(12) United States Patent
Xu et al.

(10) Patent No.: US 7,270,980 B2
(45) Date of Patent: Sep. 18, 2007

(54) COMPOUNDS FOR IMMUNODIAGNOSIS OF PROSTATE CANCER AND METHODS FOR THEIR USE

(75) Inventors: Jiangchun Xu, Bellevue, WA (US); Davin C. Dillon, Redmond, WA (US); Jennifer Lynn Mitcham, Redmond, WA (US)

(73) Assignee: Corixa Corporation, Hamilton, MT (US)

( * ) Notice: Subject to any disclaimer, the term of this patent is extended or adjusted under 35 U.S.C. 154(b) by 584 days.

(21) Appl. No.: 09/232,880

(22) Filed: Jan. 15, 1999

(65) Prior Publication Data

US 2002/0182596 A1 Dec. 5, 2002

Related U.S. Application Data

(63) Continuation-in-part of application No. 09/159,822, filed on Sep. 23, 1998, now abandoned, which is a continuation-in-part of application No. 09/116,134, filed on Jul. 14, 1998, which is a continuation-in-part of application No. 09/030,606, filed on Feb. 25, 1998, which is a continuation-in-part of application No. 09/020,747, filed on Feb. 9, 1998, now abandoned, which is a continuation-in-part of application No. 08/904,809, filed on Aug. 1, 1997, which is a continuation-in-part of application No. 08/806,596, filed on Feb. 25, 1997, now abandoned.

(51) Int. Cl.

| | |
|---|---|
| *C12P 19/34* | (2006.01) |
| *C12Q 1/00* | (2006.01) |
| *C12Q 1/68* | (2006.01) |
| *G01N 33/567* | (2006.01) |
| *G01N 33/574* | (2006.01) |
| *G01N 33/53* | (2006.01) |
| *G01N 33/537* | (2006.01) |
| *A61K 38/00* | (2006.01) |
| *C07K 14/00* | (2006.01) |
| *C07K 16/00* | (2006.01) |
| *C07K 17/00* | (2006.01) |
| *C07K 2/00* | (2006.01) |
| *C07K 4/00* | (2006.01) |
| *C07K 5/00* | (2006.01) |

(52) U.S. Cl. ............................. 435/91.2; 435/4; 435/6; 435/7.21; 435/7.23; 435/7.92; 435/85; 435/87; 435/89; 435/91.1; 435/91.5; 435/91.51; 436/63; 436/64; 436/174; 536/1.11; 536/18.7; 536/22.1; 536/23.1

(58) Field of Classification Search ............. 435/6, 435/4, 7.21, 7.23, 85, 87, 89, 91.1, 91.2, 435/91.5, 91.51, 7.92; 436/63, 64, 174; 536/1.11, 536/18.7, 22.1, 23.1, 23.5

See application file for complete search history.

(56) References Cited

U.S. PATENT DOCUMENTS 5,786,148 A * 7/1998 Bandman et al.

FOREIGN PATENT DOCUMENTS

| EP | 652 014 A1 | 5/1995 |
|---|---|---|
| WO | WO93/14755 | 8/1993 |
| WO | WO93/25224 | 12/1993 |
| WO | WO94/09820 | 5/1994 |
| WO | WO95/04548 | 2/1995 |
| WO | WO95/30758 | 11/1995 |
| WO | WO96/21671 | 7/1996 |
| WO | WO98/37093 | * 8/1998 |
| WO | WO98/37418 | * 8/1998 |
| WO | WO98/45420 | * 10/1998 |

OTHER PUBLICATIONS

Nucleic acid database, Accession #V58522, 1998.*
Nucleic acid database, Accession #V61287, 1999.*
Tockman et al. Considerations in Bringing a Cancer Biomarker to Clinical Application. Cancer Research (Suppl.) 52:2711s-2718s, May 1, 1992.*
Tascilar et al. Role of tumor markers and mutations in cells and pancreatic juice in the diagnosis of pancreatic cancer. Annals of Oncology 10,Suppl. 4:S107-S110, 1999).*
Nucleic acid database, Accession #V62429, 1998.*
Alexeyev et al., "Improved antibiotic-resistance gene cassettes and omega elements for *Escherichia coli* vector construction and in vitro deletion/insertion mutagenesis," *Gene 160*: 63-67, 1995.
Blok et al., "Isolation of cDNAs That Are Differentially Expressed Between Androgen-Dependent and Androgen-Independent Prostate Carcinoma Cells Using Differential Display PCR," *The Prostate 26*: 213-224, 1995.
Database EMBL Accession No. AA453562, Jun. 11, 1997, Hillier et al., "Homo Sapiens cDNA Clone 788180."
El-Shirbiny, Prostatic Specific Antigen, *Advances In Clinical Chemistry 31*: 99-133, 1994.
Robson et al., "Identification of prostatic androgen regulated genes using the differential display technique," *Proceedings Of The American Association For Cancer Research Meeting 86*, 36: p. 266, Abstract No. 1589, 1995.
Short et al., "λ ZAP: a bacteriophage λ expression vector with in vivo excision properties," *Nucleic Acids Research 16*(15): 7583-7600, 1988.

\* cited by examiner

*Primary Examiner*—Alana M. Harris
(74) *Attorney, Agent, or Firm*—Seed IP Law Group PLLC

(57) ABSTRACT

Compounds and methods for diagnosing prostate cancer are provided. The inventive compounds include polypeptides containing at least a portion of a prostate tumor protein. The inventive polypeptides may be used to generate antibodies useful for the diagnosis and monitoring of prostate cancer. Nucleic acid sequences for preparing probes, primers, and polypeptides are also provided.

5 Claims, 6 Drawing Sheets

SEQUENCE LISTING

<160> NUMBER OF SEQ ID NOS: 338

<210> SEQ ID NO 1
<211> LENGTH: 814
<212> TYPE: DNA
<213> ORGANISM: Homo sapien
<220> FEATURE:
<221> NAME/KEY: misc_feature
<222> LOCATION: (1)...(814)
<223> OTHER INFORMATION: n = A,T,C or G

<400> SEQUENCE: 1

```
tttttttttt tttttcacag tataacagct ctttatttct gtgagttcta ctaggaaatc      60
atcaaatctg agggttgtct ggaggacttc aatacacctc cccccatagt gaatcagctt     120
ccaggggtc cagtccctct ccttacttca tccccatccc atgccaaagg aagaccctcc      180
ctccttggct cacagccttc tctaggcttc ccagtgcctc caggacagag tgggttatgt     240
tttcagctcc atccttgctg tgagtgtctg gtgcgttgtg cctccagctt ctgctcagtg     300
cttcatggac agtgtccagc acatgtcact ctccactctc tcagtgtgga tccactagtt     360
ctagagcggc cgccaccgcg gtggagctcc agcttttgtt cccttagtg agggttaatt      420
gcgcgcttgg cgtaatcatg gtcataactg tttcctgtgt gaaattgtta tccgctcaca     480
attccacaca acatacgagc cggaagcata agtgtaaag cctggggtgc ctaatgagtg      540
anctaactca cattaattgc gttgcgctca ctgnccgctt tccagtcngg aaaactgtcg     600
tgccagctgc attaatgaat cggccaacgc ncggggaaaa gcggtttgcg ttttgggggc     660
tcttccgctt ctcgctcact nantcctgcg ctcggtcntt cggctgcggg gaacggtatc     720
actcctcaaa ggnggtatta cggttatccn naaatcnggg gatacccngg aaaaaanttt     780
aacaaagggg cancaaaggg cngaaacgta aaaa                                 814
```

<210> SEQ ID NO 2
<211> LENGTH: 816
<212> TYPE: DNA
<213> ORGANISM: Homo sapien
<220> FEATURE:
<221> NAME/KEY: misc_feature
<222> LOCATION: (1)...(816)
<223> OTHER INFORMATION: n = A,T,C or G

<400> SEQUENCE: 2

```
acagaaatgt tggatggtgg agcacctttc tatacgactt acaggacagc agatggggaa      60
ttcatggctg ttggagcaat agaacccag ttctacgagc tgctgatcaa aggacttgga     120
ctaaagtctg atgaacttcc caatcagatg agcatggatg attggccaga atgaagaag      180
aagtttgcag atgtatttgc aaagaagacg aaggcagagt ggtgtcaaat ctttgacggc     240
acagatgcct gtgtgactcc ggttctgact tttgaggagt tgttcatca tgatcacaac      300
aaggaacggg gctcgtttat caccagtgag gagcaggacg tgagccccg ccctgcacct      360
ctgctgttaa acaccccagc catcccttct ttcaaaaggg atccactagt tctagaagcg     420
gccgccaccg cggtggagct ccagcttttg ttcccttag tgagggttaa ttgcgcgctt      480
ggcgtaatca tggtcatagc tgtttcctgt gtgaaattgt tatccgctca caattccccc     540
aacatacgag ccggaacata agtgttaaag cctggggtgc ctaatgantg agctaactcn     600
cattaattgc gttgcgctca ctgcccgctt tccagtcggg aaaactgtcg tgccactgcn     660
ttantgaatc ngccaccccc cggggaaaagg cggttgcntt ttgggcctct tccgctttcc     720
```

```
tcgctcattg atcctngcnc ccggtcttcg gctgcggnga acggttcact cctcaaaggc    780
ggtntnccgg ttatccccaa acngggata cccnga                               816
```

<210> SEQ ID NO 3
<211> LENGTH: 773
<212> TYPE: DNA
<213> ORGANISM: Homo sapien
<220> FEATURE:
<221> NAME/KEY: misc_feature
<222> LOCATION: (1)...(773)
<223> OTHER INFORMATION: n = A,T,C or G

<400> SEQUENCE: 3

```
cttttgaaag aagggatggc tggggtgttt aacagcagag gtgcagggcg ggggctcacg     60
tcctgctcct cactggtgat aaacgagccc cgttccttgt tgtgatcatg atgaacaacc    120
tcctcaaaag tcagaaccgg agtcacacag gcatctgtgc cgtcaaagat ttgacaccac    180
tctgccttcg tcttctttgc aaatacatct gcaaacttct tcttcatttc tggccaatca    240
tccatgctca tctgattggg aagttcatca gactttagtc canntccttt gatcagcagc    300
tcgtagaact ggggttctat tgctccaaca gccatgaatt cccccatctgc tgtcctgtaa    360 gtcgtataga aaggtgctcc accatccaac atgttctgtc ctcgaggggg ggcccggtac    420
ccaattcgcc ctatantgag tcgtattacg cgcgctcact ggccgtcgtt ttacaacgtc    480
gtgactggga aaaccctggg cgttaccaac ttaatcgcct tgcagcacat ccccctttcg    540
ccagctgggc gtaatancga aaaggcccgc accgatcgcc cttccaacag ttgcgcacct    600
gaatgggnaa atgggacccc cctgttaccg cgcattnaac cccgcnggg tttngttgtt    660 accccccacnt nnaccgctta cactttgcca gcgccttanc gcccgctccc tttcnccttt    720
cttcccttcc tttcncnccn ctttcccccg ggtttcccc cntcaaaccc cna           773
```

<210> SEQ ID NO 4
<211> LENGTH: 828
<212> TYPE: DNA
<213> ORGANISM: Homo sapien
<220> FEATURE:
<221> NAME/KEY: misc_feature
<222> LOCATION: (1)...(828)
<223> OTHER INFORMATION: n = A,T,C or G

<400> SEQUENCE: 4

```
cctcctgagt cctactgacc tgtgctttct ggtgtggagt ccagggctgc taggaaaagg     60
aatgggcaga cacaggtgta tgccaatgtt tctgaaatgg gtataatttc gtcctctcct    120
tcggaacact ggctgtctct gaagacttct cgctcagttt cagtgaggac acacacaaag    180
acgtgggtga ccatgttgtt tgtggggtgc agagatggga ggggtggggc ccaccctgga    240
agagtggaca gtgacacaag gtggacactc tctacagatc actgaggata agctggagcc    300
acaatgcatg aggcacacac acagcaagga tgacnctgta aacatagccc acgctgtcct    360 gnggcactg ggaagcctan atnaggccgt gagcanaaag aagggagga tccactagtt    420 ctanagcggc cgccaccgcg gtgganctcc anctttttgtt cccttttagtg agggttaatt    480 gcgcgcttgg cntaatcatg gtcatanctn tttcctgtgt gaaattgtta ccgctcaca    540 attccacaca acatacganc cggaaacata aantgtaaac ctggggtgcc taatgantga    600
ctaactcaca ttaattgcgt tgcgctcact gcccgcttc caatcnggaa acctgtcttg    660
ccncttgcat tnatgaatcn gccaaccccc ggggaaaagc gtttgcgttt tgggcgctct    720
```

-continued

| | |
|---|---|
| tccgcttcct cnctcantta ntccctncnc tcggtcattc cggctgcngc aaaccggttc | 780 |
| accncctcca aagggggtat tccggtttcc ccnaatccgg gganancc | 828 |

<210> SEQ ID NO 5
<211> LENGTH: 834
<212> TYPE: DNA
<213> ORGANISM: Homo sapien
<220> FEATURE:
<221> NAME/KEY: misc_feature
<222> LOCATION: (1)...(834)
<223> OTHER INFORMATION: n = A,T,C or G

<400> SEQUENCE: 5

| | |
|---|---|
| tttttttttt tttttactga tagatggaat ttattaagct tttcacatgt gatagcacat | 60 |
| agttttaatt gcatccaaag tactaacaaa aactctagca atcaagaatg gcagcatgtt | 120 |
| attttataac aatcaacacc tgtggctttt aaaatttggt tttcataaga taatttatac | 180 |
| tgaagtaaat ctagccatgc ttttaaaaaa tgctttaggt cactccaagc ttggcagtta | 240 |
| acatttggca taaacaataa taaaacaatc acaatttaat aaataacaaa tacaacattg | 300 |
| taggccataa tcatatacag tataaggaaa aggtggtagt gttgagtaag cagttattag | 360 |
| aatagaatac cttggcctct atgcaaatat gtctagacac tttgattcac tcagccctga | 420 |
| cattcagttt tcaaagtagg agacaggttc tacagtatca ttttacagtt tccaacacat | 480 |
| tgaaaacaag tagaaaatga tgagttgatt tttattaatg cattacatcc tcaagagtta | 540 |
| tcaccaaccc ctcagttata aaaaattttc aagttatatt agtcatataa cttggtgtgc | 600 |
| ttattttaaa ttagtgctaa atggattaag tgaagacaac aatggtcccc taatgtgatt | 660 |
| gatattggtc atttttacca gcttctaaat ctnaactttc aggcttttga actggaacat | 720 |
| tgnatnacag tgttccanag ttncaaccta ctggaacatt acagtgtgct tgattcaaaa | 780 |
| tgttattttg ttaaaaatta aattttaacc tggtggaaaa ataatttgaa atna | 834 |

<210> SEQ ID NO 6
<211> LENGTH: 818
<212> TYPE: DNA
<213> ORGANISM: Homo sapien
<220> FEATURE:
<221> NAME/KEY: misc_feature
<222> LOCATION: (1)...(818)
<223> OTHER INFORMATION: n = A,T,C or G

<400> SEQUENCE: 6

| | |
|---|---|
| tttttttttt tttttttttt aagaccctca tcaatagatg gagacataca gaaatagtca | 60 |
| aaccacatct acaaaatgcc agtatcaggc ggcggcttcg aagccaaagt gatgtttgga | 120 |
| tgtaaagtga atattagtt ggcggatgaa gcagatagtg aggaaagttg agccaataat | 180 |
| gacgtgaagt ccgtggaagc ctgtggctac aaaaaatgtt gagccgtaga tgccgtcgga | 240 |
| aatggtgaag ggagactcga agtactctga ggcttgtagg agggtaaaat agagacccag | 300 |
| taaaattgta ataagcagtg cttgaattat ttggtttcgg ttgttttcta ttagactatg | 360 |
| gtgagctcag gtgattgata ctcctgatgc gagtaatacg gatgtgttta ggagtgggac | 420 |
| ttctagggga tttagcgggg tgatgcctgt tggggccag tgcctccta gttgggggt | 480 |
| aggggctagg ctgagtggt aaaaggctca gaaaaatcct gcgaagaaaa aaacttctga | 540 |
| ggtaataaat aggattatcc cgtatcgaag gccttttgg acaggtggtg tgtggtggcc | 600 |
| ttggtatgtg ctttctcgtg ttacatcgcg ccatcattgg tatatggtta gtgtgttggg | 660 |
| ttantanggc ctantatgaa gaactttggg antggaatta aatcaatngc ttggccggaa | 720 |

```
gtcattanga nggctnaaaa ggccctgtta ngggtctggg ctnggtttta cccnacccat    780
ggaatncncc ccccggacna ntgnatccct attcttaa                            818

<210> SEQ ID NO 7
<211> LENGTH: 817
<212> TYPE: DNA
<213> ORGANISM: Homo sapien
<220> FEATURE:
<221> NAME/KEY: misc_feature
<222> LOCATION: (1)...(817)
<223> OTHER INFORMATION: n = A,T,C or G

<400> SEQUENCE: 7
tttttttttt tttttttttt tggctctaga gggggtagag ggggtgctat agggtaaata     60
cgggccctat ttcaaagatt tttaggggaa ttaattctag gacgatgggt atgaaactgt    120
ggtttgctcc acagatttca gagcattgac cgtagtatac ccccggtcgt gtagcggtga    180
aagtggtttg gtttagacgt ccgggaattg catctgtttt taagcctaat gtggggacag    240
ctcatgagtg caagacgtct tgtgatgtaa ttattatacn aatgggggct tcaatcggga    300
gtactactcg attgtcaacg tcaaggagtc gcaggtcgcc tggttctagg aataatgggg    360
gaagtatgta ggaattgaag attaatccgc cgtagtcggt gttctcctag gttcaatacc    420
attggtggcc aattgatttg atggtaaggg gagggatcgt tgaactcgtc tgttatgtaa    480 aggatnccttt ngggatggga aggcnataa ggactangga tnaatggcgg gcangatatt    540
tcaaacngtc tctanttcct gaaacgtctg aaatgttaat aanaattaan tttngttatt    600
gaatnttnng gaaagggct tacaggacta gaaaccaaat angaaaanta atnntaangg    660
cnttatcntn aaaggtnata accnctccta tnatcccacc caatngnatt ccccacncnn    720
acnattggat ncccanttc canaaanggc cnccccccgg tgnanncnc cttttgttcc    780 cttnantgan ggttattcnc ccctngcntt atcancc                            817

<210> SEQ ID NO 8
<211> LENGTH: 799
<212> TYPE: DNA
<213> ORGANISM: Homo sapien
<220> FEATURE:
<221> NAME/KEY: misc_feature
<222> LOCATION: (1)...(799)
<223> OTHER INFORMATION: n = A,T,C or G

<400> SEQUENCE: 8
catttccggg tttactttct aaggaaagcc gagcggaagc tgctaacgtg ggaatcggtg     60
cataaggaga actttctgct ggcacgcgct agggacaagc gggagagcga ctccgagcgt    120
ctgaagcgca cgtcccagaa ggtggacttg cactgaaaac agctgggaca catccgcgag    180
tacgaacagc gcctgaaagt gctggagcgg gaggtccagc agtgtagccg cgtcctgggg    240
tgggtggccg angcctganc cgctctgcct tgctgccccc angtgggccg ccacccctg     300 acctgcctgg gtccaaacac tgagccctgc tggcggactt caaggganaac ccccacangg    360 ggattttgct cctanantaa ggctcatctg ggcctcggcc cccccacctg gttggccttg    420
tctttgangt gagccccatg tccatctggg ccactgtcng gaccacctt nggagtgtt    480 ctccttacaa ccacannatg cccggctcct cccggaaacc antccancc tgngaaggat    540 caagncctgn atccactnnt nctanaaccg gccnccncg cngtggaacc cnccttntgt    600 tcctttctcnt tnagggttaa tnncgccttg gccttnccan ngtcctncnc nttttccnnt    660
```

| | |
|---|---|
| gttnaaattg ttangcnccc nccnntcccn cnncnncnan cccgacccnn annttnnann | 720 |
| ncctgggggt nccnncngat tgacccnncc nccctntant tgcnttnggg nncnntgccc | 780 |
| ctttccctct ngggannncg | 799 |

<210> SEQ ID NO 9
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 9

| | |
|---|---|
| acgccttgat cctcccaggc tgggactggt tctgggagga gccgggcatg ctgtggtttg | 60 |
| taangatgac actcccaaag gtggtcctga cagtgccca gatggacatg gggctcacct | 120 |
| caaggacaag gccaccaggt gcgggggccg aagcccacat gatccttact ctatgagcaa | 180 |
| aatcccctgt gggggcttct ccttgaagtc cgccancagg gctcagtctt tggacccang | 240 |
| caggtcatgg ggttgtngnc caactggggg ccncaacgca aaanggcnca gggcctcngn | 300 |
| cacccatccc angacgcggc tacactnctg gacctcccnc tccaccactt tcatgcgctg | 360 |
| ttcntacccg cgnatntgtc ccanctgttt cngtgccnac tccancttct nggacgtgcg | 420 |
| ctacatacgc ccggantcnc nctcccgctt tgtccctatc cacgtnccan caacaaattt | 480 |
| cnccntantg caccnattcc cacntttnnc agntttccnc nncgngcttc cttntaaaag | 540 |
| ggttganccc cggaaaatnc cccaaggggg ggggccngg tacccaactn ccccctnata | 600 |
| gctgaantcc ccatnaccnn gnctcnatgg anccntcct tttaannacn ttctnaactt | 660 |
| gggaananncc ctcgnccntn ccccntnaa tcccnccttg cnangnncnt ccccnntcc | 720 |
| ncccnnntg gcntntnann cnaaaaaggc ccnnnancaa tctcctnncn cctcanttcg | 780 |
| ccanccctcg aaatcggccn c | 801 |

<210> SEQ ID NO 10
<211> LENGTH: 789
<212> TYPE: DNA
<213> ORGANISM: Homo sapien
<220> FEATURE:
<221> NAME/KEY: misc_feature
<222> LOCATION: (1)...(789)
<223> OTHER INFORMATION: n = A,T,C or G

<400> SEQUENCE: 10

| | |
|---|---|
| cagtctatnt ggccagtgtg gcagctttcc ctgtggctgc cggtgccaca tgcctgtccc | 60 |
| acagtgtggc cgtggtgaca gcttcagccg ccctcaccgg gttcaccttc tcagccctgc | 120 |
| agatcctgcc ctacacactg gcctccctct accaccggga gaagcaggtg ttcctgccca | 180 |
| aataccgagg ggacactgga ggtgctagca gtgaggacag cctgatgacc agcttcctgc | 240 |
| caggccctaa gcctggagct cccttcccta atggacacgt gggtgctgga ggcagtggcc | 300 |
| tgctcccacc tccaccgcg ctctgcgggg cctctgcctg tgatgtctcc gtacgtgtgg | 360 |
| tggtgggtga gcccaccgan gccagggtgg ttccgggccg gggcatctgc ctggacctcg | 420 |
| ccatcctgga tagtgcttcc tgctgtccca ngtggcccca tccctgttta tgggctccat | 480 |
| tgtccagctc agccagtctg tcactgccta tatggtgtct gccgcaggcc tgggtctggt | 540 |
| cccatttact ttgctacaca ggtantattt gacaagaacg anttggccaa atactcagcg | 600 |
| ttaaaaaatt ccagcaacat tgggggtgga aggcctgcct cactgggtcc aactccccgc | 660 |

```
tcctgttaac cccatggggc tgccggcttg gccgccaatt tctgttgctg ccaaantnat        720
gtggctctct gctgccacct gttgctggct gaagtgcnta cngcncanct nggggggtng        780 ggngttccc                                                                789

<210> SEQ ID NO 11
<211> LENGTH: 772
<212> TYPE: DNA
<213> ORGANISM: Homo sapien
<220> FEATURE:
<221> NAME/KEY: misc_feature
<222> LOCATION: (1)...(772)
<223> OTHER INFORMATION: n = A,T,C or G

<400> SEQUENCE: 11
cccaccctac ccaaatatta gacaccaaca cagaaaagct agcaatggat tcccttctac         60
tttgttaaat aaataagtta aatatttaaa tgcctgtgtc tctgtgatgg caacagaagg        120
accaacaggc cacatcctga taaaaggtaa gagggggggtg gatcagcaaa aagacagtgc       180
tgtgggctga ggggacctgg ttcttgtgtg ttgcccctca ggactcttcc cctacaaata       240
actttcatat gttcaaatcc catggaggag tgtttcatcc tagaaactcc catgcaagag       300
ctacattaaa cgaagctgca ggttaagggg cttanagatg ggaaaccagg tgactgagtt       360
tattcagctc ccaaaaaccc ttctctaggt gtgtctcaac taggaggcta gctgttaacc       420
ctgagcctgg gtaatccacc tgcagagtcc ccgcattcca gtgcatggaa cccttctggc       480
ctccctgtat aagtccagac tgaaaccccc ttggaaggnc tccagtcagg cagccctana       540
aactggggaa aaaagaaaag gacgccccan cccccagctg tgcanctacg cacctcaaca       600
gcacagggtg gcagcaaaaa aaccacttta ctttggcaca aacaaaaact ngggggggca       660
accccggcac cccnangggg gttaacagga ancgggnaa cntggaaccc aattnaggca        720
ggcccnccac cccnaatntt gctgggaaat ttttcctccc ctaaattntt tc               772

<210> SEQ ID NO 12
<211> LENGTH: 751
<212> TYPE: DNA
<213> ORGANISM: Homo sapien
<220> FEATURE:
<221> NAME/KEY: misc_feature
<222> LOCATION: (1)...(751)
<223> OTHER INFORMATION: n = A,T,C or G

<400> SEQUENCE: 12
gccccaattc cagctgccac accacccacg gtgactgcat tagttcggat gtcatacaaa        60
agctgattga agcaaccctc tacttttggg tcgtgagcct tttgcttggt gcaggtttca       120
ttggctgtgt tggtgacgtt gtcattgcaa cagaatgggg gaaaggcact gttctctttg       180
aagtanggtg agtcctcaaa atccgtatag ttggtgaagc cacagcactt gagcccttttc      240 atggtggtgt tccacacttg agtgaagtct tcctgggaac cataatcttt cttgatggca       300
ggcactacca gcaacgtcag ggaagtgctc agccattgtg gtgtacacca aggcgaccac       360
agcagctgcn acctcagcaa tgaagatgan gaggangatg aagaagaacg tcncgagggc       420
acacttgctc tcagtcttan caccatanca gcccntgaaa accaananca aagaccacna       480
cnccggctgc gatgaagaaa tnaccccncg ttgacaaact tgcatggcac tgggancCac       540
agtggcccna aaaatcttca aaaggatgc cccatcnatt gacccccaa atgcccactg        600 ccaacagggg ctgcccccacn cncnnaacga tganccnatt gnacaagatc tncntggtct     660
```

```
tnatnaacnt gaaccctgcn tngtggctcc tgttcaggnc cnnggcctga cttctnaann      720
aangaactcn gaagncccca cnggananne g                                    751
```

<210> SEQ ID NO 13
<211> LENGTH: 729
<212> TYPE: DNA
<213> ORGANISM: Homo sapien
<220> FEATURE:
<221> NAME/KEY: misc_feature
<222> LOCATION: (1)...(729)
<223> OTHER INFORMATION: n = A,T,C or G

<400> SEQUENCE: 13

```
gagccaggcg tccctctgcc tgcccactca gtggcaacac ccgggagctg ttttgtcctt      60
tgtggancct cagcagtncc ctctttcaga actcantgcc aagancccctg aacaggagcc    120 accatgcagt gcttcagctt cattaagacc atgatgatcc tcttcaattt gctcatcttt    180
ctgtgtggtg cagccctgtt ggcagtgggc atctgggtgt caatcgatgg gcatccttt     240 ctgaagatct tcgggccact gtcgtccagt gccatgcagt ttgtcaacgt gggctacttc    300
ctcatcgcag ccggcgttgt ggtcttagct ctaggtttcc tgggctgcta tggtgctaag    360
actgagagca agtgtgccct cgtgacgttc ttcttcatcc tcctcctcat cttcattgct    420
gaggttgcaa tgctgtggtc gccttggtgt acaccacaat ggctgagcac ttcctgacgt    480
tgctggtaat gcctgccatc aanaaaagat tatgggttcc caggaanact tcactcaagt    540
gttggaacac caccatgaaa gggctcaagt gctgtggctt cnnccaacta tacgatttt     600 gaagantcac ctacttcaaa gaaaanagtg cctttcccc atttctgttg caattgacaa     660
acgtccccaa cacagccaat tgaaaacctg cacccaaccc aaangggtcc ccaaccanaa    720 attnaaggg                                                            729
```

<210> SEQ ID NO 14
<211> LENGTH: 816
<212> TYPE: DNA
<213> ORGANISM: Homo sapien
<220> FEATURE:
<221> NAME/KEY: misc_feature
<222> LOCATION: (1)...(816)
<223> OTHER INFORMATION: n = A,T,C or G

<400> SEQUENCE: 14

```
tgctcttcct caaagttgtt cttgttgcca taacaaccac cataggtaaa gcgggcgcag      60
tgttcgctga agggttgta gtaccagcgc gggatgctct ccttgcagag tcctgtgtct     120
ggcaggtcca cgcagtgccc tttgtcactg gggaaatgga tgcgctggag ctcgtcaaag    180
ccactcgtgt atttttcaca ggcagcctcg tccgacgcgt cggggcagtt gggggtgtct    240
tcacactcca ggaaactgtc natgcagcag ccattgctgc agcggaactg ggtgggctga    300
cangtgccag agcacactgg atggcgcctt tccatgnnan gggccctgng gaaagtccc     360 tganccccan anctgcctct caaangcccc accttgcaca ccccgacagg ctagaatgga    420
atcttcttcc cgaaaggtag ttnttcttgt tgcccaancc anccccntaa acaaactctt    480
gcanatctgc tccgnggggg tcntantacc ancgtgggaa aagaaacccca ggcngcgaac    540 caancttgtt tggatncgaa gcataatct nctnttctgc ttggtggaca gcaccantna    600
ctgtnnanct ttagnccntg gtcctcntgg gttgnncttg aacctaatcn ccnntcaact    660
gggacaaggt aantngccnt cctttnaatt cccnancntn cccccctggtt tggggttttn    720 cncnctccta ccccagaaan nccgtgttcc cccccaacta ggggccnaaa ccnttnttc     780
```

<210> SEQ ID NO 15
<211> LENGTH: 783
<212> TYPE: DNA
<213> ORGANISM: Homo sapien
<220> FEATURE:
<221> NAME/KEY: misc_feature
<222> LOCATION: (1)...(783)
<223> OTHER INFORMATION: n = A,T,C or G

<400> SEQUENCE: 15

| | | |
|---|---|---|
| ccaaggcctg ggcaggcata nacttgaagg tacaacccca ggaacccctg gtgctgaagg | 60 |
| atgtggaaaa cacagattgg cgcctactgc ggggtgacac ggatgtcagg gtagagagga | 120 |
| aagacccaaa ccaggtggaa ctgtggggac tcaaggaang cacctacctg ttccagctga | 180 |
| cagtgactag ctcagaccac ccagaggaca cggccaacgt cacagtcact gtgctgtcca | 240 |
| ccaagcagac agaagactac tgcctcgcat ccaacaangt gggtcgctgc cggggctctt | 300 |
| tcccacgctg gtactatgac cccacggagc agatctgcaa gagtttcgtt tatggaggct | 360 |
| gcttgggcaa caagaacaac taccttcggg aagaagagtg cattctancc tgtcngggtg | 420 |
| tgcaaggtgg gcctttgana ngcanctctg gggctcangc gactttcccc cagggcccct | 480 |
| ccatggaaag gcgccatcca ntgttctctg gcacctgtca gcccacccag ttccgctgca | 540 |
| ncaatggctg ctgcatcnac antttcctng aattgtgaca acaccccca ntgccccaa | 600 |
| ccctcccaac aaagcttccc tgttnaaaaa tacnccantt ggcttttnac aaacnccgg | 660 |
| cnccctccntt ttccccnntn aacaaagggc nctngcnttt gaactgcccn aacccnggaa | 720 |
| tctnccnngg aaaaantncc ccccctggtt cctnnaancc cctccncnaa anctnccccc | 780 |
| ccc | 783 |

<210> SEQ ID NO 16
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 16

| | | |
|---|---|---|
| gccccaattc cagctgccac accacccacg gtgactgcat tagttcggat gtcatacaaa | 60 |
| agctgattga agcaaccctc tacttttttgg tcgtgagcct tttgcttggt gcaggtttca | 120 |
| ttggctgtgt tggtgacgtt gtcattgcaa cagaatgggg gaaaggcact gttctctttg | 180 |
| aagtagggtg agtcctcaaa atccgtatag ttggtgaagc cacagcactt gagccctttc | 240 |
| atggtggtgt tccacacttg agtgaagtct tcctgggaac cataatcttt cttgatggca | 300 |
| ggcactacca gcaacgtcag gaagtgctca gccattgtgg tgtacaccaa ggcgaccaca | 360 |
| gcagctgcaa cctcagcaat gaagatgagg aggaggatga agaagaacgt cncgagggca | 420 |
| cacttgctct ccgtcttagc accatagcag cccangaaac caagagcaaa gaccacaacg | 480 |
| ccngctgcga atgaaagaaa ntacccacgt tgacaaactg catggccact ggacgacagt | 540 |
| tggcccgaan atcttcagaa aagggatgcc ccatcgattg aacacccana tgcccactgc | 600 |
| cnacagggct gcnccncncn gaaagaatga gccattgaag aaggatcntc ntggtcttaa | 660 |
| tgaactgaaa ccntgcatgg tggcccctgt tcagggctct tggcagtgaa ttctganaaa | 720 |

| aaggaacngc ntnagccccc ccaaangana aaacaccccc gggtgttgcc ctgaattggc | 780 |
| ggccaaggan ccctgccccn g | 801 |

<210> SEQ ID NO 17
<211> LENGTH: 740
<212> TYPE: DNA
<213> ORGANISM: Homo sapien
<220> FEATURE:
<221> NAME/KEY: misc_feature
<222> LOCATION: (1)...(740)
<223> OTHER INFORMATION: n = A,T,C or G

<400> SEQUENCE: 17

| gtgagagcca ggcgtccctc tgcctgccca ctcagtggca acacccggga gctgttttgt | 60 |
| cctttgtgga gcctcagcag ttccctcttt cagaactcac tgccaagagc cctgaacagg | 120 |
| agccaccatg cagtgcttca gcttcattaa gaccatgatg atcctcttca atttgctcat | 180 |
| ctttctgtgt ggtgcagccc tgttggcagt gggcatctgg gtgtcaatcg atggggcatc | 240 |
| ctttctgaag atcttcgggc cactgtcgtc cagtgccatg cagtttgtca acgtgggcta | 300 |
| cttcctcatc gcagccggcg ttgtggtctt tgctcttggt ttcctgggct gctatggtgc | 360 |
| taagacggag agcaagtgtg ccctcgtgac gttcttcttc atcctcctcc tcatcttcat | 420 |
| tgctgaagtt gcagctgctg tggtcgcctt ggtgtacacc acaatggctg aaccattcct | 480 |
| gacgttgctg gtantgcctg ccatcaanaa agattatggg ttcccaggaa aaattcactc | 540 |
| aantntggaa caccnccatg aaaagggctc caatttctgn tggcttcccc aactataccg | 600 |
| gaattttgaa agantcnccc tacttccaaa aaaaaanant tgccttttcc cccnttctgt | 660 |
| tgcaatgaaa acntcccaan acngccaatn aaaacctgcc cnnncaaaaa ggntcncaaa | 720 |
| caaaaaaant nnaagggttn | 740 |

<210> SEQ ID NO 18
<211> LENGTH: 802
<212> TYPE: DNA
<213> ORGANISM: Homo sapien
<220> FEATURE:
<221> NAME/KEY: misc_feature
<222> LOCATION: (1)...(802)
<223> OTHER INFORMATION: n = A,T,C or G

<400> SEQUENCE: 18

| ccgctggttg cgctggtcca gngnagccac gaagcacgtc agcatacaca gcctcaatca | 60 |
| caaggtcttc cagctgccgc acattacgca gggcaagagc ctccagcaac actgcatatg | 120 |
| ggatacactt tactttagca gccagggtga caactgagag gtgtcgaagc ttattcttct | 180 |
| gagcctctgt tagtggagga agattccggg cttcagctaa gtagtcagcg tatgtcccat | 240 |
| aagcaaacac tgtgagcagc cggaaggtag aggcaaagtc actctcagcc agctctctaa | 300 |
| cattgggcat gtccagcagt tctccaaaca cgtagacacc agnggcctcc agcacctgat | 360 |
| ggatgagtgt ggccagcgct gcccccttgg ccgacttggc taggagcaga aattgctcct | 420 |
| ggttctgccc tgtcaccttc acttccgcac tcatcactgc actgagtgtg gggacttgg | 480 |
| gctcaggatg tccagagacg tggttccgcc ccctcnctta atgacaccgn ccanncaacc | 540 |
| gtcggctccc gccgantgng ttcgtcgtnc ctgggtcagg gtctgctggc cnctacttgc | 600 |
| aancttcgtc nggcccatgg aattcaccnc accggaactn gtangatcca ctnnttctat | 660 |
| aaccggncgc caccgcnnnt ggaactccac tcttnttncc tttacttgag ggttaaggtc | 720 |
| acccttnncg ttaccttggt ccaaaccntn ccntgtgtcg anatngtnaa tcnggnccna | 780 |

| | |
|---|---|
| tnccanccnc atangaagcc ng | 802 |

<210> SEQ ID NO 19
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 19

| | |
|---|---|
| cnaagcttcc aggtnacggg ccgcnaancc tgacccnagg tancanaang cagncngcgg | 60 |
| gagcccaccg tcacgnggng gngtctttat nggaggggc ggagccacat cnctggacnt | 120 |
| cntgacccca actccccncc ncncantgca gtgatgagtg cagaactgaa ggtnacgtgg | 180 |
| caggaaccaa gancaaannc tgctccnntc caagtcggcn naggggcgg ggctggccac | 240 |
| gcncatcct cnagtgctgn aaagcccnn cctgtctact tgtttggaga acngcnnnga | 300 |
| catgcccagn gttanataac nggcngagag tnantttgcc tctcccttcc ggctgcgcan | 360 |
| cgngtntgct tagnggacat aacctgacta cttaactgaa cccngaatc tnccncccct | 420 |
| ccactaagct cagaacaaaa aacttcgaca ccactcantt gtcacctgnc tgctcaagta | 480 |
| aagtgtaccc catncccaat gtntgctnga ngctctgncc tgcnttangt tcggtcctgg | 540 |
| gaagacctat caattnaagc tatgtttctg actgcctctt gctccctgna acaancnacc | 600 |
| cnncnntcca aggggggnc ggcccccaat cccccaacc ntnaattnan tttanccccn | 660 |
| ccccngggcc cggccttta cnancntcnn nnacnggna aaaccnnngc tttncccaac | 720 |
| nnaatccncc t | 731 |

<210> SEQ ID NO 20
<211> LENGTH: 754
<212> TYPE: DNA
<213> ORGANISM: Homo sapien
<220> FEATURE:
<221> NAME/KEY: misc_feature
<222> LOCATION: (1)...(754)
<223> OTHER INFORMATION: n = A,T,C or G

<400> SEQUENCE: 20

| | |
|---|---|
| tttttttttt tttttttttt taaaaacccc ctccattnaa tgnaaacttc cgaaattgtc | 60 |
| caaccccctc ntccaaatnn ncntttccgg gnggggttc caaacccaan ttannttgg | 120 |
| annttaaatt aaatnttnnt tggnggnnna anccnaatgt nangaaagtt naacccanta | 180 |
| tnancttnaa tncctggaaa ccngtngntt ccaaaaatnt ttaaccctta antccctccg | 240 |
| aaatngttna nggaaaaccc aanttctcnt aaggttgttt gaaggntnaa tnaaaanccc | 300 |
| nnccaattgt ttttngccac gcctgaatta attggnttcc gntgttttcc nttaaaanaa | 360 |
| ggnnanccc ggttantnaa tccccccnc cccaattata ccganttttt ttngaattgg | 420 |
| ganccncgg gaattaacgg ggnnnntccc tnttggggg cnggnncccc ccccntcggg | 480 |
| ggttngggnc aggncnnaat tgtttaaggg tccgaaaaat ccctccnaga aaaaanctc | 540 |
| ccaggntgag nntngggttt nccccccccc canggcccct ctcgnanagt tggggtttgg | 600 |
| ggggcctggg attttntttc ccctnttncc tccccccccc ccnggganag aggttngngt | 660 |
| tttgntcnnc ggccccncn aaganctttt ccganttnan ttaaatccnt gcctggcga | 720 |
| agtccnttgn agggntaaan ggcccccctnn cggg | 754 |

<210> SEQ ID NO 21
<211> LENGTH: 755
<212> TYPE: DNA
<213> ORGANISM: Homo sapien
<220> FEATURE:
<221> NAME/KEY: misc_feature
<222> LOCATION: (1)...(755)
<223> OTHER INFORMATION: n = A,T,C or G

<400> SEQUENCE: 21

```
atcancccat gaccccnaac nngggaccnc tcanccggnc nnncnaccnc cggccnatca        60
nngtnagnnc actncnnttn natcacnccc cnccnactac gcccncnanc cnacgcncta       120
nncanatncc actganngcg cgangtngan ngagaaanct nataccanag ncaccanacn       180
ccagctgtcc nanaangcct nnnatacngg nnnatccaat ntgnaccctc cnaagtattn       240
nncnncanat gattttcctn anccgattac ccntnccccc tanccctcc ccccaacna         300
cgaaggcnct ggnccaagg nngcgncncc ccgctagntc cccnncaagt cncncncta         360
aactcanccn nattacncgc ttcntgagta tcactccccg aatctcaccc tactcaactc       420
aaaaanatcn gatacaaaat aatncaagcc tgnttatnac actntgactg ggtctctatt       480
ttagnggtcc ntnaancntc ctaatacttc cagtctncct tcnccaattt ccnaanggct       540
ctttcngaca gcatntttg gttcccnntt gggttcttan ngaattgccc ttcntngaac        600
gggctcntct tttccttcgg ttancctggn ttcnnccggc cagttattat ttcccntttt       660
aaattcntnc cntttantt tggcnttcna aaccccggc cttgaaaacg gcccctggt         720
aaaaggttgt tttganaaaa tttttgtttt gttcc                                  755
```

<210> SEQ ID NO 22
<211> LENGTH: 849
<212> TYPE: DNA
<213> ORGANISM: Homo sapien
<220> FEATURE:
<221> NAME/KEY: misc_feature
<222> LOCATION: (1)...(849)
<223> OTHER INFORMATION: n = A,T,C or G

<400> SEQUENCE: 22

```
tttttttttt tttttangtg tngtcgtgca ggtagaggct tactacaant gtgaanacgt        60
acgctnggan taangcgacc cganttctag ganncnccct aaaatcanac tgtgaagatn       120
atcctgnnna cggaanggtc accggnngat nntgctaggg tgnccnctcc cannncnttn       180
cataactcng nggccctgcc caccaccttc ggcggcccng ngccgggcc cgggtcattn        240
gnnttaaccn cactnngcna ncggtttccn ncccnncng acccngggcga tccggggtnc      300
tctgtcttcc cctgnagncn anaaantggg ccncggnccc ctttacccct nnacaagcca       360
cngccntcta nccncngccc ccctccant nnggggact gccnanngct ccgttnctng         420
nnaccccnnn gggtncctcg gttgtcgant cnaccgnang ccanggattc cnaaggaagg       480
tgcgttnttg gccctaccc ttcgctncgg nncacccttc ccgacnanga nccgctcccg       540
cncnncgnng cctcnnctcg caacaccngc nctcntcngt ncggnnnccc ccccacccgc       600
nccctcncnc ngncgnancn ctcnccncc gtctcannca ccaccccgcc ccgccaggcc       660
ntcanccacn ggnngacnng nagncnnntc gcnccgcgcn cgncnccct cgccncngaa       720
ctncntcngg ccantnncgc tcaanccnna cnaaacgccg ctgcgcggcc cgnagcgncc       780
ncctccncga gtcctcccgn cttccnaccc angnnttccn cgaggacacn nnaccccgcc       840
nncangcgg                                                              849
```

<210> SEQ ID NO 23
<211> LENGTH: 872
<212> TYPE: DNA
<213> ORGANISM: Homo sapien
<220> FEATURE:
<221> NAME/KEY: misc_feature
<222> LOCATION: (1)...(872)
<223> OTHER INFORMATION: n = A,T,C or G

<400> SEQUENCE: 23

| | | | | |
|---|---|---|---|---|
| gcgcaaacta tacttcgctc gnactcgtgc gcctcgctnc tcttttcctc cgcaaccatg | 60 |
| tctgacnanc ccgattnggc ngatatcnan aagntcganc agtccaaact gantaacaca | 120 |
| cacacncnan aganaaatcc nctgccttcc anagtanacn attgaacnng agaaccangc | 180 |
| nggcgaatcg taatnaggcg tgcgccgcca atntgtcncc gtttattntn ccagcntcnc | 240 |
| ctnccnaccc tacntcttcn nagctgtcnn accccctngtn cgnaccccc naggtcggga | 300 |
| tcgggttttnn nntgaccgng cnnccccctcc ccccntccat nacganccnc ccgcaccacc | 360 |
| nanngcncgc ncccognnct cttcgccncc ctgtcctntn ccoctgtngc ctggcncngn | 420 |
| accgcattga ccctcgccnn ctncnngaaa ncgnanacgt ccgggttgnn annancgctg | 480 |
| tgggnnngcg tctgcnccgc gttccttccn ncnncttcca ccatcttcnt tacngggtct | 540 |
| ccncgccntc tcnnncacnc cctggacgcg tntcctntgc cccccttnac tccccocctt | 600 |
| cgncgtgncc cgnccccacc ntcatttnca nacgntcttc acaannncct ggntnnctcc | 660 |
| cnancngncn gtcanccnag ggaaggggngg ggnnccnntg nttgacgttg ngngangtc | 720 |
| cgaanantcc tcnccntcan cnctaccoct cgggcgnnct ctcgttncc aacttancaa | 780 |
| ntctcccccg ngngcncntc tcagcctcnc ccncccocnct ctctgcantg tnctctgctc | 840 |
| tnaccnntac gantnttcgn cnccctcttt cc | 872 |

<210> SEQ ID NO 24
<211> LENGTH: 815
<212> TYPE: DNA
<213> ORGANISM: Homo sapien
<220> FEATURE:
<221> NAME/KEY: misc_feature
<222> LOCATION: (1)...(815)
<223> OTHER INFORMATION: n = A,T,C or G

<400> SEQUENCE: 24

| | | | | |
|---|---|---|---|---|
| gcatgcaagc ttgagtattc tatagngtca cctaaatanc ttggcntaat catggtcnta | 60 |
| nctgncttcc tgtgtcaaat gtatacnaan tanatatgaa tctnatntga caagannnta | 120 |
| tcntncatta gtaacaantg tnntgtccat cctgtcngan canattccca tnnattncgn | 180 |
| cgcattcncn gcncantatn taatngggaa ntcnnntnnn ncaccnncat ctatcntncc | 240 |
| gcnccctgac tggnagagat ggatnanttc tnntntgacc nacatgttca tcttggattn | 300 |
| aananccccc cgcngnccac cggttngnng cnagccnntc ccaagacctc ctgtggaggt | 360 |
| aacctgcgtc aganncatca aacntgggaa acccgcnncc angtnnaagt ngnnncanan | 420 |
| gatcccgtcc aggntttnacc atcccttcnc agcgcccoct ttngtgcctt anagngnagc | 480 |
| gtgtccnanc cntcaacat ganacgcgcc agnccanccg caattnggca caatgtcgnc | 540 |
| gaaccccccta gggggantna tncaaancco caggattgtc cncncangaa atcccncanc | 600 |
| cccncccctac ccnncttgg gacngtgacc aantcccgga gtccagtcc ggccngnctc | 660 |
| ccccaccggt nncontgggg gggtgaanct cngnntcanc cngncgaggn ntcgnaagga | 720 |

```
accggncctn ggncgaanng ancnntcnga agngccncnt cgtataaccc ccccctcncca    780 nccnacngnt agntccccc cngggtncgg aangg                                815

<210> SEQ ID NO 25
<211> LENGTH: 775
<212> TYPE: DNA
<213> ORGANISM: Homo sapien
<220> FEATURE:
<221> NAME/KEY: misc_feature
<222> LOCATION: (1)...(775)
<223> OTHER INFORMATION: n = A,T,C or G

<400> SEQUENCE: 25
ccgagatgtc tcgctccgtg gccttagctg tgctcgcgct actctctctt tctggcctgg     60
aggctatcca gcgtactcca aagattcagg tttactcacg tcatccagca gagaatggaa    120
agtcaaattt cctgaattgc tatgtgtctg ggtttcatcc atccgacatt gaanttgact    180
tactgaagaa tgganagaga attgaaaaag tggagcattc agacttgtct ttcagcaagg    240
actggtcttt ctatctcntg tactacactg aattcacccc cactgaaaaa gatgagtatg    300
cctgccgtgt gaaccatgtg actttgtcac agcccaagat agttaagtgg gatcgagaca    360
tgtaagcagn cnncatggaa gtttgaagat gccgcatttg gattggatga attccaaatt    420
ctgcttgctt gcnttttaat antgatatgc ntatacaccc taccctttat gnccccaaat    480
tgtaggggtt acatnantgt tcnctnggaa catgatcttc ctttataant ccnccnttcg    540
aattgcccgt cnccongttn ngaatgttc cnnaaccacg gttggctccc ccaggtcncc    600
tcttacggaa gggcctgggc cnctttcaa ggttggggga accnaaaatt tcncttntgc    660
ccncccncca cnntcttgng nncncanttt ggaaccctc cnattcccct tggcctcnna    720
nccttnncta anaaaactn aaancgtngc naaanntttn acttcccccc ttacc        775

<210> SEQ ID NO 26
<211> LENGTH: 820
<212> TYPE: DNA
<213> ORGANISM: Homo sapien
<220> FEATURE:
<221> NAME/KEY: misc_feature
<222> LOCATION: (1)...(820)
<223> OTHER INFORMATION: n = A,T,C or G

<400> SEQUENCE: 26
anattantac agtgtaatct tttcccagag gtgtgtanag ggaacggggc ctagaggcat     60
cccanagata ncttatanca acagtgcttt gaccaagagc tgctgggcac atttcctgca    120
gaaaaggtgg cggtccccat cactcctcct ctcccatagc catcccagag gggtgagtag    180
ccatcangcc ttcggtggga gggagtcang gaaacaacan accacagagc anacagacca    240
ntgatgacca tgggcgggag cgagcctctt ccctgnaccg gggtggcana ngangccta    300 nctgaggggt cacactataa acgttaacga ccnagatnan cacctgcttc aagtgcaccc    360
ttcctacctg acnaccagng accnnnaact gcngcctggg gacagcnctg ggancagcta    420
acnnagcact cacctgcccc cccatggccg tncgcntccc tggtcctgnc aagggaagct    480
ccctgttgga attncgggga naccaaggga nccccctcct ccanctgtga aggaaaaann    540
gatgaaattt tncccttccg gccnntcccc tcttcccttta cacgcccct nntactcntc    600 tccctctntt ntcctgncnc acttttnacc ccnnatttc ccttnattga tcggannctn    660
ganattccac tnncgcctnc cntcnatcng naanacnaaa nactntctna cccngggat    720 gggnncctcg ntcatcctct cttttcnct accncnntt ctttgcctct ccttngatca    780
```

```
tccaaccntc gntggccntn cccccccnnn tcctttnccc            820

<210> SEQ ID NO 27
<211> LENGTH: 818
<212> TYPE: DNA
<213> ORGANISM: Homo sapien
<220> FEATURE:
<221> NAME/KEY: misc_feature
<222> LOCATION: (1)...(818)
<223> OTHER INFORMATION: n = A,T,C or G

<400> SEQUENCE: 27
tctgggtgat ggcctcttcc tcctcaggga cctctgactg ctctgggcca aagaatctct    60
tgtttcttct ccgagcccca ggcagcggtg attcagccct gcccaacctg attctgatga   120
ctgcggatgc tgtgacggac ccaaggggca aatagggtcc caggtccag ggaggggcgc    180
ctgctgagca cttccgcccc tcaccctgcc cagcccctgc catgagctct ggctgggtc    240
tccgcctcca gggttctgct cttccangca ngccancaag tggcgctggg ccacactggc   300
ttcttcctgc cccntccctg gctctgantc tctgtcttcc tgtcctgtgc angcnccttg   360
gatctcagtt tccctcnctc anngaactct gtttctgann tcttcantta actntgantt   420
tatnaccnan tggnctgtnc tgtcnnactt taatgggccn daccggctaa tccctccctc   480
nctcccttcc anttcnnnna accngcttnc cntcntctcc ccntanccog ccgggaanc    540
ctcctttgcc ctnaccangg gccnnnaccg cccntnnctn gggggcnng gtnnctncnc    600
ctgntnnccc cnctcncnnt tncctcgtcc cnncnncgcn nngcanttc ncgtccccnn    660
tnnctcttcn ngtntcgnaa ngtctncntn tnnnnngncn ngntnntncn tccctctcnc   720
cnnntgnang tnnttnnnnc ncngnncccc nnnncnnnn nggnnntnnn tctncncngc    780
cccnncccc ngnattaagg cctccnntct ccggccnc                            818

<210> SEQ ID NO 28
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 28
aggaagggcg gagggatatt gtangggatt gagggatagg agnataangg gggaggtgtg    60
tcccaacatg angtgnngt tctcttttga angaggttg ngtttttann ccngggtgggt   120
gattnaaccc cattgtatgg agnnaaaggn tttnagggat ttttcggctc ttatcagtat   180
ntanattcct gtnaatcgga aaatnatntt tcnncnggaa aatnttgctc ccatccgnaa   240
attnctcccg ggtagtgcat nttnggggggn cngccangtt tcccaggctg ctanaatcgt   300
actaaagntt naagtgggan tncaaatgaa aacctnncac agagnatccn tacccgactg   360
tnnntttncct tcgccctntg actctgcnng agcccaatac ccnngngnat gtcnccngn    420
nnngcgncnc tgaaannnnc tcgnggctnn gancatcang gggtttcgca tcaaaagcnn   480
cgtttcncat naaggcactt tngcctcatc caaccnctng ccctcnncca tttngccgtc   540
nggttcncct acgctnntng cncctnnntn ganattttnc ccgcctngg naancctcct   600
gnaatgggta gggncttntc ttttnaccnn gnggtntact aatcnnctnc acgcntnctt   660
tctcnacccc ccccttttt caatcccanc ggcnaatggg gtctccccnn cgangggggg   720
```

-continued nnncccannc c 731

<210> SEQ ID NO 29
<211> LENGTH: 822
<212> TYPE: DNA
<213> ORGANISM: Homo sapien
<220> FEATURE:
<221> NAME/KEY: misc_feature
<222> LOCATION: (1)...(822)
<223> OTHER INFORMATION: n = A,T,C or G

<400> SEQUENCE: 29

```
actagtccag tgtggtggaa ttccattgtg ttggggncnc ttctatgant antnttagat    60
cgctcanacc tcacanccte ccnacnangc ctataangaa nannaataga nctgtncnnt   120
atntntacnc tcatanncct cnnnacccac tccctcttaa cccntactgt gcctatngcn   180
tnnctantct ntgccgcctn cnanccaccn gtgggccnac cncnngnatt ctcnatctcc   240
tcnccatntn gcctananta ngtncatacc ctatacctac nccaatgcta nnnctaancn   300
tccatnantt annntaacta ccactgacnt ngactttcnc atnanctcct aatttgaatc   360
tactctgact cccacngcct annnattagc ancntccccc nacnatntct caaccaaatc   420
ntcaacaacc tatctanctg ttcnccaacc nttncctccg atccccnnac aaccccctc    480
ccaaatacce nccacctgac ncctaaccen caccatcccg gcaagccnan ggcatttan    540
ccactggaat cacnatngga naaaaaaaac ccnaactctc tancncnnat ctccctaana   600
aatnctcctn naatttactn ncantnccat caanccccacn tgaaacnnaa ccccctgtttt  660
tanatcccctt ctttcgaaaa ccnacccttt annnccccaac ctttgggcc ccccnctnc    720
ccnaatgaag gncncccaat cnangaaacg nccntgaaaa ancaggcna anannntccg    780
canatcctat cccttanttn ggggnccctt nccngggcc cc                       822
```

<210> SEQ ID NO 30
<211> LENGTH: 787
<212> TYPE: DNA
<213> ORGANISM: Homo sapien
<220> FEATURE:
<221> NAME/KEY: misc_feature
<222> LOCATION: (1)...(787)
<223> OTHER INFORMATION: n = A,T,C or G

<400> SEQUENCE: 30

```
cggccgcctg ctctggcaca tgcctcctga atggcatcaa aagtgatgga ctgcccattg    60
ctagagaaga ccttctctcc tactgtcatt atggagccct gcagactgag ggctcccctt   120
gtctgcagga tttgatgtct gaagtcgtgg agtgtggctt ggagctcctc atctacatna   180
gctggaagcc ctggagggcc tctctcgcca gcctccccct tctctccacg ctctccangg   240
acaccagggg ctccaggcag cccattattc ccagnangac atggtgtttc tccacgcgga   300
cccatggggc ctgnaaggcc agggtctcct ttgacaccat ctctcccgtc ctgcctggca   360
ggccgtggga tccactantt ctanaacggn cgccaccncg gtgggagctc cagcttttgt   420
tcccnttaat gaaggttaat tgcncgcttg gcgtaatcat nggtcanaac tntttcctgt   480
gtgaaattgt ttntcccctc ncnattccnc ncnacatacn aacccggaan cataaagtgt   540
taaagcctgg gggtngcctn nngaatnaac tnaactcaat taattgcgtt ggctcatggc   600
ccgctttccn ttcnggaaaa ctgtcntccc ctgcnttnnt gaatcggcca cccccnggg    660
aaaagcggtt tgcnttttng ggggntcctt ccncttcccc cctcnctaan ccctncgcct   720
cggtcgtttnc nggtngcggg gaangggnat nnnctcccnc naaggggggng agnnngntat  780
``` ccccaaa 787

<210> SEQ ID NO 31
<211> LENGTH: 799
<212> TYPE: DNA
<213> ORGANISM: Homo sapien
<220> FEATURE:
<221> NAME/KEY: misc_feature
<222> LOCATION: (1)...(799)
<223> OTHER INFORMATION: n = A,T,C or G

<400> SEQUENCE: 31

```
ttttttttttt ttttttttggc gatgctactg tttaattgca ggaggtgggg gtgtgtgtac      60
catgtaccag ggctattaga agcaagaagg aaggagggag ggcagagcgc cctgctgagc     120
aacaaaggac tcctgcagcc ttctctgtct gtctcttggc gcaggcacat ggggaggcct     180
cccgcagggt gggggccacc agtccagggg tgggagcact acangggtg ggagtgggtg      240
gtggctggtn cnaatggcct gncacanatc cctacgattc ttgacacctg gatttcacca     300
ggggaccttc tgttctccca nggnaacttc ntnnatctcn aaagaacaca actgtttctt     360
cngcanttct ggctgttcat ggaaagcaca ggtgtccnat ttnggctggg acttggtaca     420
tatggttccg gcccacctct cccntcnaan aagtaattca cccccccccn ccntctnttg     480
cctgggccct taantaccca caccggaact canttantta ttcatcttng gntgggcttg     540
ntnatcnccn cctgaangcg ccaagttgaa aggccacgcc gtnccnctc cccatagnan      600
nttttnncnt canctaatgc cccccccggc aacnatccaa tcccccccn tggggccccc      660
agcccanggc ccccgnctcg ggnnnccngn cncgnantcc ccaggntctc ccantcngnc     720
ccnnngcncc cccgcacgca gaacanaagg ntgagccnc cgcannnnnn nggtnncnac      780
ctcgccccccc ccnncgnng                                                799
```

<210> SEQ ID NO 32
<211> LENGTH: 789
<212> TYPE: DNA
<213> ORGANISM: Homo sapien
<220> FEATURE:
<221> NAME/KEY: misc_feature
<222> LOCATION: (1)...(789)
<223> OTHER INFORMATION: n = A,T,C or G

<400> SEQUENCE: 32

```
tttttttttt tttttttttt tttttttttt tttttttttt tttttttttt tttttttttt      60
ttttnccnag ggcaggttta ttgacaacct cncgggacac aancaggctg gggacaggac     120
ggcaacaggc tccggcggcg gcggcggcgg ccctacctgc ggtaccaaat ntgcagcctc     180
cgctcccgct tgatnttcct ctgcagctgc aggatgccnt aaaacagggc ctcggccntn     240
ggtgggcacc ctgggattn aatttccacg gcacaatgc ggtcgcancc cctcaccacc       300
nattaggaat agtggtntta cccnccnccg ttggcncact cccntggaa accacttntc      360
gcggctccgg catctggtct taaaccttgc aaacnctggg gccctctttt tggttantnt     420
nccngccaca atcatnactc agactggcnc gggctggccc caaaaaancn ccccaaaacc    480
ggnccatgtc ttncggggt tgctgcnatn tncatcacct cccgggcnca ncaggncaac     540
ccaaaagttc ttgnggcccn caaaaaanct ccgggggnc ccagtttcaa caaagtcatc     600
cccctttggcc cccaaatcct cccccgntt nctgggtttg gaacccacg cctctnnctt      660
tggnnggcaa gntggntccc ccttcgggcc cccggtgggc ccnnctctaa ngaaaacncc    720
```

```
ntcctnnnca ccatcccccc nngnnacgnc tancaangna tcccttttt tanaaacggg    780 cccccccncg                                                          789

<210> SEQ ID NO 33
<211> LENGTH: 793
<212> TYPE: DNA
<213> ORGANISM: Homo sapien
<220> FEATURE:
<221> NAME/KEY: misc_feature
<222> LOCATION: (1)...(793)
<223> OTHER INFORMATION: n = A,T,C or G

<400> SEQUENCE: 33
gacagaacat gttggatggt ggagcacctt tctatacgac ttacaggaca gcagatgggg    60
aattcatggc tgttggagca atanaacccc agttctacga gctgctgatc aaaggacttg   120
gactaaagtc tgatgaactt cccaatcaga tgagcatgga tgattggcca gaaatgaana   180
agaagtttgc agatgtattt gcaaagaaga cgaaggcaga gtggtgtcaa atctttgacg   240
gcacagatgc ctgtgtgact ccggttctga cttttgagga ggttgttcat catgatcaca   300
acaangaacg gggctcgttt atcaccantg aggagcagga cgtgagcccc cgccctgcac   360
ctctgctgtt aaacacccca gccatccctt ctttcaaaag ggatccacta cttctagagc   420
ggncgccacc gcgtggagc tccagctttt gttcccttta gtgagggtta attgcgcgct    480
tggcgtaatc atggtcatan ctgtttcctg tgtgaaattg ttatccgctc acaattccac   540
acaacatacg anccggaagc atnaaatttt aaagcctggn ggtngcctaa tgantgaact   600
nactcacatt aattggcttt gcgctcactg cccgctttcc agtccggaaa acctgtcctt   660
gccagctgcc nttaatgaat cnggccaccc cccgggggaaa aggcngtttg cttnttgggg  720
cgcncttccc gctttctcgc ttcctgaant ccttccccc ggtctttcgg cttgcggcna   780
acggtatcna cct                                                      793

<210> SEQ ID NO 34
<211> LENGTH: 756
<212> TYPE: DNA
<213> ORGANISM: Homo sapien
<220> FEATURE:
<221> NAME/KEY: misc_feature
<222> LOCATION: (1)...(756)
<223> OTHER INFORMATION: n = A,T,C or G

<400> SEQUENCE: 34
gccgcgaccg gcatgtacga gcaactcaag ggcgagtgga accgtaaaag ccccaatctt    60
ancaagtgcg gggaanagct gggtcgactc aagctagttc ttctggagct caacttcttg   120
ccaaccacag ggaccaagct gaccaaacag cagctaattc tggcccgtga catactggag   180
atcggggccc aatggagcat cctacgcaan gacatcccct ccttcgagcg ctacatggcc   240
cagctcaaat gctactactt tgattacaan gagcagctcc ccgagtcagc ctatatgcac   300
cagctcttgg gcctcaacct cctcttcctg ctgtcccaga accgggtggc tgantnccac   360
acgganttgg ancggctgcc tgcccaanga catacanacc aatgtctaca tcnaccacca   420
gtgtcctgga gcaatactga tgganggcag ctaccncaaa gtnttcctgg ccnagggtaa   480 catccccgc cgagagctac accttcttca ttgacatcct gctcgacact atcagggatg    540
aaaatcgcng ggttgctcca gaaaggctnc aanaaatcc ttttcnctga aggcccccgg   600
atncnctagt nctagaatcg gccgccatc gcggtggan ctccaacctt tcgttncct    660 ttactgaggg ttnattgccg cccttggcgt tatcatggtc acnccngttn cctgtgttga   720
```
aattnttaac cccccacaat tccacgccna cattng 756

<210> SEQ ID NO 35
<211> LENGTH: 834
<212> TYPE: DNA
<213> ORGANISM: Homo sapien
<220> FEATURE:
<221> NAME/KEY: misc_feature
<222> LOCATION: (1)...(834)
<223> OTHER INFORMATION: n = A,T,C or G

<400> SEQUENCE: 35

| | | | | | |
|---|---|---|---|---|---|
| ggggatctct | anatcnacct | gnatgcatgg | ttgtcggtgt | ggtcgctgtc | gatgaanatg | 60 |
| aacaggatct | tgcccttgaa | gctctcggct | gctgtnttta | agttgctcag | tctgccgtca | 120 |
| tagtcagaca | cnctcttggg | caaaaaacan | caggatntga | gtcttgattt | cacctccaat | 180 |
| aatcttcngg | gctgtctgct | cggtgaactc | gatgacnang | ggcagctggt | tgtgtntgat | 240 |
| aaantccanc | angttctcct | tggtgacctc | cccttcaaag | ttgttccggc | cttcatcaaa | 300 |
| cttctnnaan | angannancc | canctttgtc | gagctggnat | ttgganaaca | cgtcactgtt | 360 |
| ggaaactgat | cccaaatggt | atgtcatcca | tcgcctctgc | tgcctgcaaa | aaacttgctt | 420 |
| ggcncaaatc | cgactccccn | tccttgaaag | aagccnatca | cacccccctc | cctggactcc | 480 |
| nncaangact | ctnccgctnc | cccntccnng | cagggttggt | ggcanccgg | gcccntgcgc | 540 |
| ttcttcagcc | agttcacnat | nttcatcagc | ccctctgcca | gctgtttnat | tccttggggg | 600 |
| ggaanccgtc | tctcccttcc | tgaannaact | ttgaccgtng | gaatagccgc | gcntcnccnt | 660 |
| acntnctggg | ccgggttcaa | antccctccn | ttgncnntcn | cctcgggcca | ttctggattt | 720 |
| nccnaacttt | ttccttcccc | cnccccncgg | ngtttggntt | tttcatnggg | ccccaactct | 780 |
| gctnttggcc | antccctgg | gggcntntan | cnccccctnt | ggtcccntng | ggcc | 834 |

<210> SEQ ID NO 36
<211> LENGTH: 814
<212> TYPE: DNA
<213> ORGANISM: Homo sapien
<220> FEATURE:
<221> NAME/KEY: misc_feature
<222> LOCATION: (1)...(814)
<223> OTHER INFORMATION: n = A,T,C or G

<400> SEQUENCE: 36

| | | | | | |
|---|---|---|---|---|---|
| cggncgcttt | ccngccgcgc | cccgtttcca | tgacnaaggc | tcccttcang | ttaaatacnn | 60 |
| cctagnaaac | attaatgggt | tgctctacta | atacatcata | cnaaccagta | agcctgccca | 120 |
| naacgccaac | tcaggccatt | cctaccaaag | gaagaaaggc | tggtctctcc | accccctgta | 180 |
| ggaaaggcct | gccttgtaag | acaccacaat | ncggctgaat | ctnaagtctt | gtgttttact | 240 |
| aatgaaaaa | aaaaataaac | aanaggtttt | gttctcatgg | ctgcccaccg | cagcctggca | 300 |
| ctaaaacanc | ccagcgctca | cttctgcttg | ganaaatatt | ctttgctctt | ttggacatca | 360 |
| ggcttgatgg | tatcactgcc | acnttccac | ccagctgggc | nccccttcccc | catntttgtc | 420 |
| antganctgg | aaggcctgaa | ncttagtctc | caaaagtctc | ngcccacaag | accggccacc | 480 |
| agggangtc | ntttncagtg | gatctgccaa | anantacccn | tatcatcnnt | gaataaaaag | 540 |
| gcccctgaac | ganatgcttc | cancancctt | taagacccat | aatcctngaa | ccatggtgcc | 600 |
| cttccggtct | gatccnaaag | gaatgttcct | gggtcccant | ccctcctttg | ttncttacgt | 660 |
| tgtnttggac | ccntgctngn | atnacccaan | tganatcccn | ngaagcaccc | tnccctggc | 720 |

| | |
|---|---|
| atttganttt cntaaattct ctgccctacn nctgaaagca cnattccctn ggcnccnaan | 780 |
| ggngaactca agaaggtctn ngaaaaacca cncn | 814 |

<210> SEQ ID NO 37
<211> LENGTH: 760
<212> TYPE: DNA
<213> ORGANISM: Homo sapien
<220> FEATURE:
<221> NAME/KEY: misc_feature
<222> LOCATION: (1)...(760)
<223> OTHER INFORMATION: n = A,T,C or G

<400> SEQUENCE: 37

| | |
|---|---|
| gcatgctgct cttcctcaaa gttgttcttg ttgccataac aaccaccata ggtaaagcgg | 60 |
| gcgcagtgtt cgctgaaggg gttgtagtac cagcgcggga tgctctcctt gcagagtcct | 120 |
| gtgtctggca ggtccacgca atgccctttg tcactgggga aatggatgcg ctggagctcg | 180 |
| tcnaanccac tcgtgtattt ttcacangca gcctcctccg aagcntccgg gcagttgggg | 240 |
| gtgtcgtcac actccactaa actgtcgatn cancagccca ttgctgcagc ggaactgggt | 300 |
| gggctgacag gtgccagaac acactggatn ggcctttcca tggaagggcc tgggggaaat | 360 |
| cnccctnancc caaactgcct ctcaaaggcc accttgcaca ccccgacagg ctagaaatgc | 420 |
| actcttcttc ccaaaggtag ttgttcttgt tgcccaagca ncctccanca aaccaaaanc | 480 |
| ttgcaaaatc tgctccgtgg gggtcatnnn taccanggtt ggggaaanaa accggcngn | 540 |
| ganccncctt gtttgaatgc naaggnaata atcctcctgt cttgcttggg tggaanagca | 600 |
| caattgaact gttaacnttg ggccngnttc cnctngggtg gtctgaaact aatcaccgtc | 660 |
| actggaaaaa ggtangtgcc ttccttgaat tcccaaantt cccctngntt tgggtnnttt | 720 |
| ctcctctncc ctaaaaatcg tnttccccc ccntanggcg | 760 |

<210> SEQ ID NO 38
<211> LENGTH: 724
<212> TYPE: DNA
<213> ORGANISM: Homo sapien
<220> FEATURE:
<221> NAME/KEY: misc_feature
<222> LOCATION: (1)...(724)
<223> OTHER INFORMATION: n = A,T,C or G

<400> SEQUENCE: 38

| | |
|---|---|
| tttttttttt tttttttttt tttttttttt ttttaaaaa ccccctccat tgaatgaaaa | 60 |
| cttccnaaat tgtccaaccc cctcnnccaa atnnccattt ccgggggggg gttccaaacc | 120 |
| caaattaatt ttgganttta aattaaatnt tnattngggg aanaanccaa atgtnaagaa | 180 |
| aatttaaccc attataaact taaatnccctn gaaacccntg gnttccaaaa attttaacc | 240 |
| cttaaatccc tccgaaattg ntaanggaaa accaaattcn cctaaggctn tttgaaggtt | 300 |
| ngatttaaac ccccttnant tnttttnacc cnngnctnaa ntatttngnt tccggtgttt | 360 |
| tcctnttaan cntnggtaac tcccgntaat gaannnccct aanccaatta aaccgaattt | 420 |
| tttttgaatt ggaaattccn ngggaattna ccggggtttt tcccntttgg gggccatncc | 480 |
| cccnctttcg gggtttgggn ntaggttgaa tttttnnang ncccaaaaaa nccccccaana | 540 |
| aaaaactcc caagnnttaa ttngaatntc cccttccca ggccttttgg gaaggngggg | 600 |
| tttntggggg ccngggantt cnttccccn ttnccnccc ccccccngt aaanggttat | 660 |
| ngnntttggt ttttgggccc cttnanggac cttccggatn gaaattaaat ccccgggncg | 720 |
| gccg | 724 |

<210> SEQ ID NO 39
<211> LENGTH: 751
<212> TYPE: DNA
<213> ORGANISM: Homo sapien
<220> FEATURE:
<221> NAME/KEY: misc_feature
<222> LOCATION: (1)...(751)
<223> OTHER INFORMATION: n = A,T,C or G

<400> SEQUENCE: 39

```
tttttttttt tttttctttg ctcacattta attttattt tgattttttt taatgctgca      60
caacacaata tttatttcat ttgtttcttt tatttcattt tatttgtttg ctgctgctgt     120
tttatttatt tttactgaaa gtgagaggga acttttgtgg cctttttcc ttttctgta      180
ggccgcctta agctttctaa atttggaaca tctaagcaag ctgaanggaa aagggggttt     240
cgcaaaatca ctcgggggaa nggaaaggtt gctttgttaa tcatgcccta tggtgggtga     300
ttaactgctt gtacaattac ntttcacttt taattaattg tgctnaangc tttaattana     360
cttgggggtt ccctccccan accaaccccn ctgacaaaaa gtgccngccc tcaaatnatg     420
tcccggcnnt cnttgaaaca cacngcngaa ngttctcatt ntcccncnc caggtnaaaa     480
tgaagggtta ccatntttaa cnccacctcc acntggcnnn gcctgaatcc tcnaaaancn     540
ccctcaancn aattnctnng ccccggtcnc gcntnngtcc cnccccgggct ccgggaantn     600
cacccccnga anncnntnnc naacnaaatt ccgaaaatat tcccnntcnc tcaattcccc     660
cnnagactnt cctcnncnan cncaattttc ttttnntcac gaacncgnnc cnnaaaatgn     720
nnnncncctc cnctngtccn naatcnccan c                                   751
```

<210> SEQ ID NO 40
<211> LENGTH: 753
<212> TYPE: DNA
<213> ORGANISM: Homo sapien
<220> FEATURE:
<221> NAME/KEY: misc_feature
<222> LOCATION: (1)...(753)
<223> OTHER INFORMATION: n = A,T,C or G

<400> SEQUENCE: 40

```
gtggtatttt ctgtaagatc aggtgttcct ccctcgtagg tttagaggaa acaccctcat      60
agatgaaaac cccccgaga cagcagcact gcaactgcca agcagccggg gtaggagggg      120
cgccctatgc acagctgggc ccttgagaca gcagggcttc gatgtcaggc tcgatgtcaa      180
tggtctggaa gcggcggctg tacctgcgta ggggcacacc gtcagggccc accaggaact     240
tctcaaagtt ccaggcaacn tcgttgcgac acaccggaga ccaggtgatn agcttggggt     300
cggtcataan cgcggtggcg tcgtcgctgg gagctggcag ggcctcccgc aggaaggcna     360
ataaaaggtg cgccccgca ccgttcanct cgcacttctc naanaccatg angttgggct      420
cnaacccacc accannccgg acttccttga nggaattccc aaatctcttc gntcttgggc     480
ttctnctgat gccctanctg gttgcccngn atgccaanca ncccaaancc ccggggtcct     540
aaancaccn cctcctcntt tcatctgggt tnttntcccc ggaccntggt tcctctcaag     600
ggancccata tctcnaccan tactcaccnt ncccccccnt gnnaccanc cttctanngn     660
tcccncccg ncctctggcc cntcaaanan gcttncacna cctgggtctg ccttcccccc     720
tncctatct gnacccncn tttgtctcan tnt                                    753
```

<210> SEQ ID NO 41

```
<211> LENGTH: 341
<212> TYPE: DNA
<213> ORGANISM: Homo sapien

<400> SEQUENCE: 41
actatatcca tcacaacaga catgcttcat cccatagact tcttgacata gcttcaaatg      60
agtgaaccca tccttgattt atatacatat atgttctcag tattttggga gcctttccac     120
ttctttaaac cttgttcatt atgaacactg aaaataggaa tttgtgaaga gttaaaaagt     180
tatagcttgt ttacgtagta agttttttgaa gtctacattc aatccagaca cttagttgag    240
tgttaaactg tgattttttaa aaaatatcat ttgagaaaat tctttcagag gtattttcat    300
ttttactttt tgattaattg tgttttatat attagggtag t                        341

<210> SEQ ID NO 42
<211> LENGTH: 101
<212> TYPE: DNA
<213> ORGANISM: Homo sapien

<400> SEQUENCE: 42
acttactgaa tttagttctg tgctcttcct tatttagtgt tgtatcataa atactttgat      60
gtttcaaaca ttctaaataa ataattttca gtggcttcat a                        101

<210> SEQ ID NO 43
<211> LENGTH: 305
<212> TYPE: DNA
<213> ORGANISM: Homo sapien

<400> SEQUENCE: 43
acatctttgt tacagtctaa gatgtgttct taaatcacca ttccttcctg gtcctcaccc      60
tccagggtgg tctcacactg taattagagc tattgaggag tctttacagc aaattaagat     120
tcagatgcct tgctaagtct agagttctag agttatgttt cagaaagtct aagaaaccca     180
cctcttgaga ggtcagtaaa gaggacttaa tatttcatat ctacaaaatg accacaggat     240
tggatacaga acgagagtta tcctggataa ctcagagctg agtacctgcc cgggggccgc     300
tcgaa                                                              305

<210> SEQ ID NO 44
<211> LENGTH: 852
<212> TYPE: DNA
<213> ORGANISM: Homo sapien
<220> FEATURE:
<221> NAME/KEY: misc_feature
<222> LOCATION: (1)...(852)
<223> OTHER INFORMATION: n = A,T,C or G

<400> SEQUENCE: 44
acataaatat cagagaaaag tagtctttga aatatttacg tccaggagtt ctttgtttct      60
gattatttgg tgtgtgtttt ggtttgtgtc caaagtattg gcagcttcag ttttttcatttt    120 ctctccatcc tcgggcattc ttcccaaatt tatataccag tcttcgtcca tccacacgct     180
ccagaatttc tcttttgtag taatatctca tagctcggct gagcttttca taggtcatgc     240
tgctgttgtt cttctttttta ccccatagct gagccactgc ctctgatttc aagaacctga    300
agacgccctc agatcggtct tcccatttta ttaatcctgg gttcttgtct gggttcaaga    360
ggatgtcgcg gatgaattcc cataagtgag tccctctcgg gttgtgcttt ttggtgtggc    420
acttggcagg ggggtcttgc tccttttttca tatcaggtga ctctgcaaca ggaaggtgac   480
tggtggttgt catggagatc tgagcccggc agaaagtttt gctgtccaac aaatctactg    540
```

```
tgctaccata gttggtgtca tataaatagt tctngtcttt ccaggtgttc atgatggaag    600
gctcagtttg ttcagtcttg acaatgacat tgtgtgtgga ctggaacagg tcactactgc    660
actggccgtt ccacttcaga tgctgcaagt tgctgtagag gagntgcccc gccgtccctg    720
ccgcccgggt gaactcctgc aaactcatgc tgcaaggtg ctcgccgttg atgtcgaact     780
cntggaaagg gatacaattg gcatccagct ggttggtgtc caggaggtga tggagccact    840
cccacacctg gt                                                       852
```

```
<210> SEQ ID NO 45
<211> LENGTH: 234
<212> TYPE: DNA
<213> ORGANISM: Homo sapien

<400> SEQUENCE: 45
acaacagacc cttgctcgct aacgacctca tgctcatcaa gttggacgaa tccgtgtccg     60
agtctgacac catccggagc atcagcattg cttcgcagtg ccctaccgcg gggaactctt    120
gcctcgtttc tggctggggt ctgctggcga acggcagaat gcctaccgtg ctgcagtgcg    180
tgaacgtgtc ggtggtgtct gaggaggtct gcagtaagct ctatgacccg ctgt          234
```

```
<210> SEQ ID NO 46
<211> LENGTH: 590
<212> TYPE: DNA
<213> ORGANISM: Homo sapien
<220> FEATURE:
<221> NAME/KEY: misc_feature
<222> LOCATION: (1)...(590)
<223> OTHER INFORMATION: n = A,T,C or G

<400> SEQUENCE: 46 acttttatt taaatgttta taaggcagat ctatgagaat gatagaaaac atggtgtgta      60
atttgatagc aatattttgg agattacaga gttttagtaa ttaccaatta cacagttaaa    120
aagaagataa tatattccaa gcanatacaa aatatctaat gaaagatcaa ggcaggaaaa    180
tgantataac taattgacaa tggaaaatca attttaatgt gaattgcaca ttatccttta    240
aaagctttca aaanaaanaa ttattgcagt ctanttaatt caaacagtgt taaatggtat    300
caggataaan aactgaaggg canaaagaat taattttcac ttcatgtaac ncacccanat    360
ttacaatggc ttaaatgcan ggaaaaagca gtggaagtag ggaagtantc aaggtctttc    420
tggtctctaa tctgccttac tctttgggtg tggctttgat cctctggaga cagctgccag    480
ggctcctgtt atatccacaa tcccagcagc aagatgaagg gatgaaaaag gacacatgct    540
gccttccttt gaggagactt catctcactg gccaacactc agtcacatgt                590
```

```
<210> SEQ ID NO 47
<211> LENGTH: 774
<212> TYPE: DNA
<213> ORGANISM: Homo sapien
<220> FEATURE:
<221> NAME/KEY: misc_feature
<222> LOCATION: (1)...(774)
<223> OTHER INFORMATION: n = A,T,C or G

<400> SEQUENCE: 47 acaaggggc ataatgaagg agtggggana gattttaaag aaggaaaaaa aacgaggccc      60
tgaacagaat tttcctgnac aacgggcctt caaaataatt ttcttgggga ggttcaagac    120
gcttcactgc ttgaaactta aatggatgtg ggacanaatt ttctgtaatg accctgaggg    180
```

```
cattacagac gggactctgg gaggaaggat aaacagaaag gggacaaagg ctaatcccaa      240
aacatcaaag aaaggaaggt ggcgtcatac ctcccagcct acacagttct ccagggctct      300
cctcatccct ggaggacgac agtggaggaa caactgacca tgtccccagg ctcctgtgtg      360
ctggctcctg gtcttcagcc cccagctctg gaagcccacc ctctgctgat cctgcgtggc      420
ccacactcct tgaacacaca tccccaggtt atattcctgg acatggctga acctcctatt      480
cctacttccg agatgccttg ctccctgcag cctgtcaaaa tcccactcac cctccaaacc      540
acggcatggg aagcctttct gacttgcctg attactccag catcttggaa caatccctga      600
ttccccactc cttagaggca agatagggtg gttaagagta gggctggacc acttggagcc      660
aggctgctgg cttcaaattn tggctcattt acgagctatg ggaccttggg caagtnatct      720
tcacttctat gggcntcatt ttgttctacc tgcaaaatgg gggataataa tagt            774

<210> SEQ ID NO 48
<211> LENGTH: 124
<212> TYPE: DNA
<213> ORGANISM: Homo sapien
<220> FEATURE:
<221> NAME/KEY: misc_feature
<222> LOCATION: (1)...(124)
<223> OTHER INFORMATION: n = A,T,C or G

<400> SEQUENCE: 48
canaaattga aatttataa aaaggcattt ttctcttata tccataaaat gatataattt         60
ttgcaantat anaaatgtgt cataaattat aatgttcctt aattacagct caacgcaact      120
tggt                                                                    124

<210> SEQ ID NO 49
<211> LENGTH: 147
<212> TYPE: DNA
<213> ORGANISM: Homo sapien
<220> FEATURE:
<221> NAME/KEY: misc_feature
<222> LOCATION: (1)...(147)
<223> OTHER INFORMATION: n = A,T,C or G

<400> SEQUENCE: 49
gccgatgcta ctattttatt gcaggaggtg ggggtgtttt tattattctc tcaacagctt       60
tgtggctaca ggtggtgtct gactgcatna aaaanttttt tacgggtgat tgcaaaaatt      120
ttagggcacc catatcccaa gcantgt                                          147

<210> SEQ ID NO 50
<211> LENGTH: 107
<212> TYPE: DNA
<213> ORGANISM: Homo sapien

<400> SEQUENCE: 50
acattaaatt aataaaagga ctgttgggt tctgctaaaa cacatggctt gatatattgc         60
atggtttgag gttaggagga gttaggcata tgttttggga gagggt                      107

<210> SEQ ID NO 51
<211> LENGTH: 204
<212> TYPE: DNA
<213> ORGANISM: Homo sapien

<400> SEQUENCE: 51
gtcctaggaa gtctagggga cacacgactc tgggtcacg gggccgacac acttgcacgg        60
cgggaaggaa aggcagagaa gtgacaccgt caggggaaa tgacagaaag gaaaatcaag       120
```

```
gccttgcaag gtcagaaagg ggactcaggg cttccaccac agccctgccc cacttggcca      180
cctccctttt gggaccagca atgt                                              204

<210> SEQ ID NO 52
<211> LENGTH: 491
<212> TYPE: DNA
<213> ORGANISM: Homo sapien
<220> FEATURE:
<221> NAME/KEY: misc_feature
<222> LOCATION: (1)...(491)
<223> OTHER INFORMATION: n = A,T,C or G

<400> SEQUENCE: 52
acaaagataa catttatctt ataacaaaaa tttgatagtt ttaaaggtta gtattgtgta       60
gggtattttc caaaagacta agagataac tcaggtaaaa agttagaaat gtataaaaca      120
ccatcagaca ggttttaaa aaacaacata ttacaaaatt agacaatcat ccttaaaaaa      180
aaaacttctt gtatcaattt cttttgttca aaatgactga cttaantatt tttaaatatt      240
tcanaaacac ttcctcaaaa attttcaana tggtagcttt canatgtncc ctcagtccca      300
atgttgctca gataaataaa tctcgtgaga acttaccacc caccacaagc tttctggggc      360
atgcaacagt gtcttttctt tnctttttct tttttttttt ttacaggcac agaaactcat      420
caattttatt tggataacaa agggtctcca aattatattg aaaataaat ccaagttaat      480 atcactcttg t                                                          491

<210> SEQ ID NO 53
<211> LENGTH: 484
<212> TYPE: DNA
<213> ORGANISM: Homo sapien
<220> FEATURE:
<221> NAME/KEY: misc_feature
<222> LOCATION: (1)...(484)
<223> OTHER INFORMATION: n = A,T,C or G

<400> SEQUENCE: 53 acataaattta gcagggctaa ttaccataag atgctattta ttaanaggtn tatgatctga       60
gtattaacag ttgctgaagt ttggtatttt tatgcagcat tttctttttg ctttgataac      120
actacagaac ccttaaggac actgaaaatt agtaagtaaa gttcagaaac attagctgct      180
caatcaaatc tctacataac actatagtaa ttaaaacgtt aaaaaaaagt gttgaaatct      240
gcactagtat anaccgctcc tgtcaggata anactgcttt ggaacagaaa gggaaaaanc      300
agctttgant ttcttttgtgc tgatangagg aaaggctgaa ttaccttgtt gcctctccct      360
aatgattggc aggtcnggta aatnccaaaa catattccaa ctcaacactt cttttccncg      420
tancttgant ctgtgtattc caggancagg cggatggaat gggccagccc ncggatgttc      480 cant                                                                  484

<210> SEQ ID NO 54
<211> LENGTH: 151
<212> TYPE: DNA
<213> ORGANISM: Homo sapien

<400> SEQUENCE: 54
actaaacctc gtgcttgtga actccataca gaaaacggtg ccatccctga acacggctgg       60 ggta tactgctgac aaccgcaaca acaaaaacac aaatccttgg cactggctag            120 tcct ctcaagtgcc tttttgtttg t                                           151
```

<210> SEQ ID NO 55
<211> LENGTH: 91
<212> TYPE: DNA
<213> ORGANISM: Homo sapien

<400> SEQUENCE: 55
acctggcttg tctccggtgt gttcccggcg ccccccacgg tccccagaac ggacactttc      60
gccctccagt ggatactcga gccaaagtgg t                                    91

<210> SEQ ID NO 56
<211> LENGTH: 133
<212> TYPE: DNA
<213> ORGANISM: Homo sapien

<400> SEQUENCE: 56
ggcggatgtg cgttggttat atacaaatat gtcattttat gtaagggact tgagtatact     60 tggattttg gtatctgtgg gttgggggga cggtccagga accaataccc catggatacc    120
aagggacaac tgt                                                       133

<210> SEQ ID NO 57
<211> LENGTH: 147
<212> TYPE: DNA
<213> ORGANISM: Homo sapien
<220> FEATURE:
<221> NAME/KEY: misc_feature
<222> LOCATION: (1)...(147)
<223> OTHER INFORMATION: n = A,T,C or G

<400> SEQUENCE: 57
actctggaga acctgagccg ctgctccgcc tctgggatga ggtgatgcan gcngtggcgc      60
gactgggagc tgagcccttc cctttgcgcc tgcctcagag gattgttgcc gacntgcana    120
tctcantggg ctggatncat gcagggt                                        147

<210> SEQ ID NO 58
<211> LENGTH: 198
<212> TYPE: DNA
<213> ORGANISM: Homo sapien
<220> FEATURE:
<221> NAME/KEY: misc_feature
<222> LOCATION: (1)...(198)
<223> OTHER INFORMATION: n = A,T,C or G

<400> SEQUENCE: 58
acagggatat aggtttnaag ttattgtnat tgtaaaatac attgaatttt ctgtatactc      60
tgattacata catttatcct ttaaaaaga tgtaaatctt aatttttatg ccatctatta    120
atttaccaat gagttacctt gtaaatgaga agtcatgata gcactgaatt ttaactagtt    180
ttgacttcta agtttggt                                                  198

<210> SEQ ID NO 59
<211> LENGTH: 330
<212> TYPE: DNA
<213> ORGANISM: Homo sapien

<400> SEQUENCE: 59
acaacaaatg ggttgtgagg aagtcttatc agcaaaactg gtgatggcta ctgaaaagat     60
ccattgaaaa ttatcattaa tgattttaaa tgacaagtta tcaaaaactc actcaatttt    120
cacctgtgct agcttgctaa aatgggagtt aactctagag caaatatagt atcttctgaa    180
tacagtcaat aaatgacaaa gccagggcct acaggtggtt tccagacttt ccagacccag    240

```
cagaaggaat ctattttatc acatggatct ccgtctgtgc tcaaaatacc taatgatatt    300 tttcgtctttt attggacttc tttgaagagt                                    330
```

<210> SEQ ID NO 60
<211> LENGTH: 175
<212> TYPE: DNA
<213> ORGANISM: Homo sapien

<400> SEQUENCE: 60

```
accgtgggtg ccttctacat tcctgacggc tccttcacca acatctggtt ctacttcggc    60
gtcgtgggct ccttcctctt catcctcatc cagctggtgc tgctcatcga ctttgcgcac   120
tcctggaacc agcggtggct gggcaaggcc gaggagtgcg attcccgtgc ctggt         175
```

<210> SEQ ID NO 61
<211> LENGTH: 154
<212> TYPE: DNA
<213> ORGANISM: Homo sapien

<400> SEQUENCE: 61

```
accccacttt tcctcctgtg agcagtctgg acttctcact gctacatgat gagggtgagt    60
ggttgttgct cttcaacagt atcctcccct ttccggatct gctgagccgg acagcagtgc   120
tggactgcac agccccgggg ctccacattg ctgt                                154
```

<210> SEQ ID NO 62
<211> LENGTH: 30
<212> TYPE: DNA
<213> ORGANISM: Homo sapien

<400> SEQUENCE: 62

```
cgctcgagcc ctatagtgag tcgtattaga                                      30
```

<210> SEQ ID NO 63
<211> LENGTH: 89
<212> TYPE: DNA
<213> ORGANISM: Homo sapien

<400> SEQUENCE: 63

```
acaagtcatt tcagcaccct ttgctcttca aaactgacca tcttttatat ttaatgcttc    60
ctgtatgaat aaaaatggtt atgtcaagt                                       89
```

<210> SEQ ID NO 64
<211> LENGTH: 97
<212> TYPE: DNA
<213> ORGANISM: Homo sapien

<400> SEQUENCE: 64

```
accggagtaa ctgagtcggg acgctgaatc tgaatccacc aataaataaa ggttctgcag    60
aatcagtgca tccaggattg gtccttggat ctggggt                              97
```

<210> SEQ ID NO 65
<211> LENGTH: 377
<212> TYPE: DNA
<213> ORGANISM: Homo sapien
<220> FEATURE:
<221> NAME/KEY: misc_feature
<222> LOCATION: (1)...(377)
<223> OTHER INFORMATION: n = A,T,C or G

<400> SEQUENCE: 65

```
acaacaanaa ntcccttctt taggccactg atggaaacct ggaaccccct tttgatggca    60
gcatggcgtc ctaggccttg acacagcggc tggggtttgg gctntcccaa accgcacacc   120
ccaaccctgg tctacccaca nttctggcta tgggctgtct ctgccactga acatcagggt   180
tcggtcataa natgaaatcc caanggggac agaggtcagt agaggaagct caatgagaaa   240
ggtgctgttt gctcagccag aaaacagctg cctggcattc ccgctgaac tatgaacccg    300 tggggtgaa ctaccccan gaggaatcat gcctgggcga tgcaaggtg ccaacaggag     360 gggcgggagg agcatgt                                                  377

<210> SEQ ID NO 66
<211> LENGTH: 305
<212> TYPE: DNA
<213> ORGANISM: Homo sapien

<400> SEQUENCE: 66
acgcctttcc ctcagaattc agggaagaga ctgtcgcctg ccttcctccg ttgttgcgtg    60
agaacccgtg tgccccttcc caccatatcc accctcgctc catctttgaa ctcaaacacg   120
aggaactaac tgcaccctgg tcctctcccc agtccccagt tcaccctcca tccctcacct   180
tcctccactc taagggatat caacactgcc cagcacaggg gccctgaatt tatgtggttt    240
ttatatattt tttaataaga tgcactttat gtcatttttt aataaagtct gaagaattac   300
tgttt                                                              305

<210> SEQ ID NO 67
<211> LENGTH: 385
<212> TYPE: DNA
<213> ORGANISM: Homo sapien

<400> SEQUENCE: 67
actacacaca ctccacttgc ccttgtgaga cactttgtcc cagcacttta ggaatgctga    60
ggtcggacca gccacatctc atgtgcaaga ttgcccagca gacatcaggt ctgagagttc   120 ccctttaaa aaaggggact tgcttaaaaa agaagtctag ccacgattgt gtagagcagc    180
tgtgctgtgc tggagattca cttttgagag agttctcctc tgagacctga tctttagagg   240
ctgggcagtc ttgcacatga gatggggctg gtctgatctc agcactcctt agtctgcttg   300
cctctcccag ggccccagcc tggccacacc tgcttacagg gcactctcag atgcccatac   360
catagttctc tgctagtgg accgt                                          385

<210> SEQ ID NO 68
<211> LENGTH: 73
<212> TYPE: DNA
<213> ORGANISM: Homo sapien

<400> SEQUENCE: 68
acttaaccag atatattttt accccagatg gggatattct ttgtaaaaaa tgaaataaaa    60
gtttttttaa tgg                                                      73

<210> SEQ ID NO 69
<211> LENGTH: 536
<212> TYPE: DNA
<213> ORGANISM: Homo sapien
<220> FEATURE:
<221> NAME/KEY: misc_feature
<222> LOCATION: (1)...(536)
<223> OTHER INFORMATION: n = A,T,C or G

<400> SEQUENCE: 69
```

```
actagtccag tgtggtggaa ttccattgtg ttgggggctc tcaccctcct ctcctgcagc    60
tccagctttg tgctctgcct ctgaggagac catgcccag catctgagta ccctgctgct   120
cctgctggcc accctagctg tggccctggc ctggagcccc aaggaggagg ataggataat   180
cccgggtggc atctataacg cagacctcaa tgatgagtgg gtacagcgtg cccttcactt   240
cgccatcagc gagtataaca aggccaccaa agatgactac tacagacgtc cgctgcgggt   300
actaagagcc aggcaacaga ccgttggggg ggtgaattac ttcttcgacg tagaggtggg   360
ccgaaccata tgtaccaagt cccagcccaa cttggacacc tgtgccttcc atgaacagcc   420
agaactgcag aagaaacagt tgtgctcttt cgagatctac gaagttccct ggggagaaca   480
gaangtccct gggtgaaatc caggtgtcaa gaaatcctan ggatctgttg ccaggc       536
```

<210> SEQ ID NO 70
<211> LENGTH: 477
<212> TYPE: DNA
<213> ORGANISM: Homo sapien

<400> SEQUENCE: 70

```
atgacccta acaggggccc tctcagccct cctaatgacc tccggcctag ccatgtgatt    60
tcacttccac tccataacgc tcctcatact aggcctacta accaacacac taaccatata   120
ccaatgatgg cgcgatgtaa cacgagaaag cacataccaa ggccaccaca caccacctgt   180 ccaaaaggc cttcgatacg ggataatcct atttattacc tcagaagttt ttttcttcgc   240
agggattttt ctgagccttt taccactcca gcctagcccc tacccccaa ctaggagggc   300 actggccccc aacaggcatc acccgctaa atccctaga agtcccactc ctaaacacat   360
ccgtattact cgcatcagga gtatcaatca cctgagctca ccatagtcta atagaaaaca   420
accgaaacca aattattcaa agcactgctt attacaattt tactgggtct ctatttt       477
```

<210> SEQ ID NO 71
<211> LENGTH: 533
<212> TYPE: DNA
<213> ORGANISM: Homo sapien
<220> FEATURE:
<221> NAME/KEY: misc_feature
<222> LOCATION: (1)...(533)
<223> OTHER INFORMATION: n = A,T,C or G

<400> SEQUENCE: 71

```
agagctatag gtacagtgtg atctcagctt tgcaaacaca ttttctacat agatagtact    60
aggtattaat agatatgtaa agaaagaaat cacaccatta ataatggtaa gattggttta   120 tgtgattta gtggtatttt tggcacccct atatatgttt tccaaacttt cagcagtgat   180
attatttcca taacttaaaa agtgagtttg aaaagaaaa tctccagcaa gcatctcatt   240
taaataaagg tttgtcatct ttaaaaatac agcaatatgt gacttttaa aaaagctgtc   300 aaataggtgt gaccctacta ataattatta gaaatacatt taaaaacatc gagtacctca   360
agtcagtttg ccttgaaaaa tatcaaatat aactcttaga gaaatgtaca taaaagaatg   420
cttcgtaatt ttggagtang aggttccctc ctcaattttg tattttttaaa aagtacatgg   480 taaaaaaaaa aattcacaac agtatataag gctgtaaaat gaagaattct gcc           533
```

<210> SEQ ID NO 72
<211> LENGTH: 511
<212> TYPE: DNA
<213> ORGANISM: Homo sapien
<220> FEATURE:

<221> NAME/KEY: misc_feature
<222> LOCATION: (1)...(511)
<223> OTHER INFORMATION: n = A,T,C or G

<400> SEQUENCE: 72

```
tattacggaa aaacacacca cataattcaa ctancaaaga anactgcttc agggcgtgta    60
aaatgaaagg cttccaggca gttatctgat taaagaacac taaagagggg acaaggctaa   120
aagccgcagg atgtctacac tatancaggc gctatttggg ttggctggag gagctgtgga   180
aaacatggan agattggtgc tgganatcgc cgtggctatt cctcattgtt attacanagt   240
gaggttctct gtgtgccacc tggtttgaaa accgttctnc ataatgata gaatagtaca    300
cacatgagaa ctgaaatggc ccaaacccag aaagaaagcc caactagatc ctcagaanac   360
gcttctaggg acaataaccg atgaagaaaa gatggcctcc ttgtgccccc gtctgttatg   420
atttctctcc attgcagcna naaacccgtt cttctaagca aacncaggtg atgatggcna   480
aaatacaccc cctcttgaag naccnggagg a                                  511
```

<210> SEQ ID NO 73
<211> LENGTH: 499
<212> TYPE: DNA
<213> ORGANISM: Homo sapien
<220> FEATURE:
<221> NAME/KEY: misc_feature
<222> LOCATION: (1)...(499)
<223> OTHER INFORMATION: n = A,T,C or G

<400> SEQUENCE: 73

```
cagtgccagc actggtgcca gtaccagtac caataacagt gccagtgcca gtgccagcac    60
cagtggtggc ttcagtgctg gtgccagcct gaccgccact ctcacatttg ggctcttcgc   120
tggccttggt ggagctggtg ccagcaccag tggcagctct ggtgcctgtg gtttctccta   180
caagtgagat tttagatatt gttaatcctg ccagtctttc tcttcaagcc agggtgcatc   240
ctcagaaacc tactcaacac agcactctag gcagccacta tcaatcaatt gaagttgaca   300
ctctgcatta aatctatttg ccatttctga aaaaaaaaaa aaaaaaaggg cggccgctcg   360
antctagagg gcccgtttaa acccgctgat cagcctcgac tgtgccttct anttgccagc   420
catctgttgt ttgcccctcc cccgntgcct tccttgaccc tggaaagtgc cactcccact   480
gtcctttcct aantaaaat                                                499
```

<210> SEQ ID NO 74
<211> LENGTH: 537
<212> TYPE: DNA
<213> ORGANISM: Homo sapien
<220> FEATURE:
<221> NAME/KEY: misc_feature
<222> LOCATION: (1)...(537)
<223> OTHER INFORMATION: n = A,T,C or G

<400> SEQUENCE: 74

```
tttcatagga gaacacactg aggagatact tgaagaattt ggattcagcc gcgaagagat    60
ttatcagctt aactcagata aaatcattga agtaataag gtaaaagcta gtctctaact   120
tccaggccca cggctcaagt gaatttgaat actgcattta cagtgtagag taacacataa   180
cattgtatgc atgaaacat ggaggaacag tattacagtg tcctaccact ctaatcaaga    240
aaagaattac agactctgat tctacagtga tgattgaatt ctaaaatgg taatcattag    300
ggcttttgat ttataanact ttgggtactt atactaaatt atggtagtta tactgccttc   360
cagtttgctt gatatatttg ttgatattaa gattcttgac ttatattttg aatgggttct   420
```

```
actgaaaaan gaatgatata ttcttgaaga catcgatata catttattta cactcttgat      480
tctacaatgt agaaaatgaa ggaaatgccc caaattgtat ggtgataaaa gtcccgt        537
```

<210> SEQ ID NO 75
<211> LENGTH: 467
<212> TYPE: DNA
<213> ORGANISM: Homo sapien
<220> FEATURE:
<221> NAME/KEY: misc_feature
<222> LOCATION: (1)...(467)
<223> OTHER INFORMATION: n = A,T,C or G

<400> SEQUENCE: 75

```
caaanacaat tgttcaaaag atgcaaatga tacactactg ctgcagctca caaacacctc      60
tgcatattac acgtacctcc tcctgctcct caagtagtgt ggtctatttt gccatcatca     120
cctgctgtct gcttagaaga acggctttct gctgcaaagg agagaaatca taacagacgg     180
tggcacaagg aggccatctt ttcctcatcg gttattgtcc ctagaagcgt cttctgagga     240
tctagttggg ctttctttct gggtttgggc catttcattt ctcatgtgtg tactattcta     300
tcattattgt ataacggttt tcaaaccngt gggcacncag agaacctcac tctgtaataa     360
caatgaggaa tagccacggt gatctccagc accaaatctc tccatgttnt tccagagctc     420
ctccagccaa cccaaatagc cgctgctatn gtgtagaaca tccctgn                   467
```

<210> SEQ ID NO 76
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 76

```
aagctgacag cattcgggcc gagatgtctc gctccgtggc cttagctgtg ctcgcgctac      60
tctctctttc tggcctggag gctatccagc gtactccaaa gattcaggtt tactcacgtc     120
atccagcaga gaatggaaag tcaaatttcc tgaattgcta tgtgtctggg tttcatccat     180
ccgacattga agttgactta ctgaagaatg gagagagaat tgaaaaagtg gagcattcag     240
acttgtcttt cagcaaggac tggtctttct atctcttgta ctacactgaa ttcacccccca   300 ctgaaaaaga tgagtatgcc tgccgtgtga accatgtgac tttgtcacag cccaagatng     360
ttnagtggga tcganacatg taagcagcan catgggaggt                           400
```

<210> SEQ ID NO 77
<211> LENGTH: 248
<212> TYPE: DNA
<213> ORGANISM: Homo sapien

<400> SEQUENCE: 77

```
ctggagtgcc ttggtgtttc aagcccctgc aggaagcaga atgcaccttc tgaggcacct      60
ccagctgccc cggcggggga tgcgaggctc ggagcaccct tgcccggctg tgattgctgc     120
caggcactgt tcatctcagc ttttctgtcc ctttgctccc ggcaagcgct tctgctgaaa     180
gttcatatct ggagcctgat gtcttaacga ataaggtcc catgctccac ccgaaaaaaa     240
aaaaaaaa                                                               248
```

<210> SEQ ID NO 78

```
<211> LENGTH: 201
<212> TYPE: DNA
<213> ORGANISM: Homo sapien

<400> SEQUENCE: 78
actagtccag tgtggtggaa ttccattgtg ttgggcccaa cacaatggct acctttaaca      60
tcacccagac cccgccctgc ccgtgcccca cgctgctgct aacgacagta tgatgcttac     120
tctgctactc ggaaactatt tttatgtaat taatgtatgc tttcttgttt ataaatgcct     180
gatttaaaaa aaaaaaaaaa a                                               201

<210> SEQ ID NO 79
<211> LENGTH: 552
<212> TYPE: DNA
<213> ORGANISM: Homo sapien
<220> FEATURE:
<221> NAME/KEY: misc_feature
<222> LOCATION: (1)...(552)
<223> OTHER INFORMATION: n = A,T,C or G

<400> SEQUENCE: 79
tccttttgtt aggtttttga gacaaccta gacctaaact gtgtcacaga cttctgaatg       60
tttaggcagt gctagtaatt cctcgtaat gattctgtta ttactttcct attctttatt     120
cctctttctt ctgaagatta atgaagttga aaattgaggt ggataaatac aaaaaggtag    180
tgtgatagta aagtatcta agtgcagatg aaagtgtgtt atatatatcc attcaaaatt      240
atgcaagtta gtaattactc agggttaact aaattacttt aatatgctgt tgaacctact     300
ctgttccttg gctagaaaaa attataaaca ggactttgtt agtttgggaa gccaaattga     360
taatattcta tgttctaaaa gttgggctat acataaanta tnaagaaata tggaatttta     420
ttcccaggaa tatggggttc atttatgaat antacccggg anagaagttt tgantnaaac    480
cngttttggt taatacgtta atatgtcctn aatnaacaag gcntgactta tttccaaaaa    540
aaaaaaaaaa aa                                                        552

<210> SEQ ID NO 80
<211> LENGTH: 476
<212> TYPE: DNA
<213> ORGANISM: Homo sapien
<220> FEATURE:
<221> NAME/KEY: misc_feature
<222> LOCATION: (1)...(476)
<223> OTHER INFORMATION: n = A,T,C or G

<400> SEQUENCE: 80
acagggattt gagatgctaa ggccccagag atcgtttgat ccaaccctct tattttcaga      60
ggggaaaatg gggcctagaa gttacagagc atctagctgg tgcgctggca cccctggcct    120
cacacagact cccgagtagc tgggactaca ggcacacagt cactgaagca ggccctgttt    180
gcaattcacg ttgccacctc aacttaaac attcttcata tgtgatgtcc ttagtcacta     240
aggttaaact ttcccaccca gaaaggcaa cttagataaa atcttagagt actttcatac     300
tcttctaagt cctcttccag cctcactttg agtcctcctt gggggttgat aggaantntc    360
tcttggcttt ctcaataaaa tctctatcca tctcatgttt aatttggtac gcntaaaaat    420
gctgaaaaaa ttaaaatgtt ctggtttcnc tttaaaaaaa aaaaaaaaaa aaaaaa        476

<210> SEQ ID NO 81
<211> LENGTH: 232
<212> TYPE: DNA
<213> ORGANISM: Homo sapien
```

```
<220> FEATURE:
<221> NAME/KEY: misc_feature
<222> LOCATION: (1)...(232)
<223> OTHER INFORMATION: n = A,T,C or G

<400> SEQUENCE: 81 ttttttttttg tatgccntcn ctgtggngtt attgttgctg ccaccctgga ggagcccagt      60
ttcttctgta tctttctttt ctggggatc ttcctggctc tgcccctcca ttcccagcct      120
ctcatcccca tcttgcactt tgctagggt tggaggcgct ttcctggtag cccctcagag      180
actcagtcag cgggaataag tcctaggggt gggggtgtg gcaagccggc ct              232

<210> SEQ ID NO 82
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 82
aggcgggagc agaagctaaa gccaaagccc aagaagagtg gcagtgccag cactggtgcc      60
agtaccagta ccaataacat gccagtgcca gtgccagcac cagtggtggc ttcagtgctg     120
gtgccagcct gaccgccact ctcacatttg gctcttcgc tggccttggt ggagctggtg     180
ccagcaccag tggcagctct ggtgcctgtg gtttctccta caagtgagat tttagatatt     240
gttaatcctg ccagtctttc tcttcaagcc agggtgcatc ctcagaaacc tactcaacac     300
agcactctng gcagccacta tcaatcaatt gaagttgaca ctctgcatta aatctatttg     360
ccatttcaaa aaaaaaaaaa aaa                                              383

<210> SEQ ID NO 83
<211> LENGTH: 494
<212> TYPE: DNA
<213> ORGANISM: Homo sapien
<220> FEATURE:
<221> NAME/KEY: misc_feature
<222> LOCATION: (1)...(494)
<223> OTHER INFORMATION: n = A,T,C or G

<400> SEQUENCE: 83
accgaattgg gaccgctggc ttataagcga tcatgtcctc cagtattacc tcaacgagca      60
gggagatcga gtctatacgc tgaagaaatt tgacccgatg ggacaacaga cctgctcagc     120
ccatcctgct cggttctccc cagatgacaa atactctcga caccgaatca ccatcaagaa     180
acgcttcaag gtgctcatga cccagcaacc gcgcccgtc ctctgagggt ccttaaactg     240
atgtcttttc tgccacctgt taccccctcgg agactccgta accaaactct tcggactgtg     300
agccctgatg cctttttgcc agccatactc tttggcntcc agtctctcgt ggcgattgat     360
tatgcttgtg tgaggcaatc atggtggcat cacccatnaa gggaacacat ttganttttt     420
tttcncatat tttaaattac naccagaata nttcagaata aatgaattga aaaactctta     480
aaaaaaaaaa aaaa                                                        494

<210> SEQ ID NO 84
<211> LENGTH: 380
<212> TYPE: DNA
<213> ORGANISM: Homo sapien
<220> FEATURE:
<221> NAME/KEY: misc_feature
<222> LOCATION: (1)...(380)
```

<223> OTHER INFORMATION: n = A,T,C or G

<400> SEQUENCE: 84

```
gctggtagcc tatggcgtgg ccacggangg gctcctgagg cacgggacag tgacttccca      60
agtatcctgc gccgcgtctt ctaccgtccc tacctgcaga tcttcgggca gattccccag     120
gaggacatgg acgtggccct catggagcac agcaactgct cgtcggagcc cggcttctgg     180
gcacaccctc ctggggccca ggcgggcacc tgcgtctccc agtatgccaa ctggctggtg     240
gtgctgctcc tcgtcatctt cctgctcgtg ccaacatcc tgctggtcac ttgctcattg      300
ccatgttcag ttacacattc ggcaaagtac agggcaacag cnatctctac tgggaaggcc     360
agcgttnccg cctcatccgg                                                 380
```

<210> SEQ ID NO 85
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 85

```
gagttagctc ctccacaacc ttgatgaggt cgtctgcagt ggcctctcgc ttcataccgc      60
tnccatcgtc atactgtagg tttgccacca cctcctgcat cttggggcgg ctaatatcca    120
ggaaactctc aatcaagtca ccgtcnatna acctgtggc tggttctgtc ttccgctcgg     180
tgtgaaagga tctccagaag gagtgctcga tcttccccac acttttgatg actttattga    240
gtcgattctg catgtccagc aggaggttgt accagctctc tgacagtgag gtcaccagcc    300
ctatcatgcc nttgaacgtg ccgaagaaca ccgagccttg tgtgggggt gnagtctcac     360
ccagattctg cattaccaga nagccgtggc aaaaganatt gacaactcgc ccaggnngaa    420
aaagaacacc tcctggaagt gctngccgct cctcgtccnt tggtggnngc gcntnccttt    480
t                                                                    481
```

<210> SEQ ID NO 86
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 86

```
aacatcttcc tgtataatgc tgtgtaatat cgatccgatn ttgtctgctg agaattcatt      60
acttggaaaa gcaacttnaa gcctggacac tggtattaaa attcacaata tgcaacactt    120
taaacagtgt gtcaatctgc tcccttactt tgtcatcacc agtctgggaa taagggtatg    180
ccctattcac acctgttaaa agggcgctaa gcatttttga ttcaacatct ttttttttga    240
cacaagtccg aaaaaagcaa aagtaaacag ttnttaattt gttagccaat tcactttctt    300
catgggacag agccatttga tttaaaaagc aaattgcata atattgagct tgggagctg     360
atatntgagc ggaagantag cctttctact tcaccagaca caactccttt catattggga    420
tgttnacnaa agttatgtct cttacagatg ggatgctttt gtggcaattc tg            472
```

<210> SEQ ID NO 87
<211> LENGTH: 413

```
<212> TYPE: DNA
<213> ORGANISM: Homo sapien
<220> FEATURE:
<221> NAME/KEY: misc_feature
<222> LOCATION: (1)...(413)
<223> OTHER INFORMATION: n = A,T,C or G

<400> SEQUENCE: 87
agaaaccagt atctctnaaa acaacctctc ataccttgtg gacctaattt tgtgtgcgtg      60
tgtgtgtgcg cgcatattat atagacaggc acatctttt tactttgta aaagcttatg      120 cctctttggt atctatatct gtgaaagttt taatgatctg ccataatgtc ttggggacct    180
ttgtcttctg tgtaaatggt actagagaaa acacctatnt tatgagtcaa tctagttngt    240
tttattcgac atgaaggaaa tttccagatn acaacactna caaactctcc cttgactagg   300
ggggacaaag aaaagcanaa ctgaacatna gaaacaattn cctggtgaga aattncataa   360
acagaaattg ggtngtatat tgaaananng catcattnaa acgttttttt ttt          413

<210> SEQ ID NO 88
<211> LENGTH: 448
<212> TYPE: DNA
<213> ORGANISM: Homo sapien
<220> FEATURE:
<221> NAME/KEY: misc_feature
<222> LOCATION: (1)...(448)
<223> OTHER INFORMATION: n = A,T,C or G

<400> SEQUENCE: 88
cgcagcgggt cctctctatc tagctccagc ctctcgcctg ccccactccc cgcgtcccgc      60
gtcctagccn accatggccg ggcccctgcg cgccccgctg ctcctgctgg ccatcctggc    120
cgtggccctg gccgtgagcc ccgcggccgg ctccagtccc ggcaagccgc cgcgcctggt    180
gggaggccca tggaccccgc gtggaagaag aaggtgtgcg gcgtgcactg gactttgccg   240
tcggcnanta caacaaaccc gcaacnactt ttaccnagcn cgcgctgcag gttgtgccgc    300
cccaancaaa ttgttactng gggtaantaa ttcttggaag ttgaacctgg gccaaacnng   360
tttaccagaa ccnagccaat tngaacaatt nccctccat aacagcccct tttaaaagg     420 gaancantcc tgntcttttc caaatttt                                        448

<210> SEQ ID NO 89
<211> LENGTH: 463
<212> TYPE: DNA
<213> ORGANISM: Homo sapien
<220> FEATURE:
<221> NAME/KEY: misc_feature
<222> LOCATION: (1)...(463)
<223> OTHER INFORMATION: n = A,T,C or G

<400> SEQUENCE: 89
gaattttgtg cactggccac tgtgatggaa ccattgggcc aggatgcttt gagtttatca      60
gtagtgattc tgccaaagtt ggtgttgtaa catgagtatg taaaatgtca aaaaattagc    120
agaggtctag gtctgcatat cagcagacag tttgtccgtg tattttgtag ccttgaagtt    180
ctcagtgaca agttnnttct gatgcgaagt tctnattcca gtgttttagt cctttgcatc    240
tttnatgttn agacttgcct ctntnaaatt gcttttgtnt tctgcaggta ctatctgtgg   300
tttaacaaaa tagaannact tctctgcttn gaanatttga atatcttaca tctnaaaatn    360
aattctctcc ccatannaaa acccangccc ttgggganaat ttgaaaaang gntccttcnn   420
aattcnnana anttcagntn tcatacaaca naacnggganc ccc                     463
```

```
<210> SEQ ID NO 90
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 90
agggattgaa ggtctnttnt actgtcggac tgttcancca ccaactctac aagttgctgt      60
cttccactca ctgtctgtaa gcntnttaac ccagactgta tcttcataaa tagaacaaat     120
tcttcaccag tcacatcttc taggaccttt ttggattcag ttagtataag ctcttccact     180
tcctttgtta agacttcatc tggtaaagtc ttaagttttg tagaaaggaa tttaattgct     240
cgttctctaa caatgtcctc tccttgaagt atttggctga acaacccacc tnaagtccct     300
ttgtgcatcc attttaaata tacttaatag ggcattggtn cactaggtta aattctgcaa     360
gagtcatctg tctgcaaaag ttgcgttagt atatctgcca                           400

<210> SEQ ID NO 91
<211> LENGTH: 480
<212> TYPE: DNA
<213> ORGANISM: Homo sapien
<220> FEATURE:
<221> NAME/KEY: misc_feature
<222> LOCATION: (1)...(480)
<223> OTHER INFORMATION: n = A,T,C or G

<400> SEQUENCE: 91
gagctcggat ccaataatct ttgtctgagg gcagcacaca tatncagtgc catggnaact      60
ggtctacccc acatgggagc agcatgccgt agntatataa ggtcattccc tgagtcagac     120
atgcctcttt gactaccgtg tgccagtgct ggtgattctc acacacctcc nnccgctctt     180
tgtggaaaaa ctggcacttg nctggaacta gcaagacatc acttacaaat tcacccacga     240
gacacttgaa aggtgtaaca aagcgactct tgcattgctt tttgtccctc cggcaccagt     300
tgtcaatact aacccgctgg tttgcctcca tcacatttgt gatctgtagc tctggataca     360
tctcctgaca gtactgaaga acttcttctt ttgtttcaaa agcaactctt ggtgcctgtt     420
ngatcaggtt cccatttccc agtccgaatg ttcacatggc atatnttact tcccacaaaa     480

<210> SEQ ID NO 92
<211> LENGTH: 477
<212> TYPE: DNA
<213> ORGANISM: Homo sapien
<220> FEATURE:
<221> NAME/KEY: misc_feature
<222> LOCATION: (1)...(477)
<223> OTHER INFORMATION: n = A,T,C or G

<400> SEQUENCE: 92
atacagccca natcccacca cgaagatgcg cttgttgact gagaacctga tgcggtcact      60
ggtcccgctg tagccccagc gactctccac ctgctggaag cggttgatgc tgcactcctt     120
cccacgcagg cagcagcggg gccggtcaat gaactccact cgtggcttgg ggttgacggt     180
taantgcagg aagaggctga ccacctcgcg gtccaccagg atgcccgact gtgcgggacc     240
tgcagcgaaa ctcctcgatg gtcatgagcg ggaagcgaat gangcccagg gccttgccca     300
gaaccttccg cctgttctct ggcgtcacct gcagctgctg ccgctnacac tcggcctcgg     360
accagcggac aaacggcgtt gaacagccgc acctcacgga tgcccantgt gtcgcgctcc     420
```

```
aggaacggcn ccagcgtgtc caggtcaatg tcggtgaanc ctccgcgggt aatggcg      477
```

```
<210> SEQ ID NO 93
<211> LENGTH: 377
<212> TYPE: DNA
<213> ORGANISM: Homo sapien
<220> FEATURE:
<221> NAME/KEY: misc_feature
<222> LOCATION: (1)...(377)
<223> OTHER INFORMATION: n = A,T,C or G

<400> SEQUENCE: 93
gaacggctgg accttgcctc gcattgtgct gctggcagga ataccttggc aagcagctcc      60
agtccgagca gccccagacc gctgccgccc gaagctaagc ctgcctctgg ccttcccctc     120
cgcctcaatg cagaaccant agtgggagca ctgtgtttag agttaagagt gaacactgtn     180
tgattttact tgggaatttc ctctgttata tagcttttcc caatgctaat ttccaaacaa     240
caacaacaaa ataacatgtt tgcctgttna gttgtataaa agtangtgat tctgtatnta     300
aagaaaatat tactgttaca tatactgctt gcaanttctg tatttattgg tnctctggaa     360
ataaatatat tattaaa                                                    377
```

```
<210> SEQ ID NO 94
<211> LENGTH: 495
<212> TYPE: DNA
<213> ORGANISM: Homo sapien
<220> FEATURE:
<221> NAME/KEY: misc_feature
<222> LOCATION: (1)...(495)
<223> OTHER INFORMATION: n = A,T,C or G

<400> SEQUENCE: 94 cccttttgagg ggttagggtc cagttcccag tggaagaaac aggccaggag aantgcgtgc      60
cgagctgang cagatttccc acagtgaccc cagagccctg ggctatagtc tctgacccct     120
ccaaggaaag accaccttct ggggacatgg gctggagggc aggacctaga ggcaccaagg     180
gaaggcccca ttccggggct gttccccgag gaggaaggga aggggctctg tgtgcccccc     240
acgaggaana ggccctgant cctgggatca nacacccctt cacgtgtatc cccacacaaa     300
tgcaagctca ccaaggtccc ctctcagtcc cttccctaca ccctgaacgg ncactggccc     360
acacccaccc agancancca cccgccatgg ggaatgtnct caaggaatcg cngggcaacg     420
tggactctng tcccnnaagg gggcagaatc tccaatagan ggannngaacc cttgctnana     480
aaaaaaaana aaaaa                                                      495
```

```
<210> SEQ ID NO 95
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 95
ggttacttgg tttcattgcc accacttagt ggatgtcatt tagaaccatt ttgtctgctc      60
cctctggaag ccttgcgcag agcggacttt gtaattgttg gagaataact gctgaatttt     120
tagctgtttt gagttgattc gcaccactgc accacaactc aatatgaaaa ctatttnact     180
tatttattat cttgtgaaaa gtatacaatg aaaatttgt tcatactgta tttatcaagt     240
```

```
atgatgaaaa gcaatagata tatattcttt tattatgttn aattatgatt gccattatta    300
atcggcaaaa tgtggagtgt atgttctttt cacagtaata tatgcctttt gtaacttcac    360
ttggttattt tattgtaaat gaattacaaa attcttaatt taagaaaatg gtangttata    420
tttanttcan taatttcttt ccttgtttac gttaattttg aaaagaatgc at            472
```

<210> SEQ ID NO 96
<211> LENGTH: 476
<212> TYPE: DNA
<213> ORGANISM: Homo sapien
<220> FEATURE:
<221> NAME/KEY: misc_feature
<222> LOCATION: (1)...(476)
<223> OTHER INFORMATION: n = A,T,C or G

<400> SEQUENCE: 96

```
ctgaagcatt tcttcaaact tntctacttt tgtcattgat acctgtagta agttgacaat    60
gtggtgaaat tcaaaatta tatgtaactt ctactagttt tactttctcc cccaagtctt    120
ttttaactca tgattttttac acacacaatc cagaacttat tatatagcct ctaagtcttt   180
attcttcaca gtagatgatg aaagagtcct ccagtgtctt gngcanaatg ttctagntat    240
agctggatac atacngtggg agttctataa actcatacct cagtgggact naaccaaaat    300
tgtgttagtc tcaattccta ccacactgag ggagcctccc aaatcactat attcttatct    360
gcaggtactc ctccagaaaa acngacaggg caggcttgca tgaaaaagtn acatctgcgt    420
tacaaagtct atcttcctca nangtctgtn aaggaacaat ttaatcttct agcttt       476
```

<210> SEQ ID NO 97
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 97

```
actctttcta atgctgatat gatcttgagt ataagaatgc atatgtcact agaatggata    60
aaataatgct gcaaacttaa tgttcttatg caaaatggaa cgctaatgaa acacagctta    120
caatcgcaaa tcaaaactca caagtgctca tctgttgtag atttagtgta ataagactta    180
gattgtgctc cttcggatat gattgtttct canatcttgg gcaatnttcc ttagtcaaat    240
caggctacta gaattctgtt attggatatn tgagagcatg aaatttttaa naatacactt    300
gtgattatna aattaatcac aaatttcact tatacctgct atcagcagct agaaaaacat    360
ntnnttttta natcaaagta ttttgtgttt ggaantgtnn aaatgaaatc tgaatgtggg    420
ttcnatctta ttttttcccn gacnactant tncttttta gggnctattc tganccatc     479
```

<210> SEQ ID NO 98
<211> LENGTH: 461
<212> TYPE: DNA
<213> ORGANISM: Homo sapien

<400> SEQUENCE: 98

```
agtgacttgt cctccaacaa aaccccttga tcaagtttgt ggcactgaca atcagaccta    60
tgctagttcc tgtcatctat tcgctactaa atgcagactg gagggaccca aaaaggggca    120
tcaactccag ctggattatt ttggagcctg caaatctatt cctacttgta cggactttga    180
agtgattcag tttcctctac ggatgagaga ctggctcaag aatatcctca tgcagcttta    240
```

```
tgaagccact ctgaacacgc tggttatcta gatgagaaca gagaaataaa gtcagaaaat      300
ttacctggag aaaagaggct ttggctgggg accatcccat tgaaccttct cttaaggact      360
ttaagaaaaa ctaccacatg ttgtgtatcc tggtgccggc cgtttatgaa ctgaccaccc      420
tttggaataa tcttgacgct cctgaacttg ctcctctgcg a                         461

<210> SEQ ID NO 99
<211> LENGTH: 171
<212> TYPE: DNA
<213> ORGANISM: Homo sapien

<400> SEQUENCE: 99
gtggccgcgc gcaggtgttt cctcgtaccg cagggccccc tcccttcccc aggcgtccct       60
cggcgcctct gcgggcccga ggaggagcgg ctggcgggtg gggggagtgt gacccaccct      120
cggtgagaaa agccttctct agcgatctga gaggcgtgcc ttgggggtac c               171

<210> SEQ ID NO 100
<211> LENGTH: 269
<212> TYPE: DNA
<213> ORGANISM: Homo sapien

<400> SEQUENCE: 100
cggccgcaag tgcaactcca gctggggccg tgcggacgaa gattctgcca gcagttggtc       60
cgactgcgac gacggcggcg cgacagtcg caggtgcagc gcggcgcct gggtcttgc         120 aaggctgagc tgacgccgca gaggtcgtgt cacgtcccac gaccttgacg ccgtcgggga      180
cagccggaac agagcccggt gaagcgggag gcctcgggga gccctcgggg aagggcggcc      240
cgagagatac gcaggtgcag gtggccgcc                                        269

<210> SEQ ID NO 101
<211> LENGTH: 405
<212> TYPE: DNA
<213> ORGANISM: Homo sapien

<400> SEQUENCE: 101
tttttttttt ttttggaatc tactgcgagc acagcaggtc agcaacaagt ttattttgca       60
gctagcaagg taacagggta gggcatggtt acatgttcag gtcaacttcc tttgtcgtgg      120
ttgattggtt tgtctttatg ggggcggggt ggggtagggg aaacgaagca ataacatgg       180 agtgggtgca ccctccctgt agaacctggt tacaaagctt gggcagttc acctggtctg      240 tgaccgtcat tttcttgaca tcaatgttat tagaagtcag gatatctttt agagagtcca      300
ctgttctgga gggagattag ggtttcttgc caaatccaac aaaatccact gaaaagttg       360 gatgatcagt acgaataccg aggcatattc tcatatcggt ggcca                     405

<210> SEQ ID NO 102
<211> LENGTH: 470
<212> TYPE: DNA
<213> ORGANISM: Homo sapien

<400> SEQUENCE: 102
tttttttttt tttttttttt tttttttttt tttttttttt tttttttttt tttttttttt       60
ggcacttaat ccatttttat ttcaaaatgt ctacaaattt aatcccatta tacggtattt      120
tcaaaatcta aattattcaa attagccaaa tccttaccaa ataatacccca aaaatcaaaa     180 atatacttct ttcagcaaac ttgttacata aattaaaaaa atatatacgg ctggtgtttt      240
```

| | |
|---|---|
| caaagtacaa ttatcttaac actgcaaaca tttttaaggaa ctaaaataaa aaaaaacact | 300 |
| ccgcaaaggt taaagggaac aacaaattct tttacaacac cattataaaa atcatatctc | 360 |
| aaatcttagg ggaatatata cttcacacgg gatcttaact tttactcact ttgtttattt | 420 |
| ttttaaacca ttgtttgggc ccaacacaat ggaatccccc ctggactagt | 470 |

<210> SEQ ID NO 103
<211> LENGTH: 581
<212> TYPE: DNA
<213> ORGANISM: Homo sapien

<400> SEQUENCE: 103

| | |
|---|---|
| tttttttttt tttttttttga cccccctctt ataaaaaaca agttaccatt ttattttact | 60 |
| tacacatatt tattttataa ttggtattag atattcaaaa ggcagctttt aaaatcaaac | 120 |
| taaatggaaa ctgccttaga tacataattc ttaggaatta gcttaaaatc tgcctaaagt | 180 |
| gaaaatcttc tctagctctt ttgactgtaa attttttgact cttgtaaaac atccaaattc | 240 |
| attttttcttg tctttaaaat tatctaatct ttccattttt tccctattcc aagtcaattt | 300 |
| gcttctctag cctcatttcc tagctcttat ctactattag taagtggctt ttttcctaaa | 360 |
| agggaaaaca ggaagagaaa tggcacacaa aacaaacatt ttatattcat atttctacct | 420 |
| acgttaataa aatagcattt tgtgaagcca gctcaaaaga aggcttagat cctttttatgt | 480 |
| ccattttagt cactaaacga tatcaaagtg ccagaatgca aaaggtttgt gaacatttat | 540 |
| tcaaaagcta atataagata tttcacatac tcatctttct g | 581 |

<210> SEQ ID NO 104
<211> LENGTH: 578
<212> TYPE: DNA
<213> ORGANISM: Homo sapien

<400> SEQUENCE: 104

| | |
|---|---|
| tttttttttt tttttttttt tttttctctt cttttttttt gaaatgagga tcgagttttt | 60 |
| cactctctag atagggcatg aagaaaactc atctttccag ctttaaaata acaatcaaat | 120 |
| ctcttatgct atatcatatt ttaagttaaa ctaatgagtc actggcttat cttctcctga | 180 |
| aggaaatctg ttcattcttc tcattcatat agttatatca agtactacct tgcatattga | 240 |
| gaggtttttc ttctctattt acacatatat ttccatgtga atttgtatca aacctttatt | 300 |
| ttcatgcaaa ctagaaaata atgtttcttt tgcataagag aagagaacaa tatagcatta | 360 |
| caaaactgct caaattgttt gttaagttat ccattataat tagttggcag gagctaatac | 420 |
| aaatcacatt tacgacagca ataataaaac tgaagtacca gttaaatatc caaaataatt | 480 |
| aaaggaacat ttttagcctg ggtataatta gctaattcac tttacaagca tttattagaa | 540 |
| tgaattcaca tgttattatt cctagcccaa cacaatgg | 578 |

<210> SEQ ID NO 105
<211> LENGTH: 538
<212> TYPE: DNA
<213> ORGANISM: Homo sapien

<400> SEQUENCE: 105

| | |
|---|---|
| tttttttttt tttttcagta ataatcagaa caatatttat ttttatattt aaaattcata | 60 |
| gaaaagtgcc ttacatttaa taaaagtttg tttctcaaag tgatcagagg aattagatat | 120 |
| gtcttgaaca ccaatattaa tttgaggaaa atacaccaaa atacattaag taaattattt | 180 |
| aagatcatag agcttgtaag tgaaaagata aaatttgacc tcagaaactc tgagcattaa | 240 |

```
aaatccacta ttagcaaata aattactatg gacttcttgc tttaattttg tgatgaatat      300
ggggtgtcac tggtaaacca acacattctg aaggatacat tacttagtga tagattctta      360
tgtactttgc taatacgtgg atatgagttg acaagtttct ctttcttcaa tcttttaagg      420
ggcgagaaat gaggaagaaa agaaaaggat tacgcatact gttctttcta tggaaggatt      480
agatatgttt cctttgccaa tattaaaaaa ataataatgt ttactactag tgaaaccc        538

<210> SEQ ID NO 106
<211> LENGTH: 473
<212> TYPE: DNA
<213> ORGANISM: Homo sapien

<400> SEQUENCE: 106 ttttttttt ttttttagtc aagtttctat ttttattata attaaagtct tggtcatttc       60
atttattagc tctgcaactt acatatttaa attaaagaaa cgttttagac aactgtacaa     120
tttataaatg taaggtgcca ttattgagta atatattcct ccaagagtgg atgtgtccct     180
tctcccacca actaatgaac agcaacatta gtttaatttt attagtagat atacactgct     240
gcaaacgcta attctcttct ccatccccat gtgatattgt gtatatgtgt gagttggtag     300
aatgcatcac aatctacaat caacagcaag atgaagctag gctgggcttt cggtgaaaat     360
agactgtgtc tgtctgaatc aaatgatctg acctatcctc ggtggcaaga actcttcgaa     420
ccgcttcctc aaaggcgctg ccacatttgt ggctctttgc acttgtttca aaa            473

<210> SEQ ID NO 107
<211> LENGTH: 1621
<212> TYPE: DNA
<213> ORGANISM: Homo sapien

<400> SEQUENCE: 107
cgccatggca ctgcagggca tctcggtcat ggagctgtcc ggcctggccc cgggcccgtt      60
ctgtgctatg gtcctggctg acttcggggc gcgtgtggta cgcgtggacc ggcccggctc     120
ccgctacgac gtgagccgct gggccggggc caagcgctcg ctagtgctgg acctgaagca     180
gccgcgggga gccgccgtgc tgcggcgtct gtgcaagcgg tcggatgtgc tgctggagcc     240
cttccgccgc ggtgtcatgg agaaactcca gctgggccca gagattctgc agcgggaaaa     300
tccaaggctt atttatgcca ggctgagtgg atttggccag tcaggaagct tctgccggtt     360
agctggccac gatatcaact atttggcttt gtcaggtgtt ctctcaaaaa ttggcagaag     420
tggtgagaat ccgtatgccc cgctgaatct cctggctgac tttgctggtg gtggccttat     480
gtgtgcactg gcattataa tggctctttt tgaccgcaca cgcactgaca agggtcaggt     540
cattgatgca aatatggtgg aaggaacagc atatttaagt tcttttctgt ggaaaactca     600
gaaatcgagt ctgtgggaag cacctcgagg acagaacatg ttggatggtg gagcaccttt     660
ctatacgact tacaggacag cagatgggga attcatggct gttggagcaa tagaaccca     720 gttctacgag ctgctgatca aaggacttgg actaaagtct gatgaacttc ccaatcagat     780
gagcatggat gattggccag aaatgaagaa gaagtttgca gatgtatttg caaagaagac     840
gaaggcagag tggtgtcaaa tctttgacgg cacagatgcc tgtgtgactc cggttctgac     900
ttttgaggag gttgttcatc atgatcacaa caaggaacgg gctcgtttta tcaccagtga     960
ggagcaggac gtgagccccc gccctgcacc tctgctgtta aacacccag ccatcccttc     1020 tttcaaaagg gatcctttca taggagaaca cactgaggag atacttgaag aatttggatt     1080
```

-continued

```
cagccgcgaa gagatttatc agcttaactc agataaaatc attgaaagta ataaggtaaa      1140
agctagtctc taacttccag gcccacggct caagtgaatt tgaatactgc atttacagtg      1200
tagagtaaca cataacattg tatgcatgga acatggagg aacagtatta cagtgtccta      1260
ccactctaat caagaaaaga attacagact ctgattctac agtgatgatt gaattctaaa      1320
aatggttatc attagggctt ttgatttata aactttggg tacttatact aaattatggt      1380
agttattctg ccttccagtt tgcttgatat atttgttgat attaagattc ttgacttata      1440
ttttgaatgg gttctagtga aaaggaatg atatattctt gaagacatcg atatacattt      1500
atttacactc ttgattctac aatgtagaaa atgaggaaat gccacaaatt gtatggtgat      1560
aaaagtcacg tgaaacaaaa aaaaaaaaaa aaaaaaaaaa aaaaaaaaaa aaaaaaaaa      1620 a                                                                     1621
```

<210> SEQ ID NO 108
<211> LENGTH: 382
<212> TYPE: PRT
<213> ORGANISM: Homo sapien

<400> SEQUENCE: 108

```
Met Ala Leu Gln Gly Ile Ser Val Met Glu Leu Ser Gly Leu Ala Pro
 1               5                  10                  15

Gly Pro Phe Cys Ala Met Val Leu Ala Asp Phe Gly Ala Arg Val Val
             20                  25                  30

Arg Val Asp Arg Pro Gly Ser Arg Tyr Asp Val Ser Arg Leu Gly Arg
         35                  40                  45

Gly Lys Arg Ser Leu Val Leu Asp Leu Lys Gln Pro Arg Gly Ala Ala
     50                  55                  60

Val Leu Arg Arg Leu Cys Lys Arg Ser Asp Val Leu Leu Glu Pro Phe
 65                  70                  75                  80

Arg Arg Gly Val Met Glu Lys Leu Gln Leu Gly Pro Glu Ile Leu Gln
                 85                  90                  95

Arg Glu Asn Pro Arg Leu Ile Tyr Ala Arg Leu Ser Gly Phe Gly Gln
            100                 105                 110

Ser Gly Ser Phe Cys Arg Leu Ala Gly His Asp Ile Asn Tyr Leu Ala
        115                 120                 125

Leu Ser Gly Val Leu Ser Lys Ile Gly Arg Ser Gly Glu Asn Pro Tyr
    130                 135                 140

Ala Pro Leu Asn Leu Leu Ala Asp Phe Ala Gly Gly Leu Met Cys
145                 150                 155                 160

Ala Leu Gly Ile Ile Met Ala Leu Phe Asp Arg Thr Arg Thr Asp Lys
                165                 170                 175

Gly Gln Val Ile Asp Ala Asn Met Val Glu Gly Thr Ala Tyr Leu Ser
            180                 185                 190

Ser Phe Leu Trp Lys Thr Gln Lys Ser Ser Leu Trp Glu Ala Pro Arg
        195                 200                 205

Gly Gln Asn Met Leu Asp Gly Ala Pro Phe Tyr Thr Thr Tyr Arg
    210                 215                 220

Thr Ala Asp Gly Glu Phe Met Ala Val Gly Ala Ile Glu Pro Gln Phe
225                 230                 235                 240

Tyr Glu Leu Leu Ile Lys Gly Leu Gly Leu Lys Ser Asp Glu Leu Pro
                245                 250                 255

Asn Gln Met Ser Met Asp Asp Trp Pro Glu Met Lys Lys Lys Phe Ala
            260                 265                 270
```

```
Asp Val Phe Ala Lys Lys Thr Lys Ala Glu Trp Cys Gln Ile Phe Asp
        275                 280                 285
Gly Thr Asp Ala Cys Val Thr Pro Val Leu Thr Phe Glu Glu Val Val
        290                 295                 300
His His Asp His Asn Lys Glu Arg Gly Ser Phe Ile Thr Ser Glu Glu
305                 310                 315                 320
Gln Asp Val Ser Pro Arg Pro Ala Pro Leu Leu Leu Asn Thr Pro Ala
                325                 330                 335
Ile Pro Ser Phe Lys Arg Asp Pro Phe Ile Gly Glu His Thr Glu Glu
                340                 345                 350
Ile Leu Glu Glu Phe Gly Phe Ser Arg Glu Glu Ile Tyr Gln Leu Asn
            355                 360                 365
Ser Asp Lys Ile Ile Glu Ser Asn Lys Val Lys Ala Ser Leu
        370                 375                 380

<210> SEQ ID NO 109
<211> LENGTH: 1524
<212> TYPE: DNA
<213> ORGANISM: Homo sapien

<400> SEQUENCE: 109
```

| | | | | | |
|---|---|---|---|---|---|
| ggcacgaggc | tgcgccaggg | cctgagcgga | ggcggggggca | gcctcgccag | cgggggcccc | 60 |
| gggcctggcc | atgcctcact | gagccagcgc | ctgcgcctct | acctcgccga | cagctggaac | 120 |
| cagtgcgacc | tagtggctct | cacctgcttc | ctcctgggcg | tgggctgccg | gctgaccccg | 180 |
| ggtttgtacc | acctgggccg | cactgtcctc | tgcatcgact | tcatggtttt | cacggtgcgg | 240 |
| ctgcttcaca | tcttcacggt | caacaaaacag | ctggggccca | agatcgtcat | cgtgagcaag | 300 |
| atgatgaagg | acgtgttctt | cttcctcttc | ttcctcggcg | tgtggctggt | agcctatggc | 360 |
| gtggccacgg | agggctcct | gaggccacgg | gacagtgact | tcccaagtat | cctgcgccgc | 420 |
| gtcttctacc | gtccctacct | gcagatcttc | gggcagattc | cccaggagga | catggacgtg | 480 |
| gccctcatgg | agcacagcaa | ctgctcgtcg | gagcccggct | ctgggcaca | ccctcctggg | 540 |
| gcccaggcgg | gcacctgcgt | ctcccagtat | gccaactggc | tggtggtgct | gctcctcgtc | 600 |
| atcttcctgc | tcgtggccaa | catcctgctg | gtcaacttgc | tcattgccat | gttcagttac | 660 |
| acattcggca | agtacagggg | caacagcgat | ctctactgga | aggcgcagcg | ttaccgcctc | 720 |
| atccgggaat | tccactctcg | gcccgcgctg | gccccgccct | ttatcgtcat | ctcccacttg | 780 |
| cgcctcctgc | tcaggcaatt | gtgcaggcga | ccccggagcc | cccagccgtc | ctccccggcc | 840 |
| ctcgagcatt | tccgggttta | cctttctaag | gaagccgagc | ggaagctgct | aacgtgggaa | 900 |
| tcggtgcata | aggagaactt | tctgctggca | cgcgctaggg | acaagcggga | gagcgactcc | 960 |
| gagcgtctga | gcgcacgtc | ccagaaggtg | gacttggcac | tgaaacagct | gggacacatc | 1020 |
| cgcgagtacg | aacagcgcct | gaaagtgctg | gagcggagg | tccagcagtg | tagccgcgtc | 1080 |
| ctggggtggg | tggccgaggc | cctgagccgc | tctgccttgc | tgccccagg | tgggccgcca | 1140 |
| ccccctgacc | tgcctgggtc | caaagactga | gccctgctgg | cggacttcaa | ggagaagccc | 1200 |
| ccacagggga | ttttgctcct | agagtaaggc | tcatctgggc | ctcggcccccc | gcacctggtg | 1260 |
| gccttgtcct | tgaggtgagc | ccatgtccca | tctgggccac | tgtcaggacc | acctttggga | 1320 |
| gtgtcatcct | tacaaaccac | agcatgcccg | gctcctccca | gaaccagtcc | cagcctggga | 1380 |
| ggatcaaggc | ctggatcccg | ggccgttatc | catctggagg | ctgcagggtc | cttggggtaa | 1440 |
| cagggaccac | agacccctca | ccactcacag | attcctcaca | ctggggaaat | aaagccattt | 1500 | cagaggaaaa aaaaaaaaaa aaaa    1524

<210> SEQ ID NO 110
<211> LENGTH: 3410
<212> TYPE: DNA
<213> ORGANISM: Homo sapien

<400> SEQUENCE: 110

| | | | | | |
|---|---|---|---|---|---|
| gggaaccagc | ctgcacgcgc | tggctccggg | tgacagccgc | gcgcctcggc | caggatctga | 60 |
| gtgatgagac | gtgtccccac | tgaggtgccc | cacagcagca | ggtgttgagc | atgggctgag | 120 |
| aagctggacc | ggcaccaaag | ggctggcaga | aatgggcgcc | tggctgattc | ctaggcagtt | 180 |
| ggcggcagca | aggaggagag | gccgcagctt | ctggagcaga | gccgagacga | agcagttctg | 240 |
| gagtgcctga | acggccccct | gagccctacc | cgcctggccc | actatggtcc | agaggctgtg | 300 |
| ggtgagccgc | ctgctgcggc | accggaaagc | ccagctcttg | ctggtcaacc | tgctaacctt | 360 |
| tggcctggag | gtgtgtttgg | ccgcaggcat | cacctatgtg | ccgcctctgc | tgctggaagt | 420 |
| gggggtagag | gagaagttca | tgaccatggt | gctgggcatt | ggtccagtgc | tgggcctggt | 480 |
| ctgtgtcccg | ctcctaggct | cagccagtga | ccactggcgt | ggacgctatg | ccgccgccg | 540 |
| gcccttcatc | tgggcactgt | ccttgggcat | cctgctgagc | ctctttctca | tcccaagggc | 600 |
| cggctggcta | gcagggctgc | tgtgcccgga | tcccaggccc | ctggagctgg | cactgctcat | 660 |
| cctgggcgtg | gggctgctgg | acttctgtgg | ccaggtgtgc | ttcactccac | tggaggccct | 720 |
| gctctctgac | ctcttccggg | acccggacca | ctgtcgccag | gcctactctg | tctatgcctt | 780 |
| catgatcagt | cttgggggct | gcctgggcta | cctcctgcct | gccattgact | gggacaccag | 840 |
| tgccctggcc | ccctacctgg | gcacccagga | ggagtgcctc | tttggcctgc | tcaccctcat | 900 |
| cttcctcacc | tgcgtagcag | ccacactgct | ggtggctgag | gaggcagcgc | tgggccccac | 960 |
| cgagccagca | gaagggctgt | cggcccctc | cttgtcgccc | cactgctgtc | catgccgggc | 1020 |
| ccgcttggct | ttccggaacc | tgggcgccct | gcttccccgg | ctgcaccagc | tgtgctgccg | 1080 |
| catgccccgc | accctgcgcc | ggctcttcgt | ggctgagctg | tgcagctgga | tggcactcat | 1140 |
| gaccttcacg | ctgttttaca | cggatttcgt | gggcgagggg | ctgtaccagg | gcgtgccag | 1200 |
| agctgagccg | ggcaccgagg | cccggagaca | ctatgatgaa | ggcgttcgga | tgggcagcct | 1260 |
| ggggctgttc | ctgcagtgcg | ccatctccct | ggtcttctct | ctggtcatgg | accggctggt | 1320 |
| gcagcgattc | ggcactcgag | cagtctattt | ggccagtgtg | gcagctttcc | ctgtggctgc | 1380 |
| cggtgccaca | tgcctgtccc | acagtgtggc | cgtggtgaca | gcttcagccg | ccctcaccgg | 1440 |
| gttcaccttc | tcagccctgc | agatcctgcc | ctacacactg | gcctccctct | accaccggga | 1500 |
| gaagcaggtg | ttcctgccca | ataccgaggg | gacactggag | ggtgctagca | gtgaggacag | 1560 |
| cctgatgacc | agcttcctgc | caggccctaa | gcctggagct | cccttcccta | atggacacgt | 1620 |
| gggtgctgga | ggcagtggcc | tgctcccacc | tccaccgcg | ctctgcgggg | cctctgcctg | 1680 |
| tgatgtctcc | gtacgtgtgg | tggtgggtga | gccaccgag | gccagggtgg | ttccgggccg | 1740 |
| gggcatctgc | ctggacctcg | ccatcctgga | tagtgccttc | ctgctgtccc | aggtggcccc | 1800 |
| atccctgttt | atgggctcca | ttgtccagct | cagccagtct | gtcactgcct | atatggtgtc | 1860 |
| tgccgcaggc | ctgggtctgg | tcgccatttta | ctttgctaca | caggtagtat | ttgacaagag | 1920 |
| cgacttggcc | aaaatactcag | cgtagaaaac | ttccagcaca | ttggggtgga | gggcctgcct | 1980 |
| cactgggtcc | cagctccccg | ctcctgttag | ccccatgggg | ctgccgggct | ggccgccagt | 2040 |
| ttctgttgct | gccaaagtaa | tgtggctctc | tgctgccacc | ctgtgctgct | gaggtgcgta | 2100 |

```
gctgcacagc tgggggctgg ggcgtccctc tcctctctcc ccagtctcta gggctgcctg    2160
actggaggcc ttccaagggg gtttcagtct ggacttatac agggaggcca aagggctcc     2220 atgcactgga atgcggggac tctgcaggtg gattacccag gctcagggtt aacagctagc    2280
ctcctagttg agacacacct agagaagggt ttttgggagc tgaataaact cagtcacctg    2340
gtttcccatc tctaagcccc ttaacctgca gcttcgttta atgtagctct tgcatgggag    2400
tttctaggat gaaacactcc tccatgggat ttgaacatat gacttatttg tagggaaga    2460 gtcctgaggg gcaacacaca agaaccaggt cccctcagcc cacagcactg tcttttgct     2520 gatccacccc cctcttacct tttatcagga tgtggcctgt tggtccttct gttgccatca    2580
cagagacaca ggcatttaaa tatttaactt atttatttaa caaagtagaa gggaatccat    2640
tgctagcttt tctgtgttgg tgtctaatat ttgggtaggg tggggatcc ccaacaatca     2700 ggtcccctga gatagctggt cattgggctg atcattgcca gaatcttctt ctcctggggt    2760
ctggcccccc aaaatgccta acccaggacc ttggaaattc tactcatccc aaatgataat    2820
tccaaatgct gttacccaag gttagggtgt tgaaggaagg tagagggtgg ggcttcaggt    2880
ctcaacggct tccctaacca cccctcttct cttggcccag cctggttccc cccacttcca    2940
ctcccctcta ctctctctag gactgggctg atgaaggcac tgcccaaaat ttcccctacc    3000
cccaactttc ccctacccc aactttcccc accagctcca caaccctgtt tggagctact     3060
gcaggaccag aagcacaaag tgcggtttcc caagcctttg tccatctcag ccccccagagt   3120 atatctgtgc ttggggaatc tcacacagaa actcaggagc accccctgcc tgagctaagg    3180
gaggtcttat ctctcagggg gggtttaagt gccgtttgca ataatgtcgt cttatttatt    3240
tagcggggtg aatattttat actgtaagtg agcaatcaga gtataatgtt tatggtgaca    3300
aaattaaagg ctttcttata tgtttaaaaa aaaaaaaaa aaaaaaaaa aaaaaaaaa       3360 aaaaaaaara aaaaaaaaaa aaaaaaaaaa aaaaaaataa aaaaaaaaaa               3410
```

<210> SEQ ID NO 111
<211> LENGTH: 1289
<212> TYPE: DNA
<213> ORGANISM: Homo sapien

<400> SEQUENCE: 111

```
agccaggcgt ccctctgcct gcccactcag tggcaacacc cgggagctgt tttgtccttt    60
gtggagcctc agcagttccc tctttcagaa ctcactgcca agagccctga acaggagcca    120
ccatgcagtg cttcagcttc attaagacca tgatgatcct cttcaatttg ctcatctttc    180
tgtgtggtgc agcccgttg gcagtgggca tctgggtgtc aatcgatggg gcatcctttc    240
tgaagatctt cgggccactg tcgtccagtg ccatgcagtt tgtcaacgtg ggctacttcc    300
tcatcgcagc cggcgttgtg gtctttgctc ttggtttcct gggctgctat ggtgctaaga    360
ctgagagcaa gtgtgccctc gtgacgttct tcttcatcct cctcctcatc ttcattgctg    420
aggttgcagc tgctgtggtc gccttggtgt acaccacaat ggctgagcac ttcctgacgt    480
tgctggtagt gcctgccatc aagaaagatt atggttccca ggaagacttc actcaagtgt    540
ggaacaccac catgaaaggg ctcaagtgct gtggcttcac caactatacg gatttttgagg   600 actcacccta cttcaaagag aacagtgcct ttccccccatt ctgttgcaat gacaacgtca    660
ccaacacagc caatgaaacc tgcaccaagc aaaaggctca cgaccaaaaa gtagagggtt    720
gcttcaatca gcttttgtat gacatccgaa ctaatgcagt caccgtgggt ggtgtggcag    780
```

-continued

```
ctggaattgg gggcctcgag ctggctgcca tgattgtgtc catgtatctg tactgcaatc    840
tacaataagt ccacttctgc ctctgccact actgctgcca catgggaact gtgaagaggc    900
accctggcaa gcagcagtga ttggggagg ggacaggatc taacaatgtc acttgggcca    960
gaatggacct gcccttttctg ctccagactt ggggctagat agggaccact ccttttagcg   1020
atgcctgact tccttccat tggtgggtgg atgggtgggg ggcattccag agcctctaag    1080
gtagccagtt ctgttgccca ttcccccagt ctattaaacc cttgatatgc ccctaggcc    1140 tagtggtgat cccagtgctc tactggggga tgagagaaag gcattttata gcctgggcat   1200
aagtgaaatc agcagagcct ctgggtggat gtgtagaagg cacttcaaaa tgcataaacc   1260
tgttacaatg ttaaaaaaaa aaaaaaaaa                                    1289
```

<210> SEQ ID NO 112
<211> LENGTH: 315
<212> TYPE: PRT
<213> ORGANISM: Homo sapien

<400> SEQUENCE: 112

```
Met Val Phe Thr Val Arg Leu Leu His Ile Phe Thr Val Asn Lys Gln
  1               5                  10                  15

Leu Gly Pro Lys Ile Val Ile Ser Lys Met Met Lys Asp Val Phe
             20                  25                  30

Phe Phe Leu Phe Phe Leu Gly Val Trp Leu Val Ala Tyr Gly Val Ala
         35                  40                  45

Thr Glu Gly Leu Leu Arg Pro Arg Asp Ser Asp Phe Pro Ser Ile Leu
     50                  55                  60

Arg Arg Val Phe Tyr Arg Pro Tyr Leu Gln Ile Phe Gly Gln Ile Pro
 65                  70                  75                  80

Gln Glu Asp Met Asp Val Ala Leu Met Glu His Ser Asn Cys Ser Ser
                 85                  90                  95

Glu Pro Gly Phe Trp Ala His Pro Pro Gly Ala Gln Ala Gly Thr Cys
            100                 105                 110

Val Ser Gln Tyr Ala Asn Trp Leu Val Val Leu Leu Val Ile Phe
        115                 120                 125

Leu Leu Val Ala Asn Ile Leu Leu Val Asn Leu Leu Ile Ala Met Phe
    130                 135                 140

Ser Tyr Thr Phe Gly Lys Val Gln Gly Asn Ser Asp Leu Tyr Trp Lys
145                 150                 155                 160

Ala Gln Arg Tyr Arg Leu Ile Arg Glu Phe His Ser Arg Pro Ala Leu
                165                 170                 175

Ala Pro Pro Phe Ile Val Ile Ser His Leu Arg Leu Leu Leu Arg Gln
            180                 185                 190

Leu Cys Arg Arg Pro Arg Ser Pro Gln Pro Ser Ser Pro Ala Leu Glu
        195                 200                 205

His Phe Arg Val Tyr Leu Ser Lys Glu Ala Glu Arg Lys Leu Leu Thr
    210                 215                 220

Trp Glu Ser Val His Lys Glu Asn Phe Leu Leu Ala Arg Ala Arg Asp
225                 230                 235                 240

Lys Arg Glu Ser Asp Ser Glu Arg Leu Lys Arg Thr Ser Gln Lys Val
                245                 250                 255

Asp Leu Ala Leu Lys Gln Leu Gly His Ile Arg Glu Tyr Glu Gln Arg
            260                 265                 270

Leu Lys Val Leu Glu Arg Glu Val Gln Gln Cys Ser Arg Val Leu Gly
        275                 280                 285
```

```
Trp Val Ala Glu Ala Leu Ser Arg Ser Ala Leu Leu Pro Gly Gly
        290                 295                 300
Pro Pro Pro Asp Leu Pro Gly Ser Lys Asp
305             310             315

<210> SEQ ID NO 113
<211> LENGTH: 553
<212> TYPE: PRT
<213> ORGANISM: Homo sapien

<400> SEQUENCE: 113

Met Val Gln Arg Leu Trp Val Ser Arg Leu Arg His Arg Lys Ala
  1               5                  10                  15

Gln Leu Leu Val Asn Leu Leu Thr Phe Gly Leu Glu Val Cys Leu
             20                  25                  30

Ala Ala Gly Ile Thr Tyr Val Pro Pro Leu Leu Glu Val Gly Val
             35                  40                  45

Glu Glu Lys Phe Met Thr Met Val Leu Gly Ile Gly Pro Val Leu Gly
 50                  55                  60

Leu Val Cys Val Pro Leu Leu Gly Ser Ala Ser Asp His Trp Arg Gly
 65                  70                  75                  80

Arg Tyr Gly Arg Arg Pro Phe Ile Trp Ala Leu Ser Leu Gly Ile
             85                  90                  95

Leu Leu Ser Leu Phe Leu Ile Pro Arg Ala Gly Trp Leu Ala Gly Leu
                100                 105                 110

Leu Cys Pro Asp Pro Arg Pro Leu Glu Leu Ala Leu Leu Ile Leu Gly
                115                 120                 125

Val Gly Leu Leu Asp Phe Cys Gly Gln Val Cys Phe Thr Pro Leu Glu
130                 135                 140

Ala Leu Leu Ser Asp Leu Phe Arg Asp Pro Asp His Cys Arg Gln Ala
145                 150                 155                 160

Tyr Ser Val Tyr Ala Phe Met Ile Ser Leu Gly Gly Cys Leu Gly Tyr
                165                 170                 175

Leu Leu Pro Ala Ile Asp Trp Asp Thr Ser Ala Leu Ala Pro Tyr Leu
                180                 185                 190

Gly Thr Gln Glu Glu Cys Leu Phe Gly Leu Leu Thr Leu Ile Phe Leu
                195                 200                 205

Thr Cys Val Ala Ala Thr Leu Leu Val Ala Glu Glu Ala Ala Leu Gly
210                 215                 220

Pro Thr Glu Pro Ala Glu Gly Leu Ser Ala Pro Ser Leu Ser Pro His
225                 230                 235                 240

Cys Cys Pro Cys Arg Ala Arg Leu Ala Phe Arg Asn Leu Gly Ala Leu
                245                 250                 255

Leu Pro Arg Leu His Gln Leu Cys Cys Arg Met Pro Arg Thr Leu Arg
                260                 265                 270

Arg Leu Phe Val Ala Glu Leu Cys Ser Trp Met Ala Leu Met Thr Phe
                275                 280                 285

Thr Leu Phe Tyr Thr Asp Phe Val Gly Glu Gly Leu Tyr Gln Gly Val
                290                 295                 300

Pro Arg Ala Glu Pro Gly Thr Glu Ala Arg His Tyr Asp Glu Gly
305                 310                 315                 320

Val Arg Met Gly Ser Leu Gly Leu Phe Leu Gln Cys Ala Ile Ser Leu
                325                 330                 335

Val Phe Ser Leu Val Met Asp Arg Leu Val Gln Arg Phe Gly Thr Arg
```

```
                   340                 345                 350
Ala Val Tyr Leu Ala Ser Val Ala Ala Phe Pro Val Ala Ala Gly Ala
            355                 360                 365

Thr Cys Leu Ser His Ser Val Ala Val Val Thr Ala Ser Ala Ala Leu
        370                 375                 380

Thr Gly Phe Thr Phe Ser Ala Leu Gln Ile Leu Pro Tyr Thr Leu Ala
385                 390                 395                 400

Ser Leu Tyr His Arg Glu Lys Gln Val Phe Leu Pro Lys Tyr Arg Gly
                405                 410                 415

Asp Thr Gly Gly Ala Ser Ser Glu Asp Ser Leu Met Thr Ser Phe Leu
            420                 425                 430

Pro Gly Pro Lys Pro Gly Ala Pro Phe Pro Asn Gly His Val Gly Ala
        435                 440                 445

Gly Gly Ser Gly Leu Leu Pro Pro Pro Ala Leu Cys Gly Ala Ser
            450                 455                 460

Ala Cys Asp Val Ser Val Arg Val Val Val Gly Glu Pro Thr Glu Ala
465                 470                 475                 480

Arg Val Val Pro Gly Arg Gly Ile Cys Leu Asp Leu Ala Ile Leu Asp
                485                 490                 495

Ser Ala Phe Leu Leu Ser Gln Val Ala Pro Ser Leu Phe Met Gly Ser
            500                 505                 510

Ile Val Gln Leu Ser Gln Ser Val Thr Ala Tyr Met Val Ser Ala Ala
        515                 520                 525

Gly Leu Gly Leu Val Ala Ile Tyr Phe Ala Thr Gln Val Val Phe Asp
            530                 535                 540

Lys Ser Asp Leu Ala Lys Tyr Ser Ala
545                 550

<210> SEQ ID NO 114
<211> LENGTH: 241
<212> TYPE: PRT
<213> ORGANISM: Homo sapien

<400> SEQUENCE: 114

Met Gln Cys Phe Ser Phe Ile Lys Thr Met Met Ile Leu Phe Asn Leu
  1               5                  10                  15

Leu Ile Phe Leu Cys Gly Ala Ala Leu Leu Ala Val Gly Ile Trp Val
                20                  25                  30

Ser Ile Asp Gly Ala Ser Phe Leu Lys Ile Phe Gly Pro Leu Ser Ser
            35                  40                  45

Ser Ala Met Gln Phe Val Asn Val Gly Tyr Phe Leu Ile Ala Ala Gly
        50                  55                  60

Val Val Val Phe Ala Leu Gly Phe Leu Gly Cys Tyr Gly Ala Lys Thr
65                  70                  75                  80

Glu Ser Lys Cys Ala Leu Val Thr Phe Phe Ile Leu Leu Leu Ile
                85                  90                  95

Phe Ile Ala Glu Val Ala Ala Ala Val Val Ala Leu Val Tyr Thr Thr
                100                 105                 110

Met Ala Glu His Phe Leu Thr Leu Leu Val Val Pro Ala Ile Lys Lys
            115                 120                 125

Asp Tyr Gly Ser Gln Glu Asp Phe Thr Gln Val Trp Asn Thr Thr Met
        130                 135                 140

Lys Gly Leu Lys Cys Cys Gly Phe Thr Asn Tyr Thr Asp Phe Glu Asp
145                 150                 155                 160
```

```
Ser Pro Tyr Phe Lys Glu Asn Ser Ala Phe Pro Pro Phe Cys Cys Asn
            165                 170                 175

Asp Asn Val Thr Asn Thr Ala Asn Glu Thr Cys Thr Lys Gln Lys Ala
            180                 185                 190

His Asp Gln Lys Val Glu Gly Cys Phe Asn Gln Leu Leu Tyr Asp Ile
            195                 200                 205

Arg Thr Asn Ala Val Thr Val Gly Gly Val Ala Gly Ile Gly Gly
    210                 215                 220

Leu Glu Leu Ala Ala Met Ile Val Ser Met Tyr Leu Tyr Cys Asn Leu
225                 230                 235                 240

Gln

<210> SEQ ID NO 115
<211> LENGTH: 366
<212> TYPE: DNA
<213> ORGANISM: Homo sapien

<400> SEQUENCE: 115
gctctttctc tcccctcctc tgaatttaat tctttcaact tgcaatttgc aaggattaca      60
catttcactg tgatgtatat tgtgttgcaa aaaaaaaaaa gtgtctttgt ttaaaattac     120
ttggtttgtg aatccatctt gcttttttccc cattggaact agtcattaac ccatctctga    180
actggtagaa aaacatctga agagctagtc tatcagcatc tgacaggtga attggatggt    240
tctcagaacc atttcaccca gacagcctgt ttctatcctg tttaataaat tagtttgggt    300
tctctacatg cataacaaac cctgctccaa tctgtcacat aaaagtctgt gacttgaagt    360
ttagtc                                                                366

<210> SEQ ID NO 116
<211> LENGTH: 282
<212> TYPE: DNA
<213> ORGANISM: Homo sapien
<220> FEATURE:
<221> NAME/KEY: misc_feature
<222> LOCATION: (1)...(282)
<223> OTHER INFORMATION: n = A,T,C or G

<400> SEQUENCE: 116
acaaagatga accatttcct atattatagc aaaattaaaa tctacccgta ttctaatatt      60
gagaaatgag atnaaacaca atnttataaa gtctacttag agaagatcaa gtgacctcaa    120
agactttact atttcatat tttaagacac atgattatc ctatttagt aacctggttc      180 atacgttaaa caaggataa tgtgaacagc agagaggatt tgttggcaga aaatctatgt    240
tcaatctnga actatctana tcacagacat ttctattcct tt                       282

<210> SEQ ID NO 117
<211> LENGTH: 305
<212> TYPE: DNA
<213> ORGANISM: Homo sapien
<220> FEATURE:
<221> NAME/KEY: misc_feature
<222> LOCATION: (1)...(305)
<223> OTHER INFORMATION: n = A,T,C or G

<400> SEQUENCE: 117
acacatgtcg cttcactgcc ttcttagatg cttctggtca acatanagga acagggacca      60
tatttatcct ccctcctgaa acaattgcaa ataanacaa atatatgaa acaattgcaa      120 aataaggcaa atatatgaa acaacaggtc tcgagatatt ggaaatcagt caatgaagga    180
```

```
tactgatccc tgatcactgt cctaatgcag gatgtgggaa acagatgagg tcacctctgt    240
gactgcccca gcttactgcc tgtagagagt ttctangctg cagttcagac agggagaaat    300
tgggt                                                                305
```

<210> SEQ ID NO 118
<211> LENGTH: 71
<212> TYPE: DNA
<213> ORGANISM: Homo sapien
<220> FEATURE:
<221> NAME/KEY: misc_feature
<222> LOCATION: (1)...(71)
<223> OTHER INFORMATION: n = A,T,C or G

<400> SEQUENCE: 118

```
accaaggtgt ntgaatctct gacgtgggga tctctgattc ccgcacaatc tgagtggaaa     60
aantcctggg t                                                          71
```

<210> SEQ ID NO 119
<211> LENGTH: 212
<212> TYPE: DNA
<213> ORGANISM: Homo sapien
<220> FEATURE:
<221> NAME/KEY: misc_feature
<222> LOCATION: (1)...(212)
<223> OTHER INFORMATION: n = A,T,C or G

<400> SEQUENCE: 119

```
actccggttg gtgtcagcag cacgtggcat tgaacatngc aatgtggagc ccaaaccaca     60
gaaaatgggg tgaaattggc caactttcta tnaacttatg ttggcaantt tgccaccaac   120
agtaagctgg cccttctaat aaaagaaaat tgaaaggttt ctcactaanc ggaattaant   180
aatggantca aganactccc aggcctcagc gt                                 212
```

<210> SEQ ID NO 120
<211> LENGTH: 90
<212> TYPE: DNA
<213> ORGANISM: Homo sapien
<220> FEATURE:
<221> NAME/KEY: misc_feature
<222> LOCATION: (1)...(90)
<223> OTHER INFORMATION: n = A,T,C or G

<400> SEQUENCE: 120

```
actcgttgca natcaggggc cccccagagt caccgttgca ggagtccttc tggtcttgcc     60
ctccgccggc gcagaacatg ctggggtggt                                      90
```

<210> SEQ ID NO 121
<211> LENGTH: 218
<212> TYPE: DNA
<213> ORGANISM: Homo sapien
<220> FEATURE:
<221> NAME/KEY: misc_feature
<222> LOCATION: (1)...(218)
<223> OTHER INFORMATION: n = A,T,C or G

<400> SEQUENCE: 121

```
tgtancgtga anacgacaga nagggttgtc aaaaatggag aaccttgaa gtcattttga     60 gaataagatt tgctaaaaga tttggggcta aaacatggtt attgggagac atttctgaag   120
atatncangt aaaattangga atgaattcat ggttctttttg ggaattcctt tacgatngcc 180
agcatanact tcatgtgggg atancagcta cccttgta                            218
```

<210> SEQ ID NO 122
<211> LENGTH: 171
<212> TYPE: DNA
<213> ORGANISM: Homo sapien

<400> SEQUENCE: 122 tagggtgta tgcaactgta aggacaaaaa ttgagactca actggcttaa ccaataaagg       60
catttgttag ctcatggaac aggaagtcgg atggtgggc atcttcagtg ctgcatgagt      120
caccaccccg gcgggtcat ctgtgccaca ggtccctgtt gacagtgcgg t               171

<210> SEQ ID NO 123
<211> LENGTH: 76
<212> TYPE: DNA
<213> ORGANISM: Homo sapien
<220> FEATURE:
<221> NAME/KEY: misc_feature
<222> LOCATION: (1)...(76)
<223> OTHER INFORMATION: n = A,T,C or G

<400> SEQUENCE: 123
tgtagcgtga agacnacaga atggtgtgtg ctgtgctatc caggaacaca tttattatca       60
ttatcaanta ttgtgt                                                       76

<210> SEQ ID NO 124
<211> LENGTH: 131
<212> TYPE: DNA
<213> ORGANISM: Homo sapien

<400> SEQUENCE: 124
acctttcccc aaggccaatg tcctgtgtgc taactggccg gctgcaggac agctgcaatt       60
caatgtgctg ggtcatatgg aggggaggag actctaaaat agccaatttt attctcttgg     120
ttaagatttg t                                                          131

<210> SEQ ID NO 125
<211> LENGTH: 432
<212> TYPE: DNA
<213> ORGANISM: Homo sapien

<400> SEQUENCE: 125
actttatcta ctggctatga aatagatggt ggaaaattgc gttaccaact ataccactgg       60
cttgaaaaag aggtgatagc tcttcagagg acttgtgact tttgctcaga tgctgaagaa     120
ctacagtctg catttggcag aaatgaagat gaatttggat taaatgagga tgctgaagat     180
ttgcctcacc aaacaaaagt gaaacaactg agagaaaatt ttcaggaaaa agacagtgg     240 ctcttgaagt atcagtcact tttgagaatg tttcttagtt actgcatact tcatggatcc     300
catggtgggg gtcttgcatc tgtaagaatg gaattgattt tgcttttgca agaatctcag     360
caggaaacat cagaaccact attttctagc cctctgtcag agcaaacctc agtgcctctc     420
ctctttgctt gt                                                         432

<210> SEQ ID NO 126
<211> LENGTH: 112
<212> TYPE: DNA
<213> ORGANISM: Homo sapien

<400> SEQUENCE: 126
acacaacttg aatagtaaaa tagaaactga gctgaaattt ctaattcact ttctaaccat       60
agtaagaatg atatttcccc ccagggatca ccaaatattt ataaaaattt gt              112

<210> SEQ ID NO 127
<211> LENGTH: 54
<212> TYPE: DNA
<213> ORGANISM: Homo sapien

<400> SEQUENCE: 127
accacgaaac cacaaacaag atggaagcat caatccactt gccaagcaca gcag        54

<210> SEQ ID NO 128
<211> LENGTH: 323
<212> TYPE: DNA
<213> ORGANISM: Homo sapien

<400> SEQUENCE: 128
acctcattag taattgtttt gttgtttcat ttttttctaa tgtctcccct ctaccagctc   60
acctgagata acagaatgaa atggaagga cagccagatt tctcctttgc tctctgctca   120
ttctctctga agtctaggtt acccatttg gggacccatt ataggcaata acacagttc    180 ccaaagcatt tggacagttt cttgttgtgt tttagaatgg ttttcctttt tcttagcctt  240
ttcctgcaaa aggctcactc agtcccttgc ttgctcagtg gactgggctc cccagggcct  300
aggctgcctt cttttccatg tcc                                          323

<210> SEQ ID NO 129
<211> LENGTH: 192
<212> TYPE: DNA
<213> ORGANISM: Homo sapien
<220> FEATURE:
<221> NAME/KEY: misc_feature
<222> LOCATION: (1)...(192)
<223> OTHER INFORMATION: n = A,T,C or G

<400> SEQUENCE: 129
acatacatgt gtgtatattt ttaaatatca cttttgtatc actctgactt tttagcatac   60
tgaaaacaca ctaacataat ttntgtgaac catgatcaga tacaacccaa atcattcatc   120
tagcacattc atctgtgata naaagatagg tgagtttcat ttccttcacg ttggccaatg   180
gataaacaaa gt                                                      192

<210> SEQ ID NO 130
<211> LENGTH: 362
<212> TYPE: DNA
<213> ORGANISM: Homo sapien
<220> FEATURE:
<221> NAME/KEY: misc_feature
<222> LOCATION: (1)...(362)
<223> OTHER INFORMATION: n = A,T,C or G

<400> SEQUENCE: 130 cccttttta tggaatgagt agactgtatg tttgaanatt tanccacaac ctctttgaca    60
tataatgacg caacaaaaag gtgctgttta gtcctatggt tcagtttatg cccctgacaa   120
gtttccattg tgttttgccg atcttctggc taatcgtggt atcctccatg ttattagtaa   180
ttctgtattc catttgtta acgcctggta gatgtaacct gctangaggc taactttata   240
cttatttaaa agctcttatt ttgtggtcat taaaatggca atttatgtgc agcactttat   300
tgcagcagga agcacgtgtg ggttggttgt aaagctcttt gctaatctta aaaagtaatg   360
gg                                                                 362

<210> SEQ ID NO 131
<211> LENGTH: 332

<210> SEQ ID NO 131
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 131

```
cttttttgaaa gatcgtgtcc actcctgtgg acatcttgtt ttaatggagt ttcccatgca      60
gtangactgg tatggttgca gctgtccaga taaaaacatt tgaagagctc caaaatgaga     120
gttctcccag gttcgccctg ctgctccaag tctcagcagc agcctctttt aggaggcatc     180
ttctgaacta gattaaggca gcttgtaaat ctgatgtgat ttggtttatt atccaactaa     240
cttccatctg ttatcactgg agaaagccca gactccccan gacnggtacg gattgtgggc     300
atanaaggat tgggtgaagc tggcgttgtg gt                                   332
```

<210> SEQ ID NO 132
<211> LENGTH: 322
<212> TYPE: DNA
<213> ORGANISM: Homo sapien
<220> FEATURE:
<221> NAME/KEY: misc_feature
<222> LOCATION: (1)...(322)
<223> OTHER INFORMATION: n = A,T,C or G

<400> SEQUENCE: 132

```
acttttgcca ttttgtatat ataaacaatc ttgggacatt ctcctgaaaa ctaggtgtcc      60
agtggctaag agaactcgat ttcaagcaat tctgaaagga aaaccagcat gacacagaat     120
ctcaaattcc caaacagggg ctctgtggga aaaatgaggg aggacctttg tatctcgggt     180
tttagcaagt taaatgaan atgacaggaa aggcttattt atcaacaaag agaagagttg     240
ggatgcttct aaaaaaaact ttggtagaga aaataggaat gctnaatcct agggaagcct     300
gtaacaatct acaattggtc ca                                             322
```

<210> SEQ ID NO 133
<211> LENGTH: 278
<212> TYPE: DNA
<213> ORGANISM: Homo sapien
<220> FEATURE:
<221> NAME/KEY: misc_feature
<222> LOCATION: (1)...(278)
<223> OTHER INFORMATION: n = A,T,C or G

<400> SEQUENCE: 133

```
acaagccttc acaagtttaa ctaaattggg attaatcttt ctgtanttat ctgcataatt      60
cttgtttttc tttccatctg gctcctgggt tgacaatttg tggaaacaac tctattgcta     120
ctatttaaaa aaaatcacaa atctttccct ttaagctatg ttnaattcaa actattcctg     180
ctattcctgt tttgtcaaag aaattatatt tttcaaaata tgtntatttg tttgatgggt     240
cccacgaaac actaataaaa accacagaga ccagcctg                             278
```

<210> SEQ ID NO 134
<211> LENGTH: 121
<212> TYPE: DNA
<213> ORGANISM: Homo sapien
<220> FEATURE:
<221> NAME/KEY: misc_feature
<222> LOCATION: (1)...(121)
<223> OTHER INFORMATION: n = A,T,C or G

<400> SEQUENCE: 134

```
gtttanaaaa cttgtttagc tccatagagg aaagaatgtt aaactttgta ttttaaaaca        60
tgattctctg aggttaaact tggttttcaa atgttatttt tacttgtatt ttgcttttgg       120
t                                                                      121

<210> SEQ ID NO 135
<211> LENGTH: 350
<212> TYPE: DNA
<213> ORGANISM: Homo sapien
<220> FEATURE:
<221> NAME/KEY: misc_feature
<222> LOCATION: (1)...(350)
<223> OTHER INFORMATION: n = A,T,C or G

<400> SEQUENCE: 135
acttanaacc atgcctagca catcagaatc cctcaaagaa catcagtata atcctatacc        60
atancaagtg gtgactggtt aagcgtgcga caaaggtcag ctggcacatt acttgtgtgc       120
aaacttgata cttttgttct aagtaggaac tagtatacag tncctaggan tggtactcca       180
gggtgccccc caactcctgc agccgctcct ctgtgccagn ccctgnaagg aactttcgct       240
ccacctcaat caagccctgg gccatgctac ctgcaattgg ctgaacaaac gtttgctgag       300
ttcccaagga tgcaaagcct ggtgctcaac tcctgggcg tcaactcagt                   350

<210> SEQ ID NO 136
<211> LENGTH: 399
<212> TYPE: DNA
<213> ORGANISM: Homo sapien
<220> FEATURE:
<221> NAME/KEY: misc_feature
<222> LOCATION: (1)...(399)
<223> OTHER INFORMATION: n = A,T,C or G

<400> SEQUENCE: 136
tgtaccgtga agacgacaga agttgcatgg cagggacagg gcagggccga ggccaggggtt       60 gctgtgattg tatccgaata ntcctcgtga gaaaagataa tgagatgacg tgagcagcct      120
gcagacttgt gtctgccttc aanaagccag acaggaaggc cctgcctgcc ttggctctga      180
cctggcggcc agccagccag ccacaggtgg gcttcttcct tttgtggtga caacnccaag      240
aaaactgcag aggcccaggg tcaggtgtna gtgggtangt gaccataaaa caccaggtgc      300
tcccaggaac ccgggcaaag gccatcccca cctacagcca gcatgccac tggcgtgatg       360 ggtgcagang gatgaagcag ccagntgttc tgctgtggt                             399

<210> SEQ ID NO 137
<211> LENGTH: 165
<212> TYPE: DNA
<213> ORGANISM: Homo sapien
<220> FEATURE:
<221> NAME/KEY: misc_feature
<222> LOCATION: (1)...(165)
<223> OTHER INFORMATION: n = A,T,C or G

<400> SEQUENCE: 137
actggtgtgg tnggggtgga tgctggtggt anaagttgan gtgacttcan gatggtgtgt        60
ggaggaagtg tgtgaacgta gggatgtaga ngttttggcc gtgctaaatg agcttcggga      120
ttggctggtc ccactggtgg tcactgtcat tggtggggtt cctgt                      165

<210> SEQ ID NO 138
<211> LENGTH: 338
<212> TYPE: DNA
<213> ORGANISM: Homo sapien
```

```
<220> FEATURE:
<221> NAME/KEY: misc_feature
<222> LOCATION: (1)...(338)
<223> OTHER INFORMATION: n = A,T,C or G

<400> SEQUENCE: 138
actcactgga atgccacatt cacaacagaa tcagaggtct gtgaaaacat taatggctcc      60
ttaacttctc cagtaagaat cagggacttg aaatggaaac gttaacagcc acatgcccaa    120
tgctgggcag tctcccatgc cttccacagt gaaagggctt gagaaaatc acatccaatg     180 tcatgtgttt ccagccacac caaaaggtgc ttggggtgga gggctggggg catananggt    240
cangcctcag gaagcctcaa gttccattca gctttgccac tgtacattcc ccatntttaa    300
aaaaactgat gcctttttt tttttttttg taaaattc                             338

<210> SEQ ID NO 139
<211> LENGTH: 382
<212> TYPE: DNA
<213> ORGANISM: Homo sapien

<400> SEQUENCE: 139
gggaatcttg gttttggca tctggttgc ctatagccga ggccactttg acagaacaaa       60
gaaagggact tcgagtaaga aggtgattta cagccagcct agtgcccgaa gtgaaggaga    120
attcaaacag acctcgtcat tcctggtgtg agcctggtcg gctcaccgcc tatcatctgc    180
atttgcctta ctcaggtgct accggactct ggccctgat gtctgtagtt tcacaggatg     240
ccttatttgt cttctacacc ccacagggcc cctacttct tcggatgtgt ttttaataat     300
gtcagctatg tgccccatcc tccttcatgc cctccctccc tttcctacca ctgctgagtg    360
gcctggaact tgtttaaagt gt                                              382

<210> SEQ ID NO 140
<211> LENGTH: 200
<212> TYPE: DNA
<213> ORGANISM: Homo sapien
<220> FEATURE:
<221> NAME/KEY: misc_feature
<222> LOCATION: (1)...(200)
<223> OTHER INFORMATION: n = A,T,C or G

<400> SEQUENCE: 140 accaaancttt ctttctgttg tgttngattt tactataggg gtttngcttn ttctaaanat    60
acttttcatt taacancttt tgttaagtgt caggctgcac tttgctccat anaattattg    120
ttttcacatt tcaacttgta tgtgtttgtc tcttanagca ttggtgaaat cacatatttt    180
atattcagca taaaggagaa                                                 200

<210> SEQ ID NO 141
<211> LENGTH: 335
<212> TYPE: DNA
<213> ORGANISM: Homo sapien
<220> FEATURE:
<221> NAME/KEY: misc_feature
<222> LOCATION: (1)...(335)
<223> OTHER INFORMATION: n = A,T,C or G

<400> SEQUENCE: 141
actttatttt caaacactc atatgttgca aaaacacat agaaaataa agtttggtgg         60 gggtgctgac taaacttcaa gtcacagact tttatgtgac agattggagc agggtttgtt    120
atgcatgtag agaacccaaa ctaatttatt aaacaggata gaaacaggct gtctgggtga    180
```

| | |
|---|---|
| aatggttctg agaaccatcc aattcacctg tcagatgctg atanactagc tcttcagatg | 240 |
| tttttctacc agttcagaga tnggttaatg actanttcca atggggaaaa agcaagatgg | 300 |
| attcacaaac caagtaattt taaacaaaga cactt | 335 |

<210> SEQ ID NO 142
<211> LENGTH: 459
<212> TYPE: DNA
<213> ORGANISM: Homo sapien
<220> FEATURE:
<221> NAME/KEY: misc_feature
<222> LOCATION: (1)...(459)
<223> OTHER INFORMATION: n = A,T,C or G

<400> SEQUENCE: 142

| | |
|---|---|
| accaggttaa tattgccaca tatatccttt ccaattgcgg gctaaacaga cgtgtattta | 60 |
| gggttgttta aagacaaccc agcttaatat caagagaaat tgtgaccttt catggagtat | 120 |
| ctgatggaga aaacactgag tttttgacaaa tcttatttta ttcagatagc agtctgatca | 180 |
| cacatggtcc aacaacactc aaataataaa tcaaatatna tcagatgtta aagattggtc | 240 |
| ttcaaacatc atagccaatg atgccccgct tgcctatat ctctccgaca taaaaccaca | 300 |
| tcaacacctc agtggccacc aaaccattca gcacagcttc cttaactgtg agctgtttga | 360 |
| agctaccagt ctgagcacta ttgactatnt ttttcangct ctgaatagct ctaggggatct | 420 |
| cagcangggt gggaggaacc agctcaacct tggcgtant | 459 |

<210> SEQ ID NO 143
<211> LENGTH: 140
<212> TYPE: DNA
<213> ORGANISM: Homo sapien

<400> SEQUENCE: 143

| | |
|---|---|
| acatttcctt ccaccaagtc aggactcctg gcttctgtgg gagttcttat cacctgaggg | 60 |
| aaatccaaac agtctctcct agaaaggaat agtgtcacca accccaccca tctccctgag | 120 |
| accatccgac ttccctgtgt | 140 |

<210> SEQ ID NO 144
<211> LENGTH: 164
<212> TYPE: DNA
<213> ORGANISM: Homo sapien
<220> FEATURE:
<221> NAME/KEY: misc_feature
<222> LOCATION: (1)...(164)
<223> OTHER INFORMATION: n = A,T,C or G

<400> SEQUENCE: 144

| | |
|---|---|
| acttcagtaa caacatacaa taacaacatt aagtgtatat tgccatcttt gtcattttct | 60 |
| atctatacca ctctcccttc tgaaaacaan aatcactanc caatcactta tacaaatttg | 120 |
| aggcaattaa tccatatttg ttttcaataa ggaaaaaaag atgt | 164 |

<210> SEQ ID NO 145
<211> LENGTH: 303
<212> TYPE: DNA
<213> ORGANISM: Homo sapien
<220> FEATURE:
<221> NAME/KEY: misc_feature
<222> LOCATION: (1)...(303)
<223> OTHER INFORMATION: n = A,T,C or G

<400> SEQUENCE: 145

| | |
|---|---|
| acgtagacca tccaactttg tatttgtaat ggcaaacatc cagnagcaat tcctaaacaa | 60 |

```
actggagggt atttataccc aattatccca ttcattaaca tgccctcctc ctcaggctat        120
gcaggacagc tatcataagt cggcccaggc atccagatac taccatttgt ataaacttca        180
gtaggggagt ccatccaagt gacaggtcta atcaaaggag gaaatggaac ataagcccag        240
tagtaaaatn ttgcttagct gaaacagcca caaaagactt accgccgtgg tgattaccat        300
caa                                                                      303
```

<210> SEQ ID NO 146
<211> LENGTH: 327
<212> TYPE: DNA
<213> ORGANISM: Homo sapien
<220> FEATURE:
<221> NAME/KEY: misc_feature
<222> LOCATION: (1)...(327)
<223> OTHER INFORMATION: n = A,T,C or G

<400> SEQUENCE: 146

```
actgcagctc aattagaagt ggtctctgac tttcatcanc ttctccctgg gctccatgac         60
actggcctgg agtgactcat tgctctggtt ggttgagaga gctcctttgc caacaggcct        120
ccaagtcagg gctgggattt gtttcctttc cacattctag caacaatatg ctggccactt        180
cctgaacagg gagggtggga ggagccagca tggaacaagc tgccactttc taaagtagcc        240
agacttgccc ctgggcctgt cacacctact gatgaccttc tgtgcctgca ggatggaatg        300 tagggggtgag ctgtgtgact ctatggt                                           327
```

<210> SEQ ID NO 147
<211> LENGTH: 173
<212> TYPE: DNA
<213> ORGANISM: Homo sapien
<220> FEATURE:
<221> NAME/KEY: misc_feature
<222> LOCATION: (1)...(173)
<223> OTHER INFORMATION: n = A,T,C or G

<400> SEQUENCE: 147

```
acattgtttt tttgagataa agcattgana gagctctcct taacgtgaca caatggaagg         60
actggaacac atacccacat ctttgttctg agggataatt ttctgataaa gtcttgctgt        120
atattcaagc acatatgtta tatattattc agttccatgt ttatagccta gtt               173
```

<210> SEQ ID NO 148
<211> LENGTH: 477
<212> TYPE: DNA
<213> ORGANISM: Homo sapien
<220> FEATURE:
<221> NAME/KEY: misc_feature
<222> LOCATION: (1)...(477)
<223> OTHER INFORMATION: n = A,T,C or G

<400> SEQUENCE: 148

```
acaaccactt tatctcatcg aatttttaac ccaaactcac tcactgtgcc tttctatcct         60
atgggatata ttatttgatg ctccatttca tcacacatat atgaataata cactcatact        120
gccctactac ctgctgcaat aatcacattc ccttcctgtc ctgaccctga agccattggg        180
gtggtcctag tggccatcag tccangcctg caccttgagc ccttgagctc cattgctcac        240 nccanccac ctcaccgacc ccatcctctt acacagctac ctccttgctc tctaacccca        300
tagattatnt ccaaattcag tcaattaagt tactattaac actctacccg acatgtccag        360
caccactggt aagccttctc cagccaacac acacacacac acncacac acacatat           420
```
ccaggcacag gctacctcat cttcacaatc acccctttaa ttaccatgct atgtgg  477

<210> SEQ ID NO 149
<211> LENGTH: 207
<212> TYPE: DNA
<213> ORGANISM: Homo sapien

<400> SEQUENCE: 149
acagttgtat tataatatca agaaataaac ttgcaatgag agcatttaag agggaagaac  60
taacgtattt tagagagcca aggaaggttt ctgtggggag tgggatgtaa ggtggggcct  120
gatgataaat aagagtcagc caggtaagtg ggtggtgtgg tatgggcaca gtgaagaaca  180
tttcaggcag agggaacagc agtgaaa  207

<210> SEQ ID NO 150
<211> LENGTH: 111
<212> TYPE: DNA
<213> ORGANISM: Homo sapien
<220> FEATURE:
<221> NAME/KEY: misc_feature
<222> LOCATION: (1)...(111)
<223> OTHER INFORMATION: n = A,T,C or G

<400> SEQUENCE: 150
accttgattt cattgctgct ctgatggaaa cccaactatc taatttagct aaaacatggg  60
cacttaaatg tggtcagtgt ttggacttgt taactantgg catctttggg t  111

<210> SEQ ID NO 151
<211> LENGTH: 196
<212> TYPE: DNA
<213> ORGANISM: Homo sapien

<400> SEQUENCE: 151
agcgcggcag gtcatattga acattccaga tacctatcat tactcgatgc tgttgataac  60
agcaagatgg ctttgaactc agggtcacca ccagctattg gaccttacta tgaaaaccat  120
ggataccaac cggaaaaccc ctatcccgca cagcccactg tggtccccac tgtctacgag  180
gtgcatccgg ctcagt  196

<210> SEQ ID NO 152
<211> LENGTH: 132
<212> TYPE: DNA
<213> ORGANISM: Homo sapien

<400> SEQUENCE: 152
acagcacttt cacatgtaag aagggagaaa ttcctaaatg taggagaaag ataacagaac  60
cttccccttt tcatctagtg gtggaaacct gatgctttat gttgacagga atagaaccag  120
gagggagttt gt  132

<210> SEQ ID NO 153
<211> LENGTH: 285
<212> TYPE: DNA
<213> ORGANISM: Homo sapien
<220> FEATURE:
<221> NAME/KEY: misc_feature
<222> LOCATION: (1)...(285)
<223> OTHER INFORMATION: n = A,T,C or G

<400> SEQUENCE: 153
acaanaccca nganaggcca ctggccgtgg tgtcatggcc tccaaacatg aaagtgtcag  60
cttctgctct tatgtcctca tctgacaact ctttaccatt tttatcctcg ctcagcagga  120

```
gcacatcaat aaagtccaaa gtcttggact tggccttggc ttggaggaag tcatcaacac      180
cctggctagt gagggtgcgg cgccgctcct ggatgacggc atctgtgaag tcgtgcacca      240
gtctgcaggc cctgtggaag cgccgtccac acggagtnag gaatt                     285

<210> SEQ ID NO 154
<211> LENGTH: 333
<212> TYPE: DNA
<213> ORGANISM: Homo sapien

<400> SEQUENCE: 154
accacagtcc tgttgggcca gggcttcatg acccttcctg tgaaaagcca tattatcacc      60
accccaaatt tttccttaaa tatctttaac tgaaggggtc agcctcttga ctgcaaagac      120
cctaagccgg ttacacagct aactcccact ggccctgatt tgtgaaattg ctgctgcctg      180
attggcacag gagtcgaagg tgttcagctc ccctcctccg tggaacgaga ctctgatttg      240
agtttcacaa attctcgggc cacctcgtca ttgctcctct gaaataaaat ccggagaatg      300
gtcaggcctg tctcatccat atggatcttc cgg                                   333

<210> SEQ ID NO 155
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 155
actggaaata ataaaaccca catcacagtg ttgtgtcaaa gatcatcagg gcatggatgg      60
gaaagtgctt tgggaactgt aaagtgccta acacatgatc gatgattttt gttataatat      120
ttgaatcacg gtgcatacaa actctcctgc ctgctcctcc tgggcccag ccccagcccc       180 atcacagctc actgctctgt tcatccaggc ccagcatgta gtggctgatt cttcttggct      240
gcttttagcc tccanaagtt tctctgaagc caaccaaacc tctangtgta aggcatgctg      300
gccctggt                                                               308

<210> SEQ ID NO 156
<211> LENGTH: 295
<212> TYPE: DNA
<213> ORGANISM: Homo sapien

<400> SEQUENCE: 156
accttgctcg gtgcttggaa catattagga actcaaaata tgagatgata acagtgccta      60
ttattgatta ctgagagaac tgttagacat ttagttgaag attttctaca caggaactga      120
gaataggaga ttatgtttgg ccctcatatt ctctcctatc ctccttgcct cattctatgt      180
ctaatatatt ctcaatcaaa taaggttagc ataatcagga aatcgaccaa ataccaatat      240
aaaaccagat gtctatcctt aagattttca aatagaaaac aaattaacag actat          295

<210> SEQ ID NO 157
<211> LENGTH: 126
<212> TYPE: DNA
<213> ORGANISM: Homo sapien

<400> SEQUENCE: 157
acaagtttaa atagtgctgt cactgtgcat gtgctgaaat gtgaaatcca ccacatttct      60
```

| | |
|---|---|
| gaagagcaaa acaaattctg tcatgtaatc tctatcttgg gtcgtgggta tatctgtccc | 120 |
| cttagt | 126 |

<210> SEQ ID NO 158
<211> LENGTH: 442
<212> TYPE: DNA
<213> ORGANISM: Homo sapien
<220> FEATURE:
<221> NAME/KEY: misc_feature
<222> LOCATION: (1)...(442)
<223> OTHER INFORMATION: n = A,T,C or G

<400> SEQUENCE: 158

| | |
|---|---|
| acccactggt cttggaaaca cccatcctta atacgatgat ttttctgtcg tgtgaaaatg | 60 |
| aanccagcag gctgcccta gtcagtcctt ccttccagag aaaaagagat ttgagaaagt | 120 |
| gcctgggtaa ttcaccatta atttcctccc ccaaactctc tgagtcttcc cttaatattt | 180 |
| ctggtggttc tgaccaaagc aggtcatggt ttgttgagca tttgggatcc cagtgaagta | 240 |
| natgtttgta gccttgcata cttagccctt cccacgcaca aacggagtgg cagagtggtg | 300 |
| ccaaccctgt tttcccagtc cacgtagaca gattcacagt gcggaattct ggaagctgga | 360 |
| nacagacggg ctctttgcag agccgggact ctgagangga catgagggcc tctgcctctg | 420 |
| tgttcattct ctgatgtcct gt | 442 |

<210> SEQ ID NO 159
<211> LENGTH: 498
<212> TYPE: DNA
<213> ORGANISM: Homo sapien
<220> FEATURE:
<221> NAME/KEY: misc_feature
<222> LOCATION: (1)...(498)
<223> OTHER INFORMATION: n = A,T,C or G

<400> SEQUENCE: 159

| | |
|---|---|
| acttccaggt aacgttgttg tttccgttga gcctgaactg atgggtgacg ttgtaggttc | 60 |
| tccaacaaga actgaggttg cagagcgggt agggaagagt gctgttccag ttgcacctgg | 120 |
| gctgctgtgg actgttgttg attcctcact acggcccaag gttgtggaac tggcanaaag | 180 |
| gtgtgttgtt gganttgagc tcgggcggct gtggtaggtt gtgggctctt caacaggggc | 240 |
| tgctgtggtg ccgggangtg aangtgttgt gtcacttgag cttggccagc tctggaaagt | 300 |
| antanattct tcctgaaggc cagcgcttgt ggagctggca ngggtcantg ttgtgtgtaa | 360 |
| cgaaccagtg ctgctgtggg tgggtgtana tcctccacaa agcctgaagt tatggtgtcn | 420 |
| tcaggtaana atgtggtttc agtgtccctg ggcngctgtg aaggttgta nattgtcacc | 480 |
| aagggaataa gctgtggt | 498 |

<210> SEQ ID NO 160
<211> LENGTH: 380
<212> TYPE: DNA
<213> ORGANISM: Homo sapien
<220> FEATURE:
<221> NAME/KEY: misc_feature
<222> LOCATION: (1)...(380)
<223> OTHER INFORMATION: n = A,T,C or G

<400> SEQUENCE: 160

| | |
|---|---|
| acctgcatcc agcttccctg ccaaactcac aaggagacat caacctctag acagggaaac | 60 |
| agcttcagga tacttccagg agacagagcc accagcagca aaacaaatat tcccatgcct | 120 |
| ggagcatggc atagaggaag ctganaaatg tggggtctga ggaagccatt tgagtctggc | 180 |

```
cactagacat ctcatcagcc acttgtgtga agagatgccc catgacccca gatgcctctc    240
ccacccttac ctccatctca cacacttgag ctttccactc tgtataattc taacatcctg    300
gagaaaaatg gcagtttgac cgaacctgtt cacaacggta gaggctgatt tctaacgaaa    360
cttgtagaat gaagcctgga                                                380
```

<210> SEQ ID NO 161
<211> LENGTH: 114
<212> TYPE: DNA
<213> ORGANISM: Homo sapien

<400> SEQUENCE: 161

```
actccacatc ccctctgagc aggcggttgt cgttcaaggt gtatttggcc ttgcctgtca     60
cactgtccac tggccccttta tccacttggt gcttaatccc tcgaaagagc atgt         114
```

<210> SEQ ID NO 162
<211> LENGTH: 177
<212> TYPE: DNA
<213> ORGANISM: Homo sapien

<400> SEQUENCE: 162

```
actttctgaa tcgaatcaaa tgatacttag tgtagtttta atatcctcat atatatcaaa     60
gttttactac tctgataatt ttgtaaacca ggtaaccaga acatccagtc atacagcttt    120
tggtgatata taacttggca ataacccagt ctggtgatac ataaaactac tcactgt      177
```

<210> SEQ ID NO 163
<211> LENGTH: 137
<212> TYPE: DNA
<213> ORGANISM: Homo sapien
<220> FEATURE:
<221> NAME/KEY: misc_feature
<222> LOCATION: (1)...(137)
<223> OTHER INFORMATION: n = A,T,C or G

<400> SEQUENCE: 163

```
catttataca gacaggcgtg aagacattca cgacaaaaac gcgaaattct atcccgtgac     60
canagaaggc agctacggct actcctacat cctggcgtgg gtggccttcg cctgcacctt    120
catcagcggc atgatgt                                                   137
```

<210> SEQ ID NO 164
<211> LENGTH: 469
<212> TYPE: DNA
<213> ORGANISM: Homo sapien
<220> FEATURE:
<221> NAME/KEY: misc_feature
<222> LOCATION: (1)...(469)
<223> OTHER INFORMATION: n = A,T,C or G

<400> SEQUENCE: 164

```
cttatcacaa tgaatgttct cctgggcagc gttgtgatct ttgccacctt cgtgacttta     60
tgcaatgcat catgctattt catacctaat gagggagttc caggagattc aaccaggaaa    120
tgcatggatc tcaaaggaaa caaacaccca ataaactcgg agtggcagac tgacaactgt    180
gagacatgca cttgctacga aacagaaatt tcatgttgca cccttgtttc tacacctgtg    240
ggttatgaca agacaactg ccaaagaatc ttcaagaagg aggactgcaa gtatatcgtg    300
gtggagaaga aggaccccaaa aaagaccgtg tctgtcagtg aatggataat ctaatgtgct   360
tctagtaggc acagggctcc caggccaggc ctcattctcc tctggcctct aatagtcaat    420
```

```
gattgtgtag ccatgcctat cagtaaaaag atntttgagc aaacacttt              469
```

```
<210> SEQ ID NO 165
<211> LENGTH: 195
<212> TYPE: DNA
<213> ORGANISM: Homo sapien
<220> FEATURE:
<221> NAME/KEY: misc_feature
<222> LOCATION: (1)...(195)
<223> OTHER INFORMATION: n = A,T,C or G

<400> SEQUENCE: 165
acagtttttt atanatatcg acattgccgg cacttgtgtt cagtttcata aagctggtgg    60
atccgctgtc atccactatt ccttggctag agtaaaaatt attcttatag cccatgtccc   120
tgcaggccgc ccgcccgtag ttctcgttcc agtcgtcttg gcacacaggg tgccaggact   180
tcctctgaga tgagt                                                    195
```

```
<210> SEQ ID NO 166
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 166
acatcttagt agtgtggcac atcaggggc catcagggtc acagtcactc atagcctcgc     60
cgaggtcgga gtccacacca ccggtgtagg tgtgctcaat cttgggcttg gcgcccacct   120
ttggagaagg gatatgctgc acacacatgt ccacaaagcc tgtgaactcg ccaaagaatt   180
tttgcagacc agcctgagca aggggcggat gttcagcttc agctcctcct tcgtcaggtg   240
gatgccaacc tcgtctangg tccgtgggaa gctggtgtcc acntcaccta caacctgggc   300
gangatctta taaagaggct ccnagataaa ctccacgaaa cttctctggg agctgctagt   360 ngggccttt tggtgaact ttc                                             383
```

```
<210> SEQ ID NO 167
<211> LENGTH: 247
<212> TYPE: DNA
<213> ORGANISM: Homo sapien
<220> FEATURE:
<221> NAME/KEY: misc_feature
<222> LOCATION: (1)...(247)
<223> OTHER INFORMATION: n = A,T,C or G

<400> SEQUENCE: 167
acagagccag accttggcca taaatgaanc agagattaag actaaacccc aagtcganat    60
tggagcagaa actggagcaa gaagtgggcc tggggctgaa gtagagacca aggccactgc   120
tatanccata cacagagcca actctcaggc caaggcnatg gttggggcag anccagagac   180
tcaatctgan tccaaagtgg tggctggaac actggtcatg acanaggcag tgactctgac   240 tgangtc                                                             247
```

```
<210> SEQ ID NO 168
<211> LENGTH: 273
<212> TYPE: DNA
<213> ORGANISM: Homo sapien
<220> FEATURE:
<221> NAME/KEY: misc_feature
<222> LOCATION: (1)...(273)
<223> OTHER INFORMATION: n = A,T,C or G
```

<400> SEQUENCE: 168

```
acttctaagt tttctagaag tggaaggatt gtantcatcc tgaaaatggg tttacttcaa      60
aatccctcan ccttgttctt cacnactgtc tatactgana gtgtcatgtt tccacaaagg     120
gctgacacct gagcctgnat tttcactcat ccctgagaag cccttccag tagggtgggc      180
aattcccaac ttccttgcca caagcttccc aggctttctc ccctggaaaa ctccagcttg     240
agtcccagat acactcatgg gctgccctgg gca                                   273
```

<210> SEQ ID NO 169
<211> LENGTH: 431
<212> TYPE: DNA
<213> ORGANISM: Homo sapien
<220> FEATURE:
<221> NAME/KEY: misc_feature
<222> LOCATION: (1)...(431)
<223> OTHER INFORMATION: n = A,T,C or G

<400> SEQUENCE: 169

```
acagccttgg cttccccaaa ctccacagtc tcagtgcaga aagatcatct tccagcagtc      60
agctcagacc agggtcaaag gatgtgacat caacagtttc tggtttcaga acaggttcta     120
ctactgtcaa atgacccccc atacttcctc aaaggctgtg gtaagttttg cacaggtgag     180
ggcagcagaa aggggtant tactgatgga caccatcttc tctgtatact ccacactgac      240
cttgccatgg gcaaaggccc ctaccacaaa acaatagga tcactgctgg gcaccagctc      300
acgcacatca ctgacaaccg ggatggaaaa agaantgcca actttcatac atccaactgg     360
aaagtgatct gatactggat tcttaattac cttcaaaagc ttctggggc catcagctgc      420
tcgaacactg a                                                           431
```

<210> SEQ ID NO 170
<211> LENGTH: 266
<212> TYPE: DNA
<213> ORGANISM: Homo sapien
<220> FEATURE:
<221> NAME/KEY: misc_feature
<222> LOCATION: (1)...(266)
<223> OTHER INFORMATION: n = A,T,C or G

<400> SEQUENCE: 170

```
acctgtgggc tgggctgtta tgcctgtgcc ggctgctgaa agggagttca gaggtggagc      60
tcaaggagct ctgcaggcat tttgccaanc ctctccanag canagggagc aacctacact     120
ccccgctaga aagacaccag attggagtcc tgggaggggg agttggggtg ggcatttgat     180
gtatacttgt cacctgaatg aangagccag agaggaanga dacgaanatg anattggcct     240
tcaaagctag gggtctggca ggtgga                                          266
```

<210> SEQ ID NO 171
<211> LENGTH: 1248
<212> TYPE: DNA
<213> ORGANISM: Homo sapien
<220> FEATURE:
<221> NAME/KEY: misc_feature
<222> LOCATION: (1)...(1248)
<223> OTHER INFORMATION: n = A,T,C or G

<400> SEQUENCE: 171

```
ggcagccaaa tcataaacgg cgaggactgc agcccgcact cgcagccctg gcaggcggca      60
ctggtcatgg aaaacgaatt gttctgctcg ggcgtcctgg tgcatccgca gtgggtgctg     120
```

```
tcagccgcac actgttttcca gaagtgagtg cagagctcct acaccatcgg gctgggcctg    180
cacagtcttg aggccgacca agagccaggg agccagatgg tggaggccag cctctccgta    240
cggcacccag agtacaacag acccttgctc gctaacgacc tcatgctcat caagttggac    300
gaatccgtgt ccgagtctga caccatccgg agcatcagca ttgcttcgca gtgccctacc    360
gcggggaact cttgcctcgt ttctggctgg ggtctgctgg cgaacggcag aatgcctacc    420
gtgctgcagt gcgtgaacgt gtcggtggtg tctgaggagg tctgcagtaa gctctatgac    480
ccgctgtacc accccagcat gttctgcgcc ggcggagggc aagaccagaa ggactcctgc    540
aacggtgact ctggggggcc cctgatctgc aacgggtact gcagggcct tgtgtcttc    600 ggaaaagccc cgtgtggcca agttggcgtg ccaggtgtct acaccaacct ctgcaaattc    660
actgagtgga tagagaaaac cgtccaggcc agttaactct ggggactggg aacccatgaa    720
attgaccccc aaatacatcc tgcggaagga attcaggaat atctgttccc agcccctcct    780
ccctcaggcc caggagtcca ggcccccagc ccctcctccc tcaaaccaag ggtacagatc    840
cccagcccct cctccctcag acccaggagt ccagaccccc cagcccctcc tccctcagac    900
ccaggagtcc agcccctcct ccctcagacc caggagtcca gacccccag ccctcctcc    960 ctcagaccca ggggtccagg ccccaaccc ctcctccctc agactcagag gtccaagccc   1020
ccaacccntc attccccaga cccagaggtc caggtcccag cccctcntcc ctcagaccca   1080
gcggtccaat gccacctaga ctntccctgt acacagtgcc ccttgtggc acgttgaccc   1140 aaccttacca gttggttttt cattttttngt ccctttcccc tagatccaga aataaagttt   1200
aagagaagng caaaaaaaaa aaaaaaaaa aaaaaaaaa aaaaaaa                    1248
```

<210> SEQ ID NO 172
<211> LENGTH: 159
<212> TYPE: PRT
<213> ORGANISM: Homo sapien
<220> FEATURE:
<221> NAME/KEY: VARIANT
<222> LOCATION: (1)...(159)
<223> OTHER INFORMATION: Xaa = Any Amino Acid

<400> SEQUENCE: 172

```
Met Val Glu Ala Ser Leu Ser Val Arg His Pro Glu Tyr Asn Arg Pro
 1               5                  10                  15

Leu Leu Ala Asn Asp Leu Met Leu Ile Lys Leu Asp Glu Ser Val Ser
             20                  25                  30

Glu Ser Asp Thr Ile Arg Ser Ile Ser Ile Ala Ser Gln Cys Pro Thr
         35                  40                  45

Ala Gly Asn Ser Cys Leu Val Ser Gly Trp Gly Leu Leu Ala Asn Gly
     50                  55                  60

Arg Met Pro Thr Val Leu Gln Cys Val Asn Val Ser Val Val Ser Glu
 65                  70                  75                  80

Glu Val Cys Ser Lys Leu Tyr Asp Pro Leu Tyr His Pro Ser Met Phe
                 85                  90                  95

Cys Ala Gly Gly Gly Gln Xaa Gln Xaa Asp Ser Cys Asn Gly Asp Ser
            100                 105                 110

Gly Gly Pro Leu Ile Cys Asn Gly Tyr Leu Gln Gly Leu Val Ser Phe
        115                 120                 125

Gly Lys Ala Pro Cys Gly Gln Val Gly Val Pro Gly Val Tyr Thr Asn
    130                 135                 140

Leu Cys Lys Phe Thr Glu Trp Ile Glu Lys Thr Val Gln Ala Ser
145                 150                 155
```

<210> SEQ ID NO 173
<211> LENGTH: 1265
<212> TYPE: DNA
<213> ORGANISM: Homo sapien
<220> FEATURE:
<221> NAME/KEY: misc_feature
<222> LOCATION: (1)...(1265)
<223> OTHER INFORMATION: n = A,T,C or G

<400> SEQUENCE: 173

```
ggcagcccgc actcgcagcc ctggcaggcg gcactggtca tggaaaacga attgttctgc      60
tcgggcgtcc tggtgcatcc gcagtgggtg ctgtcagccg cacactgttt ccagaactcc     120
tacaccatcg ggctgggcct gcacagtctt gaggccgacc aagagccagg gagccagatg     180
gtggaggcca gcctctccgt acggcaccca gagtacaaca gacccttgct cgctaacgac     240
ctcatgctca tcaagttgga cgaatccgtg tccgagtctg acaccatccg gagcatcagc     300
attgcttcgc agtgccctac cgcggggaac tcttgcctcg tttctggctg gggtctgctg     360
gcgaacggtg agctcacggg tgtgtgtctg ccctcttcaa ggaggtcctc tgcccagtcg     420
cggggctga cccagagctc tgcgtcccag gcagaatgcc taccgtgctg cagtgcgtga     480
acgtgtcggt ggtgtctgag gaggtctgca gtaagctcta tgaccgcctg taccacccca     540
gcatgttctg cgccggcgga gggcaagacc agaaggactc ctgcaacggt gactctgggg     600
ggcccctgat ctgcaacggg tacttgcagg gccttgtgtc tttcggaaaa gccccgtgtg     660
gccaagttgg cgtgccaggt gtctacacca acctctgcaa attcactgag tggatagaga     720
aaaccgtcca ggccagttaa ctctggggac tgggaaccca tgaaattgac ccccaaatac     780
atcctgcgga aggaattcag gaatatctgt tcccagcccc tcctccctca ggcccaggag     840
tccaggcccc cagcccctcc tccctcaaac caagggtaca gatccccagc ccctcctccc     900
tcagacccag gagtccagac cccccagccc ctcctccctc agaccccagga gtccagcccc     960
tcctccntca gacccaggag tccagacccc cagcccctc ctccctcaga cccaggggtt    1020
gaggccccca acccctcctc cttcagagtc agaggtccaa gccccaacc cctcgttccc    1080
cagacccaga ggtnnaggtc ccagcccctc ttccntcaga cccagnggtc caatgccacc    1140
tagattttcc ctgncacag tgccccttg tggnangttg acccaacctt accagttggt    1200
ttttcatttt tngtccctt ccctagatc cagaaataaa gtttaagaga ngngcaaaaa    1260
aaaaa                                                                1265
```

<210> SEQ ID NO 174
<211> LENGTH: 1459
<212> TYPE: DNA
<213> ORGANISM: Homo sapien
<220> FEATURE:
<221> NAME/KEY: misc_feature
<222> LOCATION: (1)...(1459)
<223> OTHER INFORMATION: n = A,T,C or G

<400> SEQUENCE: 174

```
ggtcagccgc acactgtttc agaagtgag tgcagagctc ctacaccatc gggctgggcc      60
tgcacagtct tgaggccgac caagagccag ggagccagat ggtggaggcc agcctctccg     120
tacggcaccc agagtacaac agacccttgc tcgctaacga cctcatgctc atcaagttgg     180
acgaatccgt gtccgagtct gacaccatcc ggagcatcag cattgcttcg cagtgcccta     240
ccgcggggaa ctcttgcctc gtttctggct ggggtctgct ggcgaacggt gagctcacgg     300
```

```
gtgtgtgtct gccctcttca aggaggtcct ctgcccagtc gcgggggctg acccagagct    360
ctgcgtccca ggcagaatgc ctaccgtgct gcagtgcgtg aacgtgtcgg tggtgtctga    420
ngaggtctgc antaagctct atgacccgct gtaccacccc ancatgttct gcgccggcgg    480
agggcaagac cagaaggact cctgcaacgt gagagagggg aaagggagg gcaggcgact     540 cagggaaggg tggagaaggg ggagacagag acacacaggg ccgcatggcg agatgcagag    600
atggagagac acacagggag acagtgacaa ctagagagag aaactgagag aaacagagaa    660
ataaacacag gaataaagag aagcaaagga agagagaaac agaaacagac atggggaggc    720
agaaacacac acacatagaa atgcagttga ccttccaaca gcatgggcc tgagggcggt     780 gacctccacc aatagaaaa tcctcttata acttttgact ccccaaaaac ctgactagaa      840
atagcctact gttgacgggg agccttacca ataacataaa tagtcgattt atgcatacgt    900
tttatgcatt catgatatac ctttgttgga atttttttgat atttctaagc tacacagttc   960
gtctgtgaat ttttttaaat tgttgcaact ctcctaaaat ttttctgatg tgtttattga    1020
aaaaatccaa gtataagtgg acttgtgcat tcaaaccagg gttgttcaag ggtcaactgt   1080
gtacccagag ggaaacagtg acacagattc atagaggtga aacacgaaga gaaacaggaa   1140
aaatcaagac tctacaaaga ggctgggcag ggtggctcat gcctgtaatc ccagcacttt   1200
gggaggcgag gcaggcagat cacttgaggt aaggagttca agaccagcct ggccaaaatg   1260
gtgaaatcct gtctgtacta aaaatacaaa agttagctgg atatggtggc aggcgcctgt   1320
aatcccagct acttgggagg ctgaggcagg agaattgctt gaatatggga ggcagaggtt   1380
gaagtgagtt gagatcacac cactatactc cagctggggc aacagagtaa gactctgtct   1440
caaaaaaaaa aaaaaaaaa                                                1459

<210> SEQ ID NO 175
<211> LENGTH: 1167
<212> TYPE: DNA
<213> ORGANISM: Homo sapien
<220> FEATURE:
<221> NAME/KEY: misc_feature
<222> LOCATION: (1)...(1167)
<223> OTHER INFORMATION: n = A,T,C or G

<400> SEQUENCE: 175
gcgcagccct ggcaggcggc actggtcatg gaaaacgaat tgttctgctc gggcgtcctg     60
gtgcatccgc agtgggtgct gtcagccgca cactgtttcc agaactccta caccatcggg    120
ctgggcctgc acagtcttga ggccgaccaa gagccaggga gccagatggt ggaggccagc    180
ctctccgtac ggcacccaga gtacaacaga ctcttgctcg ctaacgacct catgctcatc    240
aagttggacg aatccgtgtc cgagtctgac accatccgga gcatcagcat tgcttcgcag    300
tgccctaccg cggggaactc ttgcctcgtn tctggctggg gtctgctggc gaacggcaga    360
atgcctaccg tgctgcactg cgtgaacgtg tcggtggtgt ctgaggangt ctgcagtaag    420
ctctatgacc cgctgtacca ccccagcatg ttctgcgccg gcgagggca agaccagaag    480 gactcctgca cgtgactc tgggggccc ctgatctgca cgggtactt gcagggcctt        540 gtgtctttcg gaaaagcccc gtgtggccaa cttggcgtgc caggtgtcta caccaacctc    600
tgcaaattca ctgagtggat agagaaaacc gtccagncca gttaactctg gggactggga    660
acccatgaaa ttgaccccca aatacatcct gcggaangaa ttcaggaata tctgttccca    720
gcccctcctc cctcaggccc aggagtccag gcccccagcc cctcctcccct caaaccaagg    780 gtacagatcc ccagcccctc ctccctcaga cccaggagtc cagacccccc agcccctcnt    840
```

```
ccntcagacc caggagtcca gccctcctc cntcagacgc aggagtccag accccccagc      900
ccntcntccg tcagacccag gggtgcaggc ccccaacccc tcntcctca gagtcagagg      960 tccaagcccc caaccctcg ttccccagac ccagaggtnc aggtcccagc ccctcctccc     1020
tcagacccag cggtccaatg ccacctagan tntccctgta cacagtgccc ccttgtggca    1080
ngttgaccca accttaccag ttggtttttc atttttgtc cctttcccct agatccagaa    1140
ataaagtnta agagaagcgc aaaaaaa                                        1167
```

```
<210> SEQ ID NO 176
<211> LENGTH: 205
<212> TYPE: PRT
<213> ORGANISM: Homo sapien
<220> FEATURE:
<221> NAME/KEY: VARIANT
<222> LOCATION: (1)...(205)
<223> OTHER INFORMATION: Xaa = Any Amino Acid

<400> SEQUENCE: 176

Met Glu Asn Glu Leu Phe Cys Ser Gly Val Leu Val His Pro Gln Trp
 1               5                  10                  15

Val Leu Ser Ala Ala His Cys Phe Gln Asn Ser Tyr Thr Ile Gly Leu
                20                  25                  30

Gly Leu His Ser Leu Glu Ala Asp Gln Glu Pro Gly Ser Gln Met Val
            35                  40                  45

Glu Ala Ser Leu Ser Val Arg His Pro Glu Tyr Asn Arg Leu Leu Leu
        50                  55                  60

Ala Asn Asp Leu Met Leu Ile Lys Leu Asp Glu Ser Val Ser Glu Ser
65                  70                  75                  80

Asp Thr Ile Arg Ser Ile Ser Ile Ala Ser Gln Cys Pro Thr Ala Gly
                85                  90                  95

Asn Ser Cys Leu Val Ser Gly Trp Gly Leu Leu Ala Asn Gly Arg Met
            100                 105                 110

Pro Thr Val Leu His Cys Val Asn Val Ser Val Val Ser Glu Xaa Val
        115                 120                 125

Cys Ser Lys Leu Tyr Asp Pro Leu Tyr His Pro Ser Met Phe Cys Ala
130                 135                 140

Gly Gly Gly Gln Asp Gln Lys Asp Ser Cys Asn Gly Asp Ser Gly Gly
                145                 150                 155                 160

Pro Leu Ile Cys Asn Gly Tyr Leu Gln Gly Leu Val Ser Phe Gly Lys
            165                 170                 175

Ala Pro Cys Gly Gln Leu Gly Val Pro Gly Val Tyr Thr Asn Leu Cys
        180                 185                 190

Lys Phe Thr Glu Trp Ile Glu Lys Thr Val Gln Xaa Ser
            195                 200                 205
```

```
<210> SEQ ID NO 177
<211> LENGTH: 1119
<212> TYPE: DNA
<213> ORGANISM: Homo sapien

<400> SEQUENCE: 177
gcgcactcgc agccctggca ggcggcactg gtcatggaaa acgaattgtt ctgctcgggc       60
gtcctggtgc atccgcagtg ggtgctgtca gccgcacact gtttccagaa ctcctacacc     120
atcgggctgg gcctgcacag tcttgaggcc gaccaagagc cagggagcca gatggtggag     180
gccagcctct ccgtacggca cccagagtac aacagaccct gctcgctaa cgacctcatg     240
```

-continued

```
ctcatcaagt tggacgaatc cgtgtccgag tctgacacca tccggagcat cagcattgct      300
tcgcagtgcc ctaccgcggg gaactcttgc ctcgtttctg gctgggtct gctggcgaac       360
gatgctgtga ttgccatcca gtcccagact gtgggaggct gggagtgtga aagctttcc       420
caaccctggc agggttgtac catttcggca acttccagtg caaggacgtc ctgctgcatc      480
ctcactgggt gctcactact gctcactgca tcacccggaa cactgtgatc aactagccag      540
caccatagtt ctccgaagtc agactatcat gattactgtg ttgactgtgc tgtctattgt      600
actaaccatg ccgatgttta ggtgaaatta gcgtcacttg ccctcaacca tcttggtatc      660
cagttatcct cactgaattg agatttcctg cttcagtgtc agccattccc acataatttc      720
tgacctacag aggtgaggga tcatatagct cttcaaggat gctggtactc ccctcacaaa      780
ttcatttctc ctgttgtagt gaaaggtgcg ccctctggag cctcccaggg tgggtgtgca      840
ggtcacaatg atgaatgtat gatcgtgttc ccattaccca aagcctttaa atccctcatg      900
ctcagtacac caggcaggt ctagcatttc ttcatttagt gtatgctgtc cattcatgca       960
accacctcag gactcctgga ttctctgcct agttgagctc ctgcatgctg cctccttggg     1020
gaggtgaggg agagggccca tggttcaatg ggatctgtgc agttgtaaca cattaggtgc     1080
ttaataaaca gaagctgtga tgttaaaaaa aaaaaaaaa                            1119
```

<210> SEQ ID NO 178
<211> LENGTH: 164
<212> TYPE: PRT
<213> ORGANISM: Homo sapien
<220> FEATURE:
<221> NAME/KEY: VARIANT
<222> LOCATION: (1)...(164)
<223> OTHER INFORMATION: Xaa = Any Amino Acid

<400> SEQUENCE: 178

```
Met Glu Asn Glu Leu Phe Cys Ser Gly Val Leu Val His Pro Gln Trp
  1               5                  10                  15

Val Leu Ser Ala Ala His Cys Phe Gln Asn Ser Tyr Thr Ile Gly Leu
             20                  25                  30

Gly Leu His Ser Leu Glu Ala Asp Gln Glu Pro Gly Ser Gln Met Val
         35                  40                  45

Glu Ala Ser Leu Ser Val Arg His Pro Glu Tyr Asn Arg Pro Leu Leu
     50                  55                  60

Ala Asn Asp Leu Met Leu Ile Lys Leu Asp Glu Ser Val Ser Glu Ser
 65                  70                  75                  80

Asp Thr Ile Arg Ser Ile Ser Ile Ala Ser Gln Cys Pro Thr Ala Gly
                 85                  90                  95

Asn Ser Cys Leu Val Ser Gly Trp Gly Leu Leu Ala Asn Asp Ala Val
            100                 105                 110

Ile Ala Ile Gln Ser Xaa Thr Val Gly Gly Trp Glu Cys Glu Lys Leu
        115                 120                 125

Ser Gln Pro Trp Gln Gly Cys Thr Ile Ser Ala Thr Ser Ser Ala Arg
    130                 135                 140

Thr Ser Cys Cys Ile Leu Thr Gly Cys Ser Leu Leu Thr Ala Ser
145                 150                 155                 160

Pro Gly Thr Leu
```

<210> SEQ ID NO 179
<211> LENGTH: 250
<212> TYPE: DNA

<213> ORGANISM: Homo sapien

<400> SEQUENCE: 179

| | | | | | |
|---|---|---|---|---|---|
| ctggagtgcc | ttggtgtttc | aagcccctgc | aggaagcaga | atgcaccttc | tgaggcacct | 60 |
| ccagctgccc | ccggccgggg | gatgcgaggc | tcggagcacc | cttgcccggc | tgtgattgct | 120 |
| gccaggcact | gttcatctca | gcttttctgt | ccctttgctc | ccggcaagcg | cttctgctga | 180 |
| aagttcatat | ctggagcctg | atgtcttaac | gaataaaggt | cccatgctcc | acccgaaaaa | 240 |
| aaaaaaaaaa | | | | | | 250 |

<210> SEQ ID NO 180
<211> LENGTH: 202
<212> TYPE: DNA
<213> ORGANISM: Homo sapien

<400> SEQUENCE: 180

| | | | | | |
|---|---|---|---|---|---|
| actagtccag | tgtggtggaa | ttccattgtg | ttgggcccaa | cacaatggct | acctttaaca | 60 |
| tcacccagac | ccgcccctg | cccgtgcccc | acgctgctgc | taacgacagt | atgatgctta | 120 |
| ctctgctact | cggaaactat | tttatgtaa | ttaatgtatg | ctttcttgtt | tataaatgcc | 180 |
| tgatttaaaa | aaaaaaaaaa | aa | | | | 202 |

<210> SEQ ID NO 181
<211> LENGTH: 558
<212> TYPE: DNA
<213> ORGANISM: Homo sapien
<220> FEATURE:
<221> NAME/KEY: misc_feature
<222> LOCATION: (1)...(558)
<223> OTHER INFORMATION: n = A,T,C or G

<400> SEQUENCE: 181

| | | | | | |
|---|---|---|---|---|---|
| tccytttgkt | naggtttkkg | agacamcock | agacctwaan | ctgtgtcaca | gacttcyngg | 60 |
| aatgtttagg | cagtgctagt | aatttcytcg | taatgattct | gttattactt | tcctnattct | 120 |
| ttattcctct | ttcttctgaa | gattaatgaa | gttgaaaatt | gaggtggata | aatacaaaaa | 180 |
| ggtagtgtga | tagtataagt | atctaagtgc | agatgaaagt | gtgttatata | tatccattca | 240 |
| aaattatgca | agttagtaat | tactcagggt | taactaaatt | actttaatat | gctgttgaac | 300 |
| ctactctgtt | ccttggctag | aaaaaattat | aaacaggact | ttgttagttt | gggaagccaa | 360 |
| attgataata | ttctatgttc | taaaagttgg | gctatacata | aattattaag | aaatatggaw | 420 |
| ttttattccc | aggaatatgg | kgttcatttt | atgaatatta | cscrggatag | awgtwtgagt | 480 |
| aaaaycagtt | ttggtwaata | ygtwaatatg | tcmtaaataa | acaakgcttt | gacttatttc | 540 |
| caaaaaaaaa | aaaaaaaa | | | | | 558 |

<210> SEQ ID NO 182
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 182

| | | | | | |
|---|---|---|---|---|---|
| acagggwttk | grggatgcta | agsccccrga | rwtygtttga | tccaaccctg | gcttwttttc | 60 |
| agagggaaa | atgggccta | gaagttacag | mscatytagy | tggtgcgmtg | gcaccctgg | 120 |
| cstcacacag | astcccgagt | agctgggact | acaggcacac | agtcactgaa | gcaggccctg | 180 |

-continued

```
ttwgcaattc acgttgccac ctccaactta acattcttc atatgtgatg tccttagtca    240
ctaaggttaa actttcccac ccagaaaagg caacttagat aaaatcttag agtactttca    300
tactmttcta agtcctcttc cagcctcact kkgagtcctm cytggggggtt gataggaant    360 ntctcttggc tttctcaata aartctctat ycatctcatg tttaatttgg tacgcatara    420
awtgstgara aaattaaaat gttctggtty mactttaaaa araaaaaaaa aaaaaaaaa    479

<210> SEQ ID NO 183
<211> LENGTH: 384
<212> TYPE: DNA
<213> ORGANISM: Homo sapien

<400> SEQUENCE: 183
aggcgggagc agaagctaaa gccaaagccc aagaagagtg gcagtgccag cactggtgcc     60
agtaccagta ccaataacag tgccagtgcc agtgccagca ccagtggtgg cttcagtgct    120
ggtgccagcc tgaccgccac tctcacattt gggctcttcg ctggccttgg tggagctggt    180
gccagcacca gtggcagctc tggtgcctgt ggtttctcct acaagtgaga ttttagatat    240
tgttaatcct gccagtcttt ctcttcaagc cagggtgcat cctcagaaac ctactcaaca    300
cagcactcta ggcagccact atcaatcaat tgaagttgac actctgcatt aratctatt     360 gccatttcaa aaaaaaaaaa aaaa                                          384

<210> SEQ ID NO 184
<211> LENGTH: 496
<212> TYPE: DNA
<213> ORGANISM: Homo sapien
<220> FEATURE:
<221> NAME/KEY: misc_feature
<222> LOCATION: (1)...(496)
<223> OTHER INFORMATION: n = A,T,C or G

<400> SEQUENCE: 184
accgaattgg gaccgctggc ttataagcga tcatgtyynt ccrgtatkac ctcaacgagc     60
agggagatcg agtctatacg ctgaagaaat ttgacccgat gggacaacag acctgctcag    120
cccatcctgc tcggttctcc ccagatgaca aatactctsg acaccgaatc accatcaaga    180
aacgcttcaa ggtgctcatg acccagcaac gcgccctgt cctctgaggg tcccttaaac     240
tgatgtcttt tctgccacct gttacccctc ggagactccg taaccaaact cttcggactg    300
tgagccctga tgccttttg ccagccatac tctttggcat ccagtctctc gtggcgattg     360
attatgcttg tgtgaggcaa tcatggtggc atcacccata aagggaacac atttgacttt    420
tttttctcat attttaaatt actacmagaw tattwmagaw waaatgawtt gaaaaactst    480
taaaaaaaaa aaaaaa                                                   496

<210> SEQ ID NO 185
<211> LENGTH: 384
<212> TYPE: DNA
<213> ORGANISM: Homo sapien

<400> SEQUENCE: 185
gctggtagcc tatggcgkgg cccacggagg ggctcctgag gccacggrac agtgacttcc     60
caagtatcyt gcgcsgcgtc ttctaccgtc cctacctgca gatcttcggg cagattcccc    120
aggaggacat ggacgtggcc ctcatggagc acagcaactg ytcgtcggag cccggcttct    180
gggcacaccc tcctggggcc caggcgggca cctgcgtctc ccagtatgcc aactggctgg    240
```

```
tggtgctgct cctcgtcatc ttcctgctcg tggccaacat cctgctggtc aacttgctca      300
ttgccatgtt cagttacaca ttcggcaaag tacagggcaa cagcgatctc tactgggaag      360
gcgcagcgtt accgcctcat ccgg                                             384
```

<210> SEQ ID NO 186
<211> LENGTH: 577
<212> TYPE: DNA
<213> ORGANISM: Homo sapien
<220> FEATURE:
<221> NAME/KEY: misc_feature
<222> LOCATION: (1)...(577)
<223> OTHER INFORMATION: n = A,T,C or G

<400> SEQUENCE: 186

```
gagttagctc ctccacaacc ttgatgaggt cgtctgcagt ggcctctcgc ttcataccgc       60
tnccatcgtc atactgtagg tttgccacca cytcctggca tcttgggcg gcntaatatt      120 ccaggaaact ctcaatcaag tcaccgtcga tgaaacctgt gggctggttc tgtcttccgc      180
tcggtgtgaa aggatctccc agaaggagtg ctcgatcttc cccacacttt tgatgacttt      240
attgagtcga ttctgcatgt ccagcaggag gttgtaccag ctctctgaca gtgaggtcac      300
cagccctatc atgccgttga mcgtgccgaa garcaccgag ccttgtgtgg gggkkgaagt      360
ctcacccaga ttctgcatta ccagagagcc gtggcaaaag acattgacaa actcgcccag      420
gtggaaaaag amcamctcct ggargtgctn gccgctcctc gtcmgttggt ggcagcgctw      480
tccttttgac acacaaacaa gttaaaggca ttttcagccc ccagaaantt gtcatcatcc      540
aagatntcgc acagcactna tccagttggg attaaat                              577
```

<210> SEQ ID NO 187
<211> LENGTH: 534
<212> TYPE: DNA
<213> ORGANISM: Homo sapien
<220> FEATURE:
<221> NAME/KEY: misc_feature
<222> LOCATION: (1)...(534)
<223> OTHER INFORMATION: n = A,T,C or G

<400> SEQUENCE: 187

```
aacatcttcc tgtataatgc tgtgtaatat cgatccgatn ttgtctgstg agaatycatw       60
actkggaaaa gmaacattaa agcctggaca ctggtattaa aattcacaat atgcaacact      120
ttaaacagtg tgtcaatctg ctcccyynac tttgtcatca ccagtctggg aakaagggta      180
tgccctattc acacctgtta aaagggcgct aagcattttt gattcaacat cttttttttt      240
gacacaagtc cgaaaaaagc aaaagtaaac agttatyaat ttgttagcca attcactttc      300
ttcatgggac agagccatyt gatttaaaaa gcaaattgca taatattgag cttygggagc      360
tgatatttga gcggaagagt agcctttcta cttcaccaga cacaactccc tttcatattg      420
ggatgttnac naaagtwatg tctctwacag atgggatgct tttgtggcaa ttctgttctg      480
aggatctccc agtttattta ccacttgcac aagaaggcgt tttcttcctc aggc           534
```

<210> SEQ ID NO 188
<211> LENGTH: 761
<212> TYPE: DNA
<213> ORGANISM: Homo sapien
<220> FEATURE:
<221> NAME/KEY: misc_feature
<222> LOCATION: (1)...(761)
<223> OTHER INFORMATION: n = A,T,C or G

<400> SEQUENCE: 188

| | |
|---|---|
| agaaaccagt atctctnaaa acaacctctc ataccttgtg gacctaattt tgtgtgcgtg | 60 |
| tgtgtgtgcg cgcatattat atagacaggc acatctttt tacttttgta aaagcttatg | 120 |
| cctctttggt atctatatct gtgaaagttt taatgatctg ccataatgtc ttggggacct | 180 |
| ttgtcttctg tgtaaatggt actagagaaa acacctatnt tatgagtcaa tctagttngt | 240 |
| tttattcgac atgaaggaaa tttccagatn acaacactna caaactctcc ctkgackarg | 300 |
| ggggacaaag aaaagcaaaa ctgamcataa raaacaatwa cctggtgaga arttgcataa | 360 |
| acagaaatwr ggtagtatat tgaarnacag catcattaaa rmgttwtktt wttctccctt | 420 |
| gcaaaaaaca tgtacngact tcccgttgag taatgccaag ttgtttttt tatnataaaa | 480 |
| cttgccttc attacatgtt tnaaagtggt gtggtgggcc aaaatattga aatgatggaa | 540 |
| ctgactgata aagctgtaca ataagcagt gtgcctaaca agcaacacag taatgttgac | 600 |
| atgcttaatt cacaaatgct aatttcatta taaatgtttg ctaaaataca ctttgaacta | 660 |
| tttttctgtn ttcccagagc tgagatntta gattttatgt agtataagt gaaaaantac | 720 |
| gaaaataata acattgaaga aaananaaaa aananaaaaa a | 761 |

<210> SEQ ID NO 189
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 189

| | |
|---|---|
| tttttttttt tttgccgatn ctactatttt attgcaggan gtgggggtgt atgcaccgca | 60 |
| caccggggct atnagaagca agaaggaagg agggagggca cagccccttg ctgagcaaca | 120 |
| aagccgcctg ctgccttctc tgtctgtctc ctggtgcagg cacatgggga gaccttcccc | 180 |
| aaggcagggg ccaccagtcc aggggtggga atacaggggg tgggangtgt gcataagaag | 240 |
| tgataggcac aggccacccg gtacagaccc ctcggctcct gacaggtnga tttcgaccag | 300 |
| gtcattgtgc cctgcccagg cacagcgtan atctggaaaa gacagaatgc tttccttttc | 360 |
| aaatttggct ngtcatngaa ngggcanttt tccaanttng gctnggtctt ggtacncttg | 420 |
| gttcggccca gctccncgtc caaaaantat tcaccennct ccnaattgct tgcnggnccc | 480 |
| cc | 482 |

<210> SEQ ID NO 190
<211> LENGTH: 471
<212> TYPE: DNA
<213> ORGANISM: Homo sapien
<220> FEATURE:
<221> NAME/KEY: misc_feature
<222> LOCATION: (1)...(471)
<223> OTHER INFORMATION: n = A,T,C or G

<400> SEQUENCE: 190

| | |
|---|---|
| tttttttttt ttttaaaaca gttttcaca acaaaattta ttagaagaat agtggttttg | 60 |
| aaaactctcg catccagtga gaactaccat acaccacatt acagctngga atgtnctcca | 120 |
| aatgtctggt caaatgatac aatggaacca ttcaatctta cacatgcacg aaagaacaag | 180 |
| cgcttttgac atacaatgca caaaaaaaaa aggggggggg gacccatgg attaaaattt | 240 |
| taagtactca tcacatacat taagacacag ttctagtcca gtcnaaaatc agaactgcnt | 300 |

```
tgaaaaattt catgtatgca atccaaccaa agaacttnat tggtgatcat gantnctcta      360
ctacatcnac cttgatcatt gccaggaacn aaaagttnaa ancacncngt acaaaaanaa      420
tctgtaattn anttcaacct ccgtacngaa aaatnttnnt tatacactcc c               471
```

<210> SEQ ID NO 191
<211> LENGTH: 402
<212> TYPE: DNA
<213> ORGANISM: Homo sapien
<220> FEATURE:
<221> NAME/KEY: misc_feature
<222> LOCATION: (1)...(402)
<223> OTHER INFORMATION: n = A,T,C or G

<400> SEQUENCE: 191

```
gagggattga aggtctgttc tastgtcggm ctgttcagcc accaactcta acaagttgct      60
gtcttccact cactgtctgt aagctttttta acccagacwg tatcttcata aatagaacaa    120
attcttcacc agtcacatct tctaggacct ttttggattc agttagtata agctcttcca    180
cttcctttgt taagacttca tctggtaaag tcttaagttt tgtagaaagg aattyaattg    240
ctcgttctct aacaatgtcc tctccttgaa gtatttggct gaacaaccca cctaaagtcc    300
ctttgtgcat ccatttttaaa tatacttaat agggcattgk tncactaggt taaattctgc    360
aagagtcatc tgtctgcaaa agttgcgtta gtatatctgc ca                       402
```

<210> SEQ ID NO 192
<211> LENGTH: 601
<212> TYPE: DNA
<213> ORGANISM: Homo sapien
<220> FEATURE:
<221> NAME/KEY: misc_feature
<222> LOCATION: (1)...(601)
<223> OTHER INFORMATION: n = A,T,C or G

<400> SEQUENCE: 192

```
gagctcggat ccaataatct ttgtctgagg gcagcacaca tatncagtgc catggnaact      60
ggtctacccc acatgggagc agcatgccgt agntatataa ggtcattccc tgagtcagac    120
atgcytyttt gaytaccgtg tgccaagtgc tggtgattct yaacacacyt ccatcccgyt    180
cttttgtgga aaaactggca cttktctgga actagcarga catcacttac aaattcaccc    240
acgagacact tgaaaggtgt aacaaagcga ytcttgcatt gcttttttgtc cctccggcac    300 cagttgtcaa tactaacccg ctggtttgcc tccatcacat ttgtgatctg tagctctgga    360
tacatctcct gacagtactg aagaacttct tcttttgttt caaaagcarc tcttggtgcc    420
tgttggatca ggttcccatt tcccagtcyg aatgttcaca tggcatattt wacttcccac    480
aaaacattgc gatttgaggc tcagcaacag caaatcctgt tccggcattg gctgcaagag    540
cctcgatgta gccggccagc gccaaggcag gcgccgtgag ccccaccagc agcagaagca    600
g                                                                     601
```

<210> SEQ ID NO 193
<211> LENGTH: 608
<212> TYPE: DNA
<213> ORGANISM: Homo sapien
<220> FEATURE:
<221> NAME/KEY: misc_feature
<222> LOCATION: (1)...(608)
<223> OTHER INFORMATION: n = A,T,C or G

<400> SEQUENCE: 193

```
atacagccca natcccacca cgaagatgcg cttgttgact gagaacctga tgcggtcact      60
```

```
ggtcccgctg tagccccagc gactctccac ctgctggaag cggttgatgc tgcactcytt    120
cccaacgcag gcagmagcgg gsccggtcaa tgaactccay tcgtggcttg gggtkgacgg    180
tkaagtgcag gaagaggctg accacctcgc ggtccaccag gatgcccgac tgtgcgggac    240
ctgcagcgaa actcctcgat ggtcatgagc gggaagcgaa tgaggcccag ggccttgccc    300
agaaccttcc gcctgttctc tggcgtcacc tgcagctgct gccgctgaca ctcggcctcg    360
gaccagcgga caaacggcrt tgaacagccg cacctcacgg atgcccagtg tgtcgcgctc    420
caggammgsc accagcgtgt ccaggtcaat gtcggtgaag ccctccgcgg gtratggcgt    480
ctgcagtgtt tttgtcgatg ttctccaggc acaggctggc cagctgcggt tcatcgaaga    540
gtcgcgcctg cgtgagcagc atgaaggcgt tgtcggctcg cagttcttct tcaggaactc    600
cacgcaat                                                             608

<210> SEQ ID NO 194
<211> LENGTH: 392
<212> TYPE: DNA
<213> ORGANISM: Homo sapien
<220> FEATURE:
<221> NAME/KEY: misc_feature
<222> LOCATION: (1)...(392)
<223> OTHER INFORMATION: n = A,T,C or G

<400> SEQUENCE: 194
gaacggctgg accttgcctc gcattgtgct tgctggcagg gaataccttg gcaagcagyt     60
ccagtccgag cagccccaga ccgctgccgc ccgaagctaa gcctgcctct ggccttcccc    120
tccgcctcaa tgcagaacca gtagtgggag cactgtgttt agagttaaga gtgaacactg    180
tttgatttta cttgggaatt tcctctgtta tatagctttt cccaatgcta atttccaaac    240
aacaacaaca aaataacatg tttgcctgtt aagttgtata aagtaggtg attctgtatt    300 taaagaaaat attactgtta catatactgc ttgcaatttc tgtatttatt gktnctstgg    360
aaataaatat agttattaaa ggttgtcant cc                                  392

<210> SEQ ID NO 195
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 195
ccsttkgagg ggtkaggkyc cagttyccga gtggaagaaa caggccagga gaagtgcgtg     60
ccgagctgag gcagatgttc ccacagtgac ccccagagcc stgggstata gtytctgacc    120
cctcncaagg aaagaccacs ttctggggac atgggctgga gggcaggacc tagaggcacc    180
aagggaaggc cccattccgg ggstgttccc cgaggaggaa gggaaggggc tctgtgtgcc    240
ccccasgagg aagaggccct gagtcctggg atcagacacc ccttcacgtg tatccccaca    300
caaatgcaag ctcaccaagg tcccctctca gtccccttcc stacaccctg amcggccact    360
gscscacacc cacccagagc acgccacccg ccatggggar tgtgctcaag gartcgcngg    420
gcarcgtgga catctngtcc cagaagggg cagaatctcc aatagangga ctgarcmstt    480
gctnanaaaa aaaaanaaaa aa                                             502

<210> SEQ ID NO 196
```

```
<211> LENGTH: 665
<212> TYPE: DNA
<213> ORGANISM: Homo sapien
<220> FEATURE:
<221> NAME/KEY: misc_feature
<222> LOCATION: (1)...(665)
<223> OTHER INFORMATION: n = A,T,C or G

<400> SEQUENCE: 196
ggttacttgg tttcattgcc accacttagt ggatgtcatt tagaaccatt ttgtctgctc      60
cctctggaag ccttgcgcag agcggacttt gtaattgttg gagaataact gctgaatttt     120
wagctgttk gagttgatts gcaccactgc acccacaact tcaatatgaa aacyawttga     180
actwatttat tatcttgtga aaagtataac aatgaaaatt tgttcatac tgtattkatc     240
aagtatgatg aaaagcaawa gatatatatt cttttattat gttaaattat gattgccatt    300
attaatcggc aaaatgtgga gtgtatgttc ttttcacagt aatatatgcc ttttgtaact     360
tcacttggtt attttattgt aaatgartta caaaattctt aatttaagar aatggtatgt     420
watatttatt tcattaattt ctttcctkgt ttacgtwaat tttgaaaaga wtgcatgatt     480
tcttgacaga aatcgatctt gatgctgtgg aagtagtttg acccacatcc ctatgagttt     540
ttcttagaat gtataaaggt tgtagcccat cnaacttcaa agaaaaaaat gaccacatac     600
tttgcaatca ggctgaaatg tggcatgctn ttctaattcc aactttataa actagcaaan     660
aagtg                                                                 665

<210> SEQ ID NO 197
<211> LENGTH: 492
<212> TYPE: DNA
<213> ORGANISM: Homo sapien
<220> FEATURE:
<221> NAME/KEY: misc_feature
<222> LOCATION: (1)...(492)
<223> OTHER INFORMATION: n = A,T,C or G

<400> SEQUENCE: 197 ttttntttt tttttttttgc aggaaggatt ccatttattg tggatgcatt ttcacaatat     60
atgtttattg gagcgatcca ttatcagtga aaagtatcaa gtgtttataa nattttagg     120
aaggcagatt cacagaacat gctngtcngc ttgcagtttt acctcgtana gatnacagag    180
aattatagtc naaccagtaa acnaggaatt tacttttcaa aagattaaat ccaaactgaa    240
caaaattcta ccctgaaact tactccatcc aaatattgga ataanagtca gcagtgatac    300
attctcttct gaactttaga ttttctagaa aaatatgtaa tagtgatcag gaagagctct    360
tgttcaaaag tacaacnaag caatgttccc ttaccatagg ccttaattca aactttgatc    420
catttcactc ccatcacggg agtcaatgct acctgggaca cttgtatttt gttcatnctg    480
ancntggctt aa                                                         492

<210> SEQ ID NO 198
<211> LENGTH: 478
<212> TYPE: DNA
<213> ORGANISM: Homo sapien
<220> FEATURE:
<221> NAME/KEY: misc_feature
<222> LOCATION: (1)...(478)
<223> OTHER INFORMATION: n = A,T,C or G

<400> SEQUENCE: 198 tttntttgn atttcantct gtannaanta ttttcattat gtttattana aaaatatnaa     60
tgtntccacn acaaatcatn ttacntnagt aagaggccan ctacattgta caacatacac    120
```

```
tgagtatatt ttgaaaagga caagtttaaa gtanacncat attgccganc atancacatt        180
tatacatggc ttgattgata tttagcacag canaaactga gtgagttacc agaaanaaat        240
natatatgtc aatcngattt aagatacaaa acagatccta tggtacatan catcntgtag        300
gagttgtggc tttatgttta ctgaaagtca atgcagttcc tgtacaaaga gatggccgta        360
agcattctag tacctctact ccatggttaa gaatcgtaca cttatgttta catatgtnca        420
gggtaagaat tgtgttaagt naanttatgg agaggtccan gagaaaaatt tgatncaa         478
```

<210> SEQ ID NO 199
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 199

```
agtgacttgt cctccaacaa aaccccttga tcaagtttgt ggcactgaca atcagaccta        60
tgctagttcc tgtcatctat tcgctactaa atgcagactg gagggaccca aaaaggggca       120
tcaactccag ctggattatt ttggagcctg caaatctatt cctacttgta cggactttga       180
agtgattcag tttcctctac ggatgagaga ctggctcaag aatatcctca tgcagcttta       240
tgaagccnac tctgaacacg ctggttatct nagatgagaa ncagagaaat aaagtcnaga       300
aaatttacct ggangaaaag aggctttngg ctggggacca tcccattgaa ccttctctta       360 anggactttta agaanaaact accacatgtn tgtngtatcc tggtgccngg ccgtttantg       420
aacntngacn ncacccttnt ggaatananat cttgacngcn tcctgaactt gctcctctgc       480
ga                                                                      482
```

<210> SEQ ID NO 200
<211> LENGTH: 270
<212> TYPE: DNA
<213> ORGANISM: Homo sapien
<220> FEATURE:
<221> NAME/KEY: misc_feature
<222> LOCATION: (1)...(270)
<223> OTHER INFORMATION: n = A,T,C or G

<400> SEQUENCE: 200

```
cggccgcaag tgcaactcca gctggggccg tgcggacgaa gattctgcca gcagttggtc        60
cgactgcgac gacggcggcg cgacagtcg caggtgcagc gcggcgcct ggggtcttgc        120 aaggctgagc tgacgccgca gaggtcgtgt cacgtcccac gaccttgacg ccgtcgggga      180
cagccggaac agagcccggt gaangcggga ggcctcgggg agcccctcgg gaagggcggc       240
ccgagagata cgcaggtgca ggtggccgcc                                        270
```

<210> SEQ ID NO 201
<211> LENGTH: 419
<212> TYPE: DNA
<213> ORGANISM: Homo sapien
<220> FEATURE:
<221> NAME/KEY: misc_feature
<222> LOCATION: (1)...(419)
<223> OTHER INFORMATION: n = A,T,C or G

<400> SEQUENCE: 201

```
tttttttttt ttttggaatc tactgcgagc acagcaggtc agcaacaagt ttattttgca        60
```

```
gctagcaagg taacagggta gggcatggtt acatgttcag gtcaacttcc tttgtcgtgg      120
ttgattggtt tgtctttatg ggggcgggt ggggtagggg aaancgaagc anaantaaca      180
tggagtgggt gcaccctccc tgtagaacct ggttacnaaa gcttgggca gttcacctgg      240 tctgtgaccg tcattttctt gacatcaatg ttattagaag tcaggatatc ttttagagag      300
tccactgtnt ctggagggag attagggttt cttgccaana tccaancaaa atccacntga      360
aaaagttgga tgatncangt acngaatacc ganggcatan ttctcatant cggtggcca      419

<210> SEQ ID NO 202
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 202 tttnttttt tttttttttt tttttttttt tttttttttt tttttttttt                 60
tggcacttaa tccattttta tttcaaaatg tctacaaant ttnaatncnc cattatacng     120
gtnattttnc aaaatctaaa nnttattcaa atntnagcca aantccttac ncaaatnnaa     180
tacncncaaa aatcaaaaat atacntntct ttcagcaaac ttngttacat aaattaaaaa     240
aatatatacg gctggtgttt tcaaagtaca attatcttaa cactgcaaac atntttnnaa     300
ggaactaaaa taaaaaaaaa cactnccgca aaggttaaag ggaacaacaa attcntttta     360
caacancnnc nattataaaa atcatatctc aaatcttagg ggaatatata cttcacacng     420
ggatcttaac ttttactnca cttttgtttat ttttttanaa ccattgtntt gggcccaaca     480
caatggnaat nccnccncnc tggactagt                                       509

<210> SEQ ID NO 203
<211> LENGTH: 583
<212> TYPE: DNA
<213> ORGANISM: Homo sapien
<220> FEATURE:
<221> NAME/KEY: misc_feature
<222> LOCATION: (1)...(583)
<223> OTHER INFORMATION: n = A,T,C or G

<400> SEQUENCE: 203
tttttttttt tttttttga ccccctctt ataaaaaaca agttaccatt ttatttact        60 tacacatatt tatttataa ttggtattag atattcaaaa ggcagctttt aaaatcaaac     120
taaatggaaa ctgccttaga tacataattc ttaggaatta gcttaaaatc tgcctaaagt     180
gaaaatcttc tctagctctt ttgactgtaa attttttgact cttgtaaaac atccaaattc     240
atttttcttg tctttaaaat tatctaatct ttccattttt tccctattcc aagtcaattt     300
gcttctctag cctcatttcc tagctcttat ctactattag taagtggctt ttttcctaaa     360
agggaaaaca ggaagagana atggcacaca aaacaaacat tttatattca tatttctacc     420
tacgttaata aaatagcatt ttgtgaagcc agctcaaaag aaggcttaga tccttttatg     480 tccatttag tcactaaacg atatcnaaag tgccagaatg caaaaggttt gtgaacattt      540
attcaaaagc taatataaga tatttcacat actcatcttt ctg                       583

<210> SEQ ID NO 204
<211> LENGTH: 589
<212> TYPE: DNA
<213> ORGANISM: Homo sapien
```

```
<220> FEATURE:
<221> NAME/KEY: misc_feature
<222> LOCATION: (1)...(589)
<223> OTHER INFORMATION: n = A,T,C or G

<400> SEQUENCE: 204
ttttttttnt tttttttttt tttttncte tctttttttt ttganaatga ggatcgagtt      60
tttcactctc tagatagggc atgaagaaaa ctcatctttc cagctttaaa ataacaatca    120
aatctcttat gctatatcat attttaagtt aaactaatga gtcactggct tatcttctcc    180
tgaaggaaat ctgttcattc ttctcattca tatagttata tcaagtacta ccttgcatat    240
tgagaggttt ttcttctcta tttacacata tatttccatg tgaatttgta tcaaacettt    300
attttcatgc aaactagaaa ataatgtntt cttttgcata agaagagaga acaatatnag    360
cattacaaaa ctgctcaaat tgtttgttaa gnttatccat tataattagt tnggcaggag    420
ctaatacaaa tcacatttac ngacnagcaa taataaaact gaagtaccag ttaaatatcc    480
aaaataatta aaggaacatt tttagcctgg gtataattag ctaattcact ttacaagcat    540
ttattnagaa tgaattcaca tgttattatt ccntagccca acacaatgg              589

<210> SEQ ID NO 205
<211> LENGTH: 545
<212> TYPE: DNA
<213> ORGANISM: Homo sapien
<220> FEATURE:
<221> NAME/KEY: misc_feature
<222> LOCATION: (1)...(545)
<223> OTHER INFORMATION: n = A,T,C or G

<400> SEQUENCE: 205
tttttntttt tttttttcagt aataatcaga acaatattta tttttatatt taaaattcat    60
agaaaagtgc cttacattta ataaagtttt gtttctcaaa gtgatcagag gaattagata   120
tngtcttgaa caccaatatt aatttgagga aaatacacca aaatacatta agtaaattat   180
ttaagatcat agagcttgta agtgaaaaga taaaatttga cctcagaaac tctgagcatt   240
aaaaatccac tattagcaaa taaattacta tggacttctt gctttaattt tgtgatgaat   300
atgggtgtc actggtaaac caacacattc tgaaggatac attacttagt gatagattct     360
tatgtacttt gctanatnac gtggatatga gttgacaagt ttctctttct tcaatctttt   420
aaggggcnga ngaaatgagg aagaaaagaa aaggattacg catactgttc tttctatngg   480
aaggattaga tatgtttcct ttgccaatat taaaaaaata ataatgttta ctactagtga   540
aaccc                                                              545

<210> SEQ ID NO 206
<211> LENGTH: 487
<212> TYPE: DNA
<213> ORGANISM: Homo sapien
<220> FEATURE:
<221> NAME/KEY: misc_feature
<222> LOCATION: (1)...(487)
<223> OTHER INFORMATION: n = A,T,C or G

<400> SEQUENCE: 206
tttttttttt tttttagtc aagtttctna ttttattat aattaaagtc ttggtcattt      60
catttattag ctctgcaact tacatattta aattaaagaa acgttnttag acaactgtna   120
caatttataa atgtaaggtg ccattattga gtanatatat tcctccaaga gtggatgtgt   180
cccttctccc accaactaat gaancagcaa cattagttta attttattag tagatnatac   240
```

```
actgctgcaa acgctaattc tcttctccat ccccatgtng atattgtgta tatgtgtgag      300
ttggtnagaa tgcatcanca atctnacaat caacagcaag atgaagctag gcntgggctt      360
tcggtgaaaa tagactgtgt ctgtctgaat caaatgatct gacctatcct cggtggcaag      420
aactcttcga accgcttcct caaaggcngc tgccacattt gtggcntctn ttgcacttgt      480
ttcaaaa                                                                 487

<210> SEQ ID NO 207
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 207
tgaattggct aaaagactgc attttttanaa ctagcaactc ttatttcttt cctttaaaaa     60
tacatagcat taaatcccaa atcctattta aagacctgac agcttgagaa ggtcactact      120
gcatttatag gaccttctgg tggttctgct gttacntttg aantctgaca atccttgana      180
atctttgcat gcagaggagg taaaaggtat tggattttca cagaggaana acacagcgca      240
gaaatgaagg ggccaggctt actgagcttg tccactggag ggctcatggg tgggacatgg      300
aaaagaaggc agcctaggcc ctggggagcc ca                                    332

<210> SEQ ID NO 208
<211> LENGTH: 524
<212> TYPE: DNA
<213> ORGANISM: Homo sapien
<220> FEATURE:
<221> NAME/KEY: misc_feature
<222> LOCATION: (1)...(524)
<223> OTHER INFORMATION: n = A,T,C or G

<400> SEQUENCE: 208
agggcgtggt gcggagggcg ttactgtttt gtctcagtaa caataaatac aaaaagactg      60
gttgtgttcc ggccccatcc aaccacgaag ttgatttctc ttgtgtgcag agtgactgat      120
tttaaaggac atggagcttg tcacaatgtc acaatgtcac agtgtgaagg gcacactcac      180
tcccgcgtga ttcacattta gcaaccaaca atagctcatg agtccatact tgtaaatact      240
tttggcagaa tacttnttga aacttgcaga tgataactaa gatccaagat atttcccaaa      300
gtaaatagaa gtgggtcata atattaatta cctgttcaca tcagcttcca tttacaagtc      360
atgagcccag acactgacat caaactaagc ccacttagac tcctcaccac cagtctgtcc      420
tgtcatcaga caggaggctg tcaccttgac caaattctca ccagtcaatc atctatccaa      480
aaaccattac ctgatccact tccggtaatg caccaccttg gtga                       524

<210> SEQ ID NO 209
<211> LENGTH: 159
<212> TYPE: DNA
<213> ORGANISM: Homo sapien

<400> SEQUENCE: 209
gggtgaggaa atccagagtt gccatggaga aaattccagt gtcagcattc ttgctccttg      60
tggccctctc ctacactctg gccagagata ccacagtcaa acctggagcc aaaaaggaca      120
caaaggactc tcgacccaaa ctgccccaga ccctctcca                             159
```

<210> SEQ ID NO 210
<211> LENGTH: 256
<212> TYPE: DNA
<213> ORGANISM: Homo sapien
<220> FEATURE:
<221> NAME/KEY: misc_feature
<222> LOCATION: (1)...(256)
<223> OTHER INFORMATION: n = A,T,C or G

<400> SEQUENCE: 210

| | | | | | |
|---|---|---|---|---|---|
| actccctggc | agacaaaggc | agaggagaga | gctctgttag | ttctgtgttg | ttgaactgcc | 60 |
| actgaatttc | tttccacttg | gactattaca | tgccanttga | gggactaatg | gaaaaacgta | 120 |
| tggggagatt | ttanccaatt | tangtntgta | aatggggaga | ctgggcagg | cgggagagat | 180 |
| ttgcagggtg | naaatgggan | ggctggtttg | ttanatgaac | agggacatag | gaggtaggca | 240 |
| ccaggatgct | aaatca | | | | | 256 |

<210> SEQ ID NO 211
<211> LENGTH: 264
<212> TYPE: DNA
<213> ORGANISM: Homo sapien
<220> FEATURE:
<221> NAME/KEY: misc_feature
<222> LOCATION: (1)...(264)
<223> OTHER INFORMATION: n = A,T,C or G

<400> SEQUENCE: 211

| | | | | | |
|---|---|---|---|---|---|
| acattgtttt | tttgagataa | agcattgaga | gagctctcct | taacgtgaca | caatggaagg | 60 |
| actggaacac | atacccacat | ctttgttctg | agggataatt | ttctgataaa | gtcttgctgt | 120 |
| atattcaagc | acatatgtta | tatattattc | agttccatgt | ttatagccta | gttaaggaga | 180 |
| ggggagatac | attcngaaag | aggactgaaa | gaaatactca | agtnggaaaa | cagaaaaaga | 240 |
| aaaaaggag | caaatgagaa | gcct | | | | 264 |

<210> SEQ ID NO 212
<211> LENGTH: 328
<212> TYPE: DNA
<213> ORGANISM: Homo sapien
<220> FEATURE:
<221> NAME/KEY: misc_feature
<222> LOCATION: (1)...(328)
<223> OTHER INFORMATION: n = A,T,C or G

<400> SEQUENCE: 212

| | | | | | |
|---|---|---|---|---|---|
| acccaaaaat | ccaatgctga | atatttggct | tcattattcc | canattcttt | gattgtcaaa | 60 |
| ggatttaatg | ttgtctcagc | ttgggcactt | cagttaggac | ctaaggatgc | cagccggcag | 120 |
| gtttatatat | gcagcaacaa | tattcaagcg | cgacaacagg | ttattgaact | tgcccgccag | 180 |
| ttnaatttca | ttcccattga | cttgggatcc | ttatcatcag | ccagagagat | tgaaaattta | 240 |
| cccctacnac | tctttactct | ctgganaggg | ccagtggtgg | tagctataag | cttggccaca | 300 |
| ttttttttc | ctttattcct | ttgtcaga | | | | 328 |

<210> SEQ ID NO 213
<211> LENGTH: 250
<212> TYPE: DNA
<213> ORGANISM: Homo sapien
<220> FEATURE:
<221> NAME/KEY: misc_feature
<222> LOCATION: (1)...(250)
<223> OTHER INFORMATION: n = A,T,C or G

<400> SEQUENCE: 213

```
acttatgagc agagcgacat atccnagtgt agactgaata aaactgaatt ctctccagtt      60
taaagcattg ctcactgaag ggatagaagt gactgccagg agggaaagta agccaaggct     120
cattatgcca aagganatat acatttcaat tctccaaact tcttcctcat tccaagagtt     180
ttcaatattt gcatgaacct gctgataanc catgttaana acaaatatc tctctnacct      240 tctcatcggt                                                            250
```

<210> SEQ ID NO 214
<211> LENGTH: 444
<212> TYPE: DNA
<213> ORGANISM: Homo sapien
<220> FEATURE:
<221> NAME/KEY: misc_feature
<222> LOCATION: (1)...(444)
<223> OTHER INFORMATION: n = A,T,C or G

<400> SEQUENCE: 214

```
acccagaatc caatgctgaa tatttggctt cattattccc agattctttg attgtcaaag      60
gatttaatgt tgtctcagct tgggcacttc agttaggacc taaggatgcc agccggcagg     120
tttatatatg cagcaacaat attcaagcgc gacaacaggt tattgaactt gcccgccagt     180
tgaatttcat tcccattgac ttgggatcct tatcatcagc canagagatt gaaaatttac     240
ccctacgact ctttactctc tggagagggc cagtggtggt agctataagc ttggccacat     300 tttttttttcc tttattcctt tgtcagagat gcgattcatc catatgctan aaaccaacag     360
agtgactttt acaaaattcc tataganatt gtgaataaaa ccttacctat agttgccatt     420
actttgctct ccctaatata cctc                                            444
```

<210> SEQ ID NO 215
<211> LENGTH: 366
<212> TYPE: DNA
<213> ORGANISM: Homo sapien
<220> FEATURE:
<221> NAME/KEY: misc_feature
<222> LOCATION: (1)...(366)
<223> OTHER INFORMATION: n = A,T,C or G

<400> SEQUENCE: 215

```
acttatgagc agagcgacat atccaagtgt anactgaata aaactgaatt ctctccagtt      60
taaagcattg ctcactgaag ggatagaagt gactgccagg agggaaagta agccaaggct     120
cattatgcca aagganatat acatttcaat tctccaaact tcttcctcat tccaagagtt     180
ttcaatattt gcatgaacct gctgataagc catgttgaga acaaatatc tctctgacct      240 tctcatcggt aagcagaggc tgtaggcaac atggaccata gcgaanaaaa aacttagtaa     300
tccaagctgt tttctacact gtaaccaggt ttccaaccaa ggtggaaatc tcctatactt     360
ggtgcc                                                                366
```

<210> SEQ ID NO 216
<211> LENGTH: 260
<212> TYPE: DNA
<213> ORGANISM: Homo sapien
<220> FEATURE:
<221> NAME/KEY: misc_feature
<222> LOCATION: (1)...(260)
<223> OTHER INFORMATION: n = A,T,C or G

<400> SEQUENCE: 216

```
ctgtataaac agaactccac tgcangaggg agggccgggc caggagaatc tccgcttgtc      60
caagacaggg gcctaaggag ggtctccaca ctgctnntaa gggctnttnc attttttttat    120
```

```
taataaaaag tnnaaaaggc ctcttctcaa cttttttccc ttnggctgga aaatttaaaa      180
atcaaaaatt tcctnaagtt ntcaagctat catatatact ntatcctgaa aaagcaacat      240
aattcttcct tccctccttt                                                  260

<210> SEQ ID NO 217
<211> LENGTH: 262
<212> TYPE: DNA
<213> ORGANISM: Homo sapien
<220> FEATURE:
<221> NAME/KEY: misc_feature
<222> LOCATION: (1)...(262)
<223> OTHER INFORMATION: n = A,T,C or G

<400> SEQUENCE: 217
acctacgtgg gtaagtttan aaatgttata atttcaggaa naggaacgca tataattgta      60
tcttgcctat aattttctat tttaataagg aaatagcaaa ttggggtggg gggaatgtag      120
ggcattctac agtttgagca aaatgcaatt aaatgtggaa ggacagcact gaaaaatttt      180
atgaataatc tgtatgatta tatgtctcta gagtagattt ataattagcc acttacccta     240
atatccttca tgcttgtaaa gt                                                262

<210> SEQ ID NO 218
<211> LENGTH: 205
<212> TYPE: DNA
<213> ORGANISM: Homo sapien
<220> FEATURE:
<221> NAME/KEY: misc_feature
<222> LOCATION: (1)...(205)
<223> OTHER INFORMATION: n = A,T,C or G

<400> SEQUENCE: 218
accaaggtgg tgcattaccg gaantggatc aangacacca tcgtggccaa cccctgagca      60
cccctatcaa ctcccttttg tagtaaactt ggaaccttgg aaatgaccag gccaagactc      120
aggcctcccc agttctactg acctttgtcc ttangtntna ngtccagggt tgctaggaaa     180
anaaatcagc agacacaggt gtaaa                                            205

<210> SEQ ID NO 219
<211> LENGTH: 114
<212> TYPE: DNA
<213> ORGANISM: Homo sapien

<400> SEQUENCE: 219
tactgttttg tctcagtaac aataaataca aaaagactgg ttgtgttccg gccccatcca      60
accacgaagt tgatttctct tgtgtgcaga gtgactgatt ttaaaggaca tgga            114

<210> SEQ ID NO 220
<211> LENGTH: 93
<212> TYPE: DNA
<213> ORGANISM: Homo sapien

<400> SEQUENCE: 220
actagccagc acaaaaggca gggtagcctg aattgctttc tgctctttac atttcttta      60 aaataagcat ttagtgctca gtccctactg agt                                    93

<210> SEQ ID NO 221
<211> LENGTH: 167
<212> TYPE: DNA
<213> ORGANISM: Homo sapien
<220> FEATURE:
```

```
<221> NAME/KEY: misc_feature
<222> LOCATION: (1)...(167)
<223> OTHER INFORMATION: n = A,T,C or G

<400> SEQUENCE: 221
actangtgca ggtgcgcaca aatatttgtc gatattccct tcatcttgga ttccatgagg      60
tcttttgccc agcctgtggc tctactgtag taagtttctg ctgatgagga gccagnatgc     120
cccccactac cttccctgac gctccccana aatcacccaa cctctgt                   167

<210> SEQ ID NO 222
<211> LENGTH: 351
<212> TYPE: DNA
<213> ORGANISM: Homo sapien

<400> SEQUENCE: 222
agggcgtggt gcggagggcg gtactgacct cattagtagg aggatgcatt ctggcacccc      60
gttcttcacc tgtcccccaa tccttaaaag gccatactgc ataaagtcaa caacagataa     120
atgtttgctg aattaaagga tggatgaaaa aaattaataa tgaattttg cataatccaa      180 ttttctcttt tatatttcta gaagaagttt ctttgagcct attagatccc gggaatcttt     240
taggtgagca tgattagaga gcttgtaggt tgcttttaca tatatctggc atatttgagt     300
ctcgtatcaa aacaatagat tggtaaaggt ggtattattg tattgataag t              351

<210> SEQ ID NO 223
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 223
aaaacaaaca aacaaaaaaa acaattcttc attcagaaaa attatcttag ggactgatat      60
tggtaattat ggtcaattta atwrtrttkt ggggcatttc cttacattgt cttgacaaga     120
ttaaaatgtc tgtgccaaaa ttttgtattt tatttggaga cttcttatca aaagtaatgc     180
tgccaaagga agtctaagga attagtagtg ttcccmtcac ttgtttggag tgtgctattc     240
taaaagattt tgatttcctg gaatgacaat tatatttaa ctttggtggg ggaaanagtt      300
ataggaccac agtcttcact tctgatactt gtaaattaat cttttattgc acttgttttg     360
accattaagc tatatgttta aaa                                             383

<210> SEQ ID NO 224
<211> LENGTH: 320
<212> TYPE: DNA
<213> ORGANISM: Homo sapien

<400> SEQUENCE: 224
cccctgaagg cttcttgtta gaaaatagta cagttacaac caataggaac aacaaaaga       60 aaagtttgt gacattgtag tagggagtgt gtaccccta ctccccatca aaaaaaaat        120 ggatacatgg ttaaaggata raagggcaat attttatcat atgttctaaa agagaaggaa     180
gagaaaatac tactttctcr aaatggaagc ccttaaaggt gctttgatac tgaaggacac     240
aaatgtggcc gtccatcctc ctttaragtt gcatgacttg gacacggtaa ctgttgcagt     300
tttaractcm gcattgtgac                                                 320
```

<210> SEQ ID NO 225
<211> LENGTH: 1214
<212> TYPE: DNA
<213> ORGANISM: Homo sapien

<400> SEQUENCE: 225

```
gaggactgca gcccgcactc gcagccctgg caggcggcac tggtcatgga aaacgaattg      60
ttctgctcgg gcgtcctggt gcatccgcag tgggtgctgt cagccgcaca ctgtttccag     120
aactcctaca ccatcgggct gggcctgcac agtcttgagg ccgaccaaga gccagggagc     180
cagatggtgg aggccagcct ctccgtacgc acccagagt acaacagacc cttgctcgct     240
aacgacctca tgctcatcaa gttggacgaa tccgtgtccg agtctgacac catccggagc     300
atcagcattg cttcgcagtg ccctaccgcg gggaactctt gcctcgtttc tggctggggt     360
ctgctggcga acggcagaat gcctaccgtg ctgcagtgcg tgaacgtgtc ggtggtgtct     420
gaggaggtct gcagtaagct ctatgacccg ctgtaccacc ccagcatgtt ctgcgccggc     480
ggagggcaag accagaagga ctcctgcaac ggtgactctg gggggcccct gatctgcaac     540
gggtacttgc agggccttgt gtctttcgga aagccccgt gtggccaagt tggcgtgcca     600
ggtgtctaca ccaacctctg caaattcact gagtggatag agaaaccgt ccaggccagt     660
taactctggg gactgggaac ccatgaaatt gaccccaaaa tacatcctgc ggaaggaatt     720
caggaatatc tgttcccagc ccctcctccc tcaggcccag gagtccaggc ccccagcccc     780
tcctccctca aaccaagggt acagatcccc agccctcct ccctcagacc caggagtcca     840
gacccccccag cccctcctcc ctcagaccca ggagtccagc cctcctccc tcagacccag     900
gagtccagac cccccagccc ctcctccctc agacccaggg tccaggccc caaccctc      960
ctccctcaga ctcagaggtc caagccccca acccctcctt cccagaccc agaggtccag    1020
gtcccagccc ctcctccctc agacccagcg gtccaatgcc acctagactc tccctgtaca    1080
cagtgccccc ttgtggcacg ttgacccaac cttaccagtt ggtttttcat tttttgtccc    1140
tttcccctag atccagaaat aaagtctaag agaagcgcaa aaaaaaaaa aaaaaaaaa     1200
aaaaaaaaaa aaaa                                                      1214
```

<210> SEQ ID NO 226
<211> LENGTH: 119
<212> TYPE: DNA
<213> ORGANISM: Homo sapien

<400> SEQUENCE: 226

```
acccagtatg tgcagggaga cggaaccccca tgtgacagcc cactccacca gggttcccaa      60
agaacctggc ccagtcataa tcattcatcc tgacagtggc aataatcacg ataaccagt      119
```

<210> SEQ ID NO 227
<211> LENGTH: 818
<212> TYPE: DNA
<213> ORGANISM: Homo sapien

<400> SEQUENCE: 227

```
acaattcata gggacgacca atgaggacag ggaatgaacc cggctctccc ccagccctga      60
tttttgctac atatgggtc ccttttcatt cttttgcaaaa acactgggtt ttctgagaac     120
acggacggtt cttagcacaa tttgtgaaat ctgtgtaraa ccgggctttg caggggagat     180
aattttcctc ctctgaagga aaggtggtga ttgacaggca gggagacagt gacaaggcta     240
gagaaagcca cgctcggcct tctctgaacc aggatggaac ggcagacccc tgaaaacgaa     300
```

| | |
|---|---|
| gcttgtcccc ttccaatcag ccacttctga gaacccccat ctaacttcct actggaaaag | 360 |
| agggcctcct caggagcagt ccaagagttt tcaaagataa cgtgacaact accatctaga | 420 |
| ggaaagggtg caccctcagc agagaagccg agagcttaac tctggtcgtt tccagagaca | 480 |
| acctgctggc tgtcttggga tgcgcccagc ctttgagagg ccactacccc atgaacttct | 540 |
| gccatccact ggacatgaag ctgaggacac tgggcttcaa cactgagttg tcatgagagg | 600 |
| gacaggctct gccctcaagc cggctgaggg cagcaaccac tctcctcccc tttctcacgc | 660 |
| aaagccattc ccacaaatcc agaccatacc atgaagcaac gagacccaaa cagtttggct | 720 |
| caagaggata tgaggactgt ctcagcctgg ctttgggctg acaccatgca cacacacaag | 780 |
| gtccacttct aggttttcag cctagatggg agtcgtgt | 818 |

<210> SEQ ID NO 228
<211> LENGTH: 744
<212> TYPE: DNA
<213> ORGANISM: Homo sapien

<400> SEQUENCE: 228

| | |
|---|---|
| actggagaca ctgttgaact tgatcaagac ccagaccacc ccaggtctcc ttcgtgggat | 60 |
| gtcatgacgt ttgacatacc tttggaacga gcctcctcct tggaagatgg aagaccgtgt | 120 |
| tcgtggccga cctggcctct cctggcctgt ttcttaagat gcggagtcac atttcaatgg | 180 |
| taggaaaagt ggcttcgtaa aatagaagag cagtcactgt ggaactacca aatggcgaga | 240 |
| tgctcggtgc acattggggt gctttgggat aaaagattta tgagccaact attctctggc | 300 |
| accagattct aggccagttt gttccactga agcttttccc acagcagtcc acctctgcag | 360 |
| gctggcagct gaatggcttg ccggtggctc tgtggcaaga tcacactgag atcgatgggt | 420 |
| gagaaggcta ggatgcttgt ctagtgttct tagctgtcac gttggctcct tccaggttgg | 480 |
| ccagacggtg ttggccactc ccttctaaaa cacaggcgcc ctcctggtga cagtgacccg | 540 |
| ccgtggtatg ccttggccca ttccagcagt cccagttatg catttcaagt ttggggtttg | 600 |
| ttcttttcgt taatgttcct ctgtgttgtc agctgtcttc atttcctggg ctaagcagca | 660 |
| tgggagatg tggaccagag atccactcct taagaaccag tggcgaaaga cactttcttt | 720 |
| cttcactctg aagtagctgg tggt | 744 |

<210> SEQ ID NO 229
<211> LENGTH: 300
<212> TYPE: DNA
<213> ORGANISM: Homo sapien

<400> SEQUENCE: 229

| | |
|---|---|
| cgagtctggg ttttgtctat aaagtttgat ccctcctttt ctcatccaaa tcatgtgaac | 60 |
| cattacacat cgaaataaaa gaaaggtggc agacttgccc aacgccaggc tgacatgtgc | 120 |
| tgcagggttg ttgttttta attattattg ttagaaacgt cacccacagt ccctgttaat | 180 |
| ttgtatgtga cagccaactc tgagaaggtc ctattttttcc acctgcagag gatccagtct | 240 |
| cactaggctc ctccttgccc tcacactgga gtctccgcca gtgtgggtgc ccactgacat | 300 |

<210> SEQ ID NO 230
<211> LENGTH: 301
<212> TYPE: DNA
<213> ORGANISM: Homo sapien

<400> SEQUENCE: 230

| | |
|---|---|
| cagcagaaca aatacaaata tgaagagtgc aaagatctca taaaatctat gctgaggaat | 60 |

-continued

```
gagcgacagt tcaaggagga gaagcttgca gagcagctca agcaagctga ggagctcagg    120
caatataaag tcctggttca cactcaggaa cgagagctga cccagttaag ggagaagttg    180
cgggaaggga gagatgcctc cctctcattg aatgagcatc tccaggccct cctcactccg    240
gatgaaccgg acaagtccca ggggcaggac ctccaagaaa cagacctcgg ccgcgaccac    300
g                                                                    301
```

<210> SEQ ID NO 231
<211> LENGTH: 301
<212> TYPE: DNA
<213> ORGANISM: Homo sapien

<400> SEQUENCE: 231

```
gcaagcacgc tggcaaatct ctgtcaggtc agctccagag aagccattag tcattttagc    60
caggaactcc aagtccacat ccttggcaac tggggacttg cgcaggttag ccttgaggat    120
ggcaacacgg gacttctcat caggaagtgg gatgtagatg agctgatcaa gacggccagg    180
tctgaggatg gcaggatcaa tgatgtcagg ccggttggta ccgccaatga tgaacacatt    240 ttttttttgtg gacatgccat ccatttctgt caggatctgg ttgatgactc ggtcagcagc    300
c                                                                    301
```

<210> SEQ ID NO 232
<211> LENGTH: 301
<212> TYPE: DNA
<213> ORGANISM: Homo sapien

<400> SEQUENCE: 232

```
agtaggtatt tcgtgagaag ttcaacacca aaactggaac atagttctcc ttcaagtgtt    60
ggcgacagcg gggcttcctg attctggaat ataactttgt gtaaattaac agccacctat    120
agaagagtcc atctgctgtg aaggagagac agagaactct gggttccgtc gtcctgtcca    180
cgtgctgtac caagtgctgg tgccagcctg ttacctgttc tcactgaaaa tctggctaat    240
gctcttgtgt atcacttctg attctgacaa tcaatcaatc aatggcctag agcactgact    300
g                                                                    301
```

<210> SEQ ID NO 233
<211> LENGTH: 301
<212> TYPE: DNA
<213> ORGANISM: Homo sapien

<400> SEQUENCE: 233

```
atgactgact tcccagtaag gctctctaag gggtaagtag gaggatccac aggatttgag    60
atgctaaggc cccagagatc gtttgatcca accctcttat tttcagaggg gaaaatgggg    120
cctagaagtt acagagcatc tagctggtgc gctggcaccc ctggcctcac acagactccc    180
gagtagctgg gactacaggc acacagtcac tgaagcaggc cctgttagca attctatgcg    240
tacaaattaa catgagatga gtagagactt tattgagaaa gcaagagaaa atcctatcaa    300
c                                                                    301
```

<210> SEQ ID NO 234
<211> LENGTH: 301
<212> TYPE: DNA
<213> ORGANISM: Homo sapien

<400> SEQUENCE: 234

```
aggtcctaca catcgagact catccatgat tgatatgaat ttaaaaatta caagcaaaga    60
cattttattc atcatgatgc tttcttttgt ttcttctttt cgttttcttc ttttcttttt   120
tcaatttcag caacatactt ctcaatttct tcaggattta aaatcttgag ggattgatct   180
cgcctcatga cagcaagttc aatgttttg ccacctgact gaaccacttc caggagtgcc    240
ttgatcacca gcttaatggt cagatcatct gcttcaatgg cttcgtcagt atagttcttc   300
t                                                                   301
```

<210> SEQ ID NO 235
<211> LENGTH: 283
<212> TYPE: DNA
<213> ORGANISM: Homo sapien

<400> SEQUENCE: 235

```
tggggctgtg catcaggcgg gtttgagaaa tattcaattc tcagcagaag ccagaatttg    60
aattccctca tctttaggg aatcatttac caggtttgga gaggattcag acagctcagg    120
tgctttcact aatgtctctg aacttctgtc cctctttgtt catggatagt ccaataaata    180
atgttatctt tgaactgatg ctcataggag agaatataag aactctgagt gatatcaaca    240
ttagggattc aaagaaatat tagatttaag ctcacactgg tca                     283
```

<210> SEQ ID NO 236
<211> LENGTH: 301
<212> TYPE: DNA
<213> ORGANISM: Homo sapien

<400> SEQUENCE: 236

```
aggtcctcca ccaactgcct gaagcacggt taaaattggg aagaagtata gtgcagcata    60 aatacttta aatcgatcag atttccctaa cccacatgca atcttcttca ccagaagagg     120
tcggagcagc atcattaata ccaagcgaaa tgcgtaatag ataaatacaa tggtatatag    180
tgggtagacg gcttcatgag tacagtgtac tgtggtatcg taatctggac ttgggttgta    240
aagcatcgtg taccagtcag aaagcatcaa tactcgacat gaacgaatat aaagaacacc    300
a                                                                   301
```

<210> SEQ ID NO 237
<211> LENGTH: 301
<212> TYPE: DNA
<213> ORGANISM: Homo sapien

<400> SEQUENCE: 237

```
cagtggtagt ggtggtggac gtggcgttgg tcgtggtgcc ttttttggtg cccgtcacaa    60
actcaatttt tgttcgctcc ttttggcct tttccaattt gtccatctca attttctggg     120
ccttggctaa tgcctcatag taggagtcct cagaccagcc atgggatca aacatatcct     180 ttgggtagtt ggtgccaagc tcgtcaatgg cacagaatgc atcagcttct cgtaaatcta    240
gggttccgaa attctttctt cctttggata atgtagttca tatccattcc ctcctttatc    300
t                                                                   301
```

<210> SEQ ID NO 238
<211> LENGTH: 301
<212> TYPE: DNA
<213> ORGANISM: Homo sapien

<400> SEQUENCE: 238

```
gggcaggttt ttttttttt ttttttgatg gtgcagaccc ttgctttatt tgtctgactt     60
```

```
gttcacagtt cagcccctg ctcagaaaac caacgggcca gctaaggaga ggaggaggca      120
ccttgagact tccggagtcg aggctctcca gggttcccca gcccatcaat cattttctgc      180
accccctgcc tgggaagcag ctccctgggg gtgggaatg gtgactaga agggatttca       240 gtgtgggacc cagggtctgt tcttcacagt aggaggtgga agggatgact aatttcttta      300
t                                                                      301

<210> SEQ ID NO 239
<211> LENGTH: 239
<212> TYPE: DNA
<213> ORGANISM: Homo sapien

<400> SEQUENCE: 239
ataagcagct agggaattct ttatttagta atgtcctaac ataaaagttc acataactgc      60
ttctgtcaaa ccatgatact gagctttgtg acaacccaga ataactaag agaaggcaaa      120 cataatacct tagagatcaa gaaacattta cacagttcaa ctgtttaaaa atagctcaac      180
attcagccag tgagtagagt gtgaatgcca gcatacacag tatacaggtc cttcaggga      239

<210> SEQ ID NO 240
<211> LENGTH: 300
<212> TYPE: DNA
<213> ORGANISM: Homo sapien

<400> SEQUENCE: 240
ggtcctaatg aagcagcagc ttccacattt taacgcaggt ttacggtgat actgtccttt      60
gggatctgcc ctccagtgga accttttaag gaagaagtgg gcccaagcta agttccacat      120
gctgggtgag ccagatgact tctgttccct ggtcactttc ttcaatgggg cgaatggggg      180
ctgccaggtt tttaaaatca tgcttcatct tgaagcacac ggtcacttca ccctcctcac      240
gctgtgggtg tactttgatg aaaatacca ctttgttggc ctttctgaag ctataatgtc       300

<210> SEQ ID NO 241
<211> LENGTH: 301
<212> TYPE: DNA
<213> ORGANISM: Homo sapien

<400> SEQUENCE: 241
gaggtctggt gctgaggtct ctgggctagg aagaggagtt ctgtggagct ggaagccaga      60
cctctttgga ggaaactcca gcagctatgt tggtgtctct gagggaatgc aacaaggctg      120
ctcctccatg tattggaaaa ctgcaaactg gactcaactg gaaggaagtg ctgctgccag      180
tgtgaagaac cagcctgagg tgacagaaac ggaagcaaac aggaacagcc agtcttttct      240
tcctcctcct gtcatacggt ctctctcaag catcctttgt tgtcaggggc ctaaaaggga      300
g                                                                      301

<210> SEQ ID NO 242
<211> LENGTH: 301
<212> TYPE: DNA
<213> ORGANISM: Homo sapien

<400> SEQUENCE: 242
ccgaggtcct gggatgcaac caatcactct gtttcacgtg acttttatca ccatacaatt      60
tgtggcattt cctcattttc tacattgtag aatcaagagt gtaaataaat gtatatcgat      120
gtcttcaaga atatatcatt cctttttcac tagaacccat tcaaaatata agtcaagaat      180
```

| | |
|---|---|
| cttaatatca acaaatatat caagcaaact ggaaggcaga ataactacca taatttagta | 240 |
| taagtaccca aagttttata aatcaaaagc cctaatgata accatttta gaattcaatc | 300 |
| a | 301 |

<210> SEQ ID NO 243
<211> LENGTH: 301
<212> TYPE: DNA
<213> ORGANISM: Homo sapien

<400> SEQUENCE: 243

| | |
|---|---|
| aggtaagtcc cagtttgaag ctcaaaagat ctggtatgag cataggctca tcgacgacat | 60 |
| ggtggcccaa gctatgaaat cagagggagg cttcatctgg gcctgtaaaa actatgatgg | 120 |
| tgacgtgcag tcggactctg tggcccaagg gtatggctct ctcggcatga tgaccagcgt | 180 |
| gctggtttgt ccagatggca agacagtaga agcagaggct gcccacggga ctgtaacccg | 240 |
| tcactaccgc atgttccaga aggacagga gacgtccacc aatcccattg cttccatttt | 300 |
| t | 301 |

<210> SEQ ID NO 244
<211> LENGTH: 300
<212> TYPE: DNA
<213> ORGANISM: Homo sapien

<400> SEQUENCE: 244

| | |
|---|---|
| gctggtttgc aagaatgaaa tgaatgattc tacagctagg acttaacctt gaaatggaaa | 60 |
| gtcatgcaat cccatttgca ggatctgtct gtgcacatgc ctctgtagag agcagcattc | 120 |
| ccagggacct tggaaacagt tgacactgta aggtgcttgc tccccaagac acatcctaaa | 180 |
| aggtgttgta atggtgaaaa cgtcttcctt ctttattgcc ccttcttatt tatgtgaaca | 240 |
| actgtttgtc ttttgtgtat cttttttaaa ctgtaaagtt caattgtgaa atgaatatc | 300 |

<210> SEQ ID NO 245
<211> LENGTH: 301
<212> TYPE: DNA
<213> ORGANISM: Homo sapien

<400> SEQUENCE: 245

| | |
|---|---|
| gtctgagtat ttaaaatgtt attgaaatta tccccaacca atgttagaaa agaaagaggt | 60 |
| tatatactta gataaaaaat gaggtgaatt actatccatt gaaatcatgc tcttagaatt | 120 |
| aaggccagga gatattgtca ttaatgtara cttcaggaca ctagagtata gcagccctat | 180 |
| gttttcaaag agcagagatg caattaaata ttgtttagca tcaaaaaggc cactcaatac | 240 |
| agctaataaa atgaaagacc taatttctaa agcaattctt tataatttac aaagttttaa | 300 |
| g | 301 |

<210> SEQ ID NO 246
<211> LENGTH: 301
<212> TYPE: DNA
<213> ORGANISM: Homo sapien

<400> SEQUENCE: 246

| | |
|---|---|
| ggtctgtcct acaatgcctg cttcttgaaa gaagtcggca ctttctagaa tagctaaata | 60 |
| acctgggctt attttaaaga actatttgta gctcagattg gttttcctat ggctaaaata | 120 |
| agtgcttctt gtgaaaatta aataaaacag ttaattcaaa gccttgatat atgttaccac | 180 |
| taacaatcat actaaatata ttttgaagta caaagtttga catgctctaa agtgacaacc | 240 |

```
caaatgtgtc ttacaaaaca cgttcctaac aaggtatgct ttacactacc aatgcagaaa      300
c                                                                      301

<210> SEQ ID NO 247
<211> LENGTH: 301
<212> TYPE: DNA
<213> ORGANISM: Homo sapien

<400> SEQUENCE: 247
aggtcctttg cagggctca tggatcagag ctcaaactgg agggaaaggc atttcgggta        60
gcctaagagg gcgactggcg gcagcacaac caaggaaggc aaggttgttt cccccacgct      120
gtgtcctgtg ttcaggtgcg acacacaatc ctcatgggaa caggatcacc catgcgctgc      180
ccttgatgat caaggttggg gcttaagtgg attaagggag gcaagttctg ggttccttgc      240
cttttcaaac catgaagtca ggctctgtat ccctcctttt cctaactgat attctaacta      300
a                                                                      301

<210> SEQ ID NO 248
<211> LENGTH: 301
<212> TYPE: DNA
<213> ORGANISM: Homo sapien

<400> SEQUENCE: 248
aggtccttgg agatgccatt tcagccgaag gactcttctw ttcggaagta caccctcact       60
attaggaaga ttcttagggg taattttttct gaggaaggaa aactagccaa cttaagaatt     120
acaggaagaa agtggtttgg aagacagcca agaaataaa agcagattaa attgtatcag       180
gtacattcca gcctgttggc aactccataa aaacatttca gattttaatc ccgaatttag      240
ctaatgagac tggattttttg ttttttatgt tgtgtgtcgc agagctaaaa actcagttcc     300
c                                                                      301

<210> SEQ ID NO 249
<211> LENGTH: 301
<212> TYPE: DNA
<213> ORGANISM: Homo sapien

<400> SEQUENCE: 249
gtccagagga agcacctggt gctgaactag gcttgccctg ctgtgaactt gcacttggag       60
ccctgacgct gctgttctcc ccgaaaaacc cgaccgacct ccgcgatctc cgtcccgccc      120
ccagggagac acagcagtga ctcagagctg gtcgcacact gtgcctccct cctcaccgcc      180
catcgtaatg aattattttg aaaattaatt ccaccatcct ttcagattct ggatggaaag      240
actgaatctt tgactcagaa ttgtttgctg aaaagaatga tgtgactttc ttagtcattt      300
a                                                                      301

<210> SEQ ID NO 250
<211> LENGTH: 301
<212> TYPE: DNA
<213> ORGANISM: Homo sapien

<400> SEQUENCE: 250
ggtctgtgac aaggacttgc aggctgtggg aggcaagtga cccttaacac tacacttctc       60
cttatcttta ttggcttgat aaacataatt atttctaaca ctagcttatt tccagttgcc      120
cataagcaca tcagtacttt tctctggctg gaatagtaaa ctaaagtatg gtacatctac      180
```

```
ctaaaagact actatgtgga ataatacata ctaatgaagt attacatgat ttaaagacta    240
caataaaacc aaacatgctt ataacattaa gaaaaacaat aaagatacat gattgaaacc    300
a                                                                   301
```

<210> SEQ ID NO 251
<211> LENGTH: 301
<212> TYPE: DNA
<213> ORGANISM: Homo sapien

<400> SEQUENCE: 251

```
gccgaggtcc tacatttggc ccagtttccc cctgcatcct ctccagggcc cctgcctcat    60
agacaacctc atagagcata ggagaactgg ttgccctggg ggcaggggga ctgtctggat    120
ggcagggtc tcaaaaatg ccactgtcac tgccaggaaa tgcttctgag cagtacacct     180
cattgggatc aatgaaaagc ttcaagaaat cttcaggctc actctcttga aggcccggaa    240
cctctggagg ggggcagtgg aatcccagct ccaggacgga tcctgtcgaa agatatcct    300
c                                                                   301
```

<210> SEQ ID NO 252
<211> LENGTH: 301
<212> TYPE: DNA
<213> ORGANISM: Homo sapien

<400> SEQUENCE: 252

```
gcaaccaatc actctgtttc acgtgacttt tatcaccata caatttgtgg catttcctca    60
ttttctacat tgtagaatca agagtgtaaa taaatgtata tcgatgtctt caagaatata    120
tcattccttt ttcactagga acccattcaa aatataagtc aagaatctta atatcaacaa    180
atatatcaag caaactggaa ggcagaataa ctaccataat ttagtataag tacccaaagt    240
tttataaatc aaaagcccta atgataacca tttttagaat tcaatcatca ctgtagaatc    300
a                                                                   301
```

<210> SEQ ID NO 253
<211> LENGTH: 301
<212> TYPE: DNA
<213> ORGANISM: Homo sapien

<400> SEQUENCE: 253

```
ttccctaaga agatgttatt ttgttgggtt ttgttccccc tccatctcga ttctcgtacc    60
caactaaaaa aaaaaaataa agaaaaaatg tgctgcgttc tgaaaaataa ctccttagct    120
tggtctgatt gttttcagac cttaaaatat aaacttgttt cacaagcttt aatccatgtg    180
gattttttt cttagagaac cacaaaacat aaaaggagca agtcggactg aatacctgtt     240
tccatagtgc ccacagggta ttcctcacat tttctccata ggaaaatgct ttttcccaag    300
g                                                                   301
```

<210> SEQ ID NO 254
<211> LENGTH: 301
<212> TYPE: DNA
<213> ORGANISM: Homo sapien

<400> SEQUENCE: 254

```
cgctgcgcct ttcccttggg ggaggggcaa ggccagaggg ggtccaagtg cagcacgagg    60
aacttgacca attcccttga agcgggtggg ttaaaccctg taaatgggaa caaaatcccc    120
ccaaatctct tcatcttacc ctggtggact cctgactgta gaattttttg gttgaaacaa    180
```

```
gaaaaaaata aagctttgga cttttcaagg ttgcttaaca ggtactgaaa gactggcctc    240
acttaaactg agccaggaaa agctgcagat ttattaatgg gtgtgttagt gtgcagtgcc    300
t                                                                   301

<210> SEQ ID NO 255
<211> LENGTH: 302
<212> TYPE: DNA
<213> ORGANISM: Homo sapien

<400> SEQUENCE: 255
agcttttttt tttttttttt tttttttttt ttcattaaaa aatagtgctc tttattataa    60
attactgaaa tgtttctttt ctgaatataa atataaatat gtgcaaagtt tgacttggat    120
tgggattttg ttgagttctt caagcatctc ctaatacccct caagggcctg agtagggggg   180
aggaaaaagg actggaggtg gaatctttat aaaaaacaag agtgattgag gcagattgta    240
aacattatta aaaacaaga aacaaacaaa aaaatagaga aaaaaccac cccaacacac      300 aa                                                                  302

<210> SEQ ID NO 256
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 256
gttccagaaa acattgaagg tggcttccca aagtctaact agggataccc cctctagcct    60
aggaccctcc tccccacacc tcaatccacc aaaccatcca taatgcaccc agataggccc    120 accccccaaaa gcctggacac cttgagcaca cagttatgac caggacagac tcatctctat   180
aggcaaatag ctgctggcaa actggcatta cctggtttgt ggggatgggg gggcaagtgt    240
gtggcctctc ggcctggtta gcaagaacat tcagggtagg cctaagttan tcgtgttagt    300
t                                                                   301

<210> SEQ ID NO 257
<211> LENGTH: 301
<212> TYPE: DNA
<213> ORGANISM: Homo sapien

<400> SEQUENCE: 257
gttgtggagg aactctggct tgctcattaa gtcctactga ttttcactat ccctgaatt     60 tcccactta tttttgtctt tcactatcgc aggccttaga agaggtctac ctgcctccag     120
tcttacctag tccagtctac cccctggagt tagaatggcc atcctgaagt gaaaagtaat    180
gtcacattac tcccttcagt gatttcttgt agaagtgcca atccctgaat gccaccaaga    240
tcttaatctt cacatctttta atcttatctc tttgactcct ctttacaccg gagaaggctc   300
c                                                                   301

<210> SEQ ID NO 258
<211> LENGTH: 301
<212> TYPE: DNA
<213> ORGANISM: Homo sapien
<220> FEATURE:
<221> NAME/KEY: misc_feature
<222> LOCATION: (1)...(301)
```

<223> OTHER INFORMATION: n = A,T,C or G

<400> SEQUENCE: 258

```
cagcagtagt agatgccgta tgccagcacg cccagcactc ccaggatcag caccagcacc    60
aggggcccag ccaccaggcg cagaagcaag ataaacagta ggctcaagac cagagccacc   120
cccagggcaa caagaatcca ataccaggac tgggcaaaat cttcaaagat cttaacactg   180
atgtctcggg cattgaggct gtcaataana cgctgatccc ctgctgtatg gtggtgtcat   240
tggtgatccc tgggagcgcc ggtggagtaa cgttggtcca tggaaagcag cgcccacaac   300
t                                                                  301
```

<210> SEQ ID NO 259
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 259

```
tcatatatgc aaacaaatgc agactangcc tcaggcagag actaaaggac atctcttggg    60
gtgtcctgaa gtgatttgga cccctgaggg cagacaccta gtaggaatc ccagtgggaa   120
gcaaagccat aaggaagccc aggattcctt gtgatcagga agtgggccag aaggtctgt   180
tccagctcac atctcatctg catgcagcac ggaccggatg cgcccactgg gtcttggctt   240
ccctcccatc ttctcaagca gtgtccttgt tgagccattt gcatccttgg ctccaggtgg   300
c                                                                  301
```

<210> SEQ ID NO 260
<211> LENGTH: 301
<212> TYPE: DNA
<213> ORGANISM: Homo sapien

<400> SEQUENCE: 260

```
ttttttttct ccctaaggaa aagaaggaa caagtctcat aaaaccaaat aagcaatggt    60
aaggtgtctt aacttgaaaa agattaggag tcactggttt acaagttata attgaatgaa   120
agaactgtaa cagccacagt tggccatttc atgccaatgg cagcaaacaa caggattaac   180
tagggcaaaa taaataagtg tgtggaagcc ctgataagtg cttaataaac agactgattc   240
actgagacat cagtacctgc ccgggcggcc gctcgagccg aattctgcag atatccatca   300
c                                                                  301
```

<210> SEQ ID NO 261
<211> LENGTH: 301
<212> TYPE: DNA
<213> ORGANISM: Homo sapien

<400> SEQUENCE: 261

```
aaatattcga gcaaatcctg taactaatgt gtctccataa aaggctttga actcagtgaa    60
tctgcttcca tccacgattc tagcaatgac ctctcggaca tcaaagctcc tcttaaggtt   120
agcaccaact attccataca attcatcagc aggaaataaa ggctcttcag aaggttcaat   180
ggtgacatcc aatttcttct gataatttag attcctcaca accttcctag ttaagtgaag   240
ggcatgatga tcatccaaag cccagtggtc acttactcca gactttctgc aatgaagatc   300
a                                                                  301
```

<210> SEQ ID NO 262
<211> LENGTH: 301
<212> TYPE: DNA
<213> ORGANISM: Homo sapien

<400> SEQUENCE: 262

```
gaggagagcc tgttacagca tttgtaagca cagaatactc caggagtatt tgtaattgtc      60
tgtgagcttc ttgccgcaag tctctcagaa atttaaaaag atgcaaatcc ctgagtcacc     120
cctagacttc ctaaaccaga tcctctgggg ctggaacctg gcactctgca tttgtaatga     180
gggctttctg gtgcacacct aatttttgtgc atctttgccc taaatcctgg attagtgccc    240
catcattacc cccacattat aatgggatag attcagagca gatactctcc agcaaagaat     300
c                                                                      301
```

<210> SEQ ID NO 263
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 263

```
tttagcttgt ggtaaatgac tcacaaaact gattttaaaa tcaagttaat gtgaattttg      60
aaaattacta cttaatccta attcacaata acaatggcat taaggtttga cttgagttgg    120
ttcttagtat tatttatggt aaataggctc ttaccacttg caaataactg gccacatcat     180
taatgactga cttcccagta aggctctcta aggggtaagt angaggatcc acaggatttg     240
agatgctaag gccccagaga tcgtttgatc caaccctctt attttcagag gggaaaatgg    300
g                                                                      301
```

<210> SEQ ID NO 264
<211> LENGTH: 301
<212> TYPE: DNA
<213> ORGANISM: Homo sapien

<400> SEQUENCE: 264

```
aaagacgtta aaccactcta ctaccacttg tggaactctc aaagggtaaa tgacaaascc      60
aatgaatgac tctaaaaaca atatttacat ttaatggttt gtagacaata aaaaaacaag    120
gtggatagat ctagaattgt aacattttaa gaaaaccata scatttgaca gatgagaaag    180
ctcaattata gatgcaaagt tataactaaa ctactatagt agtaaagaaa tacatttcac     240
acccttcata taaattcact atcttggctt gaggcactcc ataaaatgta tcacgtgcat     300
a                                                                      301
```

<210> SEQ ID NO 265
<211> LENGTH: 301
<212> TYPE: DNA
<213> ORGANISM: Homo sapien

<400> SEQUENCE: 265

```
tgcccaagtt atgtgtaagt gtatccgcac ccagaggtaa aactacactg tcatctttgt      60
cttcttgtga cgcagtattt cttctctggg gagaagccgg gaagtcttct cctggctcta    120
catattcttg gaagtctcta atcaacttt gttccatttg tttcatttct tcaggaggga     180
```

```
ttttcagttt gtcaacatgt tctctaacaa cacttgccca tttctgtaaa gaatccaaag      240
cagtccaagg ctttgacatg tcaacaacca gcataactag agtatccttc agagatacgg      300
c                                                                     301
```

<210> SEQ ID NO 266
<211> LENGTH: 301
<212> TYPE: DNA
<213> ORGANISM: Homo sapien

<400> SEQUENCE: 266

```
taccgtctgc ccttcctccc atccaggcca tctgcgaatc tacatgggtc ctcctattcg       60
acaccagatc actctttcct ctacccacag gcttgctatg agcaagagac acaacctcct      120
ctcttctgtg ttccagcttc ttttcctgtt cttcccaccc cttaagttct attcctgggg      180
atagagacac caatacccat aacctctctc ctaagcctcc ttataaccca gggtgcacag      240
cacagactcc tgacaactgg taaggccaat gaactgggag ctcacagctg gctgtgcctg      300
a                                                                     301
```

<210> SEQ ID NO 267
<211> LENGTH: 301
<212> TYPE: DNA
<213> ORGANISM: Homo sapien

<400> SEQUENCE: 267

```
aaagagcaca ggccagctca gcctgccctg gccatctaga ctcagcctgg ctccatgggg       60
gttctcagtg ctgagtccat ccaggaaaag ctcacctaga ccttctgagg ctgaatcttc      120
atcctcacag gcagcttctg agagcctgat attcctagcc ttgatggtct ggagtaaagc      180
ctcattctga ttcctctcct tcttttcttt caagttggct ttcctcacat ccctctgttc      240
aattcgcttc agcttgtctg ctttagccct catttccaga agcttcttct ctttggcatc      300
t                                                                     301
```

<210> SEQ ID NO 268
<211> LENGTH: 301
<212> TYPE: DNA
<213> ORGANISM: Homo sapien

<400> SEQUENCE: 268

```
aatgtctcac tcaactactt cccagcctac cgtggcctaa ttctgggagt tttcttctta       60
gatcttggga gagctggttc ttctaaggag aaggaggaag acagatgta actttggatc      120 tcgaagagga agtctaatgg aagtaattag tcaacggtcc ttgtttagac tcttggaata      180
tgctgggtgg ctcagtgagc ccttttggag aaagcaagta ttattcttaa ggagtaacca      240
cttcccattg ttctactttc taccatcatc aattgtatat tatgtattct ttggagaact      300
a                                                                     301
```

<210> SEQ ID NO 269
<211> LENGTH: 301
<212> TYPE: DNA
<213> ORGANISM: Homo sapien

<400> SEQUENCE: 269

```
taacaatata cactagctat cttttttaact gtccatcatt agcaccaatg aagattcaat       60
aaaattacct ttattcacac atctcaaaac aattctgcaa attcttagtg aagtttaact      120
atagtcacag accttaaata ttcacattgt tttctatgtc tactgaaaat aagttcacta      180
```

```
cttttctgga tattctttac aaaatcttat taaaattcct ggtattatca cccccaatta      240
tacagtagca caaccacctt atgtagtttt tacatgatag ctctgtagaa gtttcacatc      300
t                                                                     301
```

<210> SEQ ID NO 270
<211> LENGTH: 301
<212> TYPE: DNA
<213> ORGANISM: Homo sapien

<400> SEQUENCE: 270

```
cattgaagag cttttgcgaa acatcagaac acaagtgctt ataaaattaa ttaagcctta      60
cacaagaata catattcctt ttatttctaa ggagttaaac atagatgtag ctgatgtgga     120
gagcttgctg gtgcagtgca tattggataa cactattcat ggccgaattg atcaagtcaa     180
ccaactcctt gaactggatc atcagaagaa gggtggtgca cgatatactg cactagataa     240
tggaccaacc aactaaattc tctcaccagg ctgtatcagt aaactggctt aacagaaaac     300
a                                                                     301
```

<210> SEQ ID NO 271
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 271

```
aaaaggttct cataagatta acaatttaaa taaatatttg atagaacatt ctttctcatt      60
tttatagctc atctttaggg ttgatattca gttcatgctt cccttgctgt tcttgatcca     120
gaattgcaat cacttcatca gcctgtattc gctccaattc tctataaagt gggtccaagg     180
tgaaccacag agccacagca cacctctttc ccttggtgac tgccttcacc ccatganggt     240
tctctcctcc agatganaac tgatcatgcg cccacatttt gggttttata gaagcagtca     300
c                                                                     301
```

<210> SEQ ID NO 272
<211> LENGTH: 301
<212> TYPE: DNA
<213> ORGANISM: Homo sapien

<400> SEQUENCE: 272

```
taaattgcta agccacagat aacaccaatc aaatggaaca atcactgtc ttcaaatgtc       60 ttatcagaaa accaaatgag cctggaatct tcataatacc taaacatgcc gtatttagga     120
tccaataatt ccctcatgat gagcaagaaa aattctttgc gcaccctcc tgcatccaca      180 gcatcttctc caacaaatat aaccttgagt ggcttcttgt aatctatgtt ctttgttttc     240
ctaaggactt ccattgcatc tcctacaata ttttctctac gcaccactag aattaagcag     300
g                                                                     301
```

<210> SEQ ID NO 273
<211> LENGTH: 301
<212> TYPE: DNA
<213> ORGANISM: Homo sapien
<220> FEATURE:
<221> NAME/KEY: misc_feature
<222> LOCATION: (1)...(301)

```
<223> OTHER INFORMATION: n = A,T,C or G

<400> SEQUENCE: 273
acatgtgtgt atgtgtatct ttgggaaaan aanaagacat cttgtttayt attttttttgg      60 agagangctg ggacatggat aatcacwtaa tttgctayta tyactttaat ctgactygaa      120
gaaccgtcta aaaataaaat ttaccatgtc dtatattcct tatagtatgc ttatttcacc     180
ttytttctgt ccagagagag tatcagtgac ananatttma gggtgaamac atgmattggt    240
gggacttnty tttacngagm accctgcccg sgcgccctcg makcngantt ccgcsananc    300
t                                                                     301

<210> SEQ ID NO 274
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 274
cttatatact ctttctcaga ggcaaaagag gagatgggta atgtagacaa ttctttgagg      60
aacagtaaat gattattaga gagaangaat ggaccaagga gacagaaatt aacttgtaaa    120
tgattctctt tggaatctga atgagatcaa gaggccagct ttagcttgtg gaaaagtcca    180
tctaggtatg gttgcattct cgtcttcttt tctgcagtag ataatgaggt aaccgaaggc    240
aattgtgctt cttttgataa gaagctttct tggtcatatc aggaaattcc aganaaagtc    300
c                                                                     301

<210> SEQ ID NO 275
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 275
tcggtgtcag cagcacgtgg cattgaacat tgcaatgtgg agcccaaacc acagaaaatg     60
gggtgaaatt ggccaacttt ctattaactt atgttggcaa ttttgccacc aacagtaagc    120
tggcccttct aataaaagaa aattgaaagg tttctcacta aacggaatta agtagtggag   180
tcaagagact cccaggcctc agcgtacctg cccggcggc cgctcgaagc cgaattctgc    240
agatatccat cacactggcg gncgctcgan catgcatcta gaaggnccaa ttcgccctat   300
a                                                                     301

<210> SEQ ID NO 276
<211> LENGTH: 301
<212> TYPE: DNA
<213> ORGANISM: Homo sapien

<400> SEQUENCE: 276
tgtacacata ctcaataaat aaatgactgc attgtggtat tattactata ctgattatat     60
ttatcatgtg acttctaatt agaaaatgta tccaaaagca aaacagcaga tatacaaaat    120
taaagagaca gaagatagac attaacagat aaggcaactt atacattgag aatccaaatc    180
caatacattt aaacatttgg gaaatgaggg ggacaaatgg aagccagatc aaatttgtgt    240
```

```
aaaactattc agtatgtttc ccttgcttca tgtctgagaa ggctctcctt caatggggat    300
g                                                                    301

<210> SEQ ID NO 277
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 277
tttgttgatg tcagtatttt attacttgcg ttatgagtgc tcacctggga aattctaaag    60
atacagagga cttggaggaa gcagagcaac tgaatttaat ttaaaagaag gaaaacattg   120
gaatcatggc actcctgata ctttcccaaa tcaacactct caatgcccca ccctcgtcct   180
caccatagtg gggagactaa agtggccacg gatttgcctt angtgtgcag tgcgttctga   240
gttcnctgtc gattacatct gaccagtctc cttttccga agtccntccg ttcaatcttg    300
c                                                                    301

<210> SEQ ID NO 278
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 278
taccactaca ctccagcctg ggcaacagag caagacctgt ctcaaagcat aaaatggaat    60
aacatatcaa atgaaacagg gaaatgaag ctgacaattt atggaagcca gggcttgtca   120
cagtctctac tgttattatg cattacctgg gaatttatat aagcccttaa taataatgcc   180
aatgaacatc tcatgtgtgc tcacaatgtt ctggcactat tataagtgct tcacaggttt   240
tatgtgttct tcgtaacttt atggantagg tactcggccg cgaacacgct aagccgaatt   300
c                                                                    301

<210> SEQ ID NO 279
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 279
aaagcaggaa tgacaaagct tgcttttctg gtatgttcta ggtgtattgt gactttact    60 gttatattaa ttgccaatat aagtaaatat agattatata tgtatagtgt ttcacaaagc   120 ttagacctt accttccagc cacccacag tgcttgatat ttcagagtca gtcattggtt   180
atacatgtgt agttccaaag cacataagct agaanaanaa atatttctag ggagcactac   240
catctgtttt cacatgaaat gccacacaca tagaactcca acatcaattt cattgcacag   300
a                                                                    301

<210> SEQ ID NO 280
```

<211> LENGTH: 301
<212> TYPE: DNA
<213> ORGANISM: Homo sapien

<400> SEQUENCE: 280

```
ggtactggag ttttcctccc ctgtgaaaac gtaactactg ttgggagtga attgaggatg      60
tagaaaggtg gtggaaccaa attgtggtca atggaaatag gagaatatgg ttctcactct     120
tgagaaaaaa acctaagatt agcccaggta gttgcctgta acttcagttt ttctgcctgg     180
gtttgatata gtttagggtt ggggttagat taagatctaa attacatcag gacaaagaga     240
cagactatta actccacagt taattaagga ggtatgttcc atgtttattt gttaaagcag     300
t                                                                    301
```

<210> SEQ ID NO 281
<211> LENGTH: 301
<212> TYPE: DNA
<213> ORGANISM: Homo sapien

<400> SEQUENCE: 281

```
aggtacaaga aggggaatgg gaaagagctg ctgctgtggc attgttcaac ttggatattc      60
gccgagcaat ccaaatcctg aatgaagggg catcttctga aaaggagat ctgaatctca     120
atgtggtagc aatggcttta tcgggttata cggatgagaa gaactccctt tggagagaaa     180
tgtgtagcac actgcgatta cagctaaata acccgtattt gtgtgtcatg tttgcatttc     240
tgacaagtga aacaggatct tacgatggag ttttgtatga aaacaaagtt gcagtacctc     300
g                                                                    301
```

<210> SEQ ID NO 282
<211> LENGTH: 301
<212> TYPE: DNA
<213> ORGANISM: Homo sapien

<400> SEQUENCE: 282

```
caggtactac agaattaaaa tactgacaag caagtagttt cttggcgtgc acgaattgca      60
tccagaaccc aaaaattaag aaattcaaaa agacattttg tgggcacctg ctagcacaga     120
agcgcagaag caaagcccag gcagaaccat gctaacctta cagctcagcc tgcacagaag     180
cgcagaagca aagcccaggc agaaccatgc taaccttaca gctcagcctg cacagaagcg     240
cagaagcaaa gcccaggcag aacatgctaa ccttacagct cagcctgcac agaagcacag     300
a                                                                    301
```

<210> SEQ ID NO 283
<211> LENGTH: 301
<212> TYPE: DNA
<213> ORGANISM: Homo sapien

<400> SEQUENCE: 283

```
atctgtatac ggcagacaaa ctttatarag tgtagagagg tgagcgaaag gatgcaaaag      60
cactttgagg gctttataat aatatgctgc ttgaaaaaaa aaatgtgtag ttgatactca     120
gtgcatctcc agacatagta aggggttgct ctgaccaatc aggtgatcat tttttctatc     180
acttcccagg ttttatgcaa aaattttgtt aaattctata atggtgatat gcatcttta     240
ggaaacatat acatttttaa aaatctattt tatgtaagaa ctgacagacg aatttgctt     300
g                                                                    301
```

<210> SEQ ID NO 284
<211> LENGTH: 301
<212> TYPE: DNA
<213> ORGANISM: Homo sapien

<400> SEQUENCE: 284

| | | | | | |
|---|---|---|---|---|---|
| caggtacaaa | acgctattaa | gtggcttaga | atttgaacat | ttgtggtctt | tatttacttt | 60 |
| gcttcgtgtg | tgggcaaagc | aacatcttcc | ctaaatatat | attaccaaga | aaagcaagaa | 120 |
| gcagattagg | tttttgacaa | aacaaacagg | ccaaaagggg | gctgacctgg | agcagagcat | 180 |
| ggtgagaggc | aaggcatgag | agggcaagtt | tgttgtggac | agatctgtgc | ctactttatt | 240 |
| actggagtaa | aagaaaacaa | agttcattga | tgtcgaagga | tatatacagt | gttagaaatt | 300 |
| a | | | | | | 301 |

<210> SEQ ID NO 285
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 285

| | | | | | |
|---|---|---|---|---|---|
| acatcaccat | gatcggatcc | cccacccatt | atacgttgta | tgtttacata | aatactcttc | 60 |
| aatgatcatt | agtgttttaa | aaaaaatact | gaaaactcct | tctgcatccc | aatctctaac | 120 |
| caggaaagca | aatgctattt | acagacctgc | aagccctccc | tcaaacnaaa | ctatttctgg | 180 |
| attaaatatg | tctgacttct | tttgaggtca | cacgactagg | caaatgctat | ttacgatctg | 240 |
| caaaagctgt | tgaagagtc | aaagccccca | tgtgaacacg | atttctggac | cctgtaacag | 300 |
| t | | | | | | 301 |

<210> SEQ ID NO 286
<211> LENGTH: 301
<212> TYPE: DNA
<213> ORGANISM: Homo sapien

<400> SEQUENCE: 286

| | | | | | |
|---|---|---|---|---|---|
| taccactgca | ttccagcctg | ggtgacagag | tgagactccg | tctccaaaaa | aaactttgct | 60 |
| tgtatattat | ttttgcctta | cagtggatca | ttctagtagg | aaaggacagt | aagatttttt | 120 |
| atcaaaatgt | gtcatgccag | taagagatgt | tatattcttt | tctcatttct | tccccaccca | 180 |
| aaaataagct | accatatagc | ttataagtct | caaattttg | ccttttacta | aaatgtgatt | 240 |
| gtttctgttc | attgtgtatg | cttcatcacc | tatattaggc | aaattccatt | ttttcccttg | 300 |
| t | | | | | | 301 |

<210> SEQ ID NO 287
<211> LENGTH: 301
<212> TYPE: DNA
<213> ORGANISM: Homo sapien

<400> SEQUENCE: 287

| | | | | | |
|---|---|---|---|---|---|
| tacagatctg | ggaactaaat | attaaaaatg | agtgtggctg | gatatatgga | gaatgttggg | 60 |
| cccagaagga | acgtagagat | cagatattac | aacagctttg | ttttgagggt | tagaaatatg | 120 |
| aaatgatttg | gttatgaacg | cacagtttag | gcagcagggc | cagaatcctg | accctctgcc | 180 |
| ccgtggttat | ctcctcccca | gcttggctgc | ctcatgttat | cacagtattc | catttttgttt | 240 |

| | |
|---|---|
| gttgcatgtc ttgtgaagcc atcaagattt tctcgtctgt tttcctctca ttggtaatgc | 300 |
| t | 301 |

<210> SEQ ID NO 288
<211> LENGTH: 301
<212> TYPE: DNA
<213> ORGANISM: Homo sapien

<400> SEQUENCE: 288

| | |
|---|---|
| gtacacctaa ctgcaaggac agctgaggaa tgtaatgggc agccgctttt aaagaagtag | 60 |
| agtcaatagg aagacaaatt ccagttccag ctcagtctgg gtatctgcaa agctgcaaaa | 120 |
| gatctttaaa gacaatttca agagaatatt tccttaaagt tggcaatttg gagatcatac | 180 |
| aaaagcatct gcttttgtga tttaatttag ctcatctggc cactggaaga atccaaacag | 240 |
| tctgccttaa ttttggatga atgcatgatg gaaattcaat aatttagaaa gttaaaaaaa | 300 |
| a | 301 |

<210> SEQ ID NO 289
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 289

| | |
|---|---|
| ggtacactgt ttccatgtta tgtttctaca cattgctacc tcagtgctcc tggaaactta | 60 |
| gcttttgatg tctccaagta gtccaccttc atttaactct ttgaaactgt atcatctttg | 120 |
| ccaagtaaga gtggtggcct atttcagctg ctttgacaaa atgactggct cctgacttaa | 180 |
| cgttctataa atgaatgtgc tgaagcaaag tgcccatggt ggcggcgaan aagagaaaga | 240 |
| tgtgttttgt tttggactct ctgtggtccc ttccaatgct gtgggtttcc aaccagngga | 300 |
| a | 301 |

<210> SEQ ID NO 290
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 290

| | |
|---|---|
| acactgagct cttcttgata aatatacaga atgcttggca tatacaagat tctatactac | 60 |
| tgactgatct gttcatttct ctcacagctc ttaccccaa aagcttttcc accctaagtg | 120 |
| ttctgacctc cttttctaat cacagtaggg atagaggcag anccacctac aatgaacatg | 180 |
| gagttctatc aagaggcaga aacagcacag aatcccagtt ttaccattcg ctagcagtgc | 240 |
| tgccttgaac aaaaacattt ctccatgtct cattttcttc atgcctcaag taacagtgag | 300 |
| a | 301 |

<210> SEQ ID NO 291
<211> LENGTH: 301
<212> TYPE: DNA
<213> ORGANISM: Homo sapien

<400> SEQUENCE: 291

```
caggtaccaa tttcttctat cctagaaaca tttcatttta tgttgttgaa acataacaac      60
tatatcagct agatttttt tctatgcttt acctgctatg gaaaatttga cacattctgc     120
tttactcttt tgtttatagg tgaatcacaa aatgtatttt tatgtattct gtagttcaat     180
agccatggct gtttacttca tttaatttat ttagcataaa gacattatga aaaggcctaa     240
acatgagctt cacttcccca ctaactaatt agcatctgtt atttcttaac cgtaatgcct     300
a                                                                     301

<210> SEQ ID NO 292
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 292 acctttagt agtaatgtct aataataaat aagaaatcaa ttttataagg tccatatagc      60
tgtattaaat aattttttaag tttaaaagat aaaataccat catttttaaat gttggtattc    120 aaaaccaaag natataaccg aaaggaaaaa cagatgagac ataaaatgat ttgcnagatg     180
ggaaatatag tasttyatga atgttnatta aattccagtt ataatagtgg ctacacactc    240
tcactacaca cacagacccc acagtcctat atgccacaaa cacatttcca taacttgaaa    300
a                                                                     301

<210> SEQ ID NO 293
<211> LENGTH: 301
<212> TYPE: DNA
<213> ORGANISM: Homo sapien

<400> SEQUENCE: 293
ggtaccaagt gctggtgcca gcctgttacc tgttctcact gaaaagtctg gctaatgctc      60
ttgtgtagtc acttctgatt ctgacaatca atcaatcaat ggcctagagc actgactgtt    120
aacacaaacg tcactagcaa agtagcaaca gctttaagtc taaatacaaa gctgttctgt    180
gtgagaattt tttaaaaggc tacttgtata ataacccttg tcattttttaa tgtacctcgg    240 ccgcgaccac gctaagccga attctgcaga tatccatcac actggcggcc gctcgagcat    300
g                                                                     301

<210> SEQ ID NO 294
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 294
tgacccataa caatatacac tagctatctt tttaactgtc catcattagc accaatgaag      60
attcaataaa attacctta ttcacacatc tcaaaacaat tctgcaaatt cttagtgaag    120
tttaactata gtcacaganc ttaaatattc acattgtttt ctatgtctac tgaaaataag    180
ttcactactt ttctgggata ttctttacaa aatcttatta aaattcctgg tattatcacc    240
cccaattata cagtagcaca accaccttat gtagttttta catgatagct ctgtagaggt    300
```

| t | 301 |

<210> SEQ ID NO 295
<211> LENGTH: 305
<212> TYPE: DNA
<213> ORGANISM: Homo sapien

<400> SEQUENCE: 295

| gtactctttc tctccctcc tctgaattta attctttcaa cttgcaattt gcaaggatta | 60 |
| cacatttcac tgtgatgtat attgtgttgc aaaaaaaaaa gtgtctttgt ttaaaattac | 120 |
| ttggtttgtg aatccatctt gcttttttccc cattggaact agtcattaac ccatctctga | 180 |
| actggtagaa aaacrtctga agagctagtc tatcagcatc tgacaggtga attggatggt | 240 |
| tctcagaacc atttcaccca gacagcctgt ttctatcctg tttaataaat tagtttgggt | 300 |
| tctct | 305 |

<210> SEQ ID NO 296
<211> LENGTH: 301
<212> TYPE: DNA
<213> ORGANISM: Homo sapien

<400> SEQUENCE: 296

| aggtactatg ggaagctgct aaaataatat ttgatagtaa aagtatgtaa tgtgctatct | 60 |
| cacctagtag taaactaaaa ataaactgaa actttatgga atctgaagtt attttccttg | 120 |
| attaaataga attaataaac caatatgagg aaacatgaaa ccatgcaatc tactatcaac | 180 |
| tttgaaaaag tgattgaacg aaccacttag ctttcagatg atgaacactg ataagtcatt | 240 |
| tgtcattact ataaatttta aaatctgtta ataagatggc ctatagggag gaaaaagggg | 300 |
| c | 301 |

<210> SEQ ID NO 297
<211> LENGTH: 300
<212> TYPE: DNA
<213> ORGANISM: Homo sapien
<220> FEATURE:
<221> NAME/KEY: misc_feature
<222> LOCATION: (1)...(300)
<223> OTHER INFORMATION: n = A,T,C or G

<400> SEQUENCE: 297

| ctgagttttt aactggacgc caagcaggca aggctggaag gttttgctct ctttgtgcta | 60 |
| aggttttga aaaccttgaa ggagaatcat tttgacaaga agtacttaag agtctagaga | 120 |
| caaagangt gaaccagctg aaagctctcg ggggaanctt acatgtgttg ttaggcctgt | 180 |
| ccatcattg ggagtgcact ggccatccct caaaatttgt ctgggctggc ctgagtggtc | 240 |
| ccgcacctc ggccgcgacc acgctaagcc gaattctgca gatatccatc acactggcgg | 300 |

<210> SEQ ID NO 298
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 298

| tatgggtttt gtcacccaaa agctgatgct gagaaaggcc tccctggggc ccctcccgcg | 60 |
| ggcatctgag agacctggtg ttccagtgtt tctggaaatg ggtcccagtg ccgccggctg | 120 |

```
tgaagctctc agatcaatca cgggaagggc ctggcggtgg tggccacctg gaaccaccct    180
gtcctgtctg tttacatttc actaycaggt tttctctggg cattacnatt tgttccccta    240
caacagtgac ctgtgcattc tgctgtggcc tgctgtgtct gcaggtggct ctcagcgagg    300
t                                                                    301

<210> SEQ ID NO 299
<211> LENGTH: 301
<212> TYPE: DNA
<213> ORGANISM: Homo sapien

<400> SEQUENCE: 299
gttttgagac ggagtttcac tcttgttgcc cagactggac tgcaatggca gggtctctgc     60
tcactgcacc ctctgcctcc caggttcgag caattctcct gcctcagcct cccaggtagc    120
tgggattgca ggctcacgcc accatacccn gctaattttt ttgtattttt agtagagacg    180
gagtttcgcc atgttggcca gctggtctca aactcctgac ctcaagcgac ctgcctgcct    240
cggcctccca agtgctgga attataggca tgagtcaaca cgcccagcct aaagatattt    300
t                                                                    301

<210> SEQ ID NO 300
<211> LENGTH: 301
<212> TYPE: DNA
<213> ORGANISM: Homo sapien

<400> SEQUENCE: 300
attcagtttt atttgctgcc ccagtatctg taaccaggag tgccacaaaa tcttgccaga     60
tatgtcccac acccactggg aaaggctccc acctggctac ttcctctatc agctgggtca    120
gctgcattcc acaaggttct cagcctaatg agtttcacta cctgccagtc tcaaaactta    180
gtaaagcaag accatgacat tcccccacgg aaatcagagt ttgccccacc gtcttgttac    240
tataaagcct gcctctaaca gtccttgctt cttcacacca atcccgagcg catcccccat    300
g                                                                    301

<210> SEQ ID NO 301
<211> LENGTH: 301
<212> TYPE: DNA
<213> ORGANISM: Homo sapien

<400> SEQUENCE: 301
ttaaattttt gagaggataa aaaggacaaa taatctagaa atgtgtcttc ttcagtctgc     60
agaggacccc aggtctccaa gcaaccacat ggtcaagggc atgaataatt aaaagttggt    120
gggaactcac aaagaccctc agagctgaga cacccacaac agtgggagct cacaaagacc    180
ctcagagctg agacacccac aacagtggga gctcacaaag accctcagag ctgagacacc    240
cacaacagca cctcgttcag ctgccacatg tgtgaataag gatgcaatgt ccagaagtgt    300
t                                                                    301

<210> SEQ ID NO 302
<211> LENGTH: 301
<212> TYPE: DNA
<213> ORGANISM: Homo sapien

<400> SEQUENCE: 302
aggtacacat ttagcttgtg gtaaatgact cacaaaactg attttaaaat caagttaatg     60
```

-continued

```
tgaattttga aaattactac ttaatcctaa ttcacaataa caatggcatt aaggtttgac      120
ttgagttggt tcttagtatt atttatggta aataggctct taccacttgc aaataactgg      180
ccacatcatt aatgactgac ttcccagtaa ggctctctaa ggggtaagta ggaggatcca      240
caggatttga gatgctaagg ccccagagat cgtttgatcc aaccctctta ttttcagagg      300
g                                                                      301
```

<210> SEQ ID NO 303
<211> LENGTH: 301
<212> TYPE: DNA
<213> ORGANISM: Homo sapien

<400> SEQUENCE: 303

```
aggtaccaac tgtggaaata ggtagaggat catttttctt ttccatatca actaagttgt      60
atattgtttt ttgacagttt aacacatctt cttctgtcag agattctttc acaatagcac     120
tggctaatgg aactaccgct tgcatgttaa aaatggtggt tgtgaaatg atataggcc       180 agtaacgggt atgttttttct aactgatctt ttgctcgttc caagggacct caagacttc     240 catcgatttt atatctgggg tctagaaaag gagttaatct gttttccctc ataaattcac     300
c                                                                      301
```

<210> SEQ ID NO 304
<211> LENGTH: 301
<212> TYPE: DNA
<213> ORGANISM: Homo sapien

<400> SEQUENCE: 304

```
acatggatgt tattttgcag actgtcaacc tgaatttgta tttgcttgac attgcctaat      60
tattagtttc agtttcagct tacccacttt ttgtctgcaa catgcaraas agacagtgcc     120 cttttttagtg tatcatatca ggaatcatct cacattggtt tgtgccatta ctggtgcagt    180
gactttcagc cacttgggta aggtggagtt ggccatatgt ctccactgca aaattactga    240 ttttccttttt gtaattaata agtgtgtgtg tgaagattct ttgagatgag gtatatatct   300
c                                                                      301
```

<210> SEQ ID NO 305
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 305

```
gangtacagc gtggtcaagg taacaagaag aaaaaaatgt gagtggcatc ctgggatgag      60 caggggaca gacctggaca gacacgttgt catttgctgc tgtgggtagg aaaatgggcg     120 taaggagga gaaacagata caaaatctcc aactcagtat taaggtattc tcatgcctag    180
aatattggta gaaacaagaa tacattcata tggcaaataa ctaaccatgg tggaacaaaa    240
ttctgggatt taagttggat accaangaaa ttgtattaaa agagctgttc atggaataag   300
a                                                                      301
```

<210> SEQ ID NO 306
<211> LENGTH: 8
<212> TYPE: PRT
<213> ORGANISM: Homo sapien

<400> SEQUENCE: 306

Val Leu Gly Trp Val Ala Glu Leu
 1               5

<210> SEQ ID NO 307
<211> LENGTH: 637
<212> TYPE: DNA
<213> ORGANISM: Homo sapien

<400> SEQUENCE: 307

| acagggratg aagggaaagg gagaggatga ggaagccccc ctggggattt ggtttggtcc | 60 |
| ttgtgatcag gtggtctatg gggcttatcc ctacaaagaa gaatccagaa ataggggcac | 120 |
| attgaggaat gatacttgag cccaaagagc attcaatcat tgtttatt gccttmtttt | 180 |
| cacaccattg gtgagggagg gattaccacc ctggggttat gaagatggtt gaacacccca | 240 |
| cacatagcac cggagatatg agatcaacag tttcttagcc atagagattc acagcccaga | 300 |
| gcaggaggac gcttgcacac catgcaggat gacatggggg atgcgctcgg gattggtgtg | 360 |
| aagaagcaag gactgttaga ggcaggcttt atagtaacaa gacggtgggg caaactctga | 420 |
| tttccgtggg ggaatgtcat ggtcttgctt tactaagttt tgagactggc aggtagtgaa | 480 |
| actcattagg ctgagaacct tgtggaatgc acttgaccca sctgatagag gaagtagcca | 540 |
| ggtgggagcc tttcccagtg ggtgtgggac atatctggca agattttgtg gcactcctgg | 600 |
| ttacagatac tggggcagca aataaaactg aatcttg | 637 |

<210> SEQ ID NO 308
<211> LENGTH: 647
<212> TYPE: DNA
<213> ORGANISM: Homo sapien
<220> FEATURE:
<221> NAME/KEY: misc_feature
<222> LOCATION: (1)...(647)
<223> OTHER INFORMATION: n = A,T,C or G

<400> SEQUENCE: 308

| acgattttca ttatcatgta aatcgggtca ctcaaggggc caaccacagc tgggagccac | 60 |
| tgctcagggg aaggttcata tgggactttc tactgcccaa ggttctatac aggatataaa | 120 |
| ggngcctcac agtatagatc tggtagcaaa gaagaagaaa caaacactga tctctttctg | 180 |
| ccaccoctct gacccttggg aactcctctg accctttaga acaagcctac ctaatatctg | 240 |
| ctagagaaaa gaccaacaac ggcctcaaag gatctcttac catgaaggtc tcagctaatt | 300 |
| cttggctaag atgtgggttc cacattaggt tctgaatatg gggggaaggg tcaatttgct | 360 |
| cattttgtgt gtggataaag tcaggatgcc caggggccag agcaggggc tgcttgcttt | 420 |
| gggaacaatg gctgagcata taaccatagg ttatggggaa caaaacaaca tcaaagtcac | 480 |
| tgtatcaatt gccatgaaga cttgagggac ctgaatctac cgattcatct taaggcagca | 540 |
| ggaccagttt gagtggcaac aatgcagcag cagaatcaat ggaaacaaca gaatgattgc | 600 |
| aatgtccttt tttttctcct gcttctgact tgataaaagg ggaccgt | 647 |

<210> SEQ ID NO 309
<211> LENGTH: 460
<212> TYPE: DNA
<213> ORGANISM: Homo sapien

<400> SEQUENCE: 309

| actttatagt ttaggctgga cattggaaaa aaaaaaaagc cagaacaaca tgtgatagat | 60 |

-continued

```
aatatgattg gctgcacact tccagactga tgaatgatga acgtgatgga ctattgtatg        120
gagcacatct tcagcaagag ggggaaatac tcatcatttt tggccagcag ttgtttgatc        180
accaaacatc atgccagaat actcagcaaa ccttcttagc tcttgagaag tcaaagtccg        240
ggggaattta ttcctggcaa ttttaattgg actccttatg tgagagcagc ggctacccag        300
ctggggtggt ggagcgaacc cgtcactagt ggacatgcag tggcagagct cctggtaacc        360
acctagagga atacacaggc acatgtgtga tgccaagcgt gacacctgta gcactcaaat        420
ttgtcttgtt tttgtctttc ggtgtgtaag attcttaagt                              460
```

<210> SEQ ID NO 310
<211> LENGTH: 539
<212> TYPE: DNA
<213> ORGANISM: Homo sapien

<400> SEQUENCE: 310

```
acgggactta tcaaataaag ataggaaaag aagaaaactc aaatattata ggcagaaatg        60
ctaaaggttt taaatatgt caggattgga agaaggcatg gataaagaac aaagttcagt         120
taggaaagag aaacacagaa ggaagagaca caataaaagt cattatgtat tctgtgagaa        180
gtcagacagt aagatttgtg ggaaatgggt tggtttgttg tatggtatgt atttagcaa        240 taatctttat ggcagagaaa gctaaaatcc tttagcttgc gtgaatgatc acttgctgaa        300
ttcctcaagg taggcatgat gaaggagggt ttagaggaga cacagacaca atgaactgac        360 ctagataaa agccttagta tactcagcta ggaatagtga ttctgagggc acactgtgac        420
atgattatgt cattacatgt atggtagtga tggggatgat aggaaggaag aacttatggc        480
atattttcac ccccacaaaa gtcagttaaa tattgggaca ctaaccatcc aggtcaaga       539
```

<210> SEQ ID NO 311
<211> LENGTH: 526
<212> TYPE: DNA
<213> ORGANISM: Homo sapien
<220> FEATURE:
<221> NAME/KEY: misc_feature
<222> LOCATION: (1)...(526)
<223> OTHER INFORMATION: n = A,T,C or G

<400> SEQUENCE: 311

```
caaatttgag ccaatgacat agaattttac aaatcaagaa gcttattctg gggccatttc        60
ttttgacgtt ttctctaaac tactaaagag gcattaatga tccataaatt atattatcta       120
catttacagc atttaaaatg tgttcagcat gaaatattag ctacagggga agctaaataa       180
attaaacatg gaataaagat ttgtccttaa atataatcta caagaagact ttgatatttg       240
tttttcacaa gtgaagcatt cttataaagt gtcataacct ttttgggaa actatgggaa        300 aaaatgggga aactctgaag ggttttaagt atcttacctg aagctacaga ctccataacc       360 tctcttttaca gggagctcct gcagcccta cagaaatgag tggctgagat tcttgattgc       420
acagcaagag cttctcatct aaacccttc ccttttttagt atctgtgtat caagtataaa       480
agttctataa actgtagtnt acttatttta atccccaaag cacagt                      526
```

<210> SEQ ID NO 312
<211> LENGTH: 500
<212> TYPE: DNA
<213> ORGANISM: Homo sapien
<220> FEATURE:
<221> NAME/KEY: misc_feature
<222> LOCATION: (1)...(500)

<223> OTHER INFORMATION: n = A,T,C or G

<400> SEQUENCE: 312

```
cctctctctc cccaccccct gactctagag aactgggttt tctcccagta ctccagcaat      60
tcatttctga aagcagttga gccactttat tccaaagtac actgcagatg ttcaaactct     120
ccatttctct ttccttcca cctgccagtt ttgctgactc tcaacttgtc atgagtgtaa      180
gcattaagga cattatgctt cttcgattct gaagacaggc cctgctcatg gatgactctg     240
gcttcttagg aaaatatttt tcttccaaaa tcagtaggaa atctaaactt atccctctt     300
tgcagatgtc tagcagcttc agacatttgg ttaagaaccc atgggaaaaa aaaaaatcct     360
tgctaatgtg gtttcctttg taaaccanga ttcttatttg nctggtatag aatatcagct     420
ctgaacgtgt ggtaaagatt tttgtgtttg aatataggag aaatcagttt gctgaaaagt     480
tagtcttaat tatctattgg                                                 500
```

<210> SEQ ID NO 313
<211> LENGTH: 718
<212> TYPE: DNA
<213> ORGANISM: Homo sapien
<220> FEATURE:
<221> NAME/KEY: misc_feature
<222> LOCATION: (1)...(718)
<223> OTHER INFORMATION: n = A,T,C or G

<400> SEQUENCE: 313

```
ggagatttgt gtggtttgca gccgagggag accaggaaga tctgcatggt gggaaggacc      60
tgatgataca gaggtgagaa ataagaaagg ctgctgactt taccatctga ggccacacat     120
ctgctgaaat ggagataatt aacatcacta gaaacagcaa gatgacaata taatgtctaa     180
gtagtgacat gttttttgcac atttccagcc cttttaaata tccacacaca caggaagcac     240
aaaaggaagc acagagatcc ctgggagaaa tgcccggccg ccatcttggg tcatcgatga     300
gcctcgccct gtgcctgntc ccgcttgtga gggaaggaca ttagaaaatg aattgatgtg     360
ttccttaaag gatggcagga aaacagatcc tgttgtggat atttatttga acgggattac     420
agatttgaaa tgaagtcaca aagtgagcat taccaatgag aggaaaacag acgagaaaat     480
cttgatggtt cacaagacat gcaacaaaca aatggaata ctgtgatgac acgagcagcc     540
aactggggag gagataccac ggggcagagg tcaggattct ggccctgctg cctaactgtg     600
cgttatacca atcatttcta tttctaccct caaacaagct gtngaatatc tgacttacgg     660
ttcttntggc ccacattttc atnatccacc ccntcntttt aannttantc caaantgt     718
```

<210> SEQ ID NO 314
<211> LENGTH: 358
<212> TYPE: DNA
<213> ORGANISM: Homo sapien

<400> SEQUENCE: 314

```
gtttatttac attacagaaa aaacatcaag acaatgtata ctatttcaaa tatatccata      60
cataatcaaa tatagctgta gtacatgttt tcattggtgt agattaccac aaatgcaagg     120
caacatgtgt agatctcttg tcttattctt ttgtctataa tactgtattg tgtagtccaa     180
gctctcggta gtccagccac tgtgaaacat gctccctta gattaacctc gtggacgctc      240
ttgttgtatt gctgaactgt agtgccctgt attttgcttc tgtctgtgaa ttctgttgct     300
tctggggcat ttccttgtga tgcagaggac caccacacag atgacagcaa tctgaatt      358
```

<210> SEQ ID NO 315
<211> LENGTH: 341
<212> TYPE: DNA
<213> ORGANISM: Homo sapien

<400> SEQUENCE: 315

| | | | | | |
|---|---|---|---|---|---|
| taccacctcc | ccgctggcac | tgatgagccg | catcaccatg | gtcaccagca | ccatgaaggc | 60 |
| ataggtgatg | atgaggacat | ggaatgggcc | cccaaggatg | gtctgtccaa | agaagcgagt | 120 |
| gaccccatt | ctgaagatgt | ctggaacctc | taccagcagg | atgatgatag | ccccaatgac | 180 |
| agtcaccagc | tccccgacca | gccggatatc | gtccttaggg | gtcatgtagg | cttcctgaag | 240 |
| tagcttctgc | tgtaagaggg | tgttgtcccg | ggggctcgtg | cggttattgg | tcctgggctt | 300 |
| gaggggcgg | tagatgcagc | acatggtgaa | gcagatgatg | t | | 341 |

<210> SEQ ID NO 316
<211> LENGTH: 151
<212> TYPE: DNA
<213> ORGANISM: Homo sapien

<400> SEQUENCE: 316

| | | | | | |
|---|---|---|---|---|---|
| agactgggca | agactcttac | gccccacact | gcaatttggt | cttgttgccg | tatccattta | 60 |
| tgtgggcctt | tctcgagttt | ctgattataa | acaccactgg | agcgatgtgt | tgactggact | 120 |
| cattcaggga | gctctggttg | caatattagt | t | | | 151 |

<210> SEQ ID NO 317
<211> LENGTH: 151
<212> TYPE: DNA
<213> ORGANISM: Homo sapien

<400> SEQUENCE: 317

| | | | | | |
|---|---|---|---|---|---|
| agaactagtg | gatcctaatg | aaatacctga | acatatatt | ggcatttatc | aatggctcaa | 60 |
| atcttcattt | atctctggcc | ttaaccctgg | ctcctgaggc | tgcggccagc | agatcccagg | 120 |
| ccagggctct | gttcttgcca | cacctgcttg | a | | | 151 |

<210> SEQ ID NO 318
<211> LENGTH: 151
<212> TYPE: DNA
<213> ORGANISM: Homo sapien

<400> SEQUENCE: 318

| | | | | | |
|---|---|---|---|---|---|
| actggtggga | ggcgctgttt | agttggctgt | tttcagaggg | gtctttcgga | gggacctcct | 60 |
| gctgcaggct | ggagtgtctt | tattcctggc | gggagaccgc | acattccact | gctgaggctg | 120 |
| tgggggcggt | ttatcaggca | gtgataaaca | t | | | 151 |

<210> SEQ ID NO 319
<211> LENGTH: 151
<212> TYPE: DNA
<213> ORGANISM: Homo sapien

<400> SEQUENCE: 319

| | | | | | |
|---|---|---|---|---|---|
| aactagtgga | tccagagcta | taggtacagt | gtgatctcag | ctttgcaaac | acattttcta | 60 |
| catagatagt | actaggtatt | aatagatatg | taaagaaaga | aatcacacca | ttaataatgg | 120 |
| taagattggg | tttatgtgat | tttagtgggt | a | | | 151 |

<210> SEQ ID NO 320
<211> LENGTH: 150
<212> TYPE: DNA

-continued

```
<213> ORGANISM: Homo sapien

<400> SEQUENCE: 320
aactagtgga tccactagtc cagtgtggtg gaattccatt gtgttggggt tctagatcgc    60
gagcggctgc cctttttttt ttttttttttg gggggaatt tttttttttt aatagttatt   120
gagtgttcta cagcttacag taaataccat                                    150

<210> SEQ ID NO 321
<211> LENGTH: 151
<212> TYPE: DNA
<213> ORGANISM: Homo sapien

<400> SEQUENCE: 321
agcaactttg tttttcatcc aggttatttt aggcttagga tttcctctca cactgcagtt    60
tagggtggca ttgtaaccag ctatggcata ggtgttaacc aaaggctgag taaacatggg   120
tgcctctgag aaatcaaagt cttcatacac t                                  151

<210> SEQ ID NO 322
<211> LENGTH: 151
<212> TYPE: DNA
<213> ORGANISM: Homo sapien
<220> FEATURE:
<221> NAME/KEY: misc_feature
<222> LOCATION: (1)...(151)
<223> OTHER INFORMATION: n = A,T,C or G

<400> SEQUENCE: 322
atccagcatc ttctcctgtt tcttgccttc cttttcttc ttcttasatt ctgcttgagg     60
tttgggcttg gtcagtttgc cacagggctt ggagatggtg acagtcttct ggcattcggc   120
attgtgcagg gctcgcttca nacttccagt t                                  151

<210> SEQ ID NO 323
<211> LENGTH: 151
<212> TYPE: DNA
<213> ORGANISM: Homo sapien
<220> FEATURE:
<221> NAME/KEY: misc_feature
<222> LOCATION: (1)...(151)
<223> OTHER INFORMATION: n = A,T,C or G

<400> SEQUENCE: 323
tgaggacttg tkttcttttt ctttatttt aatcctctta ckttgtaaat atattgccta     60
nagactcant tactacccag tttgtggttt twtgggagaa atgtaactgg acagttagct   120
gttcaatyaa aaagacactt ancccatgtg g                                  151

<210> SEQ ID NO 324
<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 324
acctgtgtgg aatttcagct ttcctcatgc aaaaggattt tgtatccccg gcctacttga    60
agaagtggtc agctaaagga atccaggttg ttggttggac tgttaatacc tttgatgaaa   120
agagttacta cgaatcccat cttggttcca gctatatcac tgacagcatg gtagaagact   180
gcgaacctca cttctagact ttcacggtgg gacgaaacgg gttcagaaac tgccagggc    240
```

| | |
|---|---|
| ctcatacagg gatatcaaaa tacccttgt gctacccagg ccctggggaa tcaggtgact | 300 |
| cacacaaatg caatagttgg tcactgcatt tttacctgaa ccaaagctaa acccggtgtt | 360 |
| gccaccatgc accatggcat gccagagttc aacactgttg ctcttgaaaa ttgggtctga | 420 |
| aaaaacgcac aagagcccct gccctgccct agctgangca c | 461 |

<210> SEQ ID NO 325
<211> LENGTH: 400
<212> TYPE: DNA
<213> ORGANISM: Homo sapien

<400> SEQUENCE: 325

| | |
|---|---|
| acactgtttc catgttatgt ttctacacat tgctacctca gtgctcctgg aaacttagct | 60 |
| tttgatgtct ccaagtagtc caccttcatt taactctttg aaactgtatc atctttgcca | 120 |
| agtaagagtg gtggcctatt tcagctgctt tgacaaaatg actggctcct gacttaacgt | 180 |
| tctataaatg aatgtgctga agcaaagtgc ccatggtggc ggcgaagaag agaaagatgt | 240 |
| gttttgtttt ggactctctg tggtcccttc caatgctgtg ggtttccaac caggggaagg | 300 |
| gtcccttttg cattgccaag tgccataacc atgagcacta cgctaccatg gttctgcctc | 360 |
| ctggccaagc aggctggttt gcaagaatga aatgaatgat | 400 |

<210> SEQ ID NO 326
<211> LENGTH: 1215
<212> TYPE: DNA
<213> ORGANISM: Homo sapien

<400> SEQUENCE: 326

| | |
|---|---|
| ggaggactgc agcccgcact cgcagccctg gcaggcggca ctggtcatgg aaaacgaatt | 60 |
| gttctgctcg ggcgtcctgg tgcatccgca gtgggtgctg tcagccgcac actgtttcca | 120 |
| gaactcctac accatcgggc tgggcctgca cagtcttgag gccgaccaag agccagggag | 180 |
| ccagatggtg gaggccagcc tctccgtacg gcacccagag tacaacagac ccttgctcgc | 240 |
| taacgacctc atgctcatca gttggacga atccgtgtcc gagtctgaca ccatccggag | 300 |
| catcagcatt gcttcgcagt gccctaccgc ggggaactct tgcctcgttt ctggctgggg | 360 |
| tctgctggcg aacggcagaa tgcctaccgt gctgcagtgc gtgaacgtgt cggtggtgtc | 420 |
| tgaggaggtc tgcagtaagc tctatgaccc gctgtaccac cccagcatgt tctgcgccgg | 480 |
| cggagggcaa gaccagaagg actcctgcaa cggtgactct gggggcccc tgatctgcaa | 540 |
| cgggtacttg cagggccttg tgtctttcgg aaaagccccg tgtggccaag ttggcgtgcc | 600 |
| aggtgtctac accaacctct gcaaattcac tgagtggata gagaaaaccg tccaggccag | 660 |
| ttaactctgg ggactgggaa cccatgaaat tgacccccaa atacatcctg cggaaggaat | 720 |
| tcaggaatat ctgttcccag cccctcctcc ctcaggccca ggagtccagg ccccagccc | 780 |
| ctcctcccctc aaaccaaggg tacagatccc cagcccctcc tccctcagac ccaggagtcc | 840 |
| agaccccca gccctcctc cctcagaccc aggagtccag cccctcctcc ctcagaccca | 900 |
| ggagtccaga cccccagcc cctcctccct cagacccagg ggtccaggcc ccaacccct | 960 |
| cctccctcag actcagaggt ccaagccccc aaccctcct tccccagacc cagaggtcca | 1020 |
| ggtcccagcc cctcctccct cagacccagc ggtccaatgc cacctagact ctccctgtac | 1080 |
| acagtgcccc cttgtggcac gttgacccaa cctaccagt tggttttca ttttttgtcc | 1140 |
| cttttcccta gatccagaaa taaagtctaa gagaagcgca aaaaaaaaa aaaaaaaaa | 1200 |

```
                      aaaaaaaaaa aaaaa                                      1215
```

<210> SEQ ID NO 327
<211> LENGTH: 220
<212> TYPE: PRT
<213> ORGANISM: Homo sapien

<400> SEQUENCE: 327

```
Glu Asp Cys Ser Pro His Ser Gln Pro Trp Gln Ala Ala Leu Val Met
 1               5                  10                  15

Glu Asn Glu Leu Phe Cys Ser Gly Val Leu Val His Pro Gln Trp Val
            20                  25                  30

Leu Ser Ala Ala His Cys Phe Gln Asn Ser Tyr Thr Ile Gly Leu Gly
        35                  40                  45

Leu His Ser Leu Glu Ala Asp Gln Glu Pro Gly Ser Gln Met Val Glu
    50                  55                  60

Ala Ser Leu Ser Val Arg His Pro Glu Tyr Asn Arg Pro Leu Leu Ala
65                  70                  75                  80

Asn Asp Leu Met Leu Ile Lys Leu Asp Glu Ser Val Ser Glu Ser Asp
                85                  90                  95

Thr Ile Arg Ser Ile Ser Ile Ala Ser Gln Cys Pro Thr Ala Gly Asn
            100                 105                 110

Ser Cys Leu Val Ser Gly Trp Gly Leu Leu Ala Asn Gly Arg Met Pro
        115                 120                 125

Thr Val Leu Gln Cys Val Asn Val Ser Val Val Ser Glu Glu Val Cys
    130                 135                 140

Ser Lys Leu Tyr Asp Pro Leu Tyr His Pro Ser Met Phe Cys Ala Gly
145                 150                 155                 160

Gly Gly Gln Asp Gln Lys Asp Ser Cys Asn Gly Asp Ser Gly Gly Pro
                165                 170                 175

Leu Ile Cys Asn Gly Tyr Leu Gln Gly Leu Val Ser Phe Gly Lys Ala
            180                 185                 190

Pro Cys Gly Gln Val Gly Val Pro Gly Val Tyr Thr Asn Leu Cys Lys
        195                 200                 205

Phe Thr Glu Trp Ile Glu Lys Thr Val Gln Ala Ser
    210                 215                 220
```

<210> SEQ ID NO 328
<211> LENGTH: 234
<212> TYPE: DNA
<213> ORGANISM: Homo sapien

<400> SEQUENCE: 328

```
cgctcgtctc tggtagctgc agccaaatca taaacggcga ggactgcagc ccgcactcgc    60
agccctggca ggcggcactg gtcatggaaa acgaattgtt ctgctcgggc gtcctggtgc   120
atccgcagtg ggtgctgtca gccacacact gtttccagaa ctcctacacc atcgggctgg   180
gcctgcacag tcttgaggcc gaccaagagc cagggagcca gatggtggag gcca          234
```

<210> SEQ ID NO 329
<211> LENGTH: 77
<212> TYPE: PRT
<213> ORGANISM: Homo sapien

<400> SEQUENCE: 329

```
Leu Val Ser Gly Ser Cys Ser Gln Ile Ile Asn Gly Glu Asp Cys Ser
 1               5                  10                  15
```

```
Pro His Ser Gln Pro Trp Gln Ala Ala Leu Val Met Glu Asn Glu Leu
         20                  25                  30

Phe Cys Ser Gly Val Leu Val His Pro Gln Trp Val Leu Ser Ala Thr
             35                  40                  45

His Cys Phe Gln Asn Ser Tyr Thr Ile Gly Leu Gly Leu His Ser Leu
 50                      55                  60

Glu Ala Asp Gln Glu Pro Gly Ser Gln Met Val Glu Ala
 65                  70                  75

<210> SEQ ID NO 330
<211> LENGTH: 70
<212> TYPE: DNA
<213> ORGANISM: Homo sapien

<400> SEQUENCE: 330
cccaacacaa tggcccgatc ccatccctga ctccgccctc aggatcgctc gtctctggta    60
gctgcagcca                                                          70

<210> SEQ ID NO 331
<211> LENGTH: 22
<212> TYPE: PRT
<213> ORGANISM: Homo sapien

<400> SEQUENCE: 331

Gln His Asn Gly Pro Ile Pro Ser Leu Thr Pro Pro Ser Gly Ser Leu
 1               5                  10                  15

Val Ser Gly Ser Cys Ser
             20

<210> SEQ ID NO 332
<211> LENGTH: 2507
<212> TYPE: DNA
<213> ORGANISM: Homo sapien

<400> SEQUENCE: 332
tggtgccgct gcagccggca gagatggttg agctcatgtt cccgctgttg ctcctccttc      60
tgcccttcct tctgtatatg gctgcgcccc aaatcaggaa aatgctgtcc agtgggtgt     120
gtacatcaac tgttcagctt cctgggaaag tagttgtggt cacaggagct aatacaggta   180
tcgggaagga gacagccaaa gagctggctc agagaggagc tcgagtatat ttagcttgcc   240
gggatgtgga aaaggggaa ttggtggcca aagagatcca gaccacgaca gggaaccagc    300
aggtgttggt gcggaaactg gacctgtctg atactaagtc tattcgagct tttgctaagg   360
gcttcttagc tgaggaaaag caccttccacg ttttgatcaa caatgcagga gtgatgatgt   420
gtccgtactc gaagacagca gatggctttg agatgcacat aggagtcaac cacttgggtc   480
acttcctcct aacccatctg ctgctagaga aactaaagga atcagcccca tcaaggatag   540
taaatgtgtc ttccctcgca catcacctgg aaggatcca cttccataac tgcagggcg    600
agaaattcta caatgcaggc ctggcctact gtcacagcaa gctagccaac atcctcttca   660
cccaggaact ggcccggaga ctaaaaggct ctggcgttac gacgtattct gtacaccctg    720
gcacagtcca atctgaactg gttcggcact catctttcat gagatggatg tggtggcttt    780
tctccttttt catcaagact cctcagcagg gagcccagac cagcctgcac tgtgccttaa    840
cagaaggtct tgagattcta agtgggaatc atttcagtga ctgtcatgtg catgggtct    900
ctgcccaagc tcgtaatgag actatagcaa ggcggctgtg ggacgtcagt tgtgacctgc    960
tgggcctccc aatagactaa caggcagtgc cagttggacc caagagaaga ctgcagcaga   1020
```

```
ctacacagta cttcttgtca aaatgattct ccttcaaggt tttcaaaacc tttagcacaa    1080
agagagcaaa accttccagc cttgcctgct tggtgtccag ttaaaactca gtgtactgcc    1140
agattcgtct aaatgtctgt catgtccaga tttactttgc ttctgttact gccagagtta    1200
ctagagatat cataatagga taagaagacc ctcatatgac ctgcacagct cattttcctt    1260
ctgaaagaaa ctactaccta ggagaatcta agctatagca gggatgattt atgcaaattt    1320
gaactagctt ctttgttcac aattcagttc ctcccaacca accagtcttc acttcaagag    1380
ggccacactg caacctcagc ttaacatgaa taacaaagac tggctcagga gcagggcttg    1440
cccaggcatg gtggatcacc ggaggtcagt agttcaagac cagcctggcc aacatggtga    1500
aaccccacct ctactaaaaa ttgtgtatat cttttgtgtgt cttcctgttt atgtgtgcca    1560
agggagtatt ttcacaaagt tcaaaacagc cacaataatc agagatggag caaaccagtg    1620
ccatccagtc tttatgcaaa tgaaatgctg caaagggaag cagattctgt atatgttggt    1680
aactacccac caagagcaca tgggtagcag ggaagaagta aaaaagaga aggagaatac    1740 tggaagataa tgcacaaaat gaagggacta gttaaggatt aactagccct ttaaggatta    1800
actagttaag gattaatagc aaaagayatt aaatatgcta acatagctat ggaggaattg    1860
agggcaagca cccaggactg atgaggtctt aacaaaaacc agtgtggcaa aaaaaaaaa    1920 aaaaaaaaaa aaaatccta aaaacaaaca aacaaaaaaa acaattcttc attcagaaaa    1980
attatcttag ggactgatat tggtaattat ggtcaattta ataatatttt ggggcatttc    2040
cttacattgt cttgacaaga ttaaaatgtc tgtgccaaaa ttttgtattt tatttggaga    2100
cttcttatca aaagtaatgc tgccaaagga agtctaagga attagtagtg ttcccatcac    2160
ttgtttggag tgtgctattc taaaagattt tgatttcctg gaatgacaat tatatttaa     2220 ctttggtggg ggaaagagtt ataggaccac agtcttcact tctgatactt gtaaattaat    2280
cttttattgc acttgttttg accattaagc tatatgttta gaaatggtca ttttacggaa    2340
aaattagaaa aattctgata atagtgcaga ataaatgaat taatgttttta cttaatttat    2400 attgaactgt caatgacaaa taaaaattct ttttgattat tttttgtttt catttaccag    2460
aataaaaacg taagaattaa agtttgatt acaaaaaaaa aaaaaa                    2507

<210> SEQ ID NO 333
<211> LENGTH: 3030
<212> TYPE: DNA
<213> ORGANISM: Homo sapien

<400> SEQUENCE: 333
gcaggcgact tgcgagctgg gagcgattta aaacgctttg gattccccg gcctgggtgg      60 ggagagcgag ctgggtgccc cctagattcc ccgccccgc acctcatgag ccgaccctcg     120
gctccatgga gcccggcaat tatgccacct tggatggagc caaggatatc gaaggcttgc    180
tgggagcggg aggggggcgg aatctggtcg cccactcccc tctgaccagc cacccagcgg    240
cgcctacgct gatgcctgct gtcaactatg ccccttgga tctgccaggc tcggcggagc    300
cgccaaagca atgccaccca tgccctgggg tgccccaggg gacgtcccca gctcccgtgc    360
cttatggtta ctttggaggc gggtactact cctgccgagt gtcccggagc tcgctgaaac    420
cctgtgccca ggcagccacc ctggccgcgt acccgcggga gactcccacg gccggggaag    480
agtaccccag ycgcccccact gagtttgcct tctatccggg atatccggga acctaccagc    540
ctatggccag ttacctggac gtgtctgtgg tgcagactct gggtgctcct ggagaaccgc    600
```

-continued

```
gacatgactc cctgttgcct gtggacagtt accagtcttg ggctctcgct ggtggctgga      660
acagccagat gtgttgccag ggagaacaga acccaccagg tccctttggg aaggcagcat      720
ttgcagactc cagcgggcag caccctcctg acgcctgcgc ctttcgtcgc ggccgcaaga      780
aacgcattcc gtacagcaag gggcagttgc gggagctgga gcgggagtat gcggctaaca      840
agttcatcac caaggacaag aggcgcaaga tctcggcagc caccagcctc tcggagcgcc      900
agattaccat ctggtttcag aaccgccggg tcaaagagaa aaggttctc gccaaggtga       960
agaacagcgc taccccttaa gagatctcct tgcctgggtg ggaggagcga aagtggggt      1020
gtcctgggga ccaggaac  ctgccaagcc caggctgggg ccaaggactc tgctgagagg      1080
cccctagaga caacacccctt cccaggccac tggctgctgg actgttcctc aggagcggcc    1140
tgggtaccca gtatgtgcag ggagacggaa ccccatgtga cagcccactc caccagggtt    1200
cccaaagaac ctggcccagt cataatcatt catcctgaca gtggcaataa tcacgataac    1260
cagtactagc tgccatgatc gttagcctca tattttctat ctagagctct gtagagcact    1320
ttagaaaccg ctttcatgaa ttgagctaat tatgaataaa tttggaaggc gatccctttg    1380
cagggaagct ttctctcaga ccccccttcca ttacacctct caccctggta acagcaggaa    1440
gactgaggag aggggaacgg gcagattcgt tgtgtggctg tgatgtccgt ttagcatttt    1500
tctcagctga cagctgggta ggtggacaat tgtagaggct gtctcttcct ccctccttgt    1560
ccaccccata gggtgtaccc actggtcttg gaagcaccca tccttaatac gatgattttt    1620
ctgtcgtgtg aaaatgaagc cagcaggctg cccctagtca gtccttcctt ccagagaaaa    1680
agagatttga gaaagtgcct gggtaattca ccattaattt cctcccccaa actctctgag    1740
tcttcccctta atatttctgg tggttctgac caaagcaggt catggtttgt tgagcatttg    1800
ggatcccagt gaagtagatg tttgtagcct tgcatactta gcccttccca ggcacaaacg    1860
gagtggcaga gtggtgccaa ccctgttttc ccagtccacg tagacagatt cacagtgcgg    1920
aattctggaa gctggagaca gacgggctct ttgcagagcc gggactctga gagggacatg    1980
agggcctctg cctctgtgtt cattctctga tgtcctgtac ctgggctcag tgcccggtgg    2040
gactcatctc ctggccgcgc agcaaagcca gcgggttcgt gctggtcctt cctgcacctt    2100
aggctggggg tgggggggcct gccggcgcat tctccacgat tgagcgcaca ggcctgaagt    2160
ctggacaacc cgcagaaccg aagctccgag cagcgggtcg gtggcgagta gtgggtcgg    2220
tggcgagcag ttggtggtgg gccgcggccg ccactacctc gaggacattt ccctcccgga    2280
gccagctctc ctagaaaccc cgcggcggcc gccgcagcca agtgtttatg gcccgcggtc    2340
gggtgggatc ctagccctgt ctcctctcct gggaaggagt gagggtggga cgtgacttag    2400
acacctacaa atctatttac caaagaggag cccgggactg agggaaaagg ccaaagagtg    2460
tgagtgcatg cggactgggg gttcagggga agaggacgag gaggaggaag atgaggtcga    2520
tttcctgatt taaaaaatcg tccaagcccc gtggtccagc ttaaggtcct cggttacatg    2580
cgccgctcag agcaggtcac tttctgcctt ccacgtcctc cttcaaggaa gccccatgtg    2640
ggtagctttc aatatcgcag gttcttactc ctctgcctct ataagctcaa acccaccaac    2700
gatcgggcaa gtaaaccccc tccctcgccg acttcggaac tggcgagagt tcagcgcaga    2760
tgggcctgtg gggaggggc aagatagatg aggggagcg gcatggtgcg gggtgacccc     2820
ttggagagag gaaaaaggcc acaagagggg ctgccaccgc cactaacgga gatggccctg    2880
gtagagacct ttgggggtct ggaacctctg gactccccat gctctaactc ccacactctg    2940
ctatcagaaa cttaaacttg aggattttct ctgttttcca ctcgcaataa aytcagagca    3000
```

```
aacaaaaaaa aaaaaaaaa aaaactcgag                                   3030

<210> SEQ ID NO 334
<211> LENGTH: 2417
<212> TYPE: DNA
<213> ORGANISM: Homo sapien

<400> SEQUENCE: 334
ggcggccgct ctagagctag tgggatcccc cgggctgcac gaattcggca cgagtgagtt     60
ggagttttac ctgtattgtt ttaatttcaa caagcctgag gactagccac aaatgtaccc    120
agtttacaaa tgaggaaaca ggtgcaaaaa ggttgttacc tgtcaaaggt cgtatgtggc    180
agagccaaga tttgagccca gttatgtctg atgaacttag cctatgctct ttaaacttct    240
gaatgctgac cattgaggat atctaaactt agatcaattg cattttccct ccaagactat    300
ttacttatca atacaataat accaccttta ccaatctatt gttttgatac gagactcaaa    360
tatgccagat atatgtaaaa gcaacctaca agctctctaa tcatgctcac ctaaaagatt    420
cccgggatct aataggctca agaaacttc ttctagaaat ataaaagaga aaattggatt    480
atgcaaaaat tcattattaa ttttttttcat ccatccttta attcagcaaa catttatctg    540
ttgttgactt tatgcagtat ggcctttta ggattgggg acaggtgaag aacggggtgc    600
cagaatgcat cctcctacta atgaggtcag tacacatttg cattttaaaa tgccctgtcc    660
agctgggcat ggtggatcat gcctgtaatc tcaacattgg aaggccaagg caggaggatt    720
gcttcagccc aggagttcaa gaccagcctg gcaacatag aaagacccca tctctcaatc    780
aatcaatcaa tgccctgtct ttgaaaataa aactctttaa gaaaggttta atgggcaggg    840
tgtggtagct catgcctata atacagcact ttggaggct gaggcaggag gatcacttta    900
gcccagaagt tcaagaccag cctgggcaac aagtgacacc tcatctcaat tttttaataa    960
aatgaataca tacataagga aagataaaaa gaaaagttta atgaaagaat acagtataaa   1020
acaaatctct tggacctaaa agtatttttg ttcaagccaa atattgtgaa tcacctctct   1080
gtgttgagga tacagaatat ctaagcccag gaaactgagc agaaagttca tgtactaact   1140
aatcaacccg aggcaaggca aaatgagac taactaatca atccgaggca aggggcaaat   1200
tagacggaac ctgactctgg tctattaagc gacaactttc cctctgttgt atttttcttt   1260
tattcaatgt aaaaggataa aaactctcta aaactaaaaa caatgtttgt caggagttac   1320
aaaccatgac caactaatta tggggaatca taaaatatga ctgtatgaga tcttgatggt   1380
ttacaaagtg tacccactgt taatcacttt aaacattaat gaacttaaaa atgaatttac   1440
ggagattgga atgtttcttt cctgttgtat tagttggctc aggctgccat aacaaaatac   1500
cacagactgg gaggcttaag taacagaaat tcatttctca cagttctggg ggctggaagt   1560
ccacgatcaa ggtgcaggaa aggcaggctt cattctgagg cccctctctt ggctcacatg   1620
tggccaccct cccactgcgt gctcacatga cctctttgtg ctcctggaaa gagggtgtgg   1680
gggacagagg gaaagagaag gagagggaac tctctggtgt ctcgtctttc aaggacccta   1740
acctgggcca ctttggccca ggcactgtgg ggtgggggt tgtggctgct ctgctctgag   1800
tggccaagat aaagcaacag aaaaatgtcc aaagctgtgc agcaaagaca agccaccgaa   1860
cagggatctg ctcatcagtg tggggacctc caagtcggcc accctggagg caagccccca   1920
cagagcccat gcaaggtggc agcagcagaa aagggaatt gtccctgtcc ttggcacatt   1980
cctcaccgac ctggtgatgc tggacactgc gatgaatggt aatgtggatg agaatatgat   2040
```

| | |
|---|---|
| ggactcccag aaaaggagac ccagctgctc aggtggctgc aaatcattac agccttcatc | 2100 |
| ctggggagga actgggggcc tggttctggg tcagagagca gcccagtgag ggtgagagct | 2160 |
| acagcctgtc ctgccagctg gatccccagt cccggtcaac cagtaatcaa ggctgagcag | 2220 |
| atcaggcttc ccggagctgg tcttgggaag ccagccctgg ggtgagttgg ctcctgctgt | 2280 |
| ggtactgaga caatattgtc ataaattcaa tgcgcccttg tatcccttt tcttttttat | 2340 |
| ctgtctacat ctataatcac tatgcatact agtctttgtt agtgtttcta ttcmacttaa | 2400 |
| tagagatatg ttatact | 2417 |

<210> SEQ ID NO 335
<211> LENGTH: 2984
<212> TYPE: DNA
<213> ORGANISM: Homo sapien

<400> SEQUENCE: 335

| | |
|---|---|
| atccctcctt ccccactctc ctttccagaa ggcacttggg gtcttatctg ttggactctg | 60 |
| aaaacacttc aggcgccctt ccaaggcttc ccaaaacccc taagcagccg cagaagcgct | 120 |
| cccgagctgc cttctcccac actcaggtga tcgagttgga gaggaagttc agccatcaga | 180 |
| agtacctgtc ggcccctgaa cgggcccacc tggccaagaa cctcaagctc acggagaccc | 240 |
| aagtgaagat atggttccag aacagacgct ataagactaa gcgaaagcag ctctcctcgg | 300 |
| agctgggaga cttggagaag cactcctctt tgccggccct gaaagaggag gccttctccc | 360 |
| gggcctccct ggtctccgtg tataacagct atccttacta cccatacctg tactgcgtgg | 420 |
| gcagctggag cccagctttt tggtaatgcc agctcaggtg acaaccatta tgatcaaaaa | 480 |
| ctgccttccc cagggtgtct ctatgaaaag cacaaggggc caaggtcagg gagcaagagg | 540 |
| tgtgcacacc aaagctattg agatttgcg tggaaatctc asattcttca ctggtgagac | 600 |
| aatgaaacaa cagagacagt gaaagtttta ataccteagt cattcccca gtgcatactg | 660 |
| taggtcattt tttttgcttc tggctacctg tttgaagggg agagagggaa aatcaagtgg | 720 |
| tattttccag cactttgtat gattttggat gagctgtaca cccaaggatt ctgttctgca | 780 |
| actccatcct cctgtgtcac tgaatatcaa ctctgaaaga gcaaacctaa caggagaaag | 840 |
| gacaaccagg atgaggatgt caccaactga attaaactta agtccagaag cctcctgttg | 900 |
| gccttggaat atggccaagg ctctctctgt ccctgtaaaa gagagggca aatagagagt | 960 |
| ctccaagaga acgccctcat gctcagcaca tatttgcatg ggaggggag atgggtggga | 1020 |
| ggagatgaaa atatcagctt ttcttattcc ttttattcc tttaaaatg gtatgccaac | 1080 |
| ttaagtattt acagggtggc ccaaatagaa caagatgcac tcgctgtgat tttaagacaa | 1140 |
| gctgtataaa cagaactcca ctgcaagagg ggggccgggg ccaggagaat ctccgcttgt | 1200 |
| ccaagacagg ggcctaagga gggtctccac actgctgcta gggctgttg cattttttta | 1260 |
| ttagtagaaa gtgaaaggc ctcttctcaa cttttttccc ttgggctgga gaatttagaa | 1320 |
| tcagaagttt cctggagttt tcaggctatc atatatactg tatcctgaaa ggcaacataa | 1380 |
| ttcttccttc cctccttta aaattttgtg ttcctttttg cagcaattac tcactaaagg | 1440 |
| gcttcatttt agtccagatt tttagtctgg ctgcacctaa cttatgcctc gcttatttag | 1500 |
| cccgagatct ggtctttttt tttttttttt ttttccgtc tccccaaagc tttatctgtc | 1560 |
| ttgacttttt aaaaaagttt gggggcagat tctgaattgg ctaaaagaca tgcattttta | 1620 |
| aaactagcaa ctcttattc tttcctttaa aaatacatag cattaaatcc caatcctat | 1680 |
| ttaaagacct gacagcttga gaaggtcact actgcattta taggaccttc tggtggttct | 1740 |

-continued

```
gctgttacgt tgaagtctg acaatccttg agaatctttg catgcagagg aggtaagagg    1800
tattggattt tcacagagga agaacacagc gcagaatgaa gggccaggct tactgagctg    1860
tccagtggag ggctcatggg tgggacatgg aaaagaaggc agcctaggcc ctggggagcc    1920
cagtccactg agcaagcaag ggactgagtg agccttttgc aggaaaaggc taagaaaaag    1980
gaaaaccatt ctaaaacaca acaagaaact gtccaaatgc tttgggaact gtgtttattg    2040
cctataatgg gtccccaaaa tgggtaacct agacttcaga gagaatgagc agagagcaaa    2100
ggagaaatct ggctgtcctt ccattttcat tctgttatct caggtgagct ggtagagggg    2160
agacattaga aaaaaatgaa acaacaaaac aattactaat gaggtacgct gaggcctggg    2220
agtctcttga ctccactact taattccgtt tagtgagaaa cctttcaatt ttcttttatt    2280
agaagggcca gcttactgtt ggtggcaaaa ttgccaacat aagttaatag aaagttggcc    2340
aatttcaccc catttctgt ggtttgggct ccacattgca atgttcaatg ccacgtgctg    2400
ctgacaccga ccggagtact agccagcaca aaaggcaggg tagcctgaat tgctttctgc    2460
tctttacatt tcttttaaaa taagcattta gtgctcagtc cctactgagt actctttctc    2520 tccctcctc tgaatttaat tctttcaact tgcaatttgc aaggattaca catttcactg    2580
tgatgtatat tgtgttgcaa aaaaaaaaaa agtgtctttt gtttaaaatt acttggtttg    2640
tgaatccatc ttgcttttc cccattggaa ctagtcatta acccatctct gaactggtag    2700
aaaaacatct gaagagctag tctatcagca tctgacaggt gaattggatg gttctcagaa    2760
ccatttcacc cagacagcct gtttctatcc tgtttaataa attagtttgg gttctctaca    2820
tgcataacaa accctgctcc aatctgtcac ataaaagtct gtgacttgaa gtttagtcag    2880 caccccacc aaactttatt tttctatgtg tttttgcaa catatgagtg ttttgaaaat    2940
aaagtaccca tgtctttatt agaaaaaaaa aaaaaaaaaa aaaa               2984
```

<210> SEQ ID NO 336
<211> LENGTH: 147
<212> TYPE: PRT
<213> ORGANISM: Homo sapien

<400> SEQUENCE: 336

```
Pro Ser Phe Pro Thr Leu Leu Ser Arg Arg His Leu Gly Ser Tyr Leu
  1               5                  10                  15

Leu Asp Ser Glu Asn Thr Ser Gly Ala Leu Pro Arg Leu Pro Gln Thr
             20                  25                  30

Pro Lys Gln Pro Gln Lys Arg Ser Arg Ala Ala Phe Ser His Thr Gln
         35                  40                  45

Val Ile Glu Leu Glu Arg Lys Phe Ser His Gln Lys Tyr Leu Ser Ala
     50                  55                  60

Pro Glu Arg Ala His Leu Ala Lys Asn Leu Lys Leu Thr Glu Thr Gln
 65                  70                  75                  80

Val Lys Ile Trp Phe Gln Asn Arg Arg Tyr Lys Thr Lys Arg Lys Gln
                 85                  90                  95

Leu Ser Ser Glu Leu Gly Asp Leu Glu Lys His Ser Ser Leu Pro Ala
            100                 105                 110

Leu Lys Glu Glu Ala Phe Ser Arg Ala Ser Leu Val Ser Val Tyr Asn
        115                 120                 125

Ser Tyr Pro Tyr Tyr Pro Tyr Leu Tyr Cys Val Gly Ser Trp Ser Pro
    130                 135                 140

Ala Phe Trp
```

-continued

```
145

<210> SEQ ID NO 337
<211> LENGTH: 9
<212> TYPE: PRT
<213> ORGANISM: Homo sapien

<400> SEQUENCE: 337

Ala Leu Thr Gly Phe Thr Phe Ser Ala
 1               5

<210> SEQ ID NO 338
<211> LENGTH: 9
<212> TYPE: PRT
<213> ORGANISM: Homo sapien

<400> SEQUENCE: 338

Leu Leu Ala Asn Asp Leu Met Leu Ile
 1               5
```

COMPOUNDS FOR IMMUNODIAGNOSIS OF PROSTATE CANCER AND METHODS FOR THEIR USE

CROSS REFERENCE TO RELATED APPLICATIONS

This application is a continuation-in-part of U.S. patent application Ser. No. 09/159,822 filed Sep. 23, 1998 now abandoned, which is a continuation-in-part of U.S. patent application Ser. No. 09/116,134, filed Jul. 14, 1998, which is a continuation-in-part of U.S. patent application Ser. No. 09/030,606, filed Feb. 25, 1998, which is a continuation-in-part of U.S. patent application Ser. No. 09/020,747, filed Feb. 9, 1998 now abandoned, which is a continuation-in-part of U.S. patent application Ser. No. 08/904,809, filed Aug. 1, 1997, which is a continuation-in-part of U.S. patent application Ser. No. 08/806,596, filed Feb. 25, 1997 now abandoned.

TECHNICAL FIELD

The present invention relates generally to cancer diagnosis and monitoring. The invention is more specifically related to polypeptides comprising at least a portion of a prostate tumor protein, and to polynucleotides encoding such polypeptides. Such polypeptides and polynucleotides may be used to generate compounds for the diagnosis and monitoring of prostate cancer.

BACKGROUND OF THE INVENTION

Prostate cancer is the most common form of cancer among males, with an estimated incidence of 30% in men over the age of 50. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men in the U.S.

In spite of considerable research into therapies for the disease, prostate cancer remains difficult to treat. Commonly, treatment is based on surgery and/or radiation therapy, but these methods are ineffective in a significant percentage of cases. Two previously identified prostate specific proteins—prostate specific antigen (PSA) and prostatic acid phosphatase (PAP)—have limited therapeutic and diagnostic potential. For example, PSA levels do not always correlate well with the presence of prostate cancer, being positive in a percentage of non-prostate cancer cases, including benign prostatic hyperplasia (BPH). Furthermore, PSA measurements correlate with prostate volume, and do not indicate the level of metastasis.

In order to improve cancer treatment and survival, it would be beneficial to identify prostate tumor proteins that permit an earlier or more accurate diagnosis. In addition, further antigens are needed to facilitate the selection of a course of treatment and monitoring of patients. The present invention fulfills these needs and further provides other related advantages.

SUMMARY OF THE INVENTION

The present invention provides methods for diagnosis and monitoring of prostate cancer, together with kits for use in such methods. Polypeptides are disclosed which comprise at least an immunogenic portion of a prostate tumor protein or a variant thereof that differs in one or more substitutions, deletions, additions and/or insertions such that the ability of the variant to react with antigen-specific antisera is not substantially diminished. Within certain embodiments, the prostate tumor protein comprises an amino acid sequence encoded by a DNA molecule having a sequence selected from the group consisting of nucleotide sequences recited in SEQ ID NOs: 2–3, 5–107, 109–11, 115–171, 173–175, 177, 179–228, 229–305, 307–326, 328, 330, 332–335 and complements of such polynucleotides. Polynucleotides that encode all or a portion of a prostate tumor protein are also provided. Such polypeptides, polynucleotides, and compounds that bind to the polypeptides, may be used in the diagnosis and monitoring of cancer, such as prostate cancer.

In one specific aspect of the present invention, methods are provided for determining the presence or absence of prostate cancer in a patient, comprising: (a) contacting a biological sample obtained from a patient with a binding agent that is capable of binding to one of the above polypeptides; and (b) detecting in the sample an amount of polypeptide that binds to the binding agent, relative to a predetermined cut-off value, and therefrom determining the presence or absence of a cancer in the patient. In preferred embodiments, the binding agent is an antibody, most preferably a monoclonal antibody.

In related aspects, methods are provided for monitoring the progression of prostate cancer in a patient, comprising: (a) contacting a biological sample obtained from a patient with a binding agent that is capable of binding to one of the above polypeptides; (b) determining in the sample an amount of a protein or polypeptide that binds to the binding agent; (c) repeating steps (a) and (b); and comparing the amounts of polypeptide detected in steps (b) and (c).

Within related aspects, the present invention provides antibodies, preferably monoclonal antibodies, that bind to a polypeptide as described above, as well as diagnostic kits comprising such antibodies, and methods of using such antibodies to inhibit the development of prostate cancer.

The present invention further provides methods for determining the presence or absence of prostate cancer in a patient, comprising the steps of: (a) contacting a biological sample obtained from a patient with an oligonucleotide that hybridizes to a polynucleotide that encodes a prostate tumor protein, wherein the prostate tumor protein comprises an amino acid sequence that is encoded by a polynucleotide sequence selected from the group consisting of: (i) polynucleotides recited in any one of SEQ ID NOs:2–3, 5–107, 109–11, 115–171, 173–175, 177, 179–228, 229–305, 307–326, 328, 330, and 332–335; and (ii) complements of the foregoing polynucleotides; and (b) detecting in the sample a level of a polynucleotide that hybridizes to the oligonucleotide, relative to a predetermined cut-off value, and therefrom determining the presence or absence of prostate cancer in the patient. Within certain embodiments, the amount of mRNA is detected via polymerase chain reaction using, for example, at least one oligonucleotide primer that hybridizes to a polynucleotide that encodes a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide. In a preferred embodiment, at least one of the oligonucleotide primers comprises at least about 10 contiguous nucleotides of a DNA molecule having a partial sequence selected from the group consisting of SEQ ID NOs:2–3, 5–107, 109–11, 115–171, 173–175, 177, 179–228, 229–305, 307–326, 328, 330, and 332–335.

In related aspects, methods are provided for monitoring the progression of prostate cancer in a patient, comprising the steps of: (a) contacting a biological sample obtained from a patient with an oligonucleotide that hybridizes to a polynucleotide that encodes a prostate tumor protein, wherein the antigen comprises an amino acid sequence that is encoded by a polynucleotide sequence selected from the group consisting of: (i) polynucleotides recited in any one of SEQ ID NOs:2–3, 5–107, 109–11, 115–171, 173–175, 177, 179–228, 229–305, 307–326, 328, 330, and 332–335; and (ii) complements of the foregoing polynucleotides; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of prostate cancer in the patient.

In related aspects, diagnostic kits comprising the above oligonucleotide probes or primers are provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

In FIG. 2A, data is presented for fibroblasts pulsed with the P2S-12 peptide, as compared to fibroblasts pulsed with a control E75 peptide. In FIG. 2B, data is presented for fibroblasts expressing P506, as compared to fibroblasts expressing HER-2/neu.

DETAILED DESCRIPTION OF THE INVENTION

Figure 1:
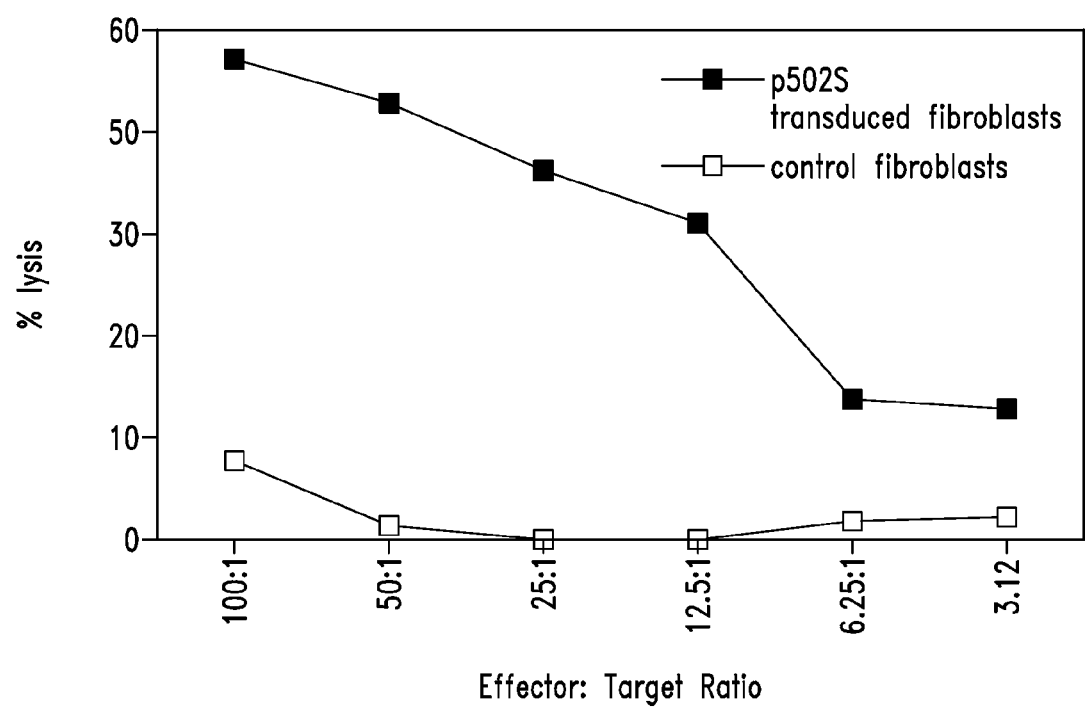
FIG. 1 is a graph illustrating the ability of T cells to kill fibroblasts expressing the representative prostate tumor polypeptide P502S, as compared to control fibroblasts. The % lysis is shown at a series of effector:target ratios, as indicated.

As noted above, the present invention is generally directed to compounds and methods for the diagnosis and monitoring of prostate cancer. The compositions described herein may include one or more prostate tumor polypeptides, nucleic acid sequences encoding such polypeptides, binding agents such as antibodies that bind to a polypeptide and/or immune system cells (e.g., T cells). Prostate tumor polypeptides of the present invention generally comprise at least a portion of a prostate tumor protein or a variant thereof, such that the therapeutic, antigenic and/or immunogenic properties of the polypeptide are not substantially diminished relative to the native prostate tumor protein. A "prostate tumor protein" is a protein that is overexpressed (i.e., mRNA and/or protein is present at a level that is at least two fold higher) in prostate tumor tissue, relative to normal prostate tissue and/or relative to other tissues (e.g., brain, heart, kidney, liver, lung, pancreas, ovary, placenta, skeletal muscle, spleen and/or thymus). Nucleic acid sequences of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a portion of a polypeptide as described above. T cells that may be employed within such compositions are generally T cells that are specific for a polypeptide as described above.

The present invention is based on the discovery of previously unknown human prostate tumor proteins. Partial sequences of polynucleotides encoding specific prostate tumor proteins (or complementary to such coding sequences) are provided in SEQ ID NOs:2–3, 5–107, 109–111, 115–171, 173–175, 177, 179–228, 229–305, 307–326, 328, 330, and 332–335.

Prostate Tumor Polynucleotides

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

Any polynucleotide that encodes a prostate tumor protein or a portion or other variant thereof as described herein is encompassed by the present invention. Preferred polynucleotides comprise at least 10 consecutive nucleotides, and preferably at least 30 consecutive nucleotides, that encode a portion of a prostate tumor protein. More preferably, a polynucleotide encodes an immunogenic portion of a prostate tumor protein. Polynucleotides complementary to any such sequences are also encompassed by the present invention.

Polynucleotides may comprise a native sequence (i.e., an endogenous sequence that encodes a prostate tumor protein or a portion thereof) or may comprise a variant of such a sequence. Polynucleotide variants may contain one or more substitutions, additions, deletions and/or insertions such that the therapeutic, antigenic and/or immunogenic properties are not substantially diminished, relative to a native prostate tumor protein. Such modifications may be readily introduced using standard mutagenesis techniques, such as oligonucleotide-directed site-specific mutagenesis as taught, for example, by Adelman et al. (*DNA,* 2:183, 1983). Preferably, the antigenicity or immunogenicity of a polypeptide variant is not substantially diminished. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native prostate tumor protein or a portion thereof. The percent identity may be readily determined by comparing sequences using computer algorithms well known to those of ordinary skill in the art, such as Megalign, using default parameters. Certain variants are substantially homologous to a native gene, or a portion or complement thereof. Such polynucleotide variants are capable of hybridizing under moderately stringent conditions to a naturally occurring DNA sequence encoding a native prostate tumor protein (or a complementary sequence). Suitable moderately stringent conditions include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5×and 0.2×SSC containing 0.1% SDS).

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, more preferably 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) Fast and sensitive multiple sequence alignments on a microcomputer *CABIOS* 5:151–153; Myers, E. W. and Muller W. (1988) Optimal alignments in linear space *CABIOS* 4:11–17; Robinson, E. D. (1971) *Comb. Theor* 11:105; Santou, N. Nes, M. (1987) The neighbor joining method. A new method for reconstructing phylogenetic trees *Mol. Biol. Evol.* 4:406–425; Sneath, P. H. A. and Sokal, R. R. (1973) *Numerical Taxonomy—the Principles and Practice of Numerical Taxonomy,* Freeman Press, San Francisco, Calif.; Wilbur, W. J. and Lipman, D. J. (1983) Rapid similarity searches of nucleic acid and protein data banks *Proc. Natl. Acad., Sci. USA* 80:726–730.

Preferably, the "percentage of sequence identity" is determined by comparing two optimally aligned sequences over a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Also included in the scope of the present invention are alleles of the genes encoding the nucleotide sequences recited herein. As used herein, an "allele" or "allellic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone or in combination with the others, one or more times in a given sequence.

Polynucleotides may be prepared using any of a variety of techniques. For example, a polynucleotide may be identified, as described in more detail below, using a PCR-based subtraction protocol. Alternatively, polypeptides may be amplified via polymerase chain reaction (PCR) from cDNA prepared from prostate tumor cells. For this approach, sequence-specific primers may be designed based on the sequences provided herein, and may be purchased or synthesized.

An amplified portion may be used to isolate a full length gene from a suitable library (e.g., a prostate tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}$P) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using techniques well known in the art (see, for example, Mullis et al., *Cold Spring Harbor Symp. Quant. Biol.* 51:263, 1987; Erlich ed., *PCR Technology*, Stockton Press, N.Y., 1989), and software well known in the art may also be employed. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Additional techniques include capture PCR (Lagerstrom et al., *PCR Methods Applic.* 1:111–19, 1991) and walking PCR (Parker et al., *Nucl. Acids. Res.* 19:3055–60, 1991). Transcription-Mediated Amplification, or TMA is another method that may be utilized for the amplification of DNA, rRNA, or mRNA, as described in Patent No. PCT/US91/03184. This autocatalytic and isothermic non-PCR based method utilizes two primers and two enzymes: RNA polymerase and reverse transcriptase. One primer contains a promoter sequence for RNA polymerase. In the first amplification, the promoter-primer hybridizes to the target rRNA at a defined site. Reverse transcriptase creates a DNA copy of the target rRNA by extension from the 3' end of the promoter-primer. The RNA in the resulting complex is degraded and a second primer binds to the DNA copy. A new strand of DNA is synthesized from the end of the primer by reverse transcriptase creating double stranded DNA. RNA polymerase recognizes the promoter sequence in the DNA template and initiates transcription. Each of the newly synthesized RNA amplicons re-enters the TMA process and serves as a template for a new round of replication leading to the expotential expansion of the RNA amplicon. Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Certain nucleic acid sequences of cDNA molecules encoding portions of prostate tumor proteins are provided in SEQ ID NOS: 1–107, 109–111, 115–171, 173–175, 177, 179–228, 229–305, 307–326, 328, 330, and 332–335. The polynucleotides recited herein, as well as full length polynucleotides comprising such sequences, other portions of such full length polynucleotides, and sequences complementary to all or a portion of such full length molecules, are specifically encompassed by the present invention.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding a prostate tumor protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo.

A portion of a sequence complementary to a coding sequence (i.e., an antisense polynucleotide) may also be used as a probe or to modulate gene expression. cDNA constructs that can be transcribed into antisense RNA may also be introduced into cells of tissues to facilitate the production of antisense RNA. An antisense polynucleotide may be used, as described herein, to inhibit expression of a prostate tumor protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches*, Futura Publishing Co. (Mt. Kisco, N.Y.; 1994)). Alternatively, an antisense molecule may be designed to hybridize with a control region of a gene (e.g., promoter, enhancer or transcription initiation site), and block transcription of the gene; or to block translation by inhibiting binding of a transcript to ribosomes.

A portion of a coding sequence or a complementary sequence may also be designed as a probe or primer to detect gene expression. Probes may be labeled by a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22–30 nucleotides in length.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating polynucleotides into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Prostrate Tumor Polypeptides

Within the context of the present invention, polypeptides may comprise at least a portion of a prostate tumor protein or a variant thereof, as described herein. As noted above, a "prostate tumor protein" is a protein that is overexpressed by prostate tumor cells, relative to normal prostate cells and/or other tissues such as brain, heart, kidney, liver, lung, pancreas, ovary, placenta, skeletal muscle, spleen and/or thymus. Such polypeptides should comprise a portion of a prostate tumor protein such that the therapeutic, antigenic and/or immunogenic properties of the polypeptide are not substantially diminished, relative to the full length protein. Within certain preferred embodiments, a polypeptide comprises an immunogenic portion of a native prostate tumor protein (i.e., the immunogenic properties of the polypeptide are not substantially diminished). As used herein, the term "polypeptide" encompasses amino acid chains of any length, including full length proteins, wherein the amino acid residues are linked by covalent peptide bonds. In addition to a portion of a prostate tumor protein, additional sequences derived from the native protein and/or heterologous sequences may be present, and such sequences may (but need not) possess further immunogenic or antigenic properties.

An "immunogenic portion," as used herein is a portion of an antigen that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a prostate tumor protein or a variant thereof. Immunogenic portions of prostate tumor proteins provided herein may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the antigen in an ELISA or other immunoassay, and do not react detectably with unrelated proteins). Such antisera and antibodies may be prepared as described herein, and using well known techniques. An immunogenic portion of a native prostate tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Alternatively, an immunogenic portion may react within such assays at a level that is diminished by less than 50%, and preferably less than 20%, relative to the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a polypeptide may comprise a variant of a native prostate tumor protein. A polypeptide "variant," as used herein, is a polypeptide that differs from a native prostate tumor protein in one or more substitutions, deletions, additions and/or insertions, such that the therapeutic, antigenic and/or immunogenic properties are not substantially diminished. Preferably, the immunogenic properties are not substantially diminished. In other words, the ability of a variant to react with antigen-specific antisera may be enhanced or unchanged, relative to the native antigen, or may be diminished by less than 50%, and preferably less than 20%, relative to the native antigen. Polypeptide variants preferably exhibit at least about 70%, more preferably at least about 90% and most preferably at least about 95% identity to polypeptides encoded by polynucleotides specifically recited herein. Identity may be determined by comparing sequences using computer algorithms well known to those of skill in the art, such as Megalign, using default parameters. For prostate tumor polypeptides with immunoreactive properties, variants may generally be identified by modifying one of the above polypeptide sequences and evaluating the reactivity of the modified polypeptide with antigen-specific antibodies or antisera as described herein. For prostate tumor polypeptides useful for the generation of diagnostic binding agents, a variant may be identified by evaluating a modified polypeptide for the ability to generate antibodies that detect the presence or absence of prostate cancer. Such modified sequences may be prepared and tested using, for example, the representative procedures described herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants containing substitutions may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by polynucleotide sequences as described above may be readily prepared from the polynucleotide sequences using any of a variety of expression vectors known to those of ordinary skill in the art. Expression may be achieved in any appropriate host cell that has been transformed or transfected with an expression vector containing a polynucleotide molecule that encodes a recombinant polypeptide. Suitable host cells include prokaryotes, yeast and higher eukaryotic cells. Preferably, the host cells employed are *E. coli*, yeast or a mammalian cell line, such as CHO cells. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc. (Foster City, Calif.), and may be operated according to the manufacturer's instructions.

Within certain specific embodiments, a polypeptide may be a fusion protein that comprises multiple polypeptides as described herein, or that comprises one polypeptide as described herein and a known prostate tumor antigen, or a variant of such an antigen. A fusion protein generally comprises at least one of the above immunogenic portions and one or more additional immunogenic prostate tumor sequences, which are joined via a peptide linkage into a single amino acid chain. The sequences may be joined directly (i.e., with no intervening amino acids) or may be joined by way of a linked sequence (e.g., Gly-Cys-Gly) that does not significantly diminish the immunogenic properties of the component polypeptides.

Fusion proteins may generally be prepared using standard techniques. For example, a fusion protein may be prepared recombinantly. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence may be incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated polynucleotide sequences are operably linked to suitable transcriptional or translational regulatory elements. The regulatory elements responsible for expression of polynucleotide are located only 5' to the polynucleotide sequence encoding the first polypeptides. Similarly, stop codons required to end translation and transcription termination signals are only present 3' to the polynucleotide sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.,* 336:86–91, 1997).

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to a prostate tumor protein. As used herein, an agent is said to "specifically bind" to a prostate tumor protein if it reacts at a detectable level (within, for example, an ELISA) with a prostate tumor protein, and does not react detectably with unrelated proteins under similar conditions. As used herein, "binding" refers to a noncovalent association between two separate molecules such that a "complex" is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents are further capable of detecting metastatic prostate tumors and differentiating between patients with and without prostate cancer, using a representative assay provided herein. In other words, antibodies or other binding agents that bind to a prostate tumor protein will generate a signal indicating the presence of prostate cancer in at least about 20% of patients with the disease, and will generate a negative signal indicating the absence of the disease in at least about 90% of individuals without the cancer. To determine whether a binding agent satisfies this requirement, biological samples (e.g., blood, blood-associated tumor cells, sera, urine, biopsies and/or prostate secretions) from patients with and without prostate cancer (as determined using standard clinical tests) may be assayed as described herein for the presence of polypeptides or polynucleotides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

If an immunogenic portion is employed, the resulting antibody should indicate the presence of prostate cancer in substantially all (i.e., at least 80%, and preferably at least 90%) of the patients for which prostate cancer would be indicated using an antibody raised against the full length antigen. The antibody should also indicate the absence of prostate cancer in substantially all of those samples that would be negative when tested with an antibody raised against the full length antigen. The representative assays provided herein, such as the two-antibody sandwich assay, may generally be employed for evaluating the ability of an antibody to detect prostate cancer.

Binding agents may be further linked to a reporter group, to facilitate diagnostic assays. Suitable reporter groups will be apparent to those of ordinary skill in the art, and include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Such antibodies may be polyclonal or monoclonal. In addition, the antibodies may be single chain, chimeric, CDR-grafted or humanized.

Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process within, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory*

Manual, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. U.S. Pat. No. 4,673,562, to Davison et al. discloses representative chelating compounds and their synthesis.

A variety of routes of administration for the antibodies and immunoconjugates may be used. Typically, administration is intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Pharmaceutical Compositions and Vaccines

Within certain aspects, polypeptides, polynucleotides and/or binding agents may be incorporated into pharmaceutical compositions or vaccines. Pharmaceutical compositions comprise one or more such compounds and a physiologically acceptable carrier. Vaccines may comprise one or more such compounds and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound within the composition or vaccine.

A pharmaceutical composition or vaccine may contain polynucleotides encoding one or more of the polypeptides as described above, such that the polypeptide is generated in situ. As noted above, the polynucleotides may be present within any of a variety of delivery systems known to those of ordinary skill in the art, including nucleic acid expression systems, bacteria and viral expression systems. Appropriate nucleic acid expression systems contain the necessary polynucleotide sequences for expression in the patient (such as a suitable promoter and terminating signal). Bacterial delivery systems involve the administration of a bacterium (such as *Bacillus-Calmette-Guerrin*) that expresses an immunogenic portion of the polypeptide on its cell surface. In a preferred embodiment, the polynucleotides may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad. Sci.* 569:86–103, 1989; Flexner et al., *Vaccine*

8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252: 431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating polynucleotides into such expression systems are well known to those of ordinary skill in the art. The polynucleotides may also be "naked," as described, for example, in Ulmer et al., *Science* 259:1745–1749, 1993 and reviewed by Cohen, *Science* 259:1691–1692, 1993. The uptake of naked polynucleotides may be increased by coating the polynucleotides onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration including, for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2, -7, or -12, may also be used as adjuvants.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Cancer Therapy

In further aspects of the present invention, the pharmaceutical compositions and vaccines described herein may be used for immunotherapy of cancer, such as prostate cancer, in a patient. Polypeptides for use within such compositions and vaccines generally comprise an immunogenic portion of a prostate tumor protein, or a variant thereof. Such polypeptides may stimulate the patient's own immune response to prostate tumor cells. Alternatively, a pharmaceutical composition or vaccine may comprise one or more fusion proteins comprising one or more such polypeptides and/or polynucleotides encoding such one or more such polypeptides. Monoclonal antibodies of the present invention may also be used as therapeutic reagents, to diminish or eliminate prostate tumors. The antibodies may be used on their own (for instance, to inhibit metastases) or coupled to one or more therapeutic agents, as described above.

Within such methods, pharmaceutical compositions and vaccines are typically administered to a patient. As used herein, a "patient" refers to any warm-blooded animal, preferably a human. A patient may be afflicted with a disease, or may be free of detectable disease. Accordingly, the above pharmaceutical compositions and vaccines may be used to prevent the development of prostate cancer or to treat a patient afflicted with prostate cancer. Prostate cancer may be diagnosed using criteria generally accepted in the art. Pharmaceutical compositions and vaccines may be administered either prior to or following surgical removal of primary tumors and/or treatment such as administration of radiotherapy or conventional chemotherapeutic drugs.

Routes and frequency of administration, as well as dosage, will vary from individual to individual, and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or polynucleotide that is effective to raise an immune response (cellular and/or humoral) against prostate tumor cells in a treated patient. A suitable immune response is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, the amount of polypeptide present in a dose (or produced in situ by the polynucleotides molecule in a dose)

ranges from about 1 pg to about 100 mg per kg of host, typically from about 10 pg to about 1 mg, and preferably from about 100 pg to about 1 µg. Suitable dose sizes will vary with the size of the patient, but will typically range from about 0.01 mL to about 5 mL. A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Polypeptides disclosed herein may also be employed in adoptive immunotherapy for the treatment of cancer. Adoptive immunotherapy may be broadly classified into either active or passive immunotherapy. In active immunotherapy, treatment relies on the in vivo stimulation of the endogenous host immune system to react against tumors with the administration of immune response-modifying agents (for example, tumor vaccines, bacterial adjuvants, and/or cytokines).

In passive immunotherapy, treatment involves the delivery of biologic reagents with established tumor-immune reactivity (such as effector cells or antibodies) that can directly or indirectly mediate antitumor effects and does not necessarily depend on an intact host immune system. Examples of effector cells include T lymphocytes (for example, CD8+ cytotoxic T-lymphocyte, CD4+ T-helper, gamma/delta T lymphocytes, tumor-infiltrating lymphocytes), killer cells (such as Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage, monocyte, fibroblast, or B-cells, may be pulsed with immunoreactive polypeptides, or polynucleotide sequence(s) may be introduced into antigen presenting cells, using a variety of standard techniques well known in the art. For example, antigen presenting cells may be transfected or transduced with a polynucleotide sequence, wherein said sequence contains a promoter region appropriate for increasing expression, and can be expressed as part of a recombinant virus or other expression system. Several viral vectors may be used to transduce an antigen presenting cell, including pox virus, vaccinia virus, and adenovirus; also, antigen presenting cells may be transfected with polynucleotide sequences disclosed herein by a variety of means, including gene-gun technology, lipid-mediated delivery, electroporation, osmotic shock, and particlate delivery mechanisms, resulting in efficient and acceptable expression levels as determined by one of ordinary skill in the art. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever, M., et al, "Therapy With Cultured T Cells: Principles Revisited," *Immunological Reviews*, 157: 177, 1997).

The polypeptides disclosed herein may also be employed to generate and/or isolate tumor-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ CTL clones may be isolated from the patient, expanded using standard tissue culture techniques, and returned to the patient.

Alternatively, peptides corresponding to immunogenic portions of the polypeptides may be employed to generate tumor reactive T cell subsets by selective in vitro stimulation and expansion of autologous T cells to provide antigen-specific T cells which may be subsequently transferred to the patient as described, for example, by Chang et al, (*Crit. Rev. Oncol. Hematol.*, 22(3), 213, 1996). Cells of the immune system, such as T cells, may be isolated from the peripheral blood of a patient, using a commercially available cell separation system, such as CellPro Incorporated's (Bothell, Wash.) CEPRATE™ system (see U.S. Pat. No. 5,240,856; U.S. Pat. No. 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

In other embodiments, T-cell and/or antibody receptors specific for the polypeptides disclosed herein can be cloned, expanded, and transferred into other vectors or effector cells for use in adoptive immunotherapy. In particular, T cells may be transfected with the appropriate genes to express the variable domains from tumor specific monoclonal antibodies as the extracellular recognition elements and joined to the T cell receptor signaling chains, resulting in T cell activation, specific lysis, and cytokine release. This enables the T cell to redirect its specificity in an MHC-independent manner. See for example, Eshhar, Z., *Cancer Immunol Immunother*, 45(3–4):131–6, 1997 and Hwu, P., et al, *Cancer Res*, 55(15):3369–73, 1995. Another embodiment may include the transfection of tumor antigen specific alpha and beta T cell receptor chains into alternate T cells, as in Cole, D J, et al, *Cancer Res*, 55(4):748–52, 1995.

In a further embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate tumors in a murine model has been demonstrated by Cheever et al, *Immunological Reviews*, 15 7:177, 1997).

Additionally, vectors expressing the disclosed polynucleotides may be introduced into stem cells taken from the patient and clonally propagated in vitro for autologous transplant back into the same patient.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a prostate tumor protein generally correlate with an improved clinical outcome. Such immune responses may generally be evaluated using standard proliferation, cytotoxicity or cytokine assays, which may be performed using samples obtained from a patient before and after treatment.

Methods for Detecting Cancer

In general, a cancer may be detected in a patient based on the presence of one or more prostate tumor proteins and/or polynucleotides encoding such proteins in a biological sample obtained from the patient. In other words, such proteins may be used as markers to indicate the presence or absence of prostate cancer. The binding agents provided herein generally permit detection of the level of protein that binds to the agent in the biological sample. Alternatively, polynucleotide primers and probes may be used to detect the level of mRNA encoding an antigen, which is also indicative of the presence or absence of prostate cancer.

There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length prostate tumor proteins and portions thereof to which the binding agent binds, as described above.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with prostate cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of prostate cancer, the signal detected from the reporter group that remains bound to the solid support is generally compared to a signal that corresponds to a predetermined cut-off value. In one preferred embodiment, the cut-off value for the detection of prostate cancer is the average mean signal obtained when the immobilized antibody is incubated with samples from patients without prostate cancer. In general, a sample generating a signal that is three standard deviations above the predetermined cut-off value is considered positive for prostate cancer. In an alternate preferred embodiment, the cut-off value is determined using a Receiver Operator Curve, according to the method of Sackett et al., *Clinical Epidemiology. A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for prostate cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of prostate cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the antigens or binding agents of the present invention. The above descriptions are intended to be exemplary only.

In another embodiment, the above polypeptides may be used as markers for the progression of prostate cancer. In this embodiment, assays as described above for the diagnosis of prostate cancer may be performed over time, and the change in the level of reactive polypeptide(s) evaluated. For example, the assays may be performed every 24–72 hours for a period of 6 months to 1 year, and thereafter performed as needed. In general, prostate cancer is progressing in those patients in whom the level of polypeptide detected by the binding agent increases over time. In contrast, the cancer is not progressing when the level of reactive polypeptide either remains constant or decreases with time.

As noted above, prostate cancer may also, or alternatively, be detected based on the level of mRNA encoding a prostate tumor protein in a biological sample. For example, at least two oligonucleotide primers may be employed in a polymerase chain reaction (PCR) based assay to amplify a portion of a prostate tumor protein cDNA derived from a biological sample, wherein at least one of the oligonucleotide primers is specific for (i.e., hybridizes to) a polynucleotide encoding the prostate tumor protein. The amplified cDNA is then separated and detected using techniques well known in the art, such as gel electrophoresis. Similarly, oligonucleotide probes that specifically hybridize to a polynucleotide encoding a prostate tumor protein may be used in a hybridization assay to detect the presence of polynucleotide encoding the antigen in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a prostate tumor protein that is at least 10 nucleotides, and preferably at least 20 nucleotides, in length. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule recited herein. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, N.Y., 1989).

One preferred assay employs RT-PCR, in which PCR is applied in conjunction with reverse transcription. Typically, RNA is extracted from a sample tissue and is reverse transcribed to produce cDNA molecules. PCR amplification using at least one specific primer generates a cDNA molecule, which may be separated and visualized using, for example, gel electrophoresis. Amplification may be performed on samples obtained from biological samples taken from a test patient and an individual who is not afflicted with prostate cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple prostate tumor protein markers may be assayed within a given sample. It will be apparent that binding agents specific for different antigens provided herein may be combined within a single assay. Further, multiple primers or probes may be used concurrently. The selection of antigen markers may be based on routine experiments to determine combinations that results in optimal sensitivity. In addition, or alternatively, assays for antigens provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a prostate tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a prostate tumor protein in a biological sample. Such kits generally comprise at least one oligonucleotide probe or primer, as described above, that hybridizes to a polynucleotide encoding a prostate tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a prostate tumor protein.

The following Examples are offered by way of illustration and not by way of limitation.

EXAMPLES

Example 1

Isolation and Characterization of Prostrate Tumor Polypeptides

This Example describes the isolation of certain prostate tumor polypeptides from a prostate tumor cDNA library.

A human prostate tumor cDNA expression library was constructed from prostate tumor poly $A^+$ RNA using a Superscript Plasmid System for cDNA Synthesis and Plasmid Cloning kit (BRL Life Technologies, Gaithersburg, Md. 20897) following the manufacturer's protocol. Specifically, prostate tumor tissues were homogenized with polytron (Kinematica, Switzerland) and total RNA was extracted using Trizol reagent (BRL Life Technologies) as directed by the manufacturer. The poly $A^+$ RNA was then purified using a Qiagen oligotex spin column mRNA purification kit (Qiagen, Santa Clarita, Calif. 91355) according to the manufacturer's protocol. First-strand cDNA was synthesized using the NotI/Oligo-dT18 primer. Double-stranded cDNA was synthesized, ligated with EcoRI/BAXI adaptors (Invitrogen, San Diego, Calif.) and digested with NotI. Following size fractionation with Chroma Spin-1000 columns (Clontech, Palo Alto, Calif.), the cDNA was ligated into the EcoRI/NotI site of pCDNA3.1 (Invitrogen) and transformed into ElectroMax *E. coli* DH10B cells (BRL Life Technologies) by electroporation.

Using the same procedure, a normal human pancreas cDNA expression library was prepared from a pool of six tissue specimens (Clontech). The cDNA libraries were characterized by determining the number of independent colonies, the percentage of clones that carried insert, the average insert size and by sequence analysis. The prostate tumor library contained $1.64 \times 10^7$ independent colonies, with 70% of clones having an insert and the average insert size being 1745 base pairs. The normal pancreas cDNA library contained $3.3 \times 10^6$ independent colonies, with 69% of clones having inserts and the average insert size being 1120 base pairs. For both libraries, sequence analysis showed that the majority of clones had a full length cDNA sequence and were synthesized from mRNA, with minimal rRNA and mitochondrial DNA contamination.

cDNA library subtraction was performed using the above prostate tumor and normal pancreas cDNA libraries, as described by Hara et al. (*Blood*, 84:189–199, 1994) with some modifications. Specifically, a prostate tumor-specific subtracted cDNA library was generated as follows. Normal pancreas cDNA library (70 µg) was digested with EcoRI, NotI, and SfuI, followed by a filling-in reaction with DNA polymerase Klenow fragment. After phenol-chloroform extraction and ethanol precipitation, the DNA was dissolved in 100 µl of $H_2O$, heat-denatured and mixed with 100 µl (100 µg) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (50 µl) was added and the biotinylation reaction was repeated. After extraction with butanol five times, the DNA was ethanol-precipitated and dissolved in 23 µl $H_2O$ to form the driver DNA.

To form the tracer DNA, 10 µg prostate tumor cDNA library was digested with BamHI and XhoI, phenol chloroform extracted and passed through Chroma spin-400 columns (Clontech). Following ethanol precipitation, the tracer DNA was dissolved in 5 µl $H_2O$. Tracer DNA was mixed with 15 µl driver DNA and 20 µl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 µl $H_2O$, mixed with 8 µl driver DNA and 20 µl of 2×hybridization buffer, and subjected to a hybridization at 68° C. for 2 hours (short hybridization [SH]). After removal of biotinylated double-stranded DNA, subtracted cDNA was ligated into BamHI/XhoI site of chloramphenicol resistant pBCSK$^+$ (Stratagene, La Jolla, Calif. 92037) and transformed into ElectroMax *E. coli* DH10B cells by electroporation to generate a prostate tumor specific subtracted cDNA library (prostate subtraction 1).

To analyze the subtracted cDNA library, plasmid DNA was prepared from 100 independent clones, randomly picked from the subtracted prostate tumor specific library and grouped based on insert size. Representative cDNA clones were further characterized by DNA sequencing with a Perkin Elmer/Applied Biosystems Division Automated Sequencer Model 373A (Foster City, Calif.). Six cDNA clones, hereinafter referred to as F-13, F-12, F1-16, H1-1, H1-9 and H1-4, were shown to be abundant in the subtracted prostate-specific cDNA library. The determined 3' and 5' cDNA sequences for F1-12 are provided in SEQ ID NO: 2 and 3, respectively, with determined 3' cDNA sequences for F1-13, F1-16, H1-1, H1-9 and H1-4 being provided in SEQ ID NO: 1 and 4–7, respectively.

The cDNA sequences for the isolated clones were compared to known sequences in the gene bank using the EMBL and GenBank databases (release 96). Four of the prostate tumor cDNA clones, F1-13, F1-16, H1-1, and H1-4, were determined to encode the following previously identified proteins: prostate specific antigen (PSA), human glandular kallikrein, human tumor expression enhanced gene, and mitochondria cytochrome C oxidase subunit II. H1-9 was found to be identical to a previously identified human autonomously replicating sequence. No significant homologies to the cDNA sequence for F1-12 were found.

Subsequent studies led to the isolation of a full-length cDNA sequence for F1-12. This sequence is provided in SEQ ID NO: 107, with the corresponding predicted amino acid sequence being provided in SEQ ID NO: 108.

To clone less abundant prostate tumor specific genes, cDNA library subtraction was performed by subtracting the prostate tumor cDNA library described above with the normal pancreas cDNA library and with the three most abundant genes in the previously subtracted prostate tumor specific cDNA library: human glandular kallikrein, prostate specific antigen (PSA), and mitochondria cytochrome C oxidase subunit II. Specifically, 1 µg each of human glandular kallikrein, PSA and mitochondria cytochrome C oxidase subunit II cDNAs in pCDNA3.1 were added to the driver DNA and subtraction was performed as described above to provide a second subtracted cDNA library hereinafter referred to as the "subtracted prostate tumor specific cDNA library with spike".

Twenty-two cDNA clones were isolated from the subtracted prostate tumor specific cDNA library with spike. The determined 3' and 5' cDNA sequences for the clones referred to as J1-17, L1-12, N1-1862, J1-13, J1-19, J1-25, J1-24, K1-58, K1-63, L1-4 and L1-14 are provided in SEQ ID NOS: 8–9, 10–11, 12–13, 14–15, 16–17, 18–19, 20–21, 22–23, 24–25, 26–27 and 28–29, respectively. The determined 3' cDNA sequences for the clones referred to as J1-12, J1-16, J1-21, K1-48, K1-55, L1-2, L1-6, N1-1858, N1-1860, N1-1861, N1-1864 are provided in SEQ ID NOS: 30–40, respectively. Comparison of these sequences with those in the gene bank as described above, revealed no significant homologies to three of the five most abundant DNA species, (J1-17, L1-12 and N1-1862; SEQ ID NOS: 8–9, 10–11 and 12–13, respectively). Of the remaining two most abundant species, one (J1-12; SEQ ID NO:30) was found to be identical to the previously identified human pulmonary surfactant-associated protein, and the other (K1-48; SEQ ID NO:33) was determined to have some homology to R. norvegicus mRNA for 2-arylpropionyl-CoA epimerase. Of the 17 less abundant cDNA clones isolated from the subtracted prostate tumor specific cDNA library with spike, four (J1-16, K1-55, L1-6 and N1-1864; SEQ ID NOS:31, 34, 36 and 40, respectively) were found to be identical to previously identified sequences, two (J1-21 and N1-1860; SEQ ID NOS: 32 and 38, respectively) were found to show some homology to non-human sequences, and two (L1-2 and N1-1861; SEQ ID NOS: 35 and 39, respectively) were found to show some homology to known human sequences. No significant homologies were found to the polypeptides J1-13, J1-19, J1-24, J1-25, K1-58, K1-63, L1-4, L1-14 (SEQ ID NOS: 14–15, 16–17, 20–21, 18–19, 22–23, 24–25, 26–27, 28–29, respectively).

Subsequent studies led to the isolation of full length cDNA sequences for J1-17, L1-12 and N1-1862 (SEQ ID NOS: 109–111, respectively). The corresponding predicted amino acid sequences are provided in SEQ ID NOS: 112–114. L1-12 is also referred to as P501 S.

In a further experiment, four additional clones were identified by subtracting a prostate tumor cDNA library with normal prostate cDNA prepared from a pool of three normal prostate poly A+ RNA (prostate subtraction 2). The determined cDNA sequences for these clones, hereinafter referred to as U1-3064, U1–3065, V1-3692 and 1A-3905, are provided in SEQ ID NO: 69–72, respectively. Comparison of the determined sequences with those in the gene bank revealed no significant homologies to U1-3065.

A second subtraction with spike (prostate subtraction spike 2) was performed by subtracting a prostate tumor specific cDNA library with spike with normal pancreas cDNA library and further spiked with PSA, J1-17, pulmonary surfactant-associated protein, mitochondrial DNA, cytochrome c oxidase subunit II, N1-1862, autonomously replicating sequence, L1-12 and tumor expression enhanced gene. Four additional clones, hereinafter referred to as V1-3686, R1-2330, 1B-3976 and V1-3679, were isolated. The determined cDNA sequences for these clones are provided in SEQ ID NO:73–76, respectively. Comparison of these sequences with those in the gene bank revealed no significant homologies to V1-3686 and R1-2330.

Further analysis of the three prostate subtractions described above (prostate subtraction 2, subtracted prostate tumor specific cDNA library with spike, and prostate subtraction spike 2) resulted in the identification of sixteen additional clones, referred to as 1G-4736, 1G-4738, 1G-4741, 1G-4744, 1G-4734, 1H-4774, 1H-4781, 1H-4785, 1H-4787, 1H-4796, 1I-4810, 1I-4811, 1J-4876, 1K-4884 and 1K-4896. The determined cDNA sequences for these clones are provided in SEQ ID NOS: 77–92, respectively. Comparison of these sequences with those in the gene bank as described above, revealed no significant homologies to 1G-4741, 1G-4734, 1I-4807, 1J-4876 and 1K-4896 (SEQ ID NOS: 79, 81, 87, 90 and 92, respectively). Further analysis of the isolated clones led to the determination of extended cDNA sequences for 1G-4736, 1G-4738, 1G-4741, 1G-4744, 1H-4774, 1H-4781, 1H-4785, 1H-4787, 1H-4796, 1I-4807, 1J-4876, 1K-4884 and 1K-4896, provided in SEQ ID NOS: 179–188 and 191–193, respectively, and to the determination of additional partial cDNA sequences for 1I-4810 and 1I-4811, provided in SEQ ID NOS: 189 and 190, respectively.

Additional studies with prostate subtraction spike 2 resulted in the isolation of three more clones. Their sequences were determined as described above and compared to the most recent Genbank. All three clones were found to have homology to known genes, which are Cysteine-rich protein, KIAA0242, and KIAA0280 (SEQ ID NO: 317, 319, and 320, respectively). Further analysis of these clones by Synteni microarray (Synteni, Palo Alto, Calif.)

demonstrated that all three clones were over-expressed in most prostate tumors and prostate BPH, as well as in the majority of normal prostate tissues tested, but low expression in all other normal tissues.

An additional subtraction was performed by subtracting a normal prostate cDNA library with normal pancreas cDNA (prostate subtraction 3). This led to the identification of six additional clones referred to as 1G-4761, 1G-4762, 1H-4766, 1H-4770, 1H-4771 and 1H-4772 (SEQ ID NOS: 93–98). Comparison of these sequences with those in the gene bank revealed no significant homologies to 1G-4761 and 1H-4771 (SEQ ID NOS: 93 and 97, respectively). Further analysis of the isolated clones led to the determination of extended cDNA sequences for 1G-4761, 1G-4762, 1H-4766 and 1H-4772 provided in SEQ ID NOS: 194–196 and 199, respectively, and to the determination of additional partial cDNA sequences for 1H-4770 and 1H-4771, provided in SEQ ID NOS: 197 and 198, respectively.

Subtraction of a prostate tumor cDNA library, prepared from a pool of polyA+ RNA from three prostate cancer patients, with a normal pancreas cDNA library (prostate subtraction 4) led to the identification of eight clones, referred to as 1D-4297, 1D-4309, 1D.1-4278, 1D-4288, 1D-4283, 1D-4304, 1D-4296 and 1D-4280, (SEQ ID NOS: 99–107). These sequences were compared to those in the gene bank as described above. No significant homologies were found to 1D-4283 and 1D-4304 (SEQ ID NOS: 103 and 104, respectively). Further analysis of the isolated clones led to the determination of extended cDNA sequences for 1D-4309, 1D.1–4278, 1D-4288, 1D-4283, 1D-4304, 1D-4296 and 1D-4280, provided in SEQ ID NOS: 200–206, respectively.

cDNA clones isolated in prostate subtraction 1 and prostate subtraction 2, described above, were colony PCR amplified and their mRNA expression levels in prostate tumor, normal prostate and in various other normal tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Two novel clones (referred to as P509S and P510S) were found to be over-expressed in prostate tumor and normal prostate and expressed at low levels in all other normal tissues tested (liver, pancreas, skin, bone marrow, brain, breast, adrenal gland, bladder, testes, salivary gland, large intestine, kidney, ovary, lung, spinal cord, skeletal muscle and colon). The determined cDNA sequences for P509S and P510S are provided in SEQ ID NO: 223 and 224, respectively. Comparison of these sequences with those in the gene bank as described above, revealed some homology to previously identified ESTs.

Additionally, the full-length cDNA sequence for P509S (SEQ ID NO: 223) is provided in SEQ ID NO: 332.

Example 2

Determination of Tissue Specificity of Prostrate Tumor Polypeptides

Using gene specific primers, mRNA expression levels for the representative prostate tumor polypeptides F1-16, H1-1, J1-17 (also referred to as P502S), L1-12 (also referred to as P501S), F1-12 (also referred to as P504S) and N1-1862 (also referred to as P503S) were examined in a variety of normal and tumor tissues using RT-PCR.

Briefly, total RNA was extracted from a variety of normal and tumor tissues using Trizol reagent as described above. First strand synthesis was carried out using 1–2 µg of total RNA with SuperScript II reverse transcriptase (BRL Life Technologies) at 42° C. for one hour. The cDNA was then amplified by PCR with gene-specific primers. To ensure the semi-quantitative nature of the RT-PCR, β-actin was used as an internal control for each of the tissues examined. First, serial dilutions of the first strand cDNAs were prepared and RT-PCR assays were performed using β-actin specific primers. A dilution was then chosen that enabled the linear range amplification of the β-actin template and which was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in four different types of tumor tissue (prostate tumor from 2 patients, breast tumor from 3 patients, colon tumor, lung tumor), and sixteen different normal tissues, including prostate, colon, kidney, liver, lung, ovary, pancreas, skeletal muscle, skin, stomach, testes, bone marrow and brain. F1-16 was found to be expressed at high levels in prostate tumor tissue, colon tumor and normal prostate, and at lower levels in normal liver, skin and testes, with expression being undetectable in the other tissues examined. H1-1 was found to be expressed at high levels in prostate tumor, lung tumor, breast tumor, normal prostate, normal colon and normal brain, at much lower levels in normal lung, pancreas, skeletal muscle, skin, small intestine, bone marrow, and was not detected in the other tissues tested. J1-17 (P502S) and L1-12 (P501S) appear to be specifically over-expressed in prostate, with both genes being expressed at high levels in prostate tumor and normal prostate but at low to undetectable levels in all the other tissues examined. N1-1862 (P503S) was found to be over-expressed in 60% of prostate tumors and detectable in normal colon and kidney. The RT-PCR results thus indicate that F1-16, H1-1, J1-17 (P502S), N1-1862 (P503S) and L1-12 (P501S) are either prostate specific or are expressed at significantly elevated levels in prostate.

Further RT-PCR studies showed that F1-12 (P504S) is over-expressed in 60% of prostate tumors, detectable in normal kidney but not detectable in all other tissues tested. Similarly, R1-2330 was shown to be over-expressed in 40% of prostate tumors, detectable in normal kidney and liver, but not detectable in all other tissues tested. U1-3064 was found to be over-expressed in 60% of prostate tumors, and also expressed in breast and colon tumors, but was not detectable in normal tissues.

RT-PCR characterization of R1-2330, U1-3064 and 1D-4279 showed that these three antigens are over-expressed in prostate and/or prostate tumors.

Northern analysis with four prostate tumors, two normal prostate samples, two BPH prostates, and normal colon, kidney, liver, lung, pancrease, skeletal muscle, brain, stomach, testes, small intestine and bone marrow, showed that L1-12 (P501 S) is over-expressed in prostate tumors and normal prostate, while being undetectable in other normal tissues tested. J1-17 (P502S) was detected in two prostate tumors and not in the other tissues tested. N1-1862 (P503S) was found to be over-expressed in three prostate tumors and to be expressed in normal prostate, colon and kidney, but not in other tissues tested. F1-12 (P504S) was found to be highly expressed in two prostate tumors and to be undetectable in all other tissues tested.

The micro-array technology described above was used to determine the expression levels of representative antigens described herein in prostate tumor, breast tumor and the following normal tissues: prostate, liver, pancreas, skin, bone marrow, brain, breast, adrenal gland, bladder, testes, salivary gland, large intestine, kidney, ovary, lung, spinal cord, skeletal muscle and colon. L1-12 (P501S) was found to be over-expressed in normal prostate and prostate tumor, with some expression being detected in normal skeletal muscle. Both J1-12 and F1-12 (P504S) were found to be over-expressed in prostate tumor, with expression being lower or undetectable in all other tissues tested. N1-1862 (P503S) was found to be expressed at high levels in prostate tumor and normal prostate, and at low levels in normal large intestine and normal colon, with expression being undetectable in all other tissues tested. R1-2330 was found to be over-expressed in prostate tumor and normal prostate, and to be expressed at lower levels in all other tissues tested. 1D-4279 was found to be over-expressed in prostate tumor and normal prostate, expressed at lower levels in normal spinal cord, and to be undetectable in all other tissues tested.

Further studies to specifically address the extent to which P501S (SEQ ID NO: 110) was expressed in breast tumor by microarray analysis revealed moderate over-expression in not only breast tumor, but also in metastatic breast tumor (2/31), with negligable to low expression in normal tissues. This data demonstrates that P501S may be over-expressed in various breast tumors as well as in prostate tumors.

Example 3

Isolation and Characterization of Prostrate Tumor Polypeptides by PCR-based Subtraction A cDNA subtraction library, containing cDNA from normal prostate subtracted with ten other normal tissue cDNAs (brain, heart, kidney, liver, lung, ovary, placenta, skeletal muscle, spleen and thymus) and then submitted to a first round of PCR amplification, was purchased from Clontech. This library was subjected to a second round of PCR amplification, following the manufacturer's protocol. The resulting cDNA fragments were subcloned into the vector pT7 Blue T-vector (Novagen, Madison, Wis.) and transformed into XL-1 Blue MRF' *E. coli* (Stratagene). DNA was isolated from independent clones and sequenced using a Perkin Elmer/Applied Biosystems Division Automated Sequencer Model 373A.

Fifty-nine positive clones were sequenced. Comparison of the DNA sequences of these clones with those in the gene bank, as described above, revealed no significant homologies to 25 of these clones, hereinafter referred to as P5, P8, P9, P18, P20, P30, P34, P36, P38, P39, P42, P49, P50, P53, P55, P60, P64, P65, P73, P75, P76, P79 and P84. The determined cDNA sequences for these clones are provided in SEQ ID NO:41–45, 47–52 and 54–65, respectively. P29, P47, P68, P80 and P82 (SEQ ID NO:46, 53 and 66–68, respectively) were found to show some degree of homology to previously identified DNA sequences. To the best of the inventors' knowledge, none of these sequences have been previously shown to be present in prostate.

Further studies using the PCR-based methodology described above resulted in the isolation of more than 180 additional clones, of which 23 clones were found to show no significant homologies to known sequences. The determined cDNA sequences for these clones are provided in SEQ ID NO: 115–123, 127, 131, 137, 145, 147–151, 153, 156–158 and 160. Twenty-three clones (SEQ ID NO: 124–126, 128–130, 132–136, 138–144, 146, 152, 154, 155 and 159) were found to show some homology to previously identified ESTs. An additional ten clones (SEQ ID NO: 161–170) were found to have some degree of homology to known genes. Larger cDNA clones containing the P20 sequence represent splice variants of a gene referred to as P703P. The determined DNA sequence for the variants referred to as DE 1, DE 13 and DE 14 are provided in SEQ ID NOS: 171, 175 and 177, respectively, with the corresponding predicted amino acid sequences being provided in SEQ ID NO: 172, 176 and 178, respectively. The determined cDNA sequence for an extended spliced form of P703 is provided in SEQ ID NO: 225. The DNA sequences for the splice variants referred to as DE2 and DE6 are provided in SEQ ID NOS: 173 and 174, respectively.

mRNA Expression levels for representative clones in tumor tissues (prostate (n=5), breast (n=2), colon and lung) normal tissues (prostate (n=5), colon, kidney, liver, lung (n=2), ovary (n=2), skeletal muscle, skin, stomach, small intestine and brain), and activated and non-activated PBMC was determined by RT-PCR as described above. Expression was examined in one sample of each tissue type unless otherwise indicated.

P9 was found to be highly expressed in normal prostate and prostate tumor compared to all normal tissues tested except for normal colon which showed comparable expression. P20, a portion of the P703P gene, was found to be highly expressed in normal prostate and prostate tumor, compared to all twelve normal tissues tested. A modest increase in expression of P20 in breast tumor (n=2), colon tumor and lung tumor was seen compared to all normal tissues except lung (1 of 2). Increased expression of P18 was found in normal prostate, prostate tumor and breast tumor compared to other normal tissues except lung and stomach. A modest increase in expression of P5 was observed in normal prostate compared to most other normal tissues. However, some elevated expression was seen in normal lung and PBMC. Elevated expression of P5 was also observed in prostate tumors (2 of 5), breast tumor and one lung tumor sample. For P30, similar expression levels were seen in normal prostate and prostate tumor, compared to six of twelve other normal tissues tested. Increased expression was seen in breast tumors, one lung tumor sample and one colon tumor sample, and also in normal PBMC. P29 was found to be over-expressed in prostate tumor (5 of 5) and normal prostate (5 of 5) compared to the majority of normal tissues. However, substantial expression of P29 was observed in normal colon and normal lung (2 of 2). P80 was found to be over-expressed in prostate tumor (5 of 5) and normal prostate (5 of 5) compared to all other normal tissues tested, with increased expression also being seen in colon tumor.

Further studies resulted in the isolation of twelve additional clones, hereinafter referred to as 10-d8, 10-h10, 11-c8, 7-g6, 8-b5, 8-b6, 8-d4, 8-d9, 8-g3, 8-h11, 9-f12 and 9-f3. The determined DNA sequences for 10-d8, 10-h10, 11-c8, 8-d4, 8-d9, 8-h11, 9-f12 and 9-f3 are provided in SEQ ID NO: 207, 208, 209, 216, 217, 220, 221 and 222, respectively. The determined forward and reverse DNA sequences for 7-g6, 8-b5, 8-b6 and 8-g3 are provided in SEQ ID NO: 210 and 211; 212 and 213; 214 and 215; and 218 and 219, respectively. Comparison of these sequences with those in the gene bank revealed no significant homologies to the sequence of 9-f3. The clones 10-d8, 11-c8 and 8-h11 were found to show some homology to previously isolated ESTs, while 10-h10, 8-b5, 8-b6, 8-d4, 8-d9, 8-g3 and 9-f12 were found to show some homology to previously identified genes. Further characterization of 7-G6 and 8-G3 showed identity to the known genes PAP and PSA, respectively.

mRNA expression levels for these clones were determined using the micro-array technology described above. The clones 7-G6, 8-G3, 8-B5, 8-B6, 8-D4, 8-D9, 9-F3, 9-F12, 9-H3, 10-A2, 10-A4, 11-C9 and 11-F2 were found to be over-expressed in prostate tumor and normal prostate, with expression in other tissues tested being low or undetectable. Increased expression of 8-F11 was seen in prostate tumor and normal prostate, bladder, skeletal muscle and colon. Increased expression of 10-H10 was seen in prostate tumor and normal prostate, bladder, lung, colon, brain and large intestine. Increased expression of 9-B1 was seen in prostate tumor, breast tumor, and normal prostate, salivary gland, large intestine and skin, with increased expression of 11-C8 being seen in prostate tumor, and normal prostate and large intestine.

An additional cDNA fragment derived from the PCR-based normal prostate subtraction, described above, was found to be prostate specific by both micro-array technology and RT-PCR. The determined cDNA sequence of this clone (referred to as 9-A11) is provided in SEQ ID NO: 226. Comparison of this sequence with those in the public databases revealed 99% identity to the known gene HOXB13.

Further studies led to the isolation of the clones 8-C6 and 8-H7. The determined cDNA sequences for these clones are provided in SEQ ID NO: 227 and 228, respectively. These sequences were found to show some homology to previously isolated ESTs.

PCR and hybridization-based methodologies were employed to obtain longer cDNA sequences for clone P20 (also referred to as P703P), yielding three additional cDNA fragments that progressively extend the 5' end of the gene. These fragments, referred to as P703PDE5, P703P6.26, and P703PX_23 (SEQ ID NO: 326, 328, and 330, with the predicted corresponding amino acid sequences in SEQ ID NO: 327, 329, and 331, respectively) contain additional 5' sequence. P703PDE5 was recovered by screening of a cDNA library (#141–26) with a portion of P703P as a probe. P703P6.26 was recovered from a mixture of three prostate tumor cDNAs and P703PX_23 was recovered from cDNA library (#438–48). Together, the additional sequences include all of the putative mature serine protease along with the majority of the putative signal sequence. Further studies using a PCR-based subtraction library of a prostate tumor pool subtracted against a pool of normal tissues (referred to as JP: PCR subtraction) resulted in the isolation of thirteen additional clones, seven of which did not share any significant homology to known Genbank sequences. The determined cDNA sequences for novel clones P711P, P712P, P774P, P775P, novel 27, P710P, and P768P are provided in SEQ ID NO: 307–311, 313, and 315, respectively. The remaining six clones (SEQ ID NO: 316, and 321–325) were shown to share homology to known genes. By microarray analysis, all thirteen clones showed three or more fold over-expression in prostate tissues, including prostate tumors, BPH, and normal prostate as compared to normal non-prostate tissues. Clones P711P, P712P, novel 23, and P768P showed over-expression in most prostate tumors and BPH tissues tested (n=29), and in the majority of normal prostate tissues (n=4), but background to low expression levels in all normal tissues. Clones P774P, P775P, and P710P showed comparatively lower expression and expression in fewer prostate tumors and BPH samples, with negative to low expression in normal prostate.

Using PCR and hybridization-based methodologies, additional cDNA sequence information was derived for two clones described above, 11-C9 and 9-F3, herein after referred to as P707P and P714P, respectively (SEQ ID NO: 333 and 334). After comparison with the most recent Genbank, P707P was found to be a splice variant of the known gene HoxB13. While there are some differences in the published sequence and the derived cDNA sequence, the differences are likely due to allelic variation. In contrast, P714P does not share homology with any know gene sequence and therefore is novel.

Additionally, clones 8-B3, P89, P98, P130, and P201 (as disclosed in U.S. patent application Ser. No. 09/020,956, filed Feb. 9, 1998) were found to be contained within one contiguous sequence, referred to as P705P (SEQ ID NO: 335, with the predicted amino acid sequence provided in SEQ ID NO: 336), which was determined to be a splice variant of the known gene NKX 3.1.

Example 4

Synthesis of Polypeptides

Polypeptides may be synthesized on a Perkin Elmer/Applied Biosystems 430A peptide synthesizer using FMOC chemistry with HPTU (O-Benzotriazole-N, N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

Example 5

Further Isolation and Characterization of Prostate Tumor Polypeptides by PCR-based Subtraction A cDNA library generated from prostate primary tumor mRNA as described above was subtracted with cDNA from normal prostate. The subtraction was performed using a PCR-based protocol (Clontech), which was modified to generate larger fragments. Within this protocol, tester and driver double stranded cDNA were separately digested with five restriction enzymes that recognize six-nucleotide restriction sites (MluI, MscI, PvuII, SalI and StuI). This digestion resulted in an average cDNA size of 600 bp, rather than the average size of 300 bp that results from digestion with RsaI according to the Clontech protocol. This modification did not affect the subtraction efficiency. Two tester populations were then created with different adapters, and the driver library remained without adapters.

The tester and driver libraries were then hybridized using excess driver cDNA. In the first hybridization step, driver was separately hybridized with each of the two tester cDNA populations. This resulted in populations of (a) unhybridized tester cDNAs, (b) tester cDNAs hybridized to other tester cDNAs, (c) tester cDNAs hybridized to driver cDNAs and (d) unhybridized driver cDNAs. The two separate hybridization reactions were then combined, and rehybridized in the presence of additional denatured driver cDNA. Following this second hybridization, in addition to populations (a) through (d), a fifth population (e) was generated in which tester cDNA with one adapter hybridized to tester cDNA with the second adapter. Accordingly, the second hybridization step resulted in enrichment of differentially expressed sequences which could be used as templates for PCR amplification with adaptor-specific primers.

The ends were then filled in, and PCR amplification was performed using adaptor-specific primers. Only population (e), which contained tester cDNA that did not hybridize to driver cDNA, was amplified exponentially. A second PCR amplification step was then performed, to reduce background and further enrich differentially expressed sequences.

This PCR-based subtraction technique normalizes differentially expressed cDNAs so that rare transcripts that are overexpressed in prostate tumor tissue may be recoverable. Such transcripts would be difficult to recover by traditional subtraction methods.

In addition to genes known to be overexpressed in prostate tumor, seventy-seven novel clones were identified. Sequences of these partial cDNAs are provided in SEQ ID NOs:229 to 305. Most of these clones had no significant homology to database sequences. Exceptions were JPTPN23 (SEQ ID NO:231; similarity to pig valosin-containing protein), JPTPN30 (SEQ ID NO:234; similarity to rat mRNA for proteasome subunit), JPTPN45 (SEQ ID NO:243; similarity to rat *norvegicus* cytosolic NADP-dependent isocitrate dehydrogenase), JPTPN46 (SEQ ID NO:244; similarity to human subclone H8 4 d4 DNA sequence), JP1D6 (SEQ ID NO:265; similarity to *G. gallus* dynein light chain-A), JP8D6 (SEQ ID NO:288); similarity to human BAC clone RG016J04), JP8F5 (SEQ ID NO:289; similarity to human subclone H8 3 b5 DNA sequence) and JP8E9 (SEQ ID NO:299; similarity to human Alu sequence).

The novel clones identified were:

| | |
|---|---|
| JPTPN13 | SEQ ID NO: 229 |
| JPTPN14 | SEQ ID NO: 230 |
| JPTPN23 | SEQ ID NO: 231 |
| JPTPN24 | SEQ ID NO: 232 |
| JPTPN25 | SEQ ID NO: 233 |
| JPTPN30 | SEQ ID NO: 234 |
| JPTPN34 | SEQ ID NO: 235 |
| JPTPN35 | SEQ ID NO: 236 |
| JPTPN36 | SEQ ID NO: 237 |
| JPTPN38 | SEQ ID NO: 238 |
| JPTPN39 | SEQ ID NO: 239 |
| JPTPN40 | SEQ ID NO: 240 |
| JPTPN41 | SEQ ID NO: 241 |
| JPTPN42 | SEQ ID NO: 242 |
| JPTPN45 | SEQ ID NO: 243 |
| JPTPN46 | SEQ ID NO: 244 |
| JPTPN51 | SEQ ID NO: 245 |
| JPTPN56 | SEQ ID NO: 246 |
| JPTPN64 | SEQ ID NO: 247 |
| JPTPN65 | SEQ ID NO: 248 |
| JPTPN67 | SEQ ID NO: 249 |
| JPTPN76 | SEQ ID NO: 250 |
| JPTPN84 | SEQ ID NO: 251 |
| JPTPN85 | SEQ ID NO: 252 |
| JPTPN86 | SEQ ID NO: 253 |
| JPTPN87 | SEQ ID NO: 254 |
| JPTPN88 | SEQ ID NO: 255 |
| JP1F1 | SEQ ID NO: 256 |
| JP1F2 | SEQ ID NO: 257 |
| JP1C2 | SEQ ID NO: 258 |
| JP1B1 | SEQ ID NO: 259 |
| JP1B2 | SEQ ID NO: 260 |
| JP1D3 | SEQ ID NO: 261 |
| JP1A4 | SEQ ID NO: 262 |
| JP1F5 | SEQ ID NO: 263 |
| JP1E6 | SEQ ID NO: 264 |
| JP1D6 | SEQ ID NO: 265 |
| JP1B5 | SEQ ID NO: 266 |
| JP1A6 | SEQ ID NO: 267 |
| JP1E8 | SEQ ID NO: 268 |
| JP1D7 | SEQ ID NO: 269 |
| JP1D9 | SEQ ID NO: 270 |
| JP1C10 | SEQ ID NO: 271 |
| JP1A9 | SEQ ID NO: 272 |
| JP1F12 | SEQ ID NO: 273 |
| JP1E12 | SEQ ID NO: 274 |
| JP1D11 | SEQ ID NO: 275 |
| JP1C11 | SEQ ID NO: 276 |
| JP1C12 | SEQ ID NO: 277 |
| JP1B12 | SEQ ID NO: 278 |
| JP1A12 | SEQ ID NO: 279 |
| JP8G2 | SEQ ID NO: 280 |
| JP8H1 | SEQ ID NO: 281 |
| JP8H2 | SEQ ID NO: 282 |
| JP8A3 | SEQ ID NO: 283 |
| JP8A4 | SEQ ID NO: 284 |
| JP8C3 | SEQ ID NO: 285 |
| JP8G4 | SEQ ID NO: 286 |
| JP8B6 | SEQ ID NO: 287 |
| JP8D6 | SEQ ID NO: 288 |
| JP8F5 | SEQ ID NO: 289 |
| JP8A8 | SEQ ID NO: 290 |
| JP8C7 | SEQ ID NO: 291 |
| JP8D7 | SEQ ID NO: 292 |
| JP8D8 | SEQ ID NO: 293 |
| JP8E7 | SEQ ID NO: 294 |
| JP8F8 | SEQ ID NO: 295 |
| JP8G8 | SEQ ID NO: 296 |
| JP8B10 | SEQ ID NO: 297 |
| JP8C10 | SEQ ID NO: 298 |
| JP8E9 | SEQ ID NO: 299 |
| JP8E10 | SEQ ID NO: 300 |
| JP8F9 | SEQ ID NO: 301 |
| JP8H9 | SEQ ID NO: 302 |
| JP8C12 | SEQ ID NO: 303 |
| JP8E11 | SEQ ID NO: 304 |
| JP8E12 | SEQ ID NO: 305 |

Additional studies using the PCR-based subtraction library consisting of a prostate tumor pool subtracted against a normal prostate pool (referred to as PT-PN PCR subtraction) yielded three additional clones. Comparison of the cDNA sequences of these clones with the most recent Genbank revealed two to be novel, herein after referred to as P715P and P767P (SEQ ID NO: 312 and 314). The remaining clone was shown to share homology to the known gene KIAA0056 (SEQ ID NO: 318). Using microarray analysis to measure mRNA expression levels in various tissues, all three clones were found to be over-expressed in prostate tumors and BPH tissues. Specifically, clone P715P was over-expressed in most prostate tumors and BPH tissues by a factor of three or greater, with elevated expression seen in the majority of normal prostate samples and in fetal tissue, but negative to low expression in all other normal tissues. Clone P767P was over-expressed in several prostate tumors and BPH tissues, with moderate expression levels in half of the normal prostate samples, and background to low expression in all other normal tissues tested.

Example 6

Peptide Priming of Mice and Propagation of CTL Lines 6.1. This Example illustrates the preparation of a CTL cell line specific for cells expressing the P502S gene.

Mice expressing the transgene for human HLA A2. 1 (provided by Dr L. Sherman, The Scripps Research Institute, La Jolla, Calif.) were immunized with P2S #12 peptide (VLGWVAEL; SEQ ID NO: 306), which is derived from the P502S gene (also referred to herein as J1-17, SEQ ID NO:8), as described by Theobald et al., *Proc. Natl. Acad. Sci. USA* 92:11993–11997, 1995 with the following modifications. Mice were immunized with 100 μg of P2S #12 and 120 μg of an I-A$^b$ binding peptide derived from hepatitis B Virus protein emulsified in incomplete Freund's adjuvant. Three weeks later these mice were sacrificed and using a nylon mesh single cell suspensions prepared. Cells were then resuspended at 6×10$^6$ cells/ml in complete media (RPMI-1640 (Gibco BRL, Gaithersburg, Md.) containing 10% FCS, 2 mM Glutamine (Gibco BRL), sodium pyruvate (Gibco BRL), non- essential amino acids (Gibco BRL, 2×10$^{-5}$ M 2-mercaptoethanol, 50 U/ml penicillin and streptomycin) and cultured in the presence of irradiated (3000 rads) P2S#12 pulsed (5 mg/ml P2S #12 and 10 mg/ml β2-microglobulin) LPS blasts (A2 transgenic spleens cells cultured in the presence of 7 μg/ml dextran sulfate and 25 μg/ml LPS for 3 days). Six days later cells (5×10$^5$/ml) were restimulated with 2.5×10$^6$/ml peptide pulsed irradiated (20,000 rads) EL4A2Kb cells (Sherman et al, *Science* 258:815–818, 1992) and 3×10$^6$/ml A2 transgenic spleen feeder cells. Cells were cultured in the presence of 20 U/ml IL-2. Cells were continued to be restimulated on a weekly basis as mentioned, in preparation for cloning the line.

P2S#12 line was cloned by limiting dilution analysis with peptide pulsed EL4 A2Kb tumor cells (1×104 cells/ well) as stimulators and A2 transgenic spleen cells as feeders ( 5×10$_5$ cells/ well) grown in the presence of 30 U/ml IL-2. On day 14, cells were restimulated as before. On day 21, clones that were growing were isolated and maintained in culture. Several of these clones demonstrated reactivity (lysis) against human fibroblasts (HLA A2.1 expressing) transduced with P502S gene significantly higher than control fibroblasts. An example is presented in FIG. 1.

This data indicates that P2S #12 represents a naturally processed epitope of the P502S protein that is expressed in the context of the human HLA A2.1 molecule.

6.2. This Example illustrates the preparation of murine CTL lines and CTL clones specific for cells expressing the P501S gene.

Figure 3:
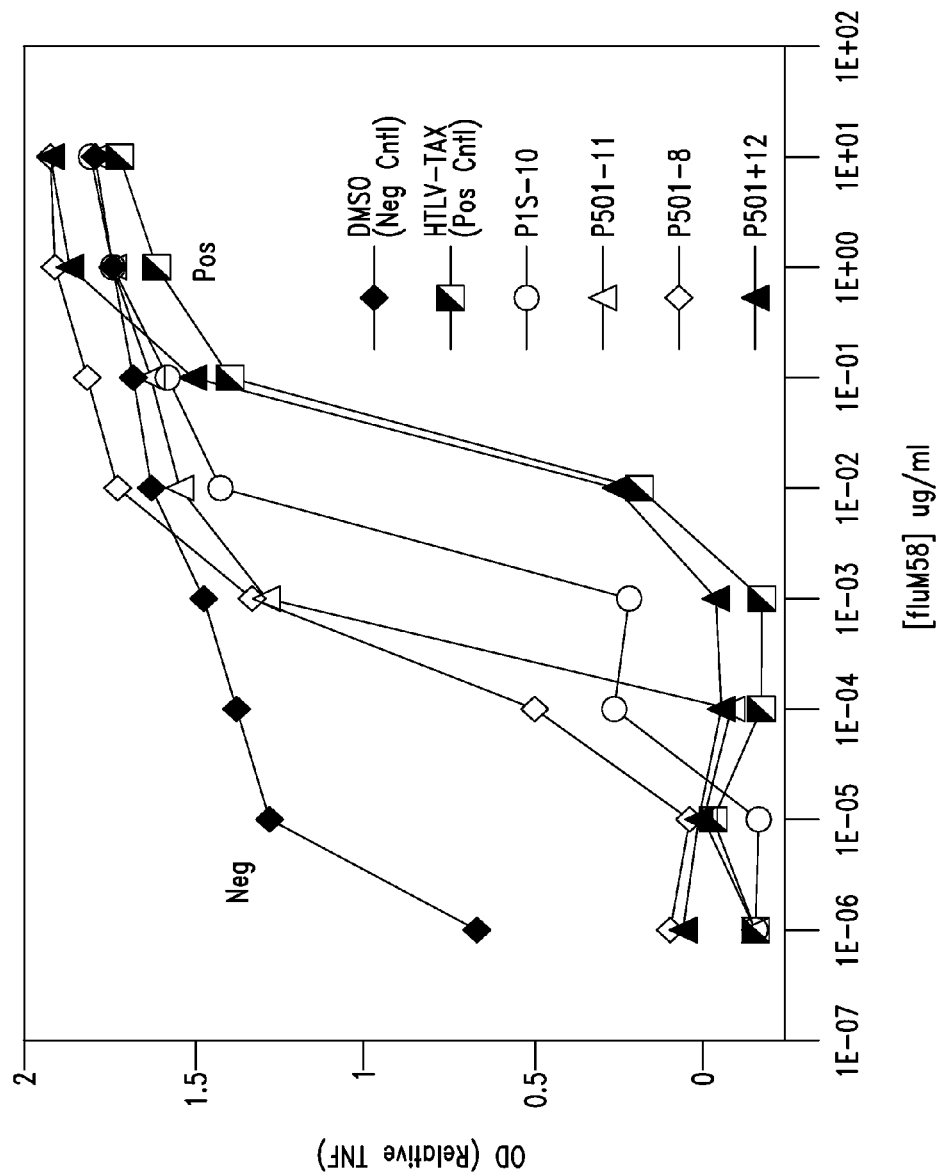
FIG. 3 represents a peptide competition binding assay showing that the P1S#10 peptide, derived from P501S, binds HLA-A2. Peptide P1S#10 inhibits HLA-A2 restricted presentation of fluM58 peptide to CTL clone D150M58 in TNF release bioassay. D150M58 CTL is specific for the HLA-A2 binding influenza matrix peptide fluM58.

This series of experiments were performed similarly to that described above. Mice were immunized with the P1S #10 peptide (SEQ ID NO: 337), which is derived from the P501S gene (also referred to herein as L1–12, SEQ ID NO:110). The P1S#10 peptide was derived by analysis of the predicted polypeptide sequence for P501S for potential HLA-A2 binding sequences as defined by published HLA-A2 binding motifs (Parker, K C, et al, *J. Immunol.*, 152:163, 1994). P1S#10 peptide was synthesized by methods described in Example 4, and empirically tested for HLA-A2 binding using a T cell based competition assay. Predicted A2 binding peptides were tested for their ability to compete HLA-A2 specific peptide presentation to an HLA-A2 restricted CTL clone (D150M58), which is specific for the HLA-A2 binding influenza matrix peptide fluM58. D150M58 CTL secretes TNF in response to self-presentation of peptide fluM58. In the competition assay, test peptides at 100–200 ug/ml were added to cultures of D150M58 CTL in order to bind HLA-A2 on the CTL. After thirty minutes, CTL cultured with test peptides, or control peptides, were tested for their antigen dose response to the fluM58 peptide in a standard TNF bioassay. FIG. 3 shows peptide P1S#10 competes HLA-A2 restricted presentation of fluM58, demonstrating that peptide P1S#10 binds HLA-A2.

Figure 4:
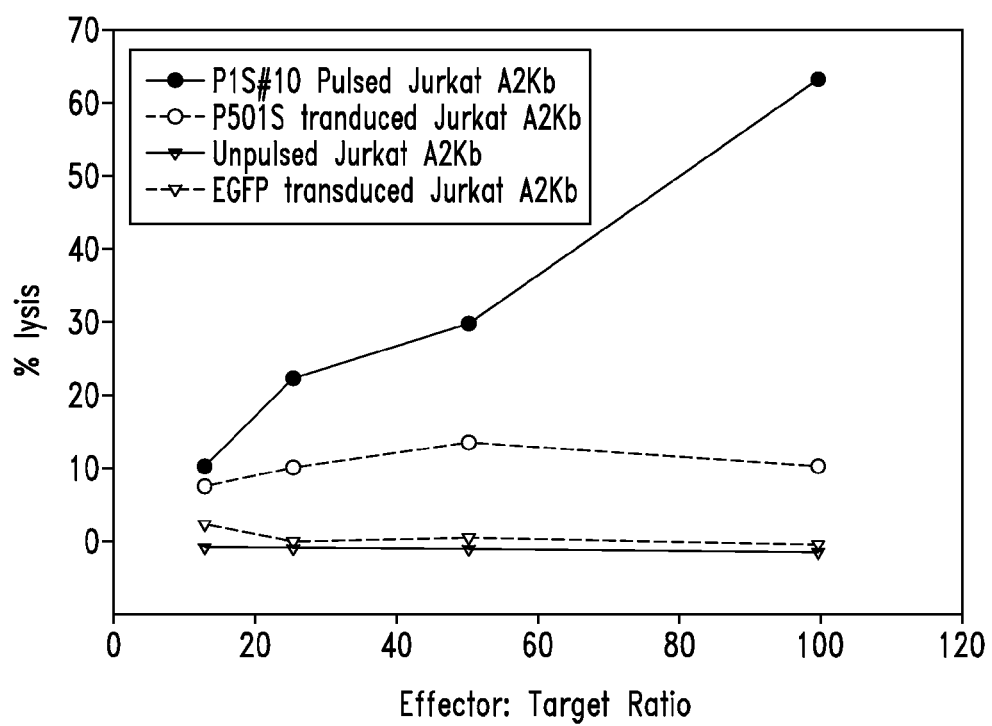
FIG. 4 is a graph illustrating the ability of T cell lines generated from P1S#10 immunized mice to specifically lyse P1S#10-pulsed Jurkat A2Kb targets and P501 S-transduced Jurkat A2Kb targets, as compared to EGFP-transduced Jurkat A2Kb. The per cent lysis is shown as a series of effector to target ratios, as indicated.

Mice expressing the transgene for human HLA A2.1 were immunized as described by Theobald et al., *Proc. Natl. Acad. Sci USA* 92:11993–11997, 1995 with the following modifications. Mice were immunized with 62.5 μg of P1S #10 and 120 μg of an I-A$^b$ binding peptide derived from Hepatitis B Virus protein emulsified in incomplete Freund's adjuvant. Three weeks later these mice were sacrificed and using a nylon mesh single cell suspensions prepared. Cells were then resuspended at 6×10$^6$ cells/ml in complete media (as described above) and cultured in the presence of irradiated (3000rads) P1S#10 pulsed (2 μg/ml P1S#10 and 10 mg/ml β2-microglobulin) LPS blasts (A2 transgenic spleens cells cultured in the presence of 7 μg/ml dextran sulfate and 25 μg/ml LPS for 3 days). Six days later cells (5×10$^5$/ml) were restimulated with 2.5×10$^6$/ml peptide-pulsed irradiated (20,000 rads) EL4A2Kb cells, as described above, and 3×10$^6$/ml A2 transgenic spleen feeder cells. Cells were cultured in the presence of 20 U/ml IL-2. Cells were restimulated on a weekly basis in preparation for cloning. After three rounds of in vitro stimulations, one line was generated that recognized P1S#10-pulsed Jurkat A2Kb targets and P501 S-transduced Jurkat targets as shown in FIG. 4.

Figure 5:
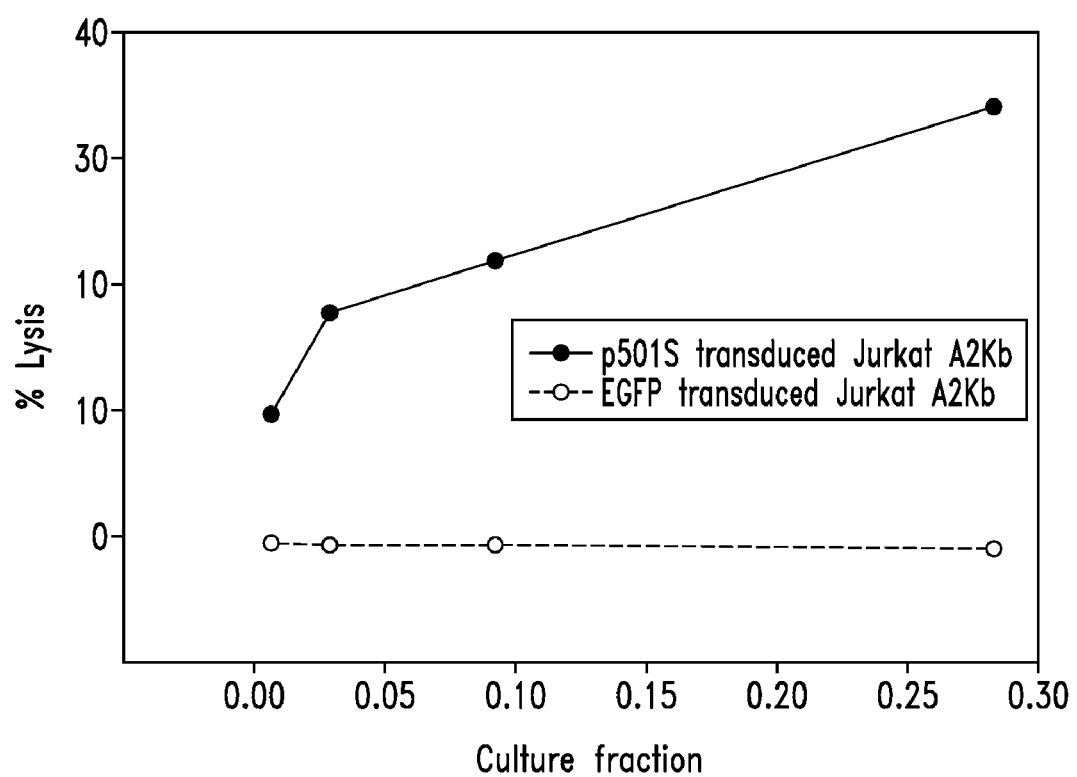
FIGS. 5 illustrates the ability of a T cell clone to recognize and specifically lyse Jurkat A2Kb cells expressing the representative prostate tumor polypeptide P501S, thereby demonstrating that the P1S#10 peptide may be a naturally processed epitope of the P501S polypeptide.

A P1S#10-specific CTL line was cloned by limiting dilution analysis with peptide pulsed EL4 A2Kb tumor cells (1×10$^4$ cells/ well) as stimulators and A2 transgenic spleen cells as feeders ( 5×10$^5$ cells/ well) grown in the presence of 30 U/ml IL-2. On day 14, cells were restimulated as before. On day 21, viable clones were isolated and maintained in culture. Five of these clones demonstrated specific cytolytic reactivity against P501S-transduced Jurkat A2Kb targets. As shown in FIG. 5, this data indicates that P1 S#10 represents a naturally processed epitope of the P501S protein that is expressed in the context of the human HLA-A2.1 molecule.

Example 7

Ability of Human T Cells to Recognize Prostate Tumor Polypeptides

This Example illustrates the ability of T cells specific for a prostate tumor polypeptide to recognize human tumor.

Figure 2A:
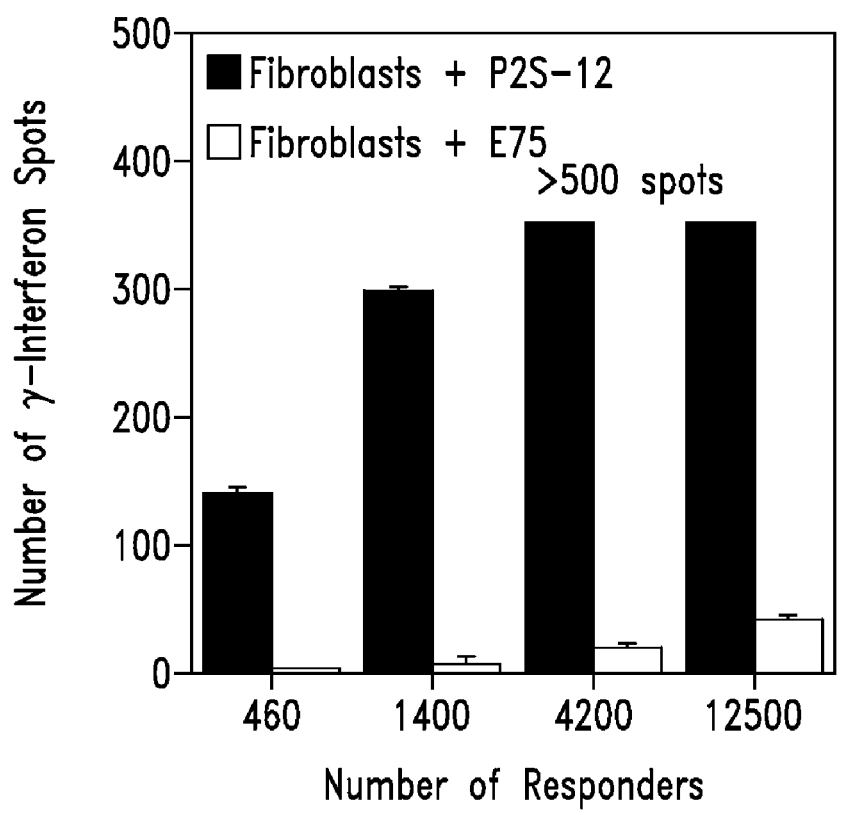
FIGS. 2A and 2B are graphs illustrating the ability of T cells to recognize cells expressing the representative prostate tumor polypeptide P502S. In each case, the number of γ-interferon spots is shown for different numbers of responders.
Figure 2B:
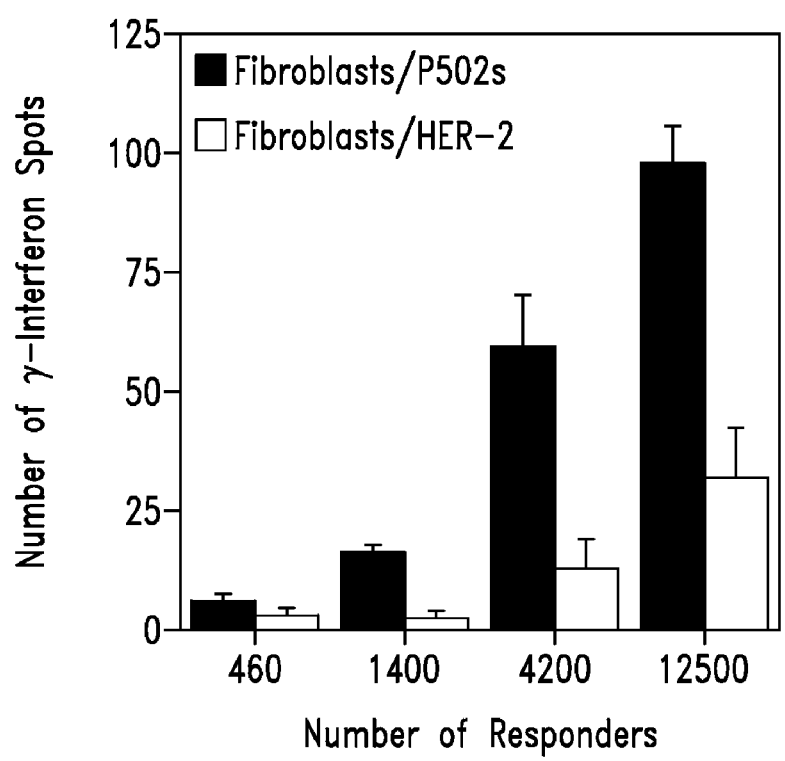

Human CD8$^+$ T cells were primed in vitro to the P2S-12 peptide (VLGWVAEL; SEQ ID NO:306) derived from the P502S (J1-17) gene using dendritic cells according to protocol set forth by Van Tsai et al., *Critical Reviews in Immunology* 18:65–75, 1998. The resulting CD8$^+$ T cell microcultures were tested for their ability to recognize the P2S-12 peptide presented by autologous fibroblasts or fibroblasts which were transduced to express the P502S gene in a γ-interferon ELISPOT assay (see Lalvani et al., *J. Experimental Medicine* 186:859–865, 1997). Briefly, titrating numbers of T cells were assayed in duplicate on 10$^4$ fibroblasts in the presence of 3 μg/ml human β$_2$-microglobulin and 1 μg/ml P2S-12 peptide or control E75 peptide. In addition, T cells were simultaneously assayed on autologous fibroblasts transduced with the P502S gene or as a control, fibroblasts transduced with HER-2/neu. Prior to the assay, the fibroblasts were treated with 10 ng/ml γ-interferon for 48 hours to upregulate class I MHC expression. One of the microcultures (#5) demonstrated strong recognition of both peptide pulsed fibroblasts as well as transduced fibroblasts in a γ-interferon ELISPOT assay. FIG. 2A demonstrates that there was a strong increase in the number of γ-interferon spots with increasing numbers of T cells on fibroblasts pulsed with the P2S-12 peptide (solid bars) but not with the control E75 peptide (open bars). This shows the ability of these T cells to specifically recognize the P2S-12 peptide. In FIG. 2B, this microculture also demonstrated an increase in the number of γ-interferon spots with increasing numbers of T cells on fibroblasts transduced to express the P502S gene but not the HER-2/neu gene. These results provide additional confirmatory evidence that the P2S-12 peptide is a naturally processed epitope of the P502S protein. Furthermore, this also demonstrates that there exists in the human T cell repertoire, high affinity T cells which are capable of recognizing this epitope. These T cells should also be capable of recognizing human tumors which express the P502S gene.

Example 8

Priming of CTL In Vivo using Naked DNA Immunization with a Novel Prostrate Antigen The novel prostate tumor antigen L1-12, as described above, is also referred to as P501S. HLA A2Kb Tg mice, (provided by Dr L. Sherman, The Scripps Research Institute, La Jolla, Calif.) were immunized with 100 ug VR10132-P501 S either intramuscularly or intradermally. The mice were immunized three times, with a two week interval between immunizations. Two weeks after the last immunization, immune spleen cells were cultured with Jurkat A2Kb-P501 S transduced stimulator cells. CTL lines were stimulated weekly. After two weeks of in vitro stimulation, CTL activity was assessed against P501S transduced targets. The results show that 2/8 mice developed strong anti-P501S CTL responses. These results demonstrate that P501S contains at least one naturally processed A2-restricted CTL epitope.

Example 9

Generation of Human CTL In Vitro using Whole Gene Priming and Stimulation Techniques with Novel Prostrate Tumor Antigen The novel prostate antigen L1-12, as described above, is also referred to as P501S. Using in vitro whole-gene priming with P501S-retrovirally transduced autologous fibroblasts, (see, for example, Yee et al, *The Journal of Immunology,* 157(9):4079–86, 1996) human CTL lines were derived that specifically recognize autologous fibroblasts transduced with P501 S, as determined by interferon-γ ELI SPOT analysis (as described above). Using a panel of HLA-mismatched fibroblast lines transduced with P501S, these CTL lines were shown to be restricted HLA-A2 class I allele. Specifically, dendritic cells (DC) were differentiated from monocyte cultures derived from PBMC of normal human donors by growth for five days in RPMI medium containing 10% human serum and 50 ng/ml human GM-CSF and 30 ng/ml human IL-4. Following culture, D C were infected overnight with recombinant P501S vaccinia virus at a multiplicity of infection (M.O.I) of five, and matured overnight by the addition of 3 ug/ml. CD40 ligand. Virus was inactivated by U.V. irradiation and CD8+ T cells were isolated using a magnetic bead system, and priming cultures were initiated using standard culture techniques. Cultures were restimulated every 7–10 days using autologous primary fibroblasts retrovirally transduced with P501S. Following four stimulations cycles, CD8+ T cell lines could be identified that specifically produced interferon-γ when stimulated with P501 S-transduced autologous fibroblasts; the P501S-specific activity could be sustained by the continued stimulation of the cultures with P501S-transduced fibroblasts in the presence of IL-15. A panel of HLA-mismatched fibroblast lines transduced with P501S were generated to define the restriction allele of the response. By measuring Interferon-γ in an ELISPOT assay, the P501S specific response was shown to be restricted by HLA-A2. These results demonstrate that a CD8+ CTL response to P501S can be elicited.

Example 10

Identification of a Naturally Processed CTL Epitope Contained within a Novel Prostrate Tumor Antigen The novel prostate antigen P20, as described above, is also referred to as P703P. The 9-mer peptide, p5, having an amino acid sequence of LLANDLMLI, (SEQ ID NO: 338) was derived from the P703P antigen. The p5 peptide is immunogenic in human HLA-A2 donors and is a naturally processed epitope. Antigen specific CD8+ T cells can be primed following repeated in vitro stimulations with monocytes pulsed with p5 peptide. These CTL specifically recognize p5-pulsed target cells in both ELISPOT (described above), and chromium release assays. Additionally, in HLA-A2 transgenic mice (described above), immunization with p5 leads to the generation of CTL lines which recognize a variety of P703P transduced target cells expressing either HLA-A2Kb or HLA-A2. Specifically, HLA-A2 transgenic mice were immunized subcutaneously in the footpad with 100 ug of p5 peptide formulated together with 140 ug of hepatitis B virus core peptide (a Th peptide) in Freund's incomplete adjuvant. Three weeks post immunization, spleen cells from immunized mice were stimulated in vitro with peptide-pulsed LPS blasts. CTL activity was assessed by chromium release assay five days after primary in vitro stimulation. Retrovirally transduced cells expressing P703P, or control antigen, and HLA-A2Kb were used as targets. CTL lines specifically recognized both p5-pulsed targets as well as P703P-expressing targets have been identified.

Human in vitro priming experiments have been conducted that demonstrate the p5 peptide is immunogenic in humans. Dendritic cells (DC) were differentiated from monocyte cultures derived from PBMC of normal human donors by culturing for five days in RPMI medium containing 10% human serum and 50 ng/ml human GM-CSF and 30 ng/ml human IL-4. Following culture, the DC were pulsed with p5 peptide and cultured with GM-CSF and IL-4 together with CD8+ T cell enriched PBMC. CTL lines were restimulated in a weekly basis using p5-pulsed monocytes in subsequent stimulations. Five to six weeks after initiation of the CTL cultures, CTL recognition of p5-pulsed target cells was demonstrated.

From the foregoing, it will be appreciated that, although specific embodiments of the invention have been described herein for the purposes of illustration, various modifications may be made without deviating from the spirit and scope of the invention. Accordingly, the present invention is not limited except as by the appended claims.

The invention claimed is:

1. A method for detecting the presence of prostate cancer in a patient, comprising the steps of:
   (a) detecting in a biological sample the level of expression of a mRNA encoding a prostate tumor protein, wherein the prostate tumor protein comprises an amino acid sequence encoded by SEQ ID NO: 107; and
   (b) comparing the level of expression detected in the biological sample to a predetermined cut-off value, and thereby detecting the presence or absence of prostate cancer, wherein an increase in the level of expression in the biological sample compared to a non-cancerous sample is indicative of the presence of prostate cancer.

2. The method of claim 1, wherein step (a) comprises an amplification reaction.

3. The method of claim 2, wherein the amplification reaction is a reverse transcription polymerase chain reaction.

4. The method of claim 2, wherein the amplification reaction is a transcription-mediated amplification reaction.

5. The method of claim 1, wherein the biological sample is blood, sera, urine, biopsies or prostate secretions.

* * * * *